United States Patent
Treen et al.

(10) Patent No.: US 12,376,898 B2
(45) Date of Patent: Aug. 5, 2025

(54) NON-INVASIVE, UNIFORM AND NON-UNIFORM RF METHODS AND SYSTEMS RELATED APPLICATIONS

(71) Applicant: CYNOSURE, LLC, Westford, MA (US)

(72) Inventors: Jeffrey Michael Treen, Nashua, NH (US); Daniel B. Masse, Windham, NH (US); James Boll, Montclair, NJ (US); Jeffrey Simon, Everett, MA (US); David Sonnenshein, Dorchester Center, MA (US); Samuel Bruce, Malden, MA (US)

(73) Assignee: CYNOSURE, LLC, Westford, MA (US)

( * ) Notice: Subject to any disclaimer, the term of this patent is extended or adjusted under 35 U.S.C. 154(b) by 156 days.

(21) Appl. No.: 16/731,004

(22) Filed: Dec. 30, 2019

(65) Prior Publication Data

US 2020/0352633 A1    Nov. 12, 2020

Related U.S. Application Data

(63) Continuation-in-part of application No. 16/238,483, filed on Jan. 2, 2019, which is a continuation-in-part of application No. 15/640,710, filed on Jul. 3, 2017.
(Continued)

(51) Int. Cl.
*A61B 18/14* (2006.01)
*A61B 18/00* (2006.01)

(52) U.S. Cl.
CPC .... *A61B 18/14* (2013.01); *A61B 2018/00077* (2013.01); *A61B 2018/00136* (2013.01);
(Continued)

(58) Field of Classification Search
CPC .. A61B 2018/1465; A61B 2018/00464; A61B 2018/147; A61B 2018/0016;
(Continued)

(56) References Cited

U.S. PATENT DOCUMENTS

D246,053 S    10/1977  Staub et al.
D281,721 S    12/1985  Scanlan
(Continued)

FOREIGN PATENT DOCUMENTS

DE    478672    7/1929
DE    3627221   2/1988
(Continued)

OTHER PUBLICATIONS

[No author] The Effect of Heat on Collagen and Neocollagenesis, Ultherapy.com, Mar. 6, 2013, 1 page, http://www.ultherapy.com/uploads/document/professional/Effects-of-Temperature-on-Collagen.pdf.
(Continued)

*Primary Examiner* — Kaitlyn E Smith
*Assistant Examiner* — Christine A Dedoulis
(74) *Attorney, Agent, or Firm* — K&L GATES LLP

(57) ABSTRACT

Systems and methods utilizing RF energy to treat a patient's skin or other target tissues are provided herein. In various aspects, the methods and systems described herein can provide a RF-based treatment in which RF energy can be selectively controlled to facilitate heating uniformity during one or more of body sculpting treatment (lipolysis), skin tightening treatment (laxity improvement), cellulite treatment, all by way of non-limiting examples. In various aspects, the systems may include a flexible applicator comprising a plurality of layers, the plurality of layers comprises a first dielectric layer, a second dielectric layer, and a conductive layer, wherein the first dielectric layer and the
(Continued)

second dielectric layer sandwich the conductive layer, the plurality of layers define a plurality of kerfs, an inner region and N regions extending from the inner region, wherein the plurality of kerfs divide the applicator into N regions.

31 Claims, 58 Drawing Sheets

Related U.S. Application Data

(60) Provisional application No. 62/514,778, filed on Jun. 2, 2017, provisional application No. 62/357,920, filed on Jul. 1, 2016.

(52) U.S. Cl.
CPC ............ *A61B 2018/00464* (2013.01); *A61B 2018/00714* (2013.01); *A61B 2018/1465* (2013.01)

(58) Field of Classification Search
CPC ........... A61B 2018/00458; A61B 2018/00559; A61N 1/0484; A61N 1/40; A61N 1/403
See application file for complete search history.

(56) References Cited

U.S. PATENT DOCUMENTS

| | | |
|---|---|---|
| D296,006 S | 5/1988 | Asche |
| D320,271 S | 9/1991 | Jones |
| D320,856 S | 10/1991 | Scheller |
| 5,246,746 A | 9/1993 | Michalske et al. |
| D346,866 S | 5/1994 | Lotuaco |
| D351,227 S | 10/1994 | Patton et al. |
| D352,350 S | 11/1994 | Rambo et al. |
| D360,705 S | 7/1995 | Martin |
| 5,458,597 A | 10/1995 | Edwards et al. |
| 5,478,303 A | 12/1995 | Foley-Nolan et al. |
| 5,505,728 A | 4/1996 | Ellman et al. |
| 5,514,131 A | 5/1996 | Edwards et al. |
| 5,562,503 A | 10/1996 | Ellman et al. |
| 5,571,101 A | 11/1996 | Ellman et al. |
| D376,423 S | 12/1996 | Monea |
| 5,594,686 A | 1/1997 | Hazen et al. |
| 5,599,347 A | 2/1997 | Hart et al. |
| 5,613,966 A | 3/1997 | Makower et al. |
| 5,620,441 A | 4/1997 | Gref et al. |
| D379,507 S | 5/1997 | Haber et al. |
| D382,342 S | 8/1997 | Rosen |
| 5,662,680 A | 9/1997 | Desal |
| 5,679,401 A | 10/1997 | Bawden |
| 5,683,387 A | 11/1997 | Garito et al. |
| 5,685,878 A | 11/1997 | Falwell et al. |
| D388,170 S | 12/1997 | Sjostrom |
| 5,709,675 A | 1/1998 | Williams |
| 5,713,942 A | 2/1998 | Stern et al. |
| D393,067 S | 3/1998 | Geary et al. |
| 5,733,282 A | 3/1998 | Ellman et al. |
| D393,715 S | 4/1998 | Strickland |
| 5,741,250 A | 4/1998 | Garito et al. |
| 5,755,716 A | 5/1998 | Garito et al. |
| 5,766,171 A | 6/1998 | Silvestrini |
| 5,769,702 A | 6/1998 | Hanson |
| 5,792,216 A * | 8/1998 | Kappel ............... A61F 7/0097 5/423 |
| 5,807,392 A | 9/1998 | Eggers |
| 5,814,044 A | 9/1998 | Hooven |
| 5,833,689 A | 11/1998 | Long |
| 5,836,897 A | 11/1998 | Sakurai et al. |
| D402,030 S | 12/1998 | Roberts et al. |
| 5,871,524 A | 2/1999 | Knowlton |
| 5,891,142 A | 4/1999 | Eggers et al. |
| 5,916,158 A | 6/1999 | Webster, Jr. |
| 5,924,206 A | 7/1999 | Cote et al. |
| 5,925,039 A | 7/1999 | Landingham |
| 5,954,686 A | 9/1999 | Garito et al. |
| 5,984,918 A | 11/1999 | Garito et al. |
| 5,993,447 A | 11/1999 | Blewett et al. |
| 5,997,533 A | 12/1999 | Kohns |
| 6,001,077 A | 12/1999 | Ellman et al. |
| 6,006,755 A | 12/1999 | Edwards |
| 6,010,500 A | 1/2000 | Sherman et al. |
| D422,024 S | 3/2000 | Andrews et al. |
| 6,039,734 A | 3/2000 | Goble |
| 6,044,846 A | 4/2000 | Edwards |
| 6,050,993 A | 4/2000 | Tu et al. |
| 6,059,734 A | 5/2000 | Yoon |
| 6,063,085 A | 5/2000 | Tay et al. |
| 6,068,628 A | 5/2000 | Fanton et al. |
| 6,080,182 A | 6/2000 | Nardella et al. |
| D428,146 S | 7/2000 | Svanberg et al. |
| 6,093,186 A | 7/2000 | Goble |
| 6,102,046 A | 8/2000 | Weinstein et al. |
| 6,113,596 A | 9/2000 | Hooven et al. |
| 6,156,032 A | 12/2000 | Lennox |
| 6,159,194 A | 12/2000 | Eggers et al. |
| 6,203,762 B1 | 3/2001 | Skalla et al. |
| 6,206,842 B1 | 3/2001 | Tu et al. |
| D441,077 S | 4/2001 | Garito et al. |
| 6,214,003 B1 | 4/2001 | Morgan et al. |
| 6,228,078 B1 | 5/2001 | Eggers et al. |
| 6,228,084 B1 | 5/2001 | Kirwan, Jr. |
| 6,231,571 B1 | 5/2001 | Ellman et al. |
| 6,235,027 B1 | 5/2001 | Herzon |
| 6,238,388 B1 | 5/2001 | Ellman et al. |
| 6,238,394 B1 | 5/2001 | Garito et al. |
| 6,245,068 B1 | 6/2001 | Olsen et al. |
| 6,251,110 B1 | 6/2001 | Wampler |
| 6,280,441 B1 | 8/2001 | Ryan |
| 6,296,637 B1 | 10/2001 | Throne et al. |
| 6,312,428 B1 | 11/2001 | Eggers et al. |
| D453,222 S | 1/2002 | Garito et al. |
| 6,348,051 B1 | 2/2002 | Farin et al. |
| 6,355,032 B1 | 3/2002 | Hovda et al. |
| 6,368,324 B1 | 4/2002 | Dinger et al. |
| 6,387,092 B1 | 5/2002 | Burnside et al. |
| 6,387,093 B1 | 5/2002 | Ellman et al. |
| 6,395,001 B1 | 5/2002 | Ellman et al. |
| 6,402,742 B1 | 6/2002 | Blewett et al. |
| 6,409,726 B1 | 6/2002 | Ellman et al. |
| 6,416,512 B1 | 7/2002 | Ellman et al. |
| 6,432,105 B1 | 8/2002 | Ellman et al. |
| 6,447,509 B1 | 9/2002 | Bonnet et al. |
| 6,461,352 B2 | 10/2002 | Morgan et al. |
| 6,506,267 B1 | 1/2003 | Fujiyasu et al. |
| D471,281 S | 3/2003 | Baura et al. |
| 6,530,924 B1 | 3/2003 | Ellman et al. |
| 6,540,745 B1 | 4/2003 | Fairbourn et al. |
| 6,544,210 B1 | 4/2003 | Trudel et al. |
| 6,546,935 B2 | 4/2003 | Hooven |
| 6,562,032 B1 | 5/2003 | Ellman et al. |
| 6,562,036 B1 | 5/2003 | Ellman et al. |
| 6,565,561 B1 | 5/2003 | Goble et al. |
| 6,572,613 B1 | 6/2003 | Ellman et al. |
| 6,585,791 B1 | 7/2003 | Garito et al. |
| 6,592,580 B1 | 7/2003 | Stockert |
| 6,607,528 B1 | 8/2003 | Quick et al. |
| 6,613,047 B2 | 9/2003 | Edwards |
| 6,613,048 B2 | 9/2003 | Mulier et al. |
| 6,652,814 B1 | 11/2003 | Ellman et al. |
| 6,673,072 B1 | 1/2004 | Garito et al. |
| 6,679,881 B1 | 1/2004 | Bybee |
| 6,689,071 B2 | 2/2004 | Burbank et al. |
| 6,730,323 B1 | 5/2004 | Murley et al. |
| 6,749,608 B2 | 6/2004 | Garito et al. |
| 6,749,624 B2 | 6/2004 | Knowlton |
| 6,766,202 B2 | 7/2004 | Underwood et al. |
| 6,767,348 B2 | 7/2004 | Nakada et al. |
| D494,270 S | 8/2004 | Reschke |
| 6,802,842 B2 | 10/2004 | Ellman et al. |
| 6,830,569 B2 | 12/2004 | Thompson et al. |
| 6,837,884 B2 | 1/2005 | Woloszko |
| 6,920,883 B2 | 7/2005 | Bessette et al. |

(56) References Cited

U.S. PATENT DOCUMENTS

| | | |
|---|---|---|
| 6,926,717 B1 | 8/2005 | Garito et al. |
| 6,994,707 B2 | 2/2006 | Ellman et al. |
| 7,070,604 B1 | 7/2006 | Garito et al. |
| 7,090,649 B2 | 8/2006 | Lin |
| 7,094,231 B1 | 8/2006 | Ellman et al. |
| 7,147,634 B2 | 12/2006 | Nesbitt |
| 7,156,844 B2 | 1/2007 | Reschke et al. |
| 7,160,295 B1 | 1/2007 | Garito et al. |
| 7,163,336 B2 | 1/2007 | Blakeley, III |
| D538,936 S | 3/2007 | Bohmel et al. |
| 7,258,689 B2 | 8/2007 | Russell |
| D555,803 S | 11/2007 | Garito et al. |
| 7,422,586 B2 | 9/2008 | Morris et al. |
| 7,473,251 B2 | 1/2009 | Ellman et al. |
| 7,479,140 B2 | 1/2009 | Ellman et al. |
| 7,507,232 B1 | 3/2009 | Garito et al. |
| 7,674,261 B2 | 3/2010 | Garito et al. |
| 7,749,218 B2 | 7/2010 | Pellegrino et al. |
| D625,412 S | 10/2010 | Garito et al. |
| 7,828,794 B2 | 11/2010 | Sartor |
| 7,875,026 B1 | 1/2011 | Garito et al. |
| 7,879,032 B1 | 2/2011 | Garito et al. |
| 7,879,033 B2 | 2/2011 | Sartor et al. |
| 7,938,110 B2 | 5/2011 | Garito et al. |
| 7,947,037 B1 | 5/2011 | Garito et al. |
| 7,955,327 B2 | 6/2011 | Sartor et al. |
| 7,959,633 B2 | 6/2011 | Sartor et al. |
| 8,016,824 B2 | 9/2011 | Buchman, II et al. |
| 8,100,898 B2 | 1/2012 | Gregg |
| 8,100,902 B2 | 1/2012 | Sartor |
| 8,128,622 B2 | 3/2012 | Podhajsky et al. |
| 8,162,937 B2 | 4/2012 | Cunningham et al. |
| 8,172,835 B2 | 5/2012 | Leyh et al. |
| 8,231,620 B2 | 7/2012 | Mathonnet |
| 8,235,987 B2 | 8/2012 | Craig |
| 8,251,989 B1 | 8/2012 | Newton et al. |
| 8,317,782 B1 | 11/2012 | Ellman et al. |
| 8,321,031 B1 | 11/2012 | Ellman et al. |
| 8,359,104 B2 | 1/2013 | Epstein et al. |
| 8,449,540 B2 | 5/2013 | Sartor et al. |
| 8,454,591 B2 | 6/2013 | Leyh et al. |
| 8,460,289 B2 | 6/2013 | Sartor |
| 8,506,565 B2 | 8/2013 | DeCarlo |
| 8,540,705 B2 | 9/2013 | Mehta |
| 8,591,509 B2 | 11/2013 | Fry et al. |
| 8,597,292 B2 | 12/2013 | Kerr |
| 8,608,737 B2 | 12/2013 | Mehta et al. |
| 8,632,536 B2 | 1/2014 | Kerr et al. |
| 8,636,733 B2 | 1/2014 | Heard |
| 8,663,216 B2 | 3/2014 | Davison et al. |
| 8,663,218 B2 | 3/2014 | Heard et al. |
| 8,663,219 B2 | 3/2014 | Heard et al. |
| 8,668,688 B2 | 3/2014 | Rusin |
| 8,700,176 B2 | 4/2014 | Azar et al. |
| 8,845,630 B2 | 9/2014 | Mehta et al. |
| 8,945,124 B2 | 2/2015 | Craig |
| 8,961,511 B2 | 2/2015 | Parmer |
| 8,998,891 B2 | 4/2015 | Garito et al. |
| D752,764 S | 3/2016 | Peters |
| 9,271,785 B2 | 3/2016 | Parmer et al. |
| 9,345,531 B2 | 5/2016 | Furnish et al. |
| D762,869 S | 8/2016 | Beckman et al. |
| 9,415,235 B2 | 8/2016 | Galen et al. |
| D785,189 S | 4/2017 | Dettmar |
| D797,948 S | 9/2017 | Matsushita |
| D824,526 S | 7/2018 | Ramjit et al. |
| D834,209 S | 11/2018 | Tan |
| D870,299 S | 12/2019 | Lin |
| D889,662 S | 7/2020 | Hubelbank |
| D937,419 S | 11/2021 | Lou |
| D937,420 S | 11/2021 | Lou |
| D940,341 S | 1/2022 | Lin |
| 2001/0018606 A1 | 8/2001 | Ingle et al. |
| 2002/0032439 A1 | 3/2002 | Hareyama |
| 2002/0062142 A1 | 5/2002 | Knowlton |
| 2002/0077626 A1 | 6/2002 | Ellman et al. |
| 2002/0115991 A1 | 8/2002 | Edwards |
| 2002/0133149 A1 | 9/2002 | Bessette |
| 2002/0188284 A1 | 12/2002 | To et al. |
| 2003/0009165 A1 | 1/2003 | Edwards et al. |
| 2003/0050634 A1 | 3/2003 | Ellman et al. |
| 2003/0092978 A1* | 5/2003 | Fisher, III ............ A61N 1/0492 600/391 |
| 2003/0112204 A1 | 6/2003 | Pettersen |
| 2003/0130711 A1 | 7/2003 | Pearson et al. |
| 2003/0139741 A1 | 7/2003 | Goble et al. |
| 2003/0139753 A1 | 7/2003 | Wang et al. |
| 2003/0153906 A1 | 8/2003 | Sharkey et al. |
| 2003/0158545 A1 | 8/2003 | Hovda et al. |
| 2003/0159700 A1 | 8/2003 | Laufer et al. |
| 2003/0163178 A1 | 8/2003 | Davison et al. |
| 2003/0216727 A1 | 11/2003 | Long |
| 2003/0216728 A1 | 11/2003 | Stern et al. |
| 2003/0236487 A1 | 12/2003 | Knowlton |
| 2004/0002705 A1 | 1/2004 | Knowlton et al. |
| 2004/0030329 A1 | 2/2004 | Hagg |
| 2004/0049251 A1 | 3/2004 | Knowlton |
| 2004/0064175 A1 | 4/2004 | Lessar et al. |
| 2004/0111087 A1 | 6/2004 | Stern et al. |
| 2004/0116979 A1 | 6/2004 | Truckai et al. |
| 2004/0167516 A1 | 8/2004 | Cucin |
| 2004/0181213 A1 | 9/2004 | Gondo |
| 2004/0186535 A1 | 9/2004 | Knowlton |
| 2004/0210214 A1 | 10/2004 | Knowlton |
| 2004/0236203 A1 | 11/2004 | Salvo |
| 2005/0004564 A1 | 1/2005 | Wham et al. |
| 2005/0009889 A1 | 3/2005 | Mayer |
| 2005/0090816 A1 | 4/2005 | McClurken et al. |
| 2005/0137662 A1 | 6/2005 | Morris et al. |
| 2005/0054385 A1 | 7/2005 | Heim et al. |
| 2005/0026524 A1 | 11/2005 | Long et al. |
| 2005/0267465 A1 | 12/2005 | Hillier et al. |
| 2006/0009757 A1 | 1/2006 | Long |
| 2006/0009763 A1 | 1/2006 | Goble et al. |
| 2006/0052847 A1 | 3/2006 | Davenport et al. |
| 2006/0173518 A1 | 8/2006 | Kreinde |
| 2006/0200122 A1* | 9/2006 | Sartor .................. A61B 18/042 606/41 |
| 2006/0259102 A1 | 11/2006 | Slatkine |
| 2007/0005053 A1 | 1/2007 | Dando |
| 2007/0055226 A1 | 3/2007 | Garito et al. |
| 2007/0083247 A1 | 4/2007 | Wyeth et al. |
| 2007/0088413 A1* | 4/2007 | Weber .................... A61B 18/14 607/99 |
| 2007/0093804 A1 | 4/2007 | Kaveckis et al. |
| 2007/0093805 A1 | 4/2007 | Auth et al. |
| 2007/0106349 A1 | 5/2007 | Karni et al. |
| 2007/0112342 A1 | 5/2007 | Pearson et al. |
| 2007/0161981 A1 | 7/2007 | Sanders et al. |
| 2007/0213700 A1 | 9/2007 | Davison et al. |
| 2007/0233191 A1 | 10/2007 | Parmer |
| 2007/0282318 A1 | 12/2007 | Spooner et al. |
| 2008/0004678 A1 | 1/2008 | Kreindel |
| 2008/0058796 A1 | 3/2008 | O'Brien et al. |
| 2008/0091184 A1 | 4/2008 | Knopp et al. |
| 2008/0091185 A1 | 4/2008 | McGill et al. |
| 2008/0125775 A1* | 5/2008 | Morris ............... A61B 18/1477 606/50 |
| 2008/0183251 A1 | 7/2008 | Azar et al. |
| 2008/0262490 A1 | 10/2008 | Williams |
| 2008/0312651 A1 | 12/2008 | Pope et al. |
| 2009/0306648 A1 | 2/2009 | Dunn-Coleman et al. |
| 2009/0062786 A1 | 3/2009 | Garito et al. |
| 2009/0093864 A1 | 4/2009 | Anderson |
| 2009/0112205 A1 | 4/2009 | McGill et al. |
| 2009/0138011 A1 | 5/2009 | Epstein |
| 2009/0248022 A1 | 10/2009 | Falkenstein et al. |
| 2009/0306647 A1* | 12/2009 | Leyh .................. A61B 18/1233 606/34 |
| 2010/0023008 A1 | 1/2010 | Heard et al. |
| 2010/0030212 A1 | 2/2010 | Aramayo |
| 2010/0045427 A1 | 2/2010 | Boone, III et al. |
| 2010/0114088 A1 | 5/2010 | Buchman, II et al. |
| 2010/0211060 A1 | 8/2010 | Baron et al. |

(56) References Cited

U.S. PATENT DOCUMENTS

| | | | |
|---|---|---|---|
| 2010/0217254 A1 | 8/2010 | Mehta | |
| 2010/0228243 A1 | 9/2010 | Mehta | |
| 2010/0249772 A1 | 9/2010 | Mehta et al. | |
| 2010/0262135 A1 | 10/2010 | Berube | |
| 2010/0312233 A1 | 12/2010 | Furnish et al. | |
| 2010/0330338 A1* | 12/2010 | Boyce | H01L 23/4985 428/156 |
| 2011/0046523 A1 | 2/2011 | Altshuler et al. | |
| 2011/0087215 A1 | 4/2011 | Aldridge et al. | |
| 2011/0144729 A1 | 6/2011 | Weber | |
| 2011/0178584 A1 | 7/2011 | Parmer et al. | |
| 2012/0022512 A1 | 1/2012 | Lee et al. | |
| 2012/0265193 A1 | 10/2012 | Uschinsky et al. | |
| 2013/0006239 A1 | 1/2013 | Pikramenos et al. | |
| 2013/0123629 A1 | 5/2013 | Rosenberg et al. | |
| 2013/0226269 A1 | 8/2013 | Eckhouse et al. | |
| 2013/0245727 A1 | 9/2013 | Kothare et al. | |
| 2013/0245728 A1 | 9/2013 | Galen et al. | |
| 2014/0182879 A1* | 7/2014 | Busse | H01J 37/32541 174/98 |
| 2014/0249609 A1 | 9/2014 | Zarsky et al. | |
| 2014/0276768 A1 | 9/2014 | Juergens et al. | |
| 2015/0094914 A1 | 4/2015 | Abreu | |
| 2015/0297908 A1 | 10/2015 | Alinsod et al. | |
| 2015/0327926 A1 | 11/2015 | Parmer | |
| 2016/0135876 A1 | 5/2016 | Parmer et al. | |
| 2016/0263387 A1 | 9/2016 | Alinsod et al. | |
| 2016/0263388 A1 | 9/2016 | Alinsod et al. | |
| 2016/0263389 A1 | 9/2016 | Alinsod et al. | |
| 2016/0296278 A1 | 10/2016 | Galen et al. | |
| 2017/0071651 A1 | 3/2017 | Allan et al. | |
| 2017/0231680 A1* | 8/2017 | Mahrenholz | A61N 1/44 606/34 |
| 2017/0333249 A1 | 11/2017 | Herchman, Jr. et al. | |
| 2018/0001103 A9 | 1/2018 | Alinsod et al. | |
| 2020/0352633 A1 | 11/2020 | Treen et al. | |

FOREIGN PATENT DOCUMENTS

| | | | |
|---|---|---|---|
| DE | 9102778 | 5/1991 | |
| DE | 4423216 | 8/1995 | |
| DE | 19850663 | 3/2001 | |
| DE | 20110351 | 2/2002 | |
| DE | 10138235 | 1/2003 | |
| EP | 332308 | 9/1989 | |
| EP | 0368532 | 5/1990 | |
| EP | 0423757 | 4/1991 | |
| EP | 0480639 | 4/1992 | |
| EP | 1707147 | 10/2006 | |
| EP | 2258296 | 12/2010 | |
| EP | 2790603 | 10/2014 | |
| EP | 2670477 | 11/2015 | |
| EP | 2967711 | 1/2016 | |
| EP | 2627400 B1 * | 4/2016 | A61N 5/0616 |
| GB | 2154881 | 9/1985 | |
| GB | 2490788 | 11/2012 | |
| JP | 63-317073 | 12/1988 | |
| JP | H07-95985 | 4/1995 | |
| JP | H08-168495 | 7/1996 | |
| JP | 11-504828 | 5/1999 | |
| JP | 2009-537226 | 10/2009 | |
| JP | 2013-534167 | 2/2013 | |
| JP | 2013-544175 | 12/2013 | |
| WO | WO 96/22742 | 8/1996 | |
| WO | WO 96/39088 | 12/1996 | |
| WO | WO 97/15238 | 5/1997 | |
| WO | WO 98/16162 | 4/1998 | |
| WO | WO 98/38932 | 9/1998 | |
| WO | 02/053028 | 7/2002 | |
| WO | 03/079916 | 10/2003 | |
| WO | WO 2003/103522 | 12/2003 | |
| WO | WO 2004/090939 | 10/2004 | |
| WO | WO2007/136726 | 11/2007 | |
| WO | WO 2008/012827 | 1/2008 | |
| WO | WO 2008/112931 | 9/2008 | |
| WO | WO 2009/031995 | 3/2009 | |
| WO | WO 2009/053117 | 4/2009 | |
| WO | 2010/056771 | 5/2010 | |
| WO | 2011/113943 | 9/2011 | |
| WO | 2012052986 A2 | 4/2012 | |
| WO | WO 2012/052986 | 4/2012 | |
| WO | WO2012/073232 | 6/2012 | |
| WO | 2013/076714 | 5/2013 | |
| WO | 2015050870 A1 | 4/2015 | |
| WO | 2018/006086 | 1/2018 | |

OTHER PUBLICATIONS

Abraham, Manoj T., et al. "Monopolar Radiofrequency Skin Tightening," Facial Plastic Surgery Clinics of North America, 2007, pp. 169-177, vol. 15, Elsevier Inc.

Brunelle, et al. (2005) "A Bipolar Electode for Vascular Electrocoagulation with Alternating Current"Radiology, vol. 137, No. 1, p. 239-240, Oct. 1980.

Fitzpatrick, Richard, et al., "Multicenter Study of Noninvasive Radiofrequency for Periorbital Tissue Tightening" Lasers in Surgery and Medicine, 2003, pp. 232-242, vol. 33, Wiley-Liss, Inc., United States.

Fritz, et al. (2004) Radiofrequency Treatment for Middle and Lower Face Laxity: Arch Facial Plastic Surgery 2004, 6:370-373, 4 pages.

Gonzalex-Suarez, Ana, et al., "Thermal and Elastic Response of Subcutaneous Tissue With Different Fibrous Septa Architectures to RF Heating: Numerical Study," Lasers in Surgery and Medicine, 2015, pp. 183-195, vol. 47, Wiley Periodicals, Inc., United States.

Hantash, Basil M., et al., "Bipolar Fractional Radiofrequency Treatment Induces Neoelastogenesis and Neocollagenesis," Lasers in Surgery and Medicine, 2009, pp. 1-9, vol. 41, Wiley-Liss, Inc., United States.

Hayashi, Kei, et al., "Effect of Nonablative Laser Energy on the Joint Capsule: An in Vivo Rabbit Study Using a Holmium:YAG Laser," Lasers in Surgery and Medicine, 1997, pp. 164-171, vol. 20, Wiley-Liss, Inc., United States.

Hayashi, Kei, et al., "The Effect of Thermal Heating on the Length and Histologic Properties ofthe Glenohumeral Joint Capsule," The American Journal of Sports Medicine, 1997, pp. 107-112, vol. 25 No. 1, Sage Publications, United States.

Kist, David, et al., "Ultrastructural Evaluation of Multiple Pass Low Energy Versus Single Pass High Energy Radio-Frequency Treatment," Lasers in Surgery and Medicine, 2006, pp. 150-154, vol. 38, Wiley-Liss, Inc., United States.

Kushikata, et al. (2005) "Is Topical Anaesthesia Useful in Noninvasive Skin Tightening Using Radiofrequency?" J. Dermatologic Surgery 2005; 31:526-533, 8 pages.

Laubach, Hans J., et al., "Intense Focused Ultrasound: Evaluation of a New Treatment Modality for Precise Microcoagulation within the Skin," American Society for Dermatologic Surgery, Inc., 2008, pp. 727-734, vol. 34, Blackwell Publishing, United States.

Lin, Sung-Jan, et al., "Monitoring the Thermally Induced Structural Transitions of Collagen by Use of Second-Harmonic Generation Microscopy," Optics Letters, 2005, pp. 622-624, vol. 30 No. 6, Optical Society of America.

Paul, Malcolm, et al., "Three-Dimensional Radiofrequency Tissue Tightening: A Proposed Mechanism and Applications for Body Contouring," Aesth Platic Surgery, 2010, pp. 87-95, vol 35., Springer.

Sadick, Neil, "Tissue Tightening Technologies: Fact or Fiction," Aesthetic Surgery Journal, Mar./Apr. 2008, pp. 180-188, vol. 28 No. 2, Sage Publications, United States.

Vangsness Jr., C. Thomas, et al., "Collagen Shortening: An Experimental Approach with Heat," Clinical Orthopedics and Related Research, 1997, pp. 267-271, vol. 337, Lippincott-Raven Publishers.

White, W. Matthew, et al., "Selective Transcutaneous Delivery of Energy to Porcine Soft Tissues Using Intense Ultrasound (IUS)," Lasers in Surgery and Medicine, 2008, pp. 67-75, vol. 40, Wiley-Liss, Inc. United States.

Zelickson, Brian D.,et al., "Histological and Ultrastrcutrual Evaluation of the Effects fo Radiofrequency-Based Nonablative Dermal

(56) References Cited

OTHER PUBLICATIONS

Remodeling Device," Arch Dermatol, Feb. 2004, pp. 204-209, vol. 140, American Medical Association, United States.
Third Party Observation received in PCT/US2017/040585 dated Jan. 29, 2018; 30 pages.
Invitation To Pay Additional Fees, And, Where Applicable, Protest Fee received in PCT/US2017/040585 dated Oct. 13, 2017; 26 pages.
International Search Report and Written Opinion received in PCT/US2017/040585 dated Dec. 6, 2017; 28 pages.
World's First Wrappable RF Applicator, for Hands-Free Treatment on All Skin Types. Online, published date Oct. 8, 2020. Retrieved on Mar. 7, 2022 from URL: https://www.everythingrf.com/news/details/10987-world-s-first-wrappable-rf-applicator-for-hands-free-treatment-on-all-skin-types.
Written Opinion issued by the Intellectual Property Office of Singapore on Apr. 3, 2023 for Singapore application No. 11202107086U (9 pages).
Shin, Jae Min et al., "Radiofrequency in Clinical Dermatology", Medical Lasers, (2013), pp. 49-57.

\* cited by examiner

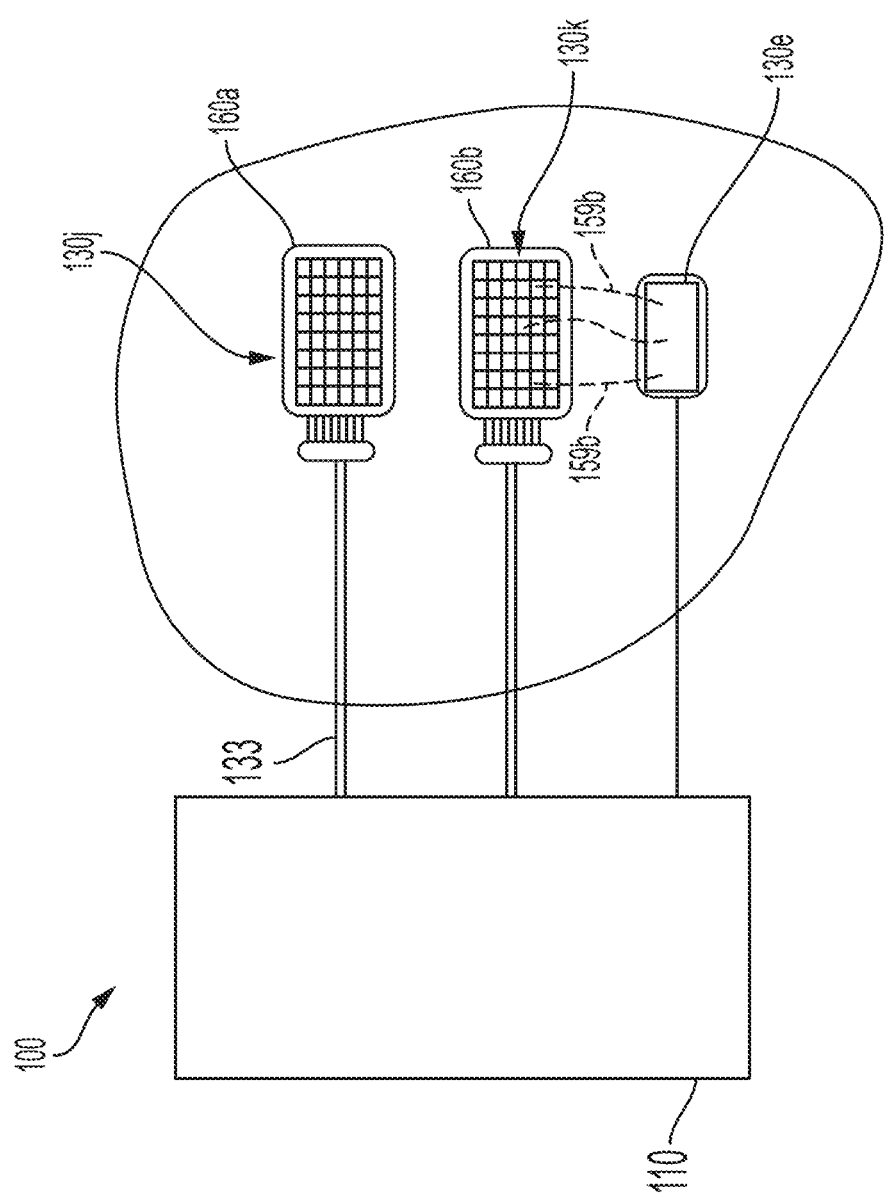

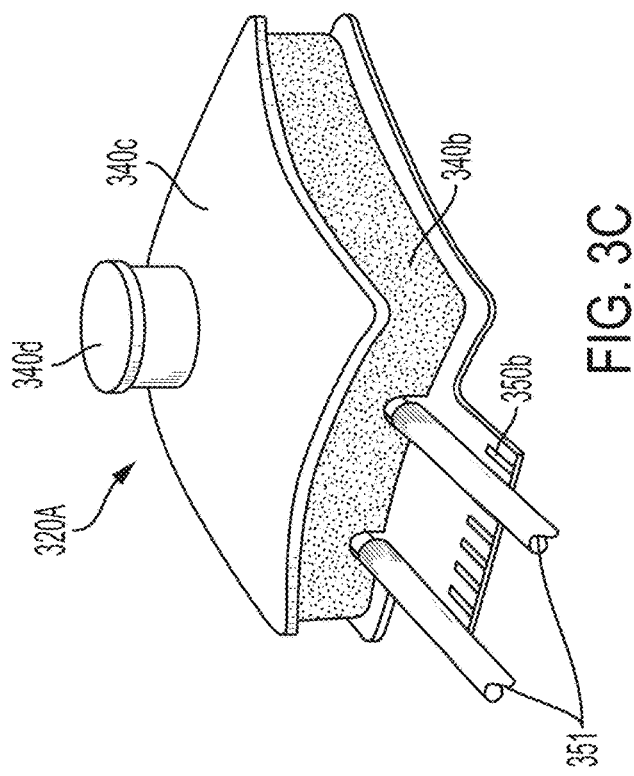
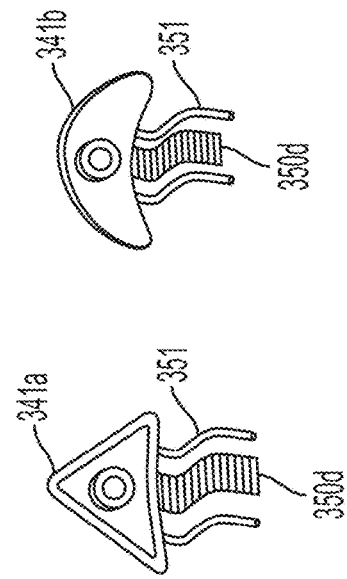
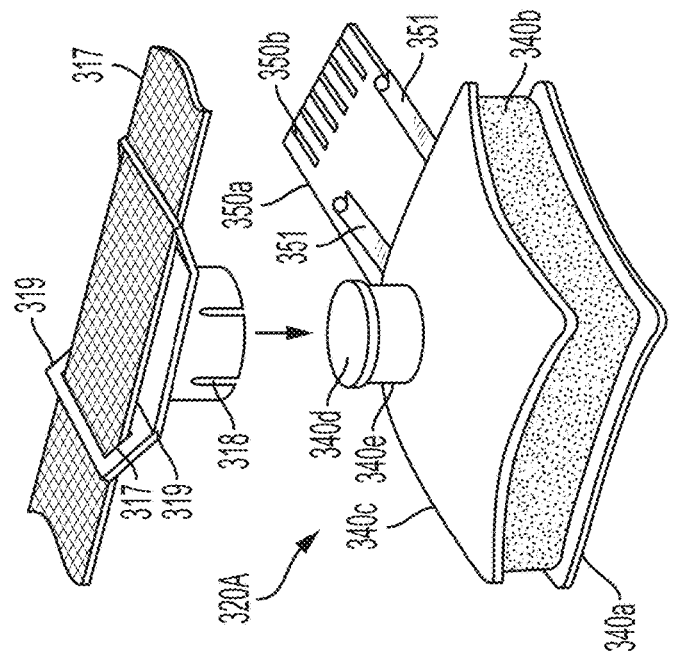
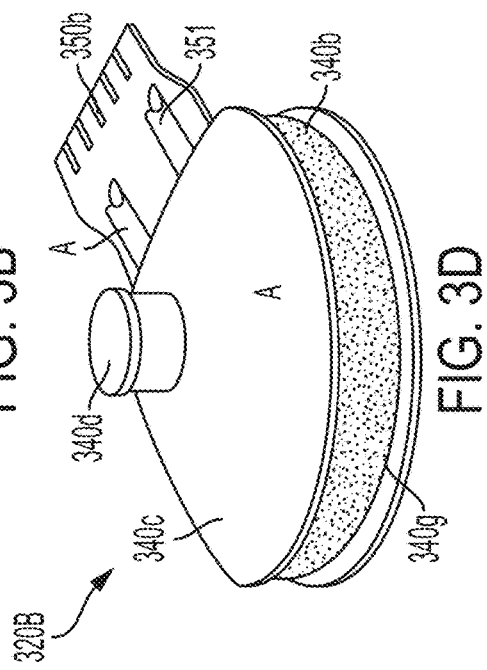

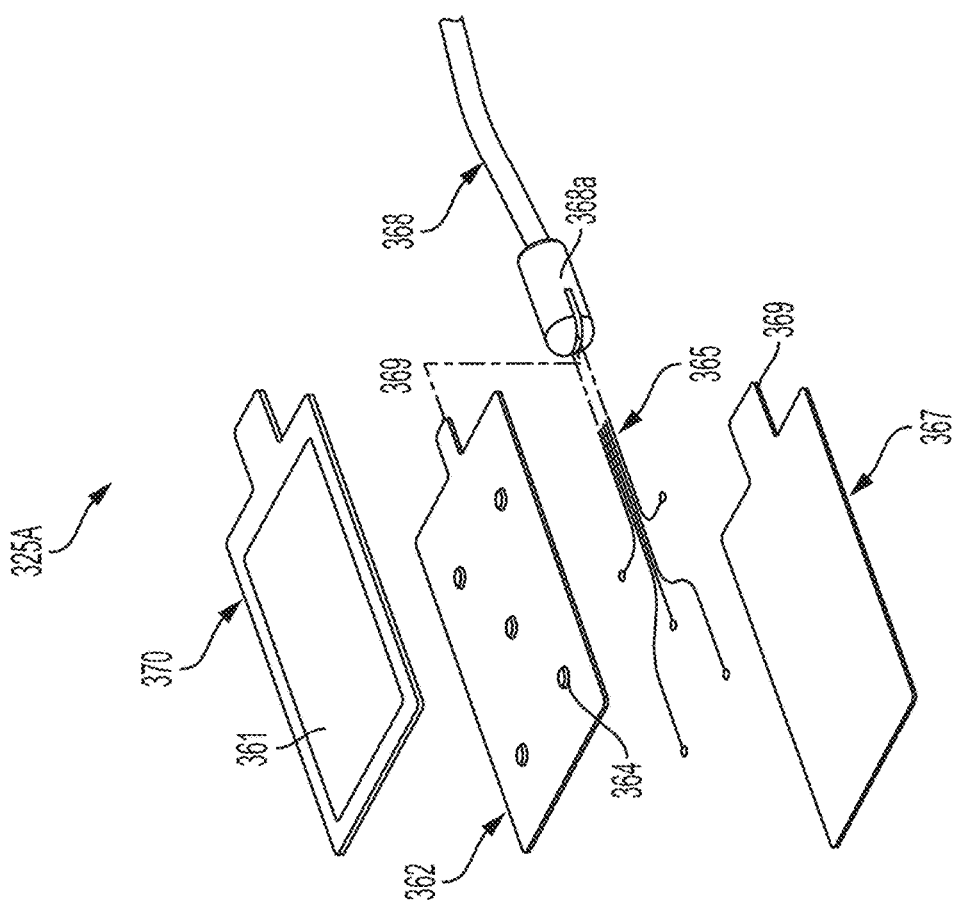
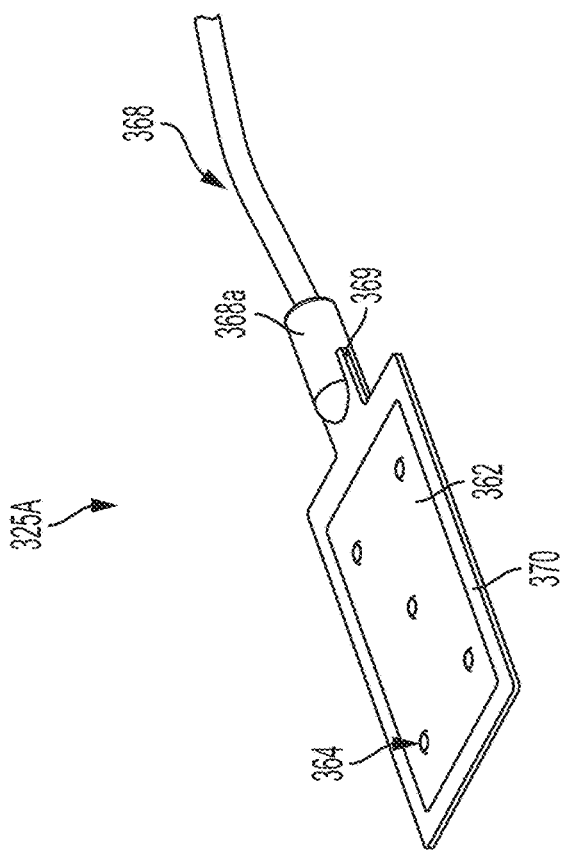

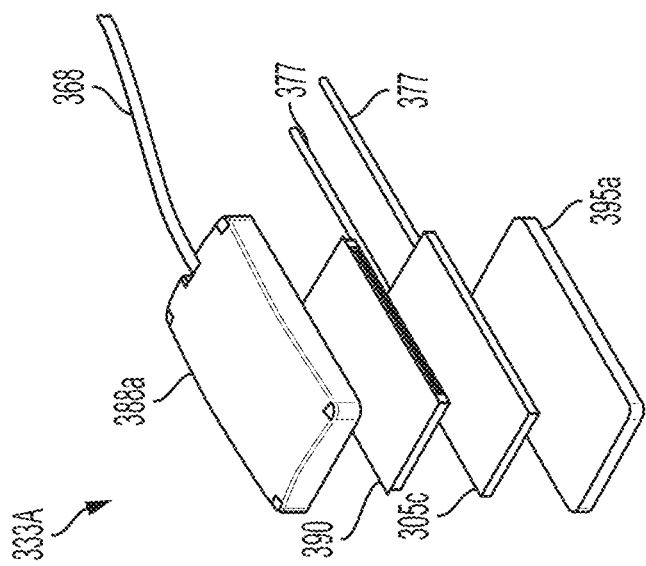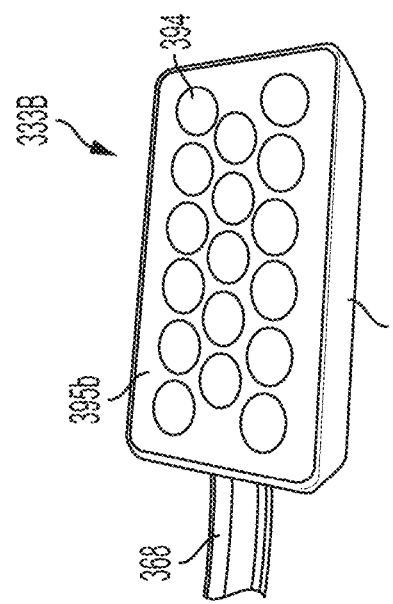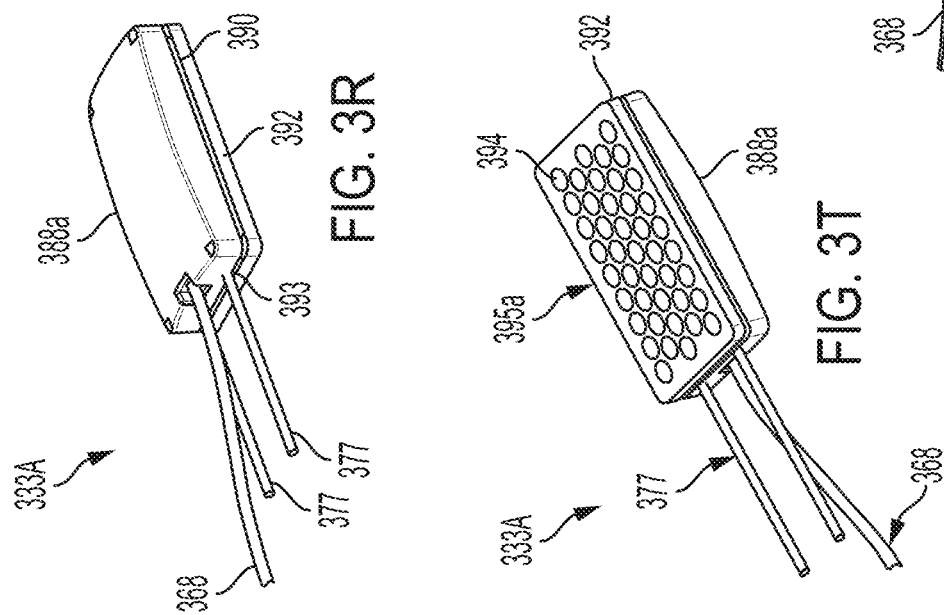

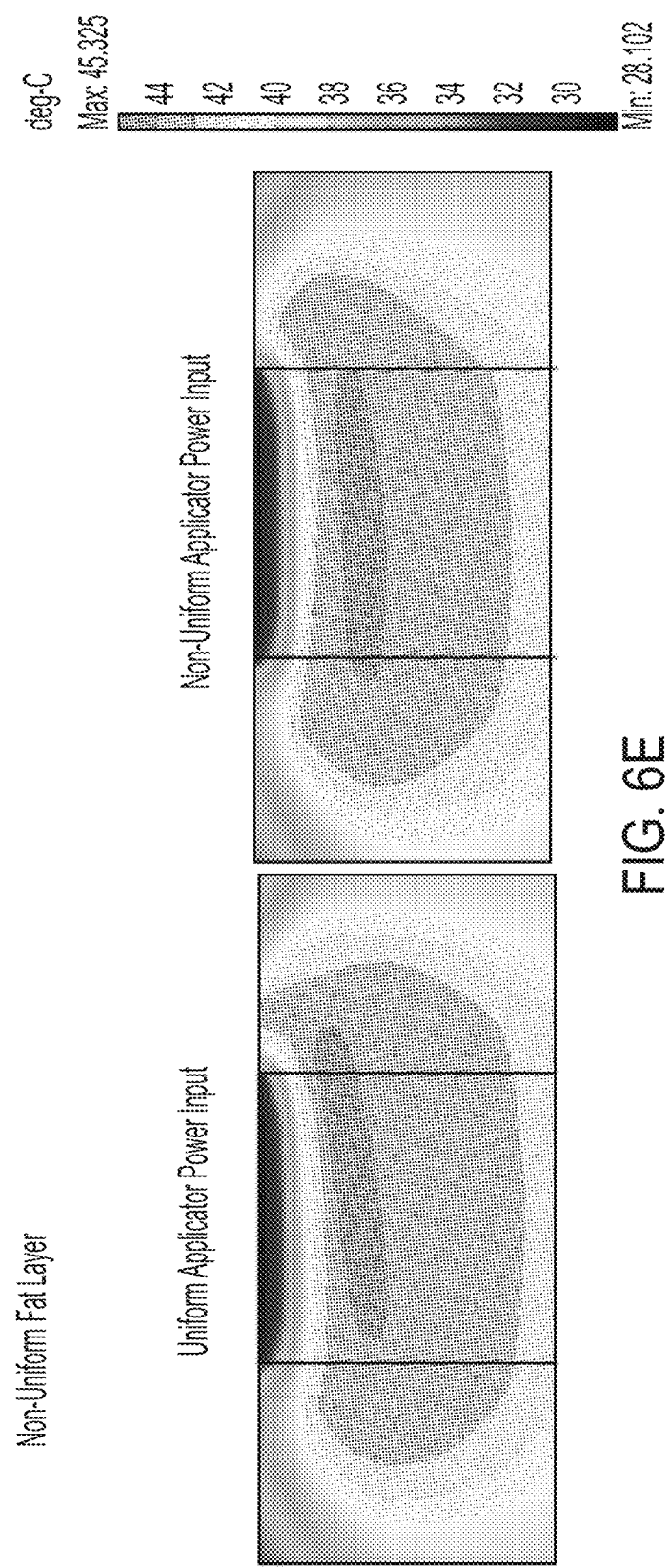

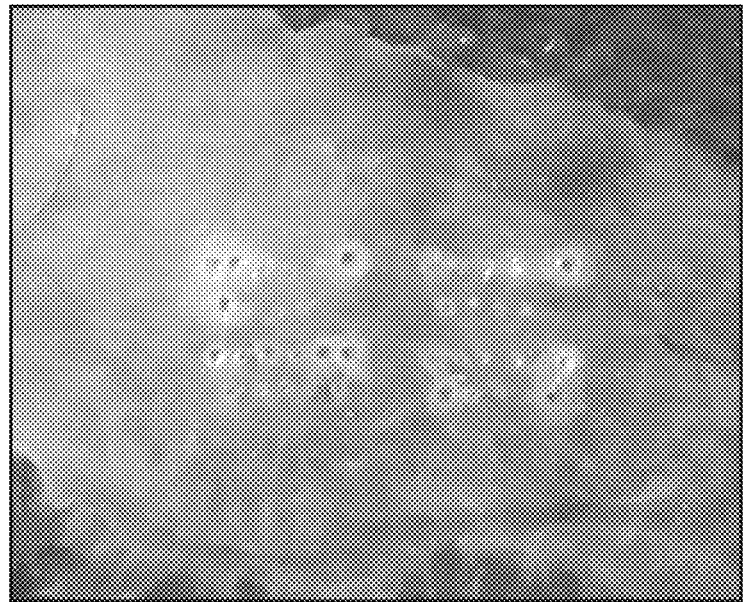
FIG. 13
 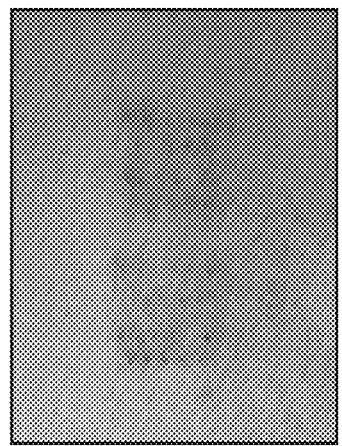 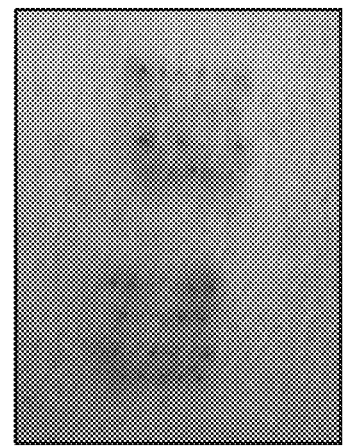
FIG. 14A  FIG. 14B  FIG. 14C

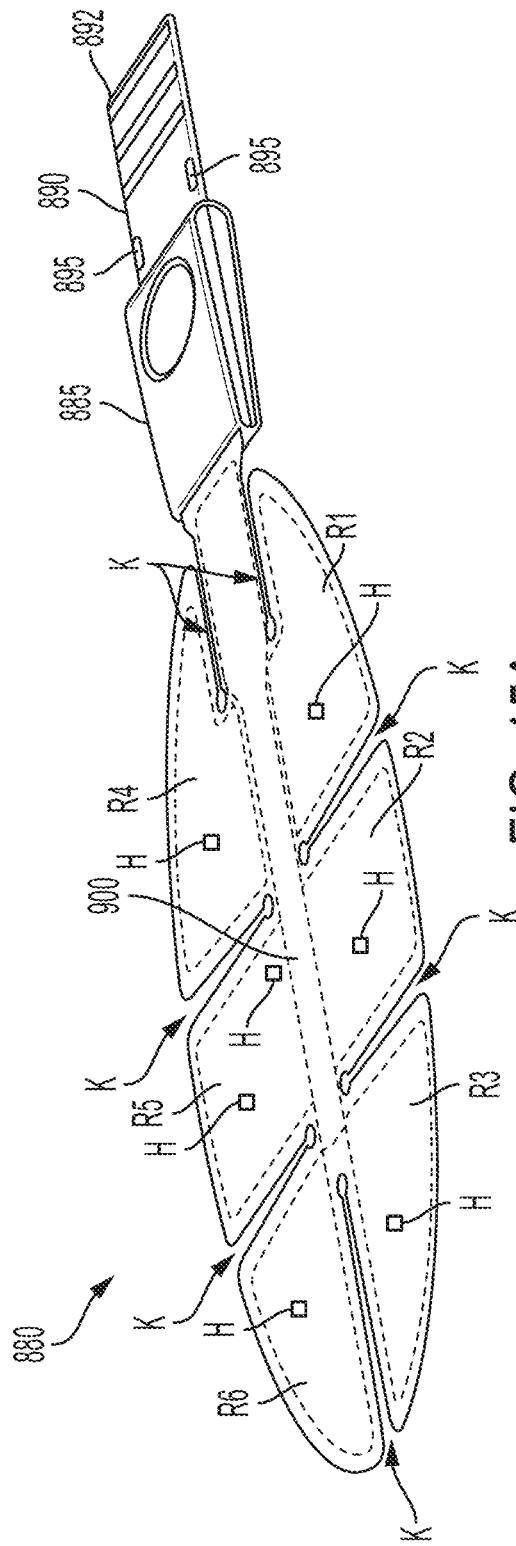
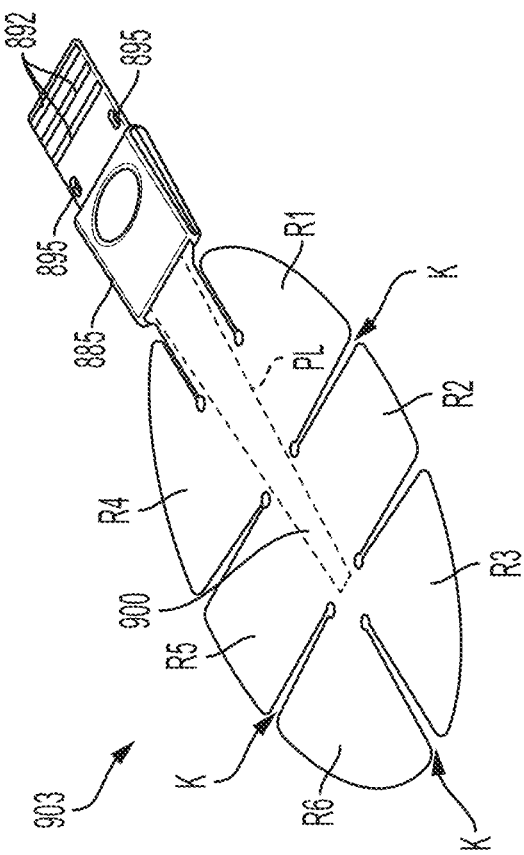
FIG. 15A
FIG. 15B

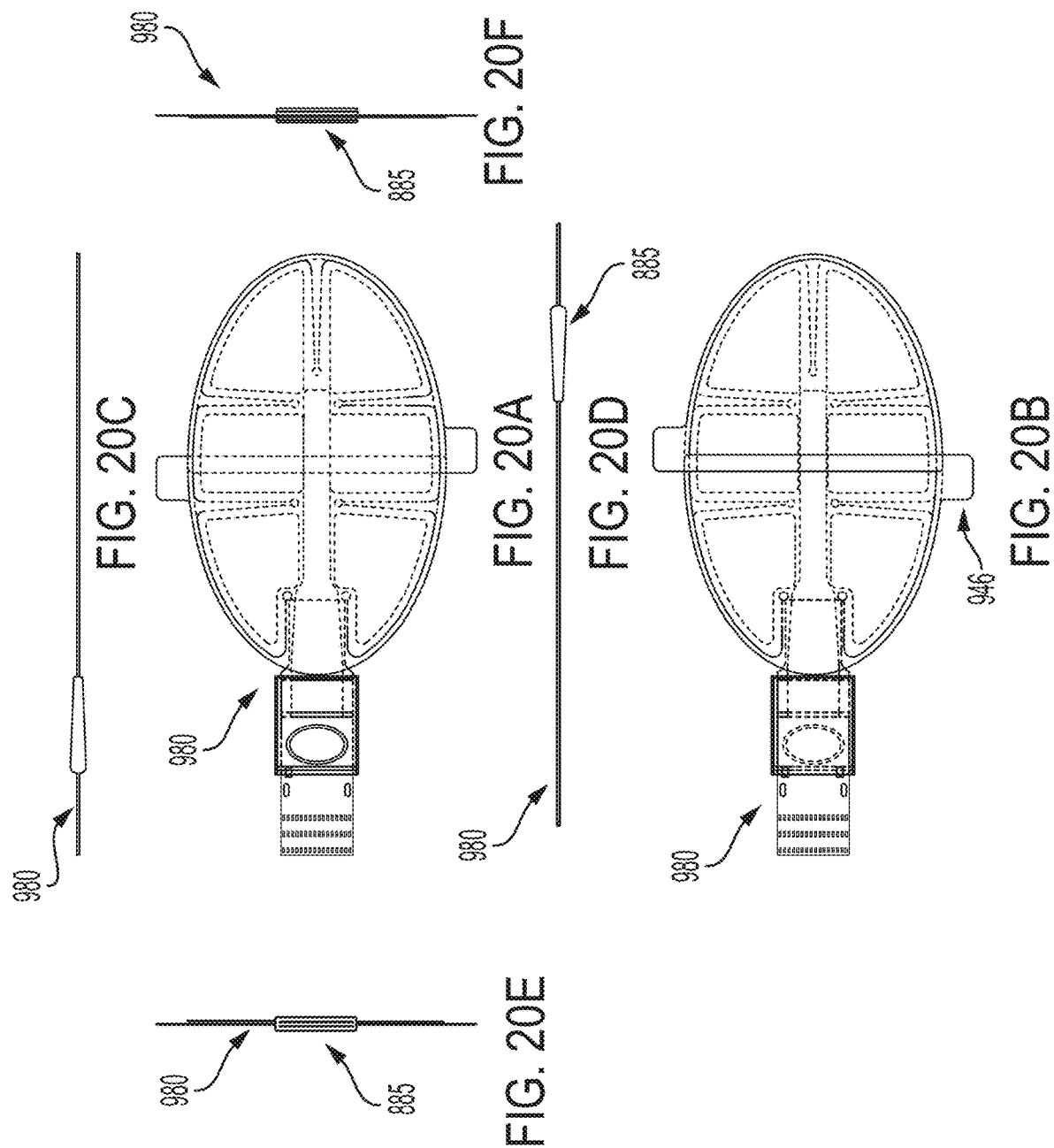

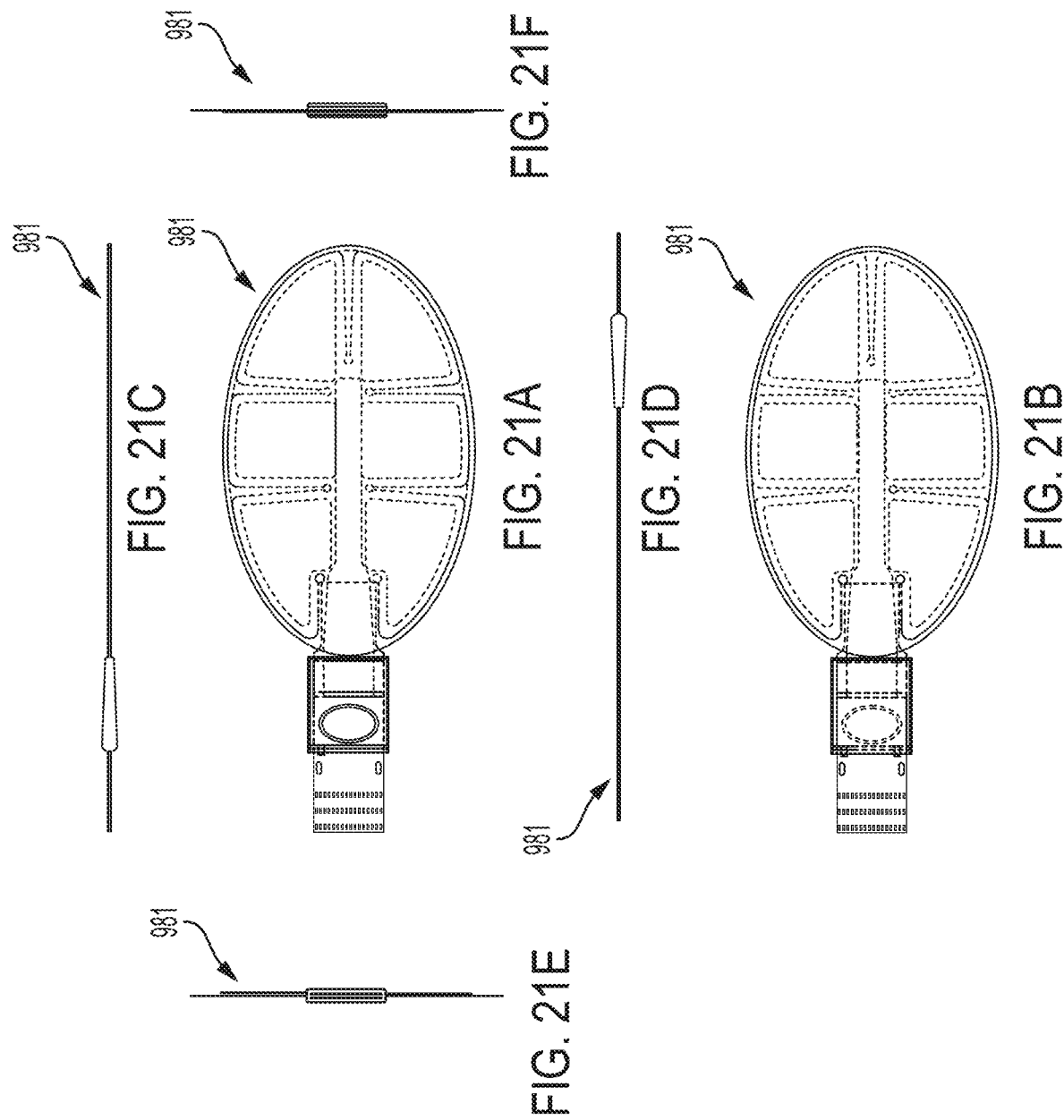

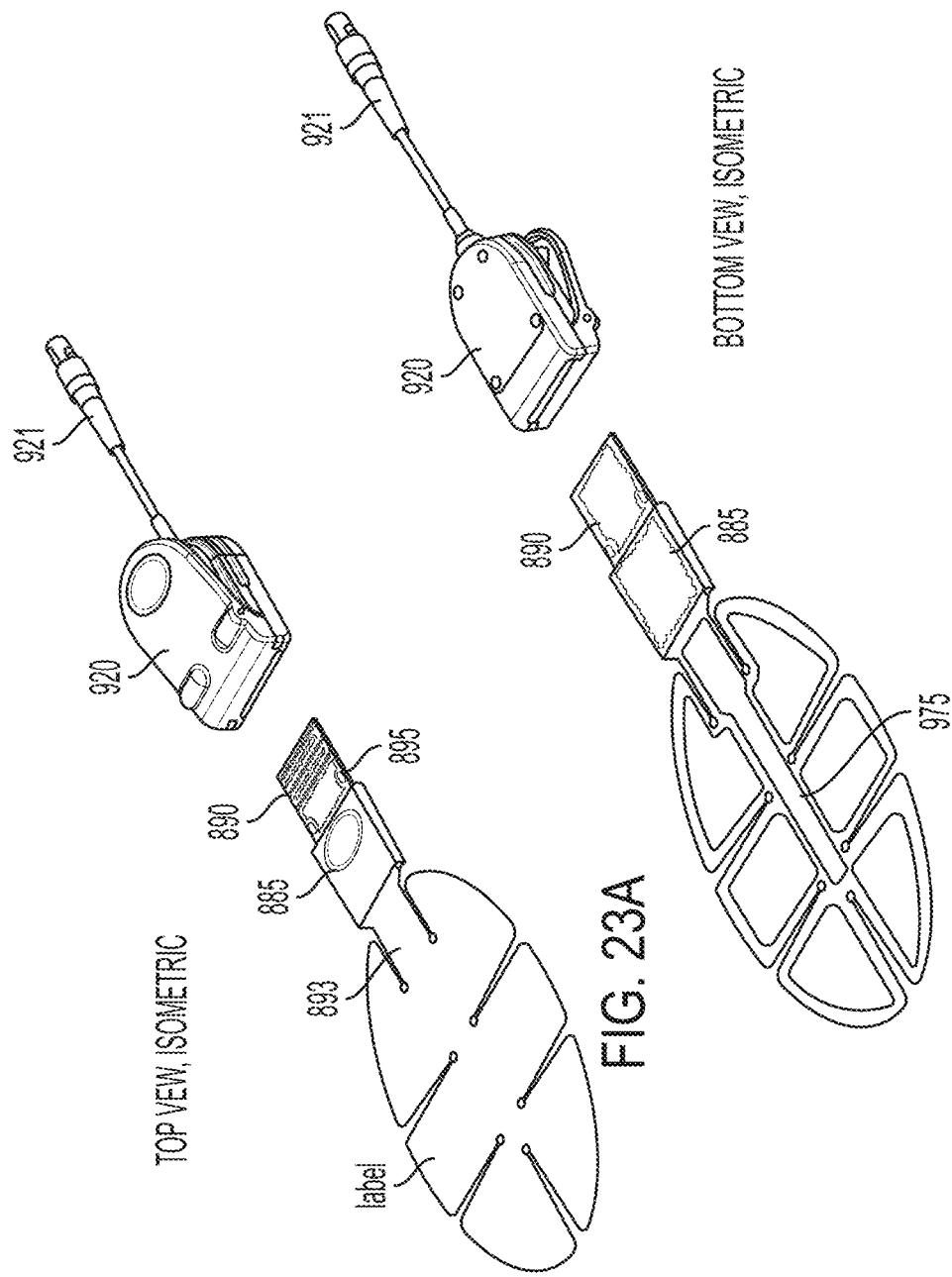

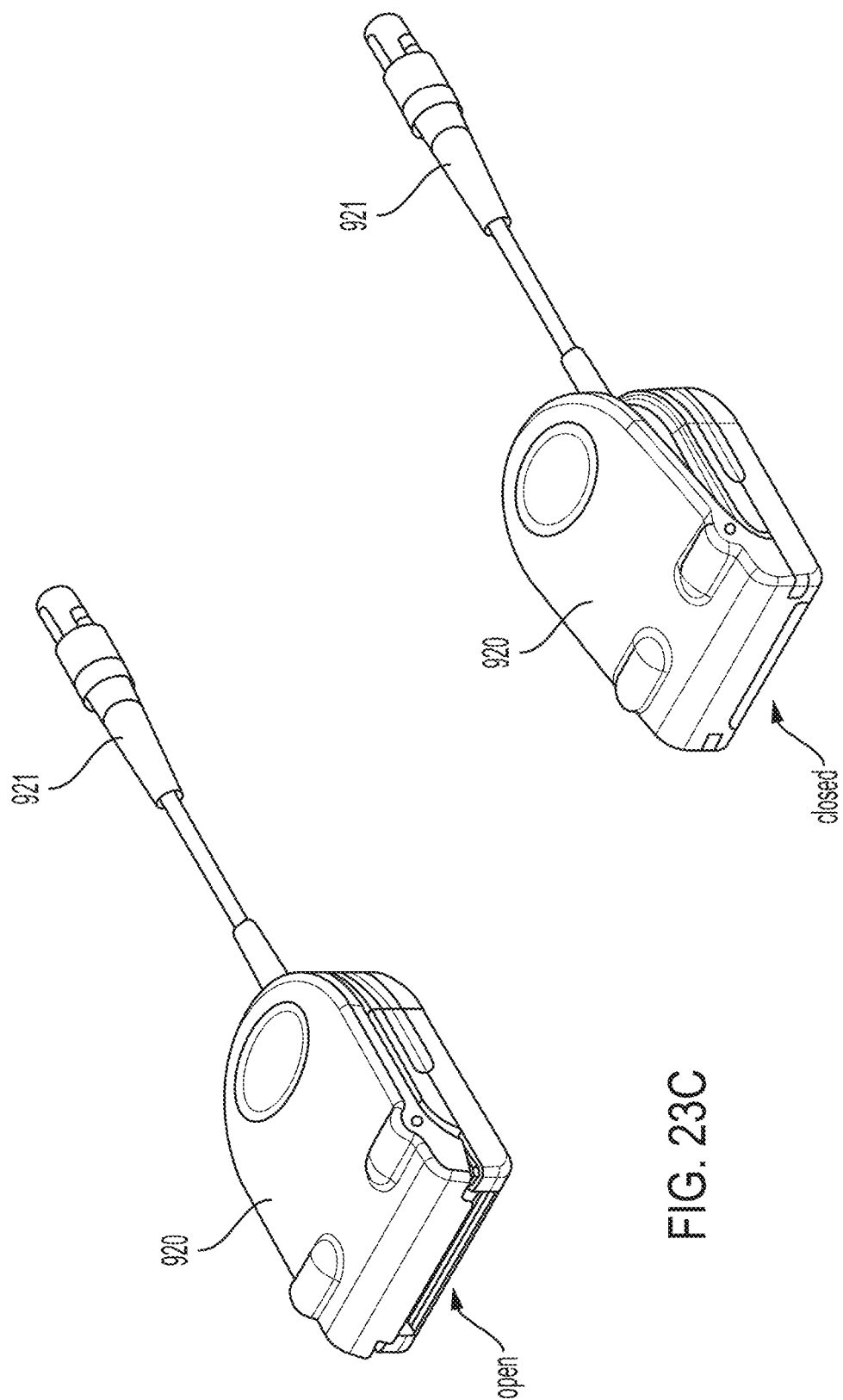

NON-INVASIVE, UNIFORM AND NON-UNIFORM RF METHODS AND SYSTEMS RELATED APPLICATIONS

RELATED APPLICATIONS

This application is a continuation-in-part of U.S. patent application Ser. No. 16/238,483 filed Jan. 2, 2019, which claims priority to U.S. patent application Ser. No. 15/640,710, filed on Jul. 3, 2017, which claims the benefit of priority to U.S. Provisional App. No. 62/357,920, filed on Jul. 1, 2016, and U.S. Provisional App. No. 62/514,778, filed on Jun. 2, 2017, each of which is incorporated herein by reference in its entirety.

FIELD

The present disclosure relates generally to systems and methods for treating a patient's skin (e.g., dermis and hypodermis) and other target tissue, including tissue at a depth below a tissue surface with radiofrequency (RF) energy.

BACKGROUND

Electrosurgical devices are known for applying RF energy to tissue so as to generate a variety of effects, including invasive procedures (e.g., for ablating or vaporizing tissue) or less-invasive procedures (e.g., to gently heat the surface of the skin). However, a need remains for improved methods and system for providing uniform and large-area application of RF energy in cosmetic and/or aesthetic applications, for example, in order to improve the appearance of skin so that it is (or appears) tightened/smoothed and/or to reduce fat present in subcutaneous tissue (e.g., hypodermis).

SUMMARY

Systems and methods utilizing RF energy to treat a patient's skin (e.g., dermis and hypodermis) or other target tissue at a depth below a tissue surface with RF energy are described herein. In various aspects, the present teachings can provide a non-invasive, cooled (or uncooled) RF-based treatment to achieve one or more of body sculpting (lipolysis), skin tightening (laxity improvement), cellulite treatment apparatus, vaginal laxity treatment or rejuvenation, urinary incontinence treatment, fecal incontinence treatment, and treatment of other genitourinary conditions, by way of non-limiting examples.

In various aspects, the non-invasive treatment of unwanted fat, the improvement in skin laxity/tightness and the improvement in the appearance of cellulite can be accomplished by the application RF energy (e.g., 500 kHz, 1 Mhz, or other) delivered to the surface of the patient's tissue (e.g., skin, vaginal wall, esophagus) via a water-cooled treatment electrode or electrode array operating in either monopolar or bipolar mode, the RF energy propagating from the tissue surface into the deeper tissue layers. In accordance with various aspects of the present teachings, cooling the superficial layers and selectively controlling the deposition of RF energy can heat the tissue below the surface and can help ensure heating uniformity, patient safety and tolerance, and consistent clinical results.

In accordance with various aspects of the present teachings, systems and methods described herein can be one or more of:

1. user-friendly and/or hands-free (e.g., after initial set-up);
2. provide patient safety and/or comfort through cooling of the upper layers of the tissue and/or modulation of RF energy and/or modulation of cooling to improve a patient's tolerance; and
3. flexible so as to address a variety of anatomical features.

By way of non-limiting example, various systems and methods in accordance with the present teachings can be utilized in a hand's free manner such that an RF applicator or multiple RF applicators can be applied to the patient at the start of the treatment, energized and optionally left unattended until the completion of the procedure (e.g., patients can be left largely unattended for treatments, for example, for at least as long as 5 minutes or at least as long as 10 minutes following initial set-up). In various aspects, the methods and systems described herein can include a cooling system (e.g., via the circulation of refrigerated, temperature-controlled water adjacent to the RF source and/or electrode array) to provide patient safety (e.g., avoid burning of the skin and/or nodule formation in the tissue subsequent to heat treatment of the tissue) in accordance with FDA and IEC safety recommended safety standards, improve patient comfort, and/or increase a patient's tolerance to potentially painful effects of the RF energy during treatment. In various aspects, the methods and systems described herein can be sufficiently flexible and/or adaptable so as to be able to treat a variety of desired locations (e.g., abdomen, submental region, any of a number of areas of the face, arms, legs) on the patient's body despite inter- and intra-patient anatomical differences, differing surface areas, and complex curvatures, which can be difficult to maintain contact with during the time required to complete the treatment.

In accordance with various aspects of the present teachings, a system for treating a patient's tissue is provided, the system comprising a source of RF energy and a treatment applicator having a plurality of treatment electrodes configured to be disposed in contact with a surface of a patient's tissue (e.g., a skin surface, a mucosal surface) and to deliver RF energy thereto and a return electrode. The plurality of treatment electrodes can comprise at least two individually-addressable treatment electrodes to which different treatment RF signals can be applied, the RF signals exhibiting one or more of a power, duty cycle, pulse duration, phase, and RF frequency. The system can also include a controller configured to determine the impedance of each of the at least two individually-addressable treatment electrodes, wherein the controller is further configured to adjust the treatment RF signals applied simultaneously to the at least two individually-addressable treatment electrodes based on the impedance thereof so as to maintain uniformity of heating in a target tissue disposed below the treatment applicator. Optionally, in some aspects, the system can also include a cooling mechanism for cooling the tissue surface in contact with the plurality of electrodes. In various aspects, the at least one return electrode can be disposed on a skin surface or internally (e.g., within the urethra).

In some aspects, the different RF signals applied simultaneously to the at least two individually-addressable treatment electrodes can comprise one or more of different powers, pulse widths, duty cycles, phases, and RF frequencies. In some related aspects, the controller can be configured to reduce the power of the RF signal to the electrode of the at least two individually-addressable treatment electrodes exhibiting a lower impedance.

In various aspects, the at least two individually-addressable treatment electrodes can comprise at least two groups (e.g., clusters) of individually-addressable treatment electrodes, wherein each treatment electrode in each of group of individually-addressable treatment electrodes have the same RF signal simultaneously applied thereto as the other treatment electrodes in the group, and wherein each group of individually-addressable treatment electrodes are configured to have different RF signals applied simultaneously thereto.

In some aspects according to the present teachings, the system can also include a second treatment applicator configured to be disposed in contact with a tissue surface spaced apart from the tissue surface to which the first treatment applicator is disposed. The second treatment applicator can, in some aspects, represent the at least one return electrode, though a return electrode can also be a separate electrode. Optionally, the second treatment applicator can comprise a cooling mechanism for cooling the tissue surface in contact with the plurality of electrodes of the second treatment applicator. In some aspects, the second treatment applicator can comprise a second plurality of treatment electrodes configured to be disposed in contact with the patient's tissue surface and to deliver RF energy thereto, wherein the second plurality of treatment electrodes comprise at least two individually-addressable treatment electrodes to which different RF signals can be applied. In such aspects, the controller can be configured to activate only one of the individually-addressable treatment electrodes on each of the first and second treatment applicator at a given time, for example. Additionally, the controller can be configured to determine the impedance between each of the at least two individually-addressable treatment electrodes of the first treatment applicator and each of the at least two individually-addressable treatment electrodes of the second treatment applicator (e.g., by polling one electrode from each applicator at a time). By way of example, the controller can be configured to determine the impedance between each of the at least two individually-addressable treatment electrodes of the first treatment applicator and each of the at least two individually-addressable treatment electrodes of the second treatment applicator by generating a sub-treatment threshold RF current therebetween prior to applying treatment RF signals to the first plurality of electrodes. Additionally or alternatively, in some aspects, the controller can be configured to determine the impedance between each of the at least two individually-addressable treatment electrodes of the first treatment applicator and each of the at least two individually-addressable treatment electrodes of the second treatment applicator while applying treatment RF signals to the first plurality of electrodes so as to determine when to terminate treatment by terminating the treatment RF signals.

The return electrode can have a variety of configurations. For example, the return electrode can be a passive electrode configured to be disposed in contact with a tissue surface spaced apart from the tissue surface to which the first treatment applicator is disposed. For example, the passive electrode can be a neutral drain pad. In some related aspects, a second treatment applicator can also be provided in addition to the return electrode, the second treatment applicator configured to be disposed in contact with a tissue surface spaced apart from the tissue surfaces to which the first treatment applicator and the passive electrode are disposed, wherein the second treatment applicator comprises a second plurality of treatment electrodes configured to be disposed in contact with the patient's tissue surface and to deliver RF energy thereto.

In various aspects, the controller can be configured to separately poll each of at least two individually-addressable treatment electrodes of the first treatment applicator with a low-power sub-treatment threshold RF signal.

Methods and systems in accordance with the present teachings can provide a variety of treatments. By way of example, the RF treatment signals can be configured to reduce skin laxity by stimulating the production of collagen and/or lipolysis in fat tissue below the tissue surface (e.g., by bulk heating). By way of example, each electrode can be configured to deliver RF power in a range from about 1 $W/cm^2$ to about 5 $W/cm^2$, wherein the RF signal has a pulse width greater than about 1 second. Additionally or alternatively, the RF treatment signals can be configured to reduce the appearance of cellulite. For example, each electrode can be configured to deliver RF pulses exhibiting an energy per pulse in a range from about 10 J/cm2 to about 1000 J/cm2 and wherein the RF signal has a pulse width less than about 500 ms.

The cooling mechanism can have a variety of configurations in accordance with the present teachings. By way of example, the cooling mechanism can comprise a circulating fluid, thermoelectric elements, or a phase change material disposed in the applicator in thermal contact with the electrode. In certain aspects, the cooling mechanism can comprise a circulating fluid, with the temperature of the circulating fluid being controlled by a temperature regulator (e.g., under the influence of the controller) such that a target tissue region disposed can comprise below the tissue surface is maintain at a temperature in a range from about 42° C. to about 47° C. during a treatment time in a range from about 10 minutes to about 30 minutes. In some aspects, the circulating fluid can comprise water. In various aspects, at least a portion of a fluid pathway of the circulating fluid can be in thermal contact with a side of the electrodes that is not configured for contact with the tissue surface. Additionally or alternatively, at least a portion of a fluid pathway of the circulating fluid can be in thermal contact with the tissue surface at a location between adjacent electrodes of the plurality of treatment electrodes.

In various aspects, the system can also include one or more temperature detectors for detecting a temperature of the tissue surface around the perimeter of the electrode array, wherein the controller is further configured to adjust the RF signals (e.g., reduce the power of the treatment RF signals) applied to electrodes on a side of the applicator exhibiting the highest temperature. Additionally or alternatively, the controller can be configured to adjust the RF signals (e.g., increase the power of the treatment RF signals) applied to electrodes on a side of the applicator opposed to the side of the applicator exhibiting the lowest temperature.

In some aspects, the source of RF energy can comprise two or more individually-controllable RF energy sources, each of the individually controllable RF energy sources being configured to operate at the same fundamental frequency, but the RF signals generated thereby can have different phases and amplitudes. In such aspects, the system can comprise two or more treatment applicators each associated with one of the RF energy sources, wherein current amongst each of the two or more treatment applicators can be shared such that the two or more applicators can be disposed on two or more distinct treatment regions of the body of the subject and each of the two or more applicators can be configured to deliver a suitable amount of RF energy to each of the distinct treatment regions.

In accordance with various aspects of the present teachings, a system for treating a patient's tissue is provided, the system comprising a source of RF energy, a treatment applicator comprising a treatment electrode configured to be disposed in contact with a surface of a patient's tissue and to deliver RF energy thereto, and at least one return electrode. The system can also include a controller configured to provide an RF signal to the treatment electrode, the RF signal having a pulse duration that selectively heats septae within fat tissue while substantially avoiding conduction of heat into adjacent tissue, and an impedance tracker for monitoring the patient's tissue impedance during the pulse duration and for providing information about the patient's tissue impedance changes to the controller so that the controller can terminate the RF signal when the desired treatment is completed. Optionally, the system can include a cooling mechanism for cooling the tissue surface in contact with the electrodes.

In various related aspects, the treatment electrode can be configured to deliver RF pulses exhibiting an energy per pulse in a range from about 10 $J/cm^2$ to about 500 $J/cm^2$, wherein the RF signal has a pulse width less than about 500 ms. In some aspects, the controller can be further configured to adjust the RF signals provided to the plurality of electrodes such that second treatment RF signals are simultaneously provided to each of the plurality of electrodes, wherein the second RF signals comprise a lower RF power and longer pulse width relative to the RF treatment signals for selectively heating the septae. By way of example, the second RF treatment signals can be configured to reduce skin laxity and/or cause lipolysis (e.g., after or before the septae are selectively targeted). In various aspects, the second RF treatment signals can be configured such that each electrode simultaneously delivers RF power in a range from about 1 $W/cm^2$ to about 5 $W/cm^2$, wherein the RF signal has a pulse width greater than about 1 second.

In accordance with various aspects of the present teachings, a system for treating a patient's tissue is provided, the system comprising a source of RF energy and a treatment applicator comprising a plurality of treatment electrodes configured to be disposed in contact with a surface of a patient's tissue and to deliver RF energy thereto, wherein the plurality of treatment electrodes comprise at least two individually-addressable treatment electrodes to which treatment RF signals can be applied. The system can also, in some aspects, include at least one return electrode and optionally, a cooling mechanism for cooling the tissue surface in contact with the plurality of electrodes. A controller can be provided that is configured to sequentially provide treatment RF signals to each of the at least two individually-addressable treatment electrodes such that each of the at least two individually-addressable treatment electrodes are configured to selectively heat septae within fat tissue while substantially avoiding conduction of heat into adjacent tissue. In some aspects, each of the at least two individually-addressable treatment electrodes can be configured to deliver RF pulses having an energy in a range from about 10 $J/cm^2$ to about 500 $J/cm^2$ and wherein the RF signal has a pulse width less than about 100 ms. Additionally, the controller can be further configured to adjust the RF signals provided to the plurality of electrodes such that second treatment RF signals are simultaneously provided to each of the plurality of electrodes, wherein the second RF signals comprise a lower RF power and longer pulse width relative to the RF treatment signals for selectively heating the septae. By way of example, the second RF treatment signals can be configured to reduce skin laxity and/or cause lipolysis. In certain aspects, each electrode subject to the second RF treatment signals can simultaneously deliver RF power in a range from about 1 $W/cm^2$ to about 5 $W/cm^2$, wherein the RF signal has a pulse width greater than about 1 second.

In accordance with various aspects of the present teachings, an apparatus for treating a female genitourinary condition is provided, the apparatus comprising a probe adapted for vaginal insertion having a distal end configured to apply heat to at least a portion of a vaginal wall surface and a plurality of radiofrequency (RF) energy radiating therapeutic electrodes disposed in an array at the distal end of the probe to heat tissue either in contact with the probe or in proximity to it. At least one temperature sensor can also be incorporated into the probe to monitor the temperature of the vaginal wall surface and/or the target tissue. In various aspects, the temperature sensor can be an infrared (IR) sensor configured to detect black body radiation emitted by heated tissue or can be implemented by one or more of the electrodes operating as an impedance measuring electrode. Optionally, the probe can further comprise one or more cooling circuits to avoid overheating of the vaginal wall surface.

In some aspects, the electrodes are programmable (e.g., under the influence of a controller) such that a subset of the array components can be activated to deliver heat in a specific pattern. In various aspects, the apparatus can further comprise one or more return electrodes to provide a return path for an RF current from the therapeutic electrode. By way example, the return electrode can be a drain pad (e.g., a neutral paddle) adapted to be disposed on an external surface a patient's body (e.g., a skin surface). Alternatively, the return electrode can be disposed in a urethral catheter. Alternatively, the return electrode can be implemented by one or more electrodes in the array serving as a grounding electrode.

In certain aspects, a fixation device can also be provided to ease insertion of the probe and/or for holding the probe in place upon insertion into a patient. For example, the fixation device can comprise a locking sleeve or balloon.

In accordance with various aspects of the present teachings, a method of treating a female genitourinary condition is provided. By way of example, in various aspects a method of treating stress urinary incontinence (SUI) is provided, the method comprising delivering a controlled amount of heat to a vaginal wall surface to remodel tissue in a target region adjacent to a patient's bladder neck or urethra. In various aspects, the heating can be performed by activating one or more radio frequency (RF) energy emitting therapeutic electrodes in contact with the vaginal wall surface to transmit an RF current into the target region. In certain exemplary aspects, the therapeutic electrodes can comprise an electrode array carried by a probe, the method further comprising inserting the probe into a patient such that at least one therapeutic electrode contacts at least a portion of a vaginal wall surface. In certain aspects, the power delivered by individual electrodes in the array can be varied to ensure uniform heating of tissue in the target region. In some aspects, the electrode(s) can be configured to contact at least a portion of the anterior vaginal wall and/or the method can further comprise delivering RF energy to heat tissue between the patient's vaginal wall surface and urethra. By way of example, the method can further comprise delivering RF energy to heat tissue in a target region that extends to a treatment depth of about 2 to 9 cm, preferably about 5 to 8 cm beyond the inner vaginal wall surface.

In some related aspects, RF energy can be delivered so as to heat tissue in a target region for a period of time, preferably less than 30 minutes, or less than 10 minutes or in some instances less than five minutes. Additionally in certain aspects, the target tissue can be heated to about 40° C. to 45° C., or from about 41° C. to 43° C. Optionally, the method can comprise cooling the vaginal wall surface before, after or during heating the tissue in the target region.

In various aspects, the method can further comprise mapping the heating effects of the RF electrode by thermal imaging or impedance measurements.

In accordance with various aspects of the present teachings, a system for treating a patient's tissue is provided, the system comprising a source of RF energy, a treatment applicator comprising a treatment electrode configured to be disposed in contact with a surface of a patient's tissue (e.g., a treatment probe configured for insertion into a patient's vagina having one or more treatment electrodes) and to deliver RF energy thereto, and at least one return electrode. The system can also include a controller configured to provide an RF signal to the treatment electrode, the RF signal having a pulse duration and the treatment electrode being sized so as to apply current density sufficient to ablate the surface of the tissue in contact with the treatment electrode. Optionally, a cooling mechanism for cooling the tissue surface in contact with the electrode(s). In various aspects, the pulse duration can be less than about 100 ms. (e.g., in a range from about 5 ms. to about 35 ms.). In various aspects, the treatment electrode(s) can have a size that ranges from about 0.1 mm to about 10 mm, or from about 0.1 mm to about 5 mm.

In various aspects, the system can also include a second treatment electrode that can be disposed adjacent to the treatment electrode, the controller also being configured to provide the RF signal to the second treatment electrode, the RF signal having a pulse duration and the second treatment electrode being sized so as to apply current density sufficient to ablate the surface of the tissue in contact with the treatment electrode. In various aspects, the pitch between the treatment electrode and the second electrode can range from about 0.1 mm to about 10 mm or from about 0.5 mm to about 5 mm. In some related aspects, the treatment electrode can be addressed by the controller simultaneous with the second treatment electrode.

In various aspects, the treatment electrode can comprise a cluster of two or more electrodes, each of the electrodes in the cluster having a size that ranges from about 0.1 mm to about 10 mm, or from about 0.1 mm to about 5 mm. In such aspects, each of the two or more electrodes in the cluster can be sized so as to apply current density sufficient to ablate the surface of the tissue in contact with each treatment electrode of the cluster. Additionally, in some aspects, a second cluster of two or more electrodes can be provided, the controller being configured to provide the RF signal to the second cluster and the RF signal having a pulse duration and each of the two or more electrodes in the second cluster being sized so as to apply current density sufficient to ablate the surface of the tissue in contact with each treatment electrode of the second cluster. In various aspects, the controller can separately address the cluster and the second cluster.

In accordance with various aspects of the present teachings, a system for treating a patient's tissue is provided, the system comprising two or more treatment applicators each adapted to be disposed on a tissue surface and two or more individually controllable RF energy sources. In exemplary aspects, each of the individually controllable RF energy sources can operate at the same fundamental frequency, but the phases and the amplitudes of each of the two or more RF energy sources can be controllable relative to one another. In such aspects, each of the two or more treatment applicators can be associated with its own individually controllable RF energy source such that current can be shared amongst the two or more treatment applicators such that the two or more applicators can be placed on two or more distinct treatment regions of the body of the subject and each of the two or more applicators can be capable of delivering a suitable amount of RF energy to each of the distinct treatment regions. In various aspects, the system can also include a return electrode. Additionally, in certain aspects, each treatment applicator can comprise a plurality of treatment electrodes configured to be disposed in contact with a surface of a patient's tissue and to deliver RF energy thereto, wherein the plurality of treatment electrodes comprise at least two individually-addressable treatment electrodes to which RF signals can be applied.

In accordance with various aspects of the present teachings, a radiofrequency (RF)-based treatment system include an RF transmission cable comprising a plurality of electrical leads and an RF input port and a first applicator. The first applicator includes a plurality of electrical contacts in electrical communication with the plurality of electrical leads. The system can also include a first support comprising a tissue facing surface and a bottom surface, the tissue facing surface defining a first shape and an array of K individually addressable electrodes disposed in or on the first support and arranged relative to the tissue facing surface, each of the K electrodes in communication with at least one of the electrical contacts. In one embodiment, K is a positive integer.

In various aspects, the system can in include a first support that can be a first flexible substrate. In some aspects, the system can include electrical contacts and each addressable electrode can be flexible and can be disposed on the first support. Optionally, in some aspects, the RF-based treatment system includes a second support, the second support can include a second flexible material, where the second support can be disposed on or above the bottom surface.

In various aspects, the RF-based treatment system can include a second flexible material can be a resilient compressible foam material. Optionally, in some aspects, the RF-based treatment system can include a fluid-based cooling device defining one or more coolant flow channels, the cooling device disposed below the tissue facing surface. In some aspects, the RF-based treatment system can include coolant flow channels sized to reduce tissue surface heating when the array is activated during a tissue treatment. In some aspects, the RF-based treatment system can include a cooling device including one or more connectors extending therefrom, the cooling device sandwiched between the first support and the foam material.

In many aspects, the RF-based treatment system can include a first support which can be a flexible polymer substrate, wherein the plurality of electrical contacts is disposed on one or more edges of the polymer substrate. In some aspects, the RF-based treatment system can include an applicator kit, the applicator kit including a first applicator and M applicators, wherein each of the M applicators can be substantially the same as the first applicator, wherein the first shape of each applicator can be selected such that M+1 applicators can tile a tissue treatment surface when placed adjacent to each other. M can range from 1 to 1000 in one embodiment. In one embodiment, M is a positive integer.

In various aspects, the RF-based treatment system can include one or more temperature sensors arranged in a pattern to measure temperature of tissue during treatment, wherein one or more temperature sensors can be in communication with one or more of the plurality of electrical contacts. In some aspects, the RF-based treatment system can include an adhesive layer disposed on or near skin facing surface to temporarily attach the applicator to the skin. In certain aspects, the RF-based treatment system can include an upper housing portion disposed on the foam, wherein the upper housing portion includes an attachment member.

In many aspects, the RF-based treatment system can include the RF transmission cable with a cable length CL between the RF input port and the electrode array, wherein CL ranges from about 1 foot to about 40 feet. In some aspects, the RF-based treatment system can include a first control node disposed between and in electrical communication with the RF input port and the electrode array. In some aspects, the RF-based treatment system can include a first control node including a first controller, wherein the first controller generates control signals to turn individual electrodes in the electrode array "on" and "off."

In various aspects, the RF-based treatment system can include a distance of Y between output of first control node along RF transmission cable and connection point of RF transmission cable with first applicator. In some aspects, the RF-based treatment system can include Y ranges from about 0 to about 2 inches. In some aspects, the RF-based treatment system can include Y ranges from about 0 to about 6 inches. In various aspects, the RF-based treatment system can include Y ranges from about 0 to about 24 inches. In some aspects, the RF-based treatment system can include a first control node comprises a first controller, wherein the first controller generates control signals to measure individual current flow for one or more electrodes of the electrode array.

In many aspects, the RF-based treatment system can include a foam material and a rigid support, the foam material sandwiched between the rigid support and the first support. In various aspects, the RF-based treatment system can include, as applicable, a controller configured to provide an RF signal to the electrode array through the RF cable, the RF signal having a pulse duration that selectively heats septae within fat tissue while substantially avoiding conduction of heat into adjacent tissue.

In various aspects, the RF-based treatment system can include an impedance tracker for monitoring a patient's tissue impedance during treatment and sensing patient's tissue impedance changes and relaying them to controller so that the controller can terminate the RF signal in response to occurrence of one or more events. In some aspects, the RF-based treatment system a first support that can be a rigid housing. In some aspects, the RF-based treatment system can include the array of K individually addressable electrodes which can be a first array, and further including a second array, wherein the first array can be arranged relative to treatment regions in a first zone. In various aspects, the RF-based treatment system can include the second array which can be arranged relative to treatment regions in a first zone, wherein the first zone and second zone can be separate parts of patient's body.

In various aspects, a method of controlling an RF-based treatment system can include connecting a plurality of control nodes, wherein the first control node is master control of other nodes, synchronizing second node and third node with first node, wherein first node, second node and third node are in electrical communication with a radiofrequency (RF) transmission line; and transmitting control signals from first node to second node using serial communication protocol during an active treatment session. In some aspects, the method can include an active treatment session which can be an impedance mapping performed using an electrode array in communication with the RF transmission line. Optionally, in some aspects, the method can include phasing the second node using one or more output signals from the first node. In some aspects, the method can include measuring current signals at one or more electrodes using the third node. In various aspects, the method can include activating and deactivating electrode using the third node. In many aspects, the method can include wherein the nodes are connected using a plurality of connections, wherein one of the connections is the first node connected to a plurality of subnodes of the second node. In some aspects, the method can include wherein the active treatment session further includes an impedance mapping performed using the electrode array in communication with one or both of a second electrode array and a drain pad.

In accordance with various aspects of the present teachings, a radiofrequency (RF)-based treatment system includes a flexible applicator that includes a plurality of layers, the plurality of layers that includes a first dielectric layer, a second dielectric layer, and a conductive layer, wherein the first dielectric layer and the second dielectric layer sandwich the conductive layer, the plurality of layers define a plurality of kerfs, and an inner region and N regions extending from the inner region, wherein the plurality of kerfs divide the applicator into N regions.

In some aspects, N ranges from 2 to 12. Optionally, some aspects, the plurality of layers define one or more strain relief elements, wherein each strain relief element is a circular or elliptical hole in the plurality of layers. Optionally, in some aspects, one or more of the plurality of kerfs terminate at one or more strain relief elements, wherein the inner region is adjacent the one or more strain relief elements. Optionally, in some aspects, the inner region is a kerf-free region, wherein N is 6. Optionally, in some aspects, the plurality of N regions include a first region and a second region, wherein each of the first and second region define one or more areas, borders, or kerfs that are substantially the same.

In some aspects, the plurality of layers include a label, wherein the label includes N region identifiers, wherein each of the N region identifiers is disposed on one of the N regions. Optionally, in some aspects, the applicator defines an applicator shape, wherein applicator shape is selected from the group consisting of elliptical, circular, substantially elliptical, substantially circular, pear shaped, substantially pear shaped, submental, and combinations thereof. Optionally, in some aspects, the conductive layer includes a patterned region of copper traces in each of the N regions, wherein each of the patterned regions has one or more copper traces in electrical communication with copper traces arranged along the inner region. Optionally, in some aspects, the applicator further includes an electrical connector, the electrical connector in electrical communication with one or more addressable regions of conductive layer.

In some aspects, the system includes an RF treatment system comprising an RF generator, the RF generator having an operating frequency that ranges from about 0.5 MHz to about 10 MHz, wherein the RF generator is in electrical communication with the electrical connector. Optionally, in some aspects, the applicator further includes an electrical connector, the electrical connector in electrical communication with one or more addressable regions of conductive layer, the electrical connector comprising a plurality of electrical contacts, wherein the copper traces arranged along the inner region are in electrical communication with the electrical contacts. Optionally, in some aspects, the copper traces arranged along the inner region are arranged in a series of three or more adjacent sections that increase in width in direction towards the electrical connector. Optionally, in some aspects, the conductive layer includes a continuous copper sheet and wherein each of the N regions further includes a first region of dielectric material having a first thickness and a first area, and a second region of dielectric material having a second thickness and a second area, wherein area of each region is greater than first area disposed therein, wherein each first area is greater than each second area.

In some aspects, the system includes an RF treatment system comprising an interface device in communication with the RF treatment system, the interface device comprising a clamp and a cable adapter, wherein the clamp opens and closes to releasably connect and align with electrical connector, wherein cable adapter is in electrical communication with electric contacts of clamp. Optionally, in some aspects, the area of electrode ranges from about 50 $cm^2$ to about 600 $cm^2$. Optionally, in some aspects, the system includes a heat shield layer, wherein conductive layer includes arrangements of electrical traces, wherein heat shield layer covers a portion of inner region below which adjacent electrical traces span the portion and change in density along the portion. Optionally, in some aspects, the system includes one or more temperature sensors per each of the N regions.

In some aspects, the system includes an RF treatment system in electrical communication with the applicator and each temperature sensor, further comprising a control system, wherein control system selectively addresses each of the N regions to transmit RF energy sequentially to facilitate uniform heating according to one or more patterns. Optionally, in some aspects, the system includes an RF treatment system in electrical communication with the applicator and each temperature sensor, further comprising a control system, wherein control system selectively bypasses one or more of the N regions in response to an operator selection that the one or more N regions is positioned above a sensitive tissue region. Optionally, in some aspects, the plurality of layers further includes one or more adhesive layers, a polyamide layer, and an aqueous gel layer.

In accordance with various aspects of the present teachings, a method of treating tissue using an RF-based applicator includes providing a flexible applicator comprising an elongate inner spine region and a plurality of regions extending therefrom, wherein each of the plurality of regions is bounded by a first kerf and a second kerf; and transmitting RF energy from each of the plurality of regions according to an alternating or sequential addressing schemes to raise tissue below applicator to a target temperature during an initial heating time period. Optionally, in some aspects, the method includes shielding the inner spine region to avoid unwanted heating of target tissue below inner spine region of applicator. Optionally, in some aspects, the method includes controlling transmission of RF energy such that one or more sensitive regions below one or more of the plurality of regions is not interrogated with RF energy. In one embodiment, the method includes controlling transmission of RF energy such that one or more sensitive regions below one or more of the plurality of regions is cosmetically treated to increase or initiate lipolysis, skin tightening, and cellulite reduction. The method may be performed over a treatment time that ranges from about 10 to about 15 minutes.

Although, the disclosure relates to different aspects and embodiments, it is understood that the different aspects and embodiments disclosed herein can be integrated, combined, or used together as a combination system, or in part, as separate components, devices, and systems, as appropriate. Thus, each embodiment disclosed herein can be incorporated in each of the aspects to varying degrees as appropriate for a given implementation. Further, the various systems, probes, control nodes, applicators, controllers, components and parts of the foregoing can be used with any suitable tissue surface, cosmetic applications, and medical applications and other methods and conjunction with other devices and systems without limitation.

These and other features of the applicant's teachings are set forth herein.

BRIEF DESCRIPTION OF THE DRAWINGS

The skilled person in the art will understand that the drawings, described below, are for illustration purposes only. The drawings are not intended to limit the scope of the applicant's teachings in any way.

FIG. 1F schematically shows another exemplary system for providing RF treatment of a target region of a patient's body utilizing one or more electrodes and a drain paid in accordance with various aspects of the present teachings.

FIGS. 3B-F schematically depict various exemplary applicator embodiments suitable for treating tissue regions of various shapes in accordance with various aspects of the present teachings.

FIGS. 3G-H schematically depict various exemplary applicator embodiments suitable for adhering to a tissue surface when placed in contact therewith in accordance with various aspects of the present teachings.

FIGS. 3R-T schematically depict various views of an exemplary rigid applicator embodiment in accordance with various aspects of the present teachings.

FIG. 3U depicts an electrode array facing image of an exemplary rigid applicator embodiment in accordance with various aspects of the present teachings.

FIG. 6E depicts an exemplary plot of tissue temperature for a target region and correction of treatment zone shift during RF treatment of a fat region exhibiting a relatively non-uniform thickness in accordance with various aspects of the present teachings.

FIG. 8 is a schematic perspective view of a system for treating genitourinary conditions according to various aspects of the present teachings;

FIG. 13 depicts an exemplary fractional, ablative treatment in accordance with various aspects of the present teachings;

FIG. 14A-C depict the results of exemplary fractional, ablative treatments at different pulse durations in accordance with various aspects of the present teachings;

FIGS. 15A-15C schematically depict various exemplary flexible RF-based applicator embodiments suitable for treating tissue in accordance with various aspects of the present teachings;

FIG. 20A schematically depicts a top view of an RF-based flexible applicator in accordance with various aspects of the present teachings;

FIG. 20B schematically depicts a bottom view an RF-based flexible applicator in accordance with various aspects of the present teachings;

FIG. 20C schematically depicts a view of one side of an RF-based flexible applicator in accordance with various aspects of the present teachings;

FIG. 20D schematically depicts a view of another side of an RF-based flexible applicator in accordance with various aspects of the present teachings;

FIG. 20E schematically depicts a rear view of an RF-based flexible applicator in accordance with various aspects of the present teachings;

FIG. 20F schematically depicts a front view of an RF-based flexible applicator in accordance with various aspects of the present teachings;

FIGS. 21A-21F schematically depict the views of the flexible applicator of FIGS. 20A-20F, without a releasable liner in accordance with various aspects of the present teachings;

FIGS. 23A-23B schematically depict a top and a bottom view, respectively of a flexible applicator prior to coupling with an interface device in accordance with various aspects of the present teachings;

FIGS. 23C-23D schematically depict an interface device in and open and closed configuration in accordance with various aspects of the present teachings;

DETAILED DESCRIPTION

Figure 1A:
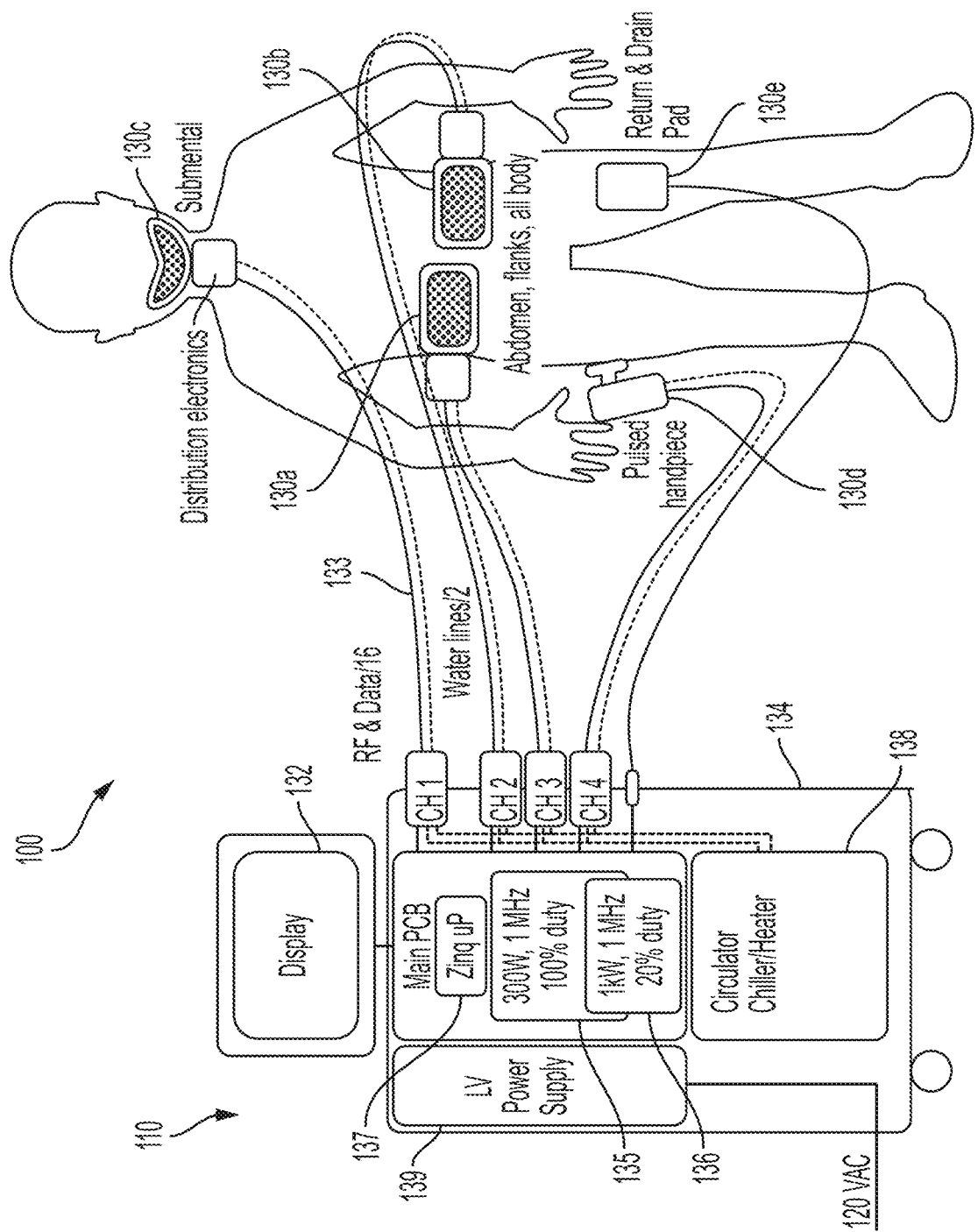
FIG. 1A schematically shows an exemplary system for providing RF treatment of various target regions of a patient's body in accordance with various aspects of the present teachings.

It will be appreciated that for clarity, the following discussion will explicate various aspects of embodiments of the applicant's teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicant's teachings may not require certain of the specifically described details in every implementation, which are set forth herein only to provide a thorough understanding of the embodiments. Similarly, it will be apparent that the described embodiments may be susceptible to alteration or variation according to common general knowledge without departing from the scope of the disclosure. The following detailed description of embodiments is not to be regarded as limiting the scope of the applicant's teachings in any manner.

The terms "about" and "substantially identical" as used herein, refer to variations in a numerical quantity that can occur, for example, through measuring or handling procedures in the real world; through inadvertent error in these procedures; through differences/faults in the manufacture of electrical elements; through electrical losses; as well as variations that would be recognized by one skilled in the art as being equivalent so long as such variations do not encompass known values practiced by the prior art. Typically, the term "about" means greater or lesser than the value or range of values stated by $\frac{1}{10}$ of the stated value, e.g., ±10%. For instance, applying a voltage of about +3V DC to an element can mean a voltage between +2.7V DC and +3.3V DC. Likewise, wherein values are said to be "substantially identical," the values may differ by up to 5%. Whether or not modified by the term "about" or "substantially" identical, quantitative values recited in the claims include equivalents to the recited values, e.g., variations in the numerical quantity of such values that can occur, but would be recognized to be equivalents by a person skilled in the art.

As discussed in detail below, systems and methods utilizing RF energy to treat a patient's skin (e.g., dermis and hypodermis), the surface of a patient's mucosal tissue (e.g., surface of vaginal tissue or surface of esophageal tissue), or other target tissue including tissue at a depth below a tissue surface (e.g., skin surface, mucosal surfaces of the vagina or esophagus) are provided and can generally comprise one or more sources of RF energy (e.g., a RF generator), a treatment applicator comprising one or more electrode arrays configured to be disposed in contact with a tissue surface, and a return electrode (e.g., a neutral pad) coupled to the tissue surface. The electrodes may include zones or regions of an applicator that include a plurality of electrical traces or patterned/gradient containing regions of materials of differing dielectric constants/properties and other combinations and configurations of electrical elements as disclosed herein. The systems and methods disclosed herein for delivering RF energy to one or more target regions can be used in one or more lumens or cavities of a patient without limitation.

In general, the methods and systems disclosed herein may be used to provide various non-medical treatments such as cosmetic treatments, aesthetic treatments, and combinations thereof. Skin tightening, such as by improving skin laxity, and body sculpting (for example, via hyperthermic treatment and via lipolysis) are examples of cosmetic and/or aesthetic treatments that may be implemented using various RF-based systems and methods such as those discussed in more detail below.

In various aspects, the systems and methods can treat unwanted fat (e.g., via lipolysis), improve skin laxity/tightness (e.g., through the stimulation of collagen), improve the appearance of cellulite (e.g., by breaking septae), and various genitourinary conditions through the application of RF energy (e.g., about 500 kHz, about 0.5 MHz, about 1 MHz, less than about 1 MHz, greater than about 1 MHz, about 1.5 MHz, about 2 MHz, about 2.5 MHz, about 3 MHz, about 3.5 MH, about 4 MHz, about 4.5 MHz, and 5.5 MHz, or other frequencies include frequencies ranging from about 0.5 MHz to about 10 MHz) delivered to the surface of the patient's tissue (e.g., skin, vaginal wall, esophagus) via treatment electrode or electrode array, the treatment electrode or electrode array is optionally water-cooled, the RF energy propagating from the surface into deeper tissue layers and returning to the RF generator via a return electrode (e.g., a large surface area neutral pad) coupled to the tissue surface at a location distant from the treatment electrode or electrode array. In accordance with various aspects of the present teachings, systems and methods are provided for utilizing RF energy to heat a relatively large area of target tissue (e.g., greater than about 24 cm$^2$, greater than about 50 cm$^2$, or greater than about 200 cm$^2$ by applying (e.g., placing, fixing) an applicator to the skin, energizing the device (e.g., activating the RF generator), while cooling the superficial layers and selectively controlling the deposition of RF energy so as to heat the tissue below the surface. In accordance with various aspects of the present teachings, the deposition of the RF energy and/or the cooling of the tissue can be provided such that the tissue below the surface is heated substantially uniformly. It will be appreciated in light of the present teachings that heating uniformity can be required to help provide for safety, patient tolerance, and uniform clinical results.

Figure 1B:
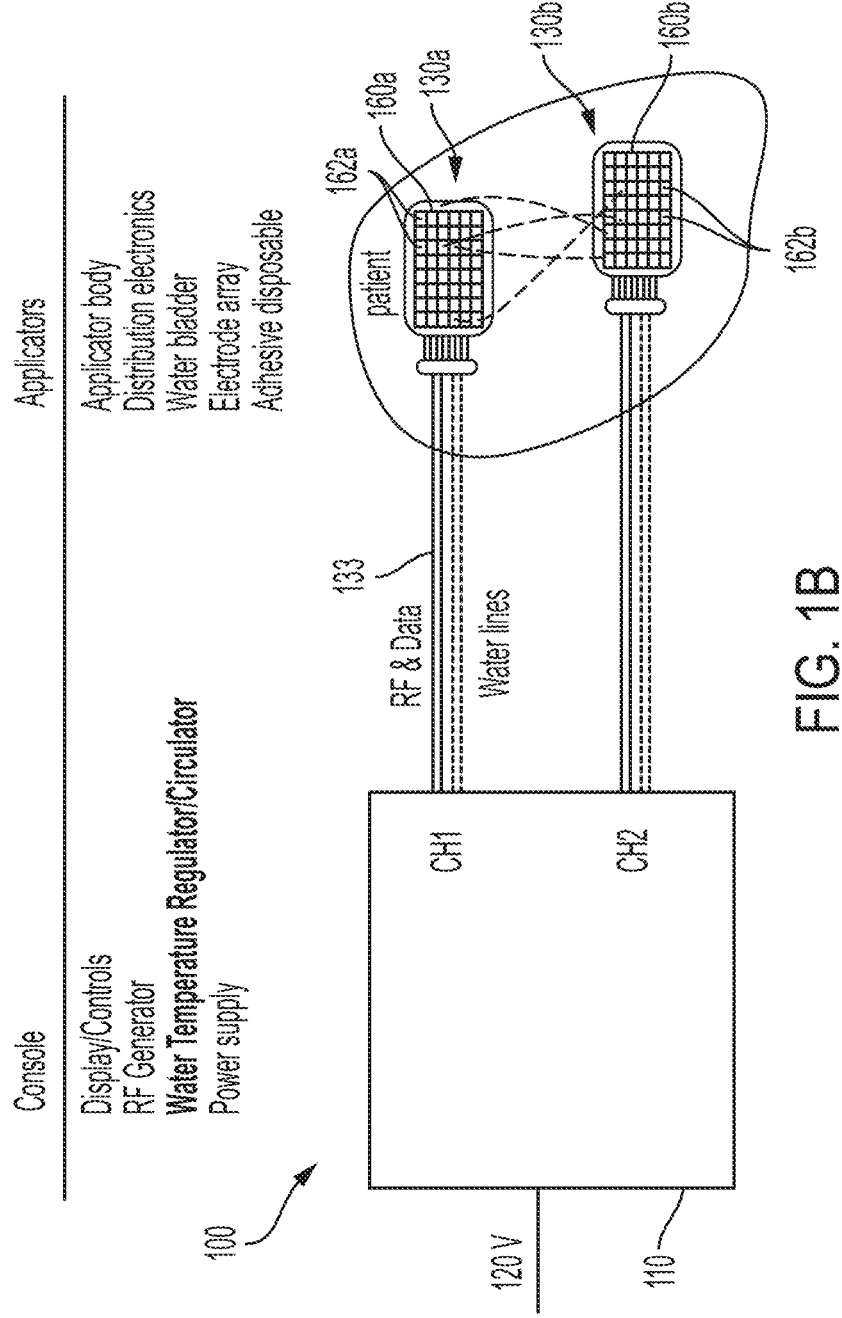
FIG. 1B schematically shows additional exemplary aspects of the system of FIG. 1A in accordance with various aspects of the present teachings.

With reference now to FIGS. 1A and 1B, an exemplary system 100 in accordance with various aspects of the present teachings is schematically depicted. As shown, the system 100 generally includes a console 110 and one or more applicators 130a-d comprising one or more electrically-conductive electrodes (e.g., comprised of metal) that are configured to be disposed in electrical contact with the patient's tissue (e.g., adjacent a region to be treated) for applying the RF energy to the tissue surface, and a return electrode (e.g., a neutral/drain pad 130e as in FIG. 1A or an active electrode array 160 as in FIG. 1B). The console 110 can have a variety of configurations and can include a display 132 (e.g., enabling reporting and/or control of various treatment parameters) and a housing 134 containing one or more RF energy generators 135, 136, a temperature-controlled water circulator 138 (e.g., including a chiller and/or a heater), and a power supply 139 (e.g., a low voltage power supply), all by way of non-limiting example. The system 100 also comprises a controller 137 (e.g., including a CPU or microprocessor) for controlling the operation of the RF energy generators 135, 136, the application of RF energy to particular electrodes 162, and/or the water temperature regulator/circulator 138 in accordance with the teachings herein. As shown, the console 110 can include a plurality of ports (e.g., CH1-4) for electrical and fluid connection of the applicators 130a-d as well as an additional port for electrical connection to the drain pad return 130e. As discussed in detail below, for example, each applicator 130a-d can include cooling water attachments and electrical connections to support serial communications between the console 110 and the applicators 130a-d, each applicator is connected to the console 110 via its own cable or umbilical 133.

Figure 1C:
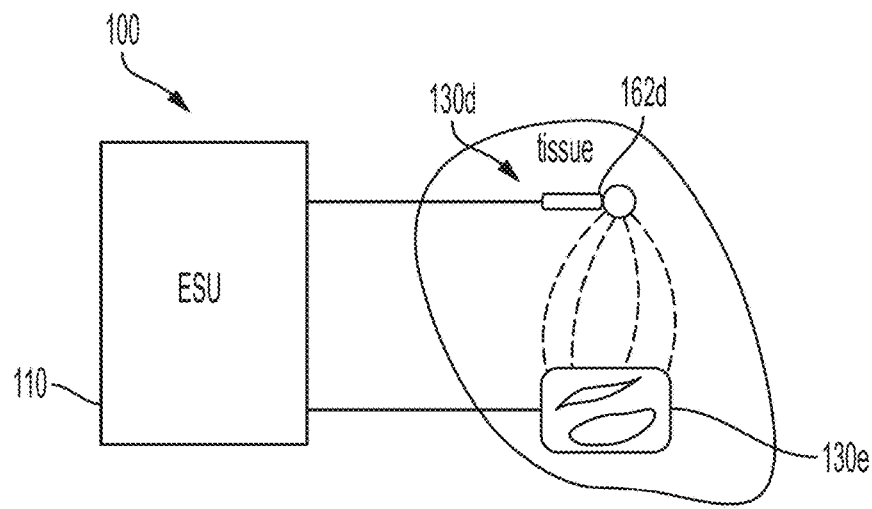
FIG. 1C schematically shows an exemplary system for providing RF treatment of a target region of a patient's body utilizing an electrode tip in accordance with various aspects of the present teachings.
Figure 1D:
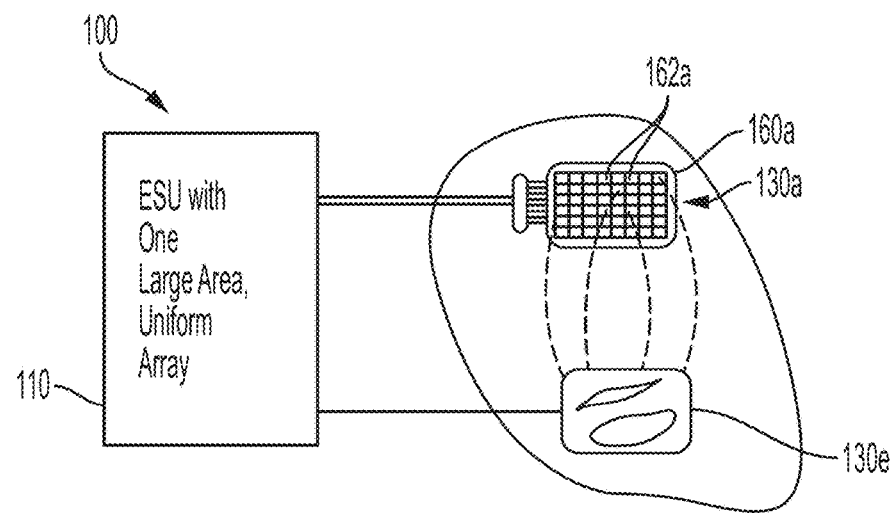
FIG. 1D schematically shows another exemplary system for providing RF treatment of a target region of a patient's body utilizing an electrode array in accordance with various aspects of the present teachings.
Figure 1E:
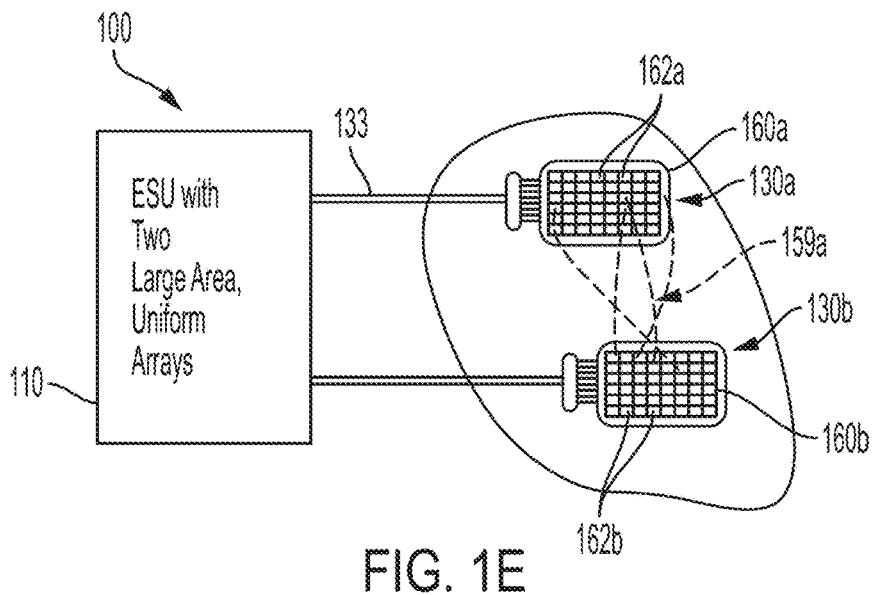
FIG. 1E schematically shows another exemplary system for providing RF treatment of a target region of a patient's body utilizing two electrode arrays in accordance with various aspects of the present teachings.
Figure 1G:
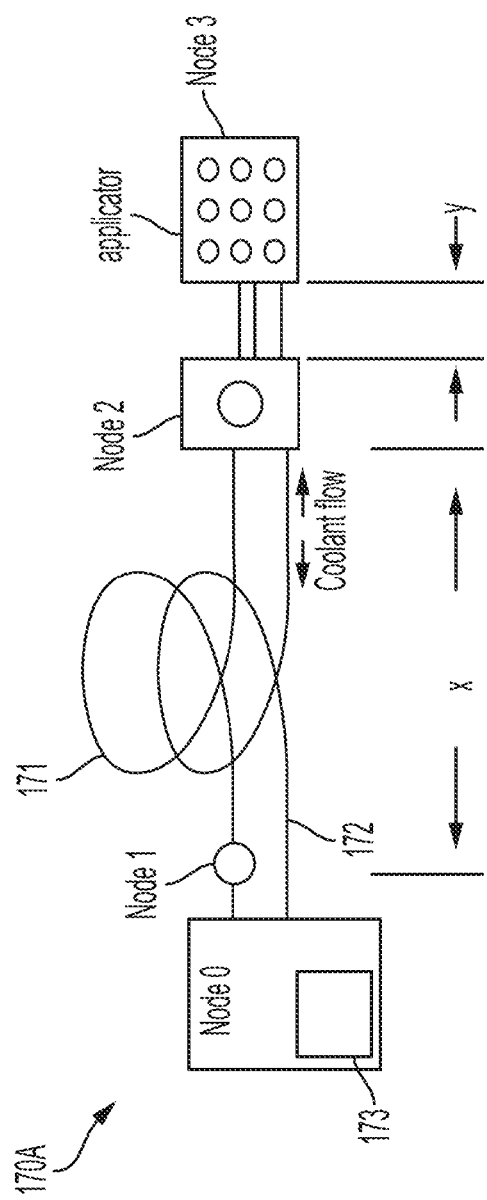
FIG. 1G schematically shows an exemplary system for providing an RF treatment that includes various nodes that represent different connections and operative components, such as control nodes, of the system in accordance with various aspects of the present teachings.

As discussed in more detail herein with regard to FIG. 1G, the length of the umbilical may also be referred to as length X. Each of the ranges recited herein may apply to the length X shown in FIG. 1G between control Node 1 and Node 2. In one embodiment, the length of the umbilical can range from about 10 feet to about 20 feet. In one embodiment, the length of the umbilical can range from about 1 foot to about 10 feet. In one embodiment, the length of the umbilical can range from about 2 feet to about 8 feet. In one embodiment, the length of the umbilical can range from about 20 feet to about 50 feet. In one embodiment, the length of the umbilical is greater than about 20 feet.

The one or more RF generators 135, 136 are generally configured to produce energy that is delivered to the applicator(s) 130a-d via one or more transmission lines extending through an umbilical 133 for application to the tissue (e.g., as modified by distribution electronics within the applicators 130a-d) and can be any known or hereafter-developed source of RF energy modified in accordance with the present teachings. Exemplary commercially-available RF sources suitable for use to be modified in accordance with the present teachings include the ForceTriad™ Energy Platform, marketed by Covidien. In some aspects, a plurality of RF energy generators can be provided, with each configured to generate RF energy of different characteristics from one another such that one or more of the generators can be utilized alone or in combination depending on the desired treatment. As shown in FIG. 1A, the system 100 includes two generators, one labeled 135 can generate RF energy of a maximum power of 300 W at 1 MHz (and can be operated at 100% duty) and the other labeled 136 can generate RF energy of a maximum power of 1 kW at 1 MHz (and can be operated at 20% duty), by way of non-limiting example.

It will be appreciated by a person skilled in the art in light of the present teachings that the various parameters of the RF energy (maximum power, frequency, duty cycle, pulse duration, etc.) can be selected depending on the desired treatment and the treatment area, as discussed otherwise herein. By way of example, it will be appreciated that one or more of the plurality of RF generators 135, 136 can be modulated to provide various powers including, for example, 300 W of RF energy that is provided to an applicator (e.g., 130a of FIG. 1B) and a return electrode (e.g., 130b if FIG. 1B) configured to cover ~200 cm$^2$ (~100 cm$^2$×2) or about 1.5 W/cm$^2$ per applicator, with each applicators 130a and 130b each providing about 1.5 W/cm$^2$.

Other suitable RF energy generators can be employed as discussed otherwise herein, for example, suitable RF energy generators can provide a wattage range of from about 0.5 W/cm$^2$ to about 5 W/cm$^2$, by way of non-limiting example. In various aspects, suitable duty cycles can vary depending on the targeted tissue type, however, in some exemplary tissue heating applications the objective can be to deliver an amount of RF energy so as to cause a temperature rise, while maintaining the treatment time as short as possible. Thus, as the duty cycle decreases, the RF energy can be increased to compensate for the reduced amount of "on time" so as not to extend the total treatment time. An exemplary duty cycle for heating skin and fat is from about 30% to about 80%, for example an about 50% RF duty cycle would be on for 5 seconds and then off for 5 seconds. Duty cycles can be modulated at varying frequencies that range from microseconds to seconds, because in some applications a faster modulation cycle can enable more precise control whereas in other application a longer modulation cycle may be desirable. The duty cycle may also be adjusted to optimize energy deposition in differing tissue layers or types: anatomical areas where large volume, deep, and highly perfused tissue target areas (e.g., fat) can allow for a relatively longer duty cycle (e.g., an 80% duty cycle as opposed to a 30% duty cycle), whereas shallower, smaller, and poorly perfused tissue (e.g., skin), the tissue can require a relatively shorter duty cycle (e.g., a 30% duty cycle is preferred over a 80% duty cycle). Applications other than bulk heating that rely on tissue impedance to select the targeted tissue can benefit strongly from very short duty cycles, even <1% duty cycle. Such short duty cycles can also be characterized as or referred to as pulsed RF.

As shown in FIGS. 1A and 1B, the exemplary system 100 can include a plurality of applicators 130a-d, representing a variously-adaptable, stand-alone system to heat and/or cool tissue safely and effectively. In various aspects, reducing and or maintaining the temperature of the surface of the patient's skin tissue, for example, by flowing water adjacent to a relatively rigid applicator (e.g., applicators 130a and 130b) or a flexible applicator (e.g., applicator 130c applied by adhesive to the skin), can be important in maintaining patient safety and comfort. As shown schematically, each applicator 130a-c can comprise a relatively rigid or flexible applicator body, distribution electronics, a water bladder or reservoir, an electrode array, and an adhesive for helping secure the applicator(s) 130a-c to the patient's skin, all by way of non-limiting example. In some additional or alternative aspects, vacuum can be used to help secure the applicator(s) to the skin. As discussed in detail below, the applicators 130a-c can have a variety of configurations but are generally configured to be coupled to the patient's tissue surface such that the RF energy delivered to the applicator 130a-c can be applied to the patient's tissue through one or more electrodes disposed in contact with the tissue surface. The applicator(s) 130a-c can also have a variety of configurations. Additional exemplary applicator configurations are described in further detail herein.

In the exemplary system 100 of FIGS. 1A and 1B, for example, applicators 130a-b can be substantially identical to one another, with one of the electrode arrays serving as the treatment electrode array and the other completing the circuit as the return electrode. In various aspects, the system 100 can be operated in a monopolar mode such that a circuit is formed by a source electrode 162a of an electrode array 160a from one applicator (e.g., 130a of FIG. 1B) with a return electrode 162b of another electrode array 160b from the other applicator (e.g., 130b of FIG. 1B). Additionally or alternatively, in some aspects, a large area drain pad 130e (also referred to herein as a "return electrode") can be attached to the tissue surface at a location distant from the treatment applicators 130a-d to disperse and/or return the RF energy applied to the patient's tissue from one or more of the "active" applicators 130a-d, as best shown in FIG. 1A. As discussed otherwise herein, as the tissue reaches the clinical endpoint for some electrode arrays, it is possible that the other arrays will not have delivered a full dose due to anatomical differences. In such cases, a power drain to an ancillary return electrode 130e can be used to boost the relative temperature of the lagging site. In some alternative aspects, bipolar operation could be achieved by activating electrodes within a single applicator array (e.g., array 160a of applicator 130a).

As shown in FIG. 1A, and discussed otherwise herein, applicator 130c can also include an electrode array and can be relatively rigid but have a shape configured to suit a particular body area. By way of non-limiting example, applicator 130c can provide an electrode array disposed within a concavity that can be configured to receive a patient's submental region such that contact is substantially maintained between the skin surface and the electrode surface when coupled to the patient's submental area. Alternatively, the applicator 130c can be relatively flexible such that it can be conformed to a curved tissue surface (e.g., the submental area, jowls, neck, and abdomen). As shown in FIG. 1A, and discussed otherwise herein, an applicator handpiece 130d having one or more electrodes can be provided that can be operated in a stamping mode. By way of example, applicator 130d can be held against a tissue surface of a particular treatment region while one or more RF pulses are applied to the tissue surface. In some aspects, the applicator 130d can be configured to provide one or more short-duration, high power RF pulses that can utilize one or more of impedance mapping, impedance tracking, and temperature monitoring as otherwise discussed herein. After treatment of one particular region is performed, the handpiece applicator 130d can be moved to another location. It will also be appreciated in light of the present teachings that more than two applicators can be used to cover larger areas.

With reference now to FIGS. 1C-1F, the electrode(s) of other exemplary applicators will now be described with reference to an electrosurgery unit (ESU) system 100 having a console 110 known in the art and modified in accordance with the present teachings. As shown in FIG. 1C, for example, the ESU 100 can be configured to concentrate the RF power and subsequent tissue heating at an electrode tip 162d (e.g., comprising a single, small area electrode) of an applicator 130d (e.g., configured to be held against the patient's tissue surface and operate in stamping mode), while a relatively large area drain pad 130e (e.g., the return electrode can have a surface area up to about 5000× the surface area of the delivery tip). In such a manner, non-uniformities in the return path can be still sufficiently safe to avoid burns due to the adequate distribution and/or dispersion of the RF power.

Referring now to FIG. 1D, in some alternative aspects the ESU 100 can instead include an applicator 130a having an electrode array 160a (e.g., comprising a plurality of individually-addressable electrodes 162a) for distributing the power uniformly over a large area, with the drain pad 130e representing the return path. As with FIG. 1C, the surface area of the return electrode 130e relative to the treatment electrode array 160a can help ensure that the RF energy is sufficiently distributed to avoid non-desired damage. However, unlike the return pad 130e shown in FIG. 1C, the return pad 130e in FIG. 1D is similar in surface area to the electrode array 130a such that benefits of large area uniformity in the return pad 130e can diminish. That is, a return pad having a larger surface area than the electrode array can generally help avoid undesirable side effects in the return pad (e.g., hot spots). With a large area treatment goal with an electrode array, shown in FIG. 1D, the size requirement of the return pad may be impractical and not possible to size to connect to a non-treated part of the body (e.g., too large to connect to a non-treated part of the body).

Additionally, as discussed in detail below, various mechanisms in accordance with the present teachings can be utilized to reduce "hot spots" on the active treatment electrode and ensure a more uniform treatment. For example, as discussed in detail below, distribution electronics of the applicator(s) 130a can be utilized to provide the same or different RF signals to the individual electrodes 162a of the electrode array 160a so as to provide improved control of the treatment procedure.

As shown in the FIG. 1E, in some aspects, the system 100 can instead utilize two electrode arrays disposed on different applicators: a first applicator 130a having a delivery treatment electrode array 160a and a second applicator 130b having a return electrode array 160b that also functions to delivery treatment energy via an electrode array. In such aspects, the return electrode array 160b can mirror the treatment electrode array 160a, likewise providing treatment energy, and can help achieve good uniformity for both skin contact areas that contact the first and second applicators, 130a and 130b. In some aspects, both treatment pads measure about ~100 cm$^2$ and each can deliver RF energy so as to provide uniform deep heating, while a third electrode is capable of draining power from a site if the two treatment sites in contact with the first and second applicators 130a, 130b heat differentially, for example, due to perfusion (as noted above with respect to FIG. 1A). RF energy, current, signals or energy 159a can flow between the applicators/electrodes as shown.

As shown in the FIG. 1F, in some aspects, the system 100 can also utilize an applicator 130j having an electrode array 160a and another applicator 130k having an electrode 160b that is used with a drain pad 130e or other drain device. The applicators 130j, 130k may attach via an umbilical 133. The applicators 130j, 130k and drain paid 130e can be used during an active treatment session to perform impedance mapping performed using an electrode array (130k or 130j) in communication with one or both of a second electrode array (130j or 130k) and a drain pad 130e. RF energy, current, signals or energy 159b can flow between an applicator 130k and the drain paid 130e as shown.

Optionally, in some exemplary aspects, the applicator(s) 130a-d can include one or more coupling features (e.g., clips) that allow the applicator to clip into a frame, the frame being attached to a belt or the like which would encircle or attach the frame (and the applicator attached thereto) to the patient surface so as to provide a hands free connection of the device to the patient for the clinician. In another embodiment, the applicator(s) 130a-d can attach directly to the skin surface via, for example, adhesive, gel, and/or mild suction.

Though the applicators of FIGS. 1D-F are generally shown as comprising generally planar arrays of electrodes (e.g., rigid or flexible arrays of electrodes) or individual electrodes in accordance with the embodiments disclosed herein, in some alternative aspects the applicator can be configured for insertion into an internal tissue site so as to provide for the application of RF energy to a mucosal tissues surface or to reach a depth below a mucosal surface (e.g., vaginal wall, esophageal lining). For example, as discussed in detail below with reference to FIGS. 8-12, the applicator can comprise a generally tubular probe that can be sized and shaped to be inserted into the vagina or esophagus for RF treatment thereof. As will be understood by a person skilled in the art in light of the discussion herein, the probe can comprise a plurality of electrodes (or groups of electrodes) that can be activated to apply RF energy to the target tissue in monopolar, bipolar, or hybrid mode. Additional examples of applicators suitable for applying and directing RF energy are also discussed herein and depicted in FIGS. 15A-15C, 17, 19A-21F, 22A, 22B, 23A, 23B, 25A-25C, 26A-26F and 27A-27C.

Operation Mode

Figure 7A:
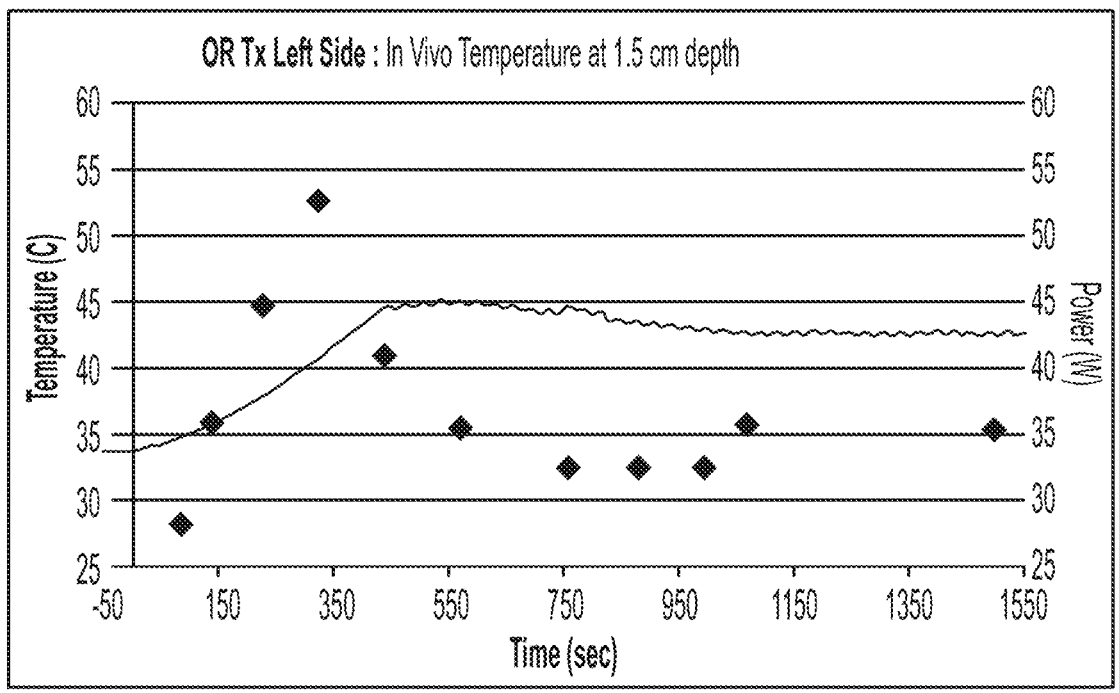
FIG. 7A depicts a plot of RF power and temperature of a target region at a depth of 1.5 cm during an exemplary treatment in accordance with various aspects of the present teachings.

The teachings herein include a variety of electrical configurations, namely, monopolar, bipolar, and a hybrid thereof. The monopolar configuration includes an active electrode (or electrode array) and an inactive electrode (e.g., a drain pad). The bipolar configuration includes two separate, active electrodes (or two separate, active electrode arrays). The hybrid configuration includes two separate, active electrodes (or two separate, active electrode arrays) and an inactive electrode (e.g., a drain pad). The exemplary electrical configurations shown in FIGS. 1C and 1D are monopolar and the electrical configuration shown in FIG. 1E is bipolar. The electrode configuration shown in FIG. 1A is hybrid. It will be appreciated that where only the pulsed handpiece 130d and the drain pad 130e as shown in FIG. 1 are used, such a configuration would be monopolar. On the other hand, using and activating only the electrodes of the electrode arrays on the two applicators 130a and 130b would be a bipolar configuration. Still another subset of the options shown in FIG. 1A utilizing the two applicators 130a, 130b and the drain pad 130e would be a hybrid configuration.

FIG. 1G is a schematic diagram showing a representation of RF-based tissue treatment system 170A according to the disclosure in which various operative and/or connecting control nodes are shown. Specifically, Node 0, Node 1, Node 2, and Node 3 are shown in sequence. As an introduction to specific roles for a given node type, Node 0 can serve as the master control node in some embodiments. Node 1 can control and direct the transmission of various DC power signals and other signals discussed in more detail herein. Further, Node 2 can control individual activation and deactivation of electrodes and other functions as described herein. Node 3 is used to designate the electrode array which receives on or more signals, power, and other parameters from one or more of the nodes to which it connects. The nodes can be referred to as control nodes or nodes interchangeably. In one embodiment, the nodes have a hierarchical architecture with Node 0 sending control signals and related signals to the other nodes to control their operation. The nodes can be considered as reference points or labels that correspond to various electronic components or other components or subassemblies of a given RF-based tissue treatment embodiment. Temperature measurements can be made using sensors disposed in the applicator in the vicinity of Node 3. Specifically, in one embodiment the temperature measurements are made using signals from such sensors and the temperature measurements are obtained at Node 1 or Node 2.

Figure 1H:
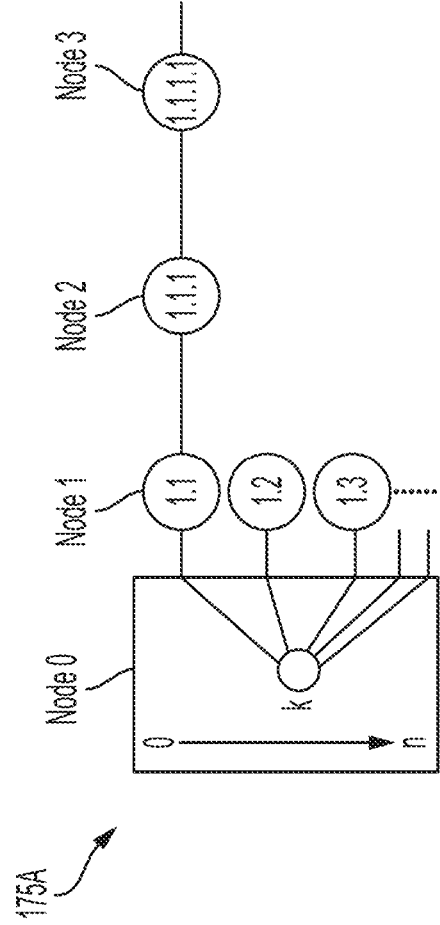
FIG. 1H schematically shows an exemplary arrangement of control nodes suitable for use with an RF-based system embodiment in accordance with various aspects of the present teachings.

Further, each of these nodes (Node 0-Node 3) can also serve as categories or grouping such that each of these four nodes has other nodes grouped with it. For example, in FIG. 1H, Node 0 can have a plurality of other Node 0's. As shown, Node 0 can have nodes 0 to n, with node k being labeled as an example node. In turn, node k, as Node 0 level node, is in communication with several Node 1 type nodes labeled as 1.1, 1.2, 1.3-1.n. A group of nodes within one of the higher-level node categories (Node 0, Node 1, Node 2, and Node 3) can be referenced as a sub-node in various embodiments. n is used as an index to identify the number of nodes for a particular node type. The set of nodes of type Node 0 has a cardinality of n. In some embodiments, the number of nodes per Node type can be greater or less than n. For example, there can be one Node 0 and twenty nodes that are of the Node 1, 2, or 3 type. In general, the number of nodes per node type can be any positive integer greater than or equal to 1.

Referring back to FIG. 1G, each node may have nodes within or connected to another node. Starting with Node 0, this node corresponds to a RF driver platform for a given RF treatment system embodiment. Node 2 is responsible for turning on/off individual electrodes in the applicator and taking local measurement of individual current flowing out of each individual electrode. The RF driver platform (Node 0) includes one or more components that provide other nodes or sub-nodes with individual commands. The RF driver platform (Node 0) can be implemented with one or more logical devices, FPGAs, circuits, circuit elements or combinations thereof. The nodes can be connected using one or more electrical connections 171, which can include one or more cables, buses, or other electrical signal connection and transmission mechanism.

Node 0 includes one or more devices that serve as a master controller or "brain" such all of the drivers, controls, signals, parameters, including phase, frequency, period, and amplitude values for drive or control signals that are directed to the other nodes and sub-nodes to which Node 0 connects are regulated and controlled in a consistent manner thereby. Thus, if Node 0 specifies a specific phase and amplitude for a signal that will drive a set of electrodes of an array of addressable electrodes at nodes of type Node 3, those outputs and other signals may be clocked and controlled by Node 0, in whole or in part.

Still referring to FIG. 1G, in one embodiment, Node 0 can include one or more control or timing components 173. The control or timing components 173 can include a system clock, a clock generator, or other device for clocking and synchronizing the nodes to which Node 0 connects such a Node 1, Node 2, and Node 3. The control or timing components 173 can include one or more of a controller, a feedback loop, a waveform generator, and one or more filters. Node 0 can include or connect to a DC power supply, an AC power supply, connections thereto or combinations thereof. The RF driver platform (Node 0) may include a master logic device disposed in a system component, such as console 110 or other consoles described herein. A coolant flow path 172 extending from Node 0 is also shown consistent with embodiments having Node 0 within the console 110. In general, the coolant flow path 172, also shown as a dotted line, relative to electrical connection between Node 0, Node 1, and Node 2 shown as a solid line, can start from any of the nodes or connect to applicator from a different source.

Node 0 controls the timing for all of the other nodes in the system such as Node 1, Node 2, and Node 3 as well as sub-nodes within each of these node types or categories. This can be performed using the one or more timing components 173. As a result, Node 0 can facilitate serial communication over an active RF treatment line with the other downstream nodes such as the type 1, type 2, and type 3 Nodes. In turn, this nodal configuration alone or together with the use of serial communication signals facilitates phase control of the various nodes and sub-nodes that are in electrical communication with Node 0. In one embodiment, the system drives the serial communication length synchronously with the fundamental RF frequency. Given that phase angle can be time varying for various waveforms, the timing control afforded by Node 0 and the timing components supports specifying a given phase on a per signal basis. In turn, this facilitates each addressable electrode, such as those shown in Node 3 to be phase tuned or adjusted. Further, such an implementation of timing and phase control using Node 0 supports any phasing scenario with regard to Node 1 and other nodes.

The RF-based treatment systems described and depicted herein including those described with regard to FIGS. 1H-K including Node 0, and any sub-nodes thereof, are designed to phase Node 1 and any sub-nodes of the Node 1 category. Node 0 may output one or more signals with a set phase or phase relationship. In one embodiment, Node 1 is disposed in, near, or about the RF generator.

In various embodiments, Node 1 controls one or more (or all) of the DC voltage; the RF Drive signal, and the relative phasing of the RF drive signal. In addition, in various embodiments, Node 1 specifies frequency and pulse form (Sine, triangle, sq. wave, chirp, sawtooth, etc.) of RF drive signal and other signal parameters.

There could be any of a number of these nodes in the generator (e.g., one per applicator, multiple nodes per applicator, or multiple applicators per node). These Node 1 nodes (or sub-nodes) are labeled 1.1, 1.2, 1.3 . . . 1.n, etc. as shown in FIGS. 1H-K. As was the case with Node 0, and the other nodes described and depicted herein, Node 1 can serve as category or node type for all nodes that are part of or performing RF generator operations or functions. The use of sub-nodes is only to convey the idea that the sub-nodes are one type of node, but each sub-node is a node in its own right which can connect to other nodes. The hierarchy of nodes is without limit and any given node of a particular function, electrode connections, applicator connections, etc. can define another node category to group nodes with similar functions and/or connections. Thus, nodes can map to one or more applicators and vice versa, without limitation.

As noted herein, Node 0 can facilitate serial communication over an active RF treatment line with the other control nodes or other components to which it is connected. In addition, differential serial communication between Node 1 and Node 2 can be implemented using twisted pair conductors as shown in the node-based system 170C depicted in FIG. 1J. As shown, exemplary node 1.1 of Node 1 connects to Node 2 through one or more twisted pair conductors. In turn, each Node 2 connects to one node in Node 3 as shown. A limited number of twisted pairs (e.g., from 1 to 20 twisted pairs) delivering RF power and control signals to the distribution electronics (Node 2) allows for no practical restriction on the length of the electrical connections 171 between Node 1 and 2 and being twisted improves noise immunity thereby reducing the likelihood of contaminating control signal integrity.

In addition, having the distribution electronics (Node 2) remote from the platform (Node 0), and close to the applicator's electrodes (Node3), allows for the improved fidelity in controlling and reading the individual electrodes. Long lead lengths from the distribution electronics to the individual electrodes will blur the control of individual electrodes by fostering cross-talk between individual channels and reducing the performance of the mapping and treatment capabilities of this architecture. In this way, controlling the length of the lead improves mapping and treatment performance.

In various embodiments, Node 1 has one or more outputs. This can be seen in the node configuration 170B shown In FIG. 1I. The outputs of Node 1 include one or more of the main RF drive signals to power electrode for treatment; communication signals or data between node 1 and node 2; and the DC power to power node 2. In one embodiment, Node 1 provides patient isolation/electrical safety to prevent any dangerous currents from getting to the patient. In one embodiment, Node 1 is configured to prevent the transmission of any harmful alternating current. In one embodiment, the nodal connections shown in FIG. 1I are configure for a typical treatment regimen using RF energy.

Each individual Node 1 sub-node (1.1, 1.2, 1.3, . . . 1.m) can be phased individually such that one or more or all output signals from Node 1 are set with all of the same phase, differing phases, or phase groupings among node subsets prior to such signals being transmitted to Node 2. As shown in FIG. 1I, each node of the Node 1 type, nodes 1.1, 1.2, 1.3, 1.4, . . . 1.m. each connect to a Node 2 type node on a 1 for 1 basis. In turn, each node in the Node 2 group of nodes (node 1.1.1 . . . 1.n.1) branches to multiple node 3 type nodes.

Figure 1I:
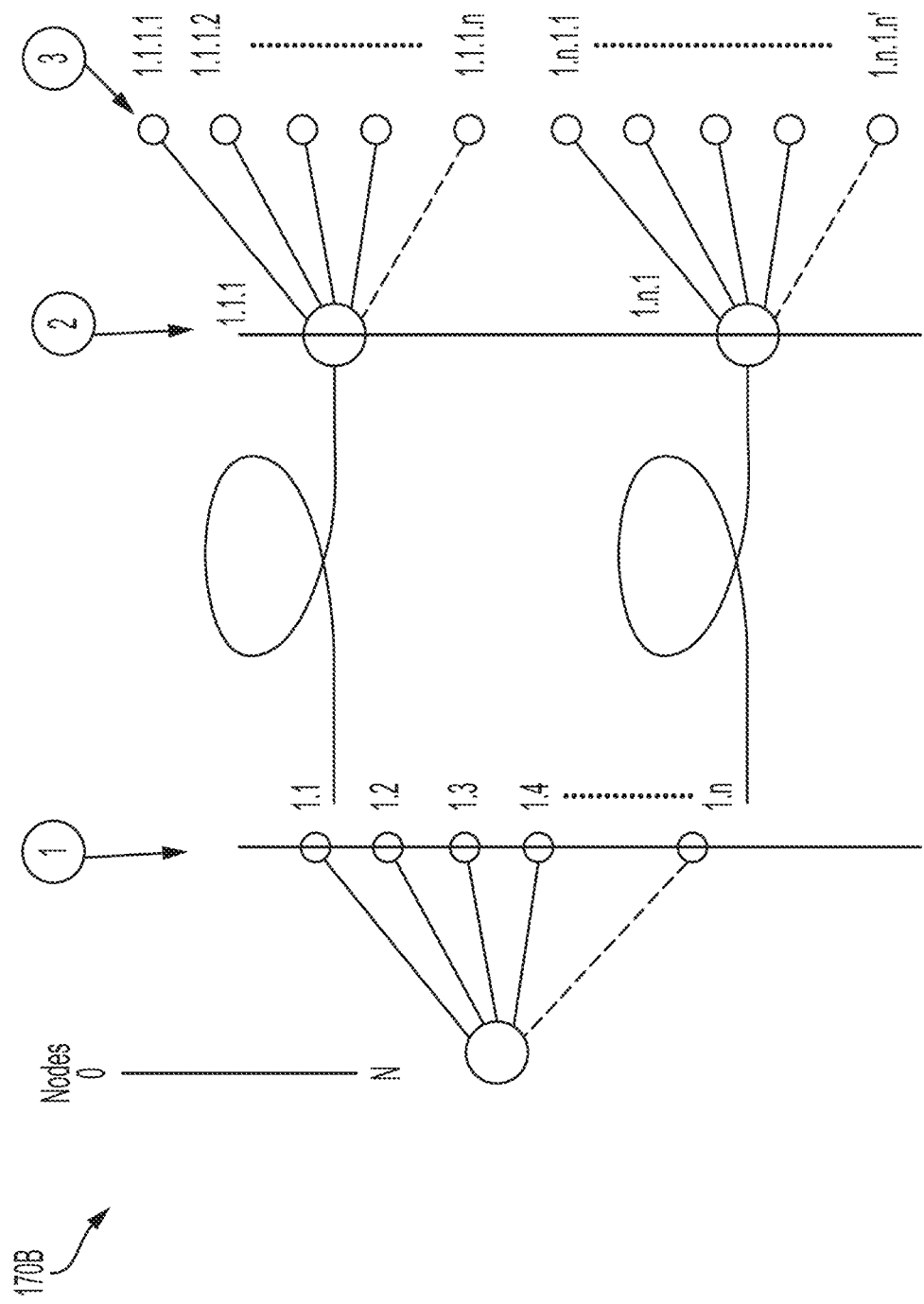
FIG. 1I schematically shows an exemplary arrangement of nodes suitable for use with an RF-based system embodiment in accordance with various aspects of the present teachings.
Figure 1J:
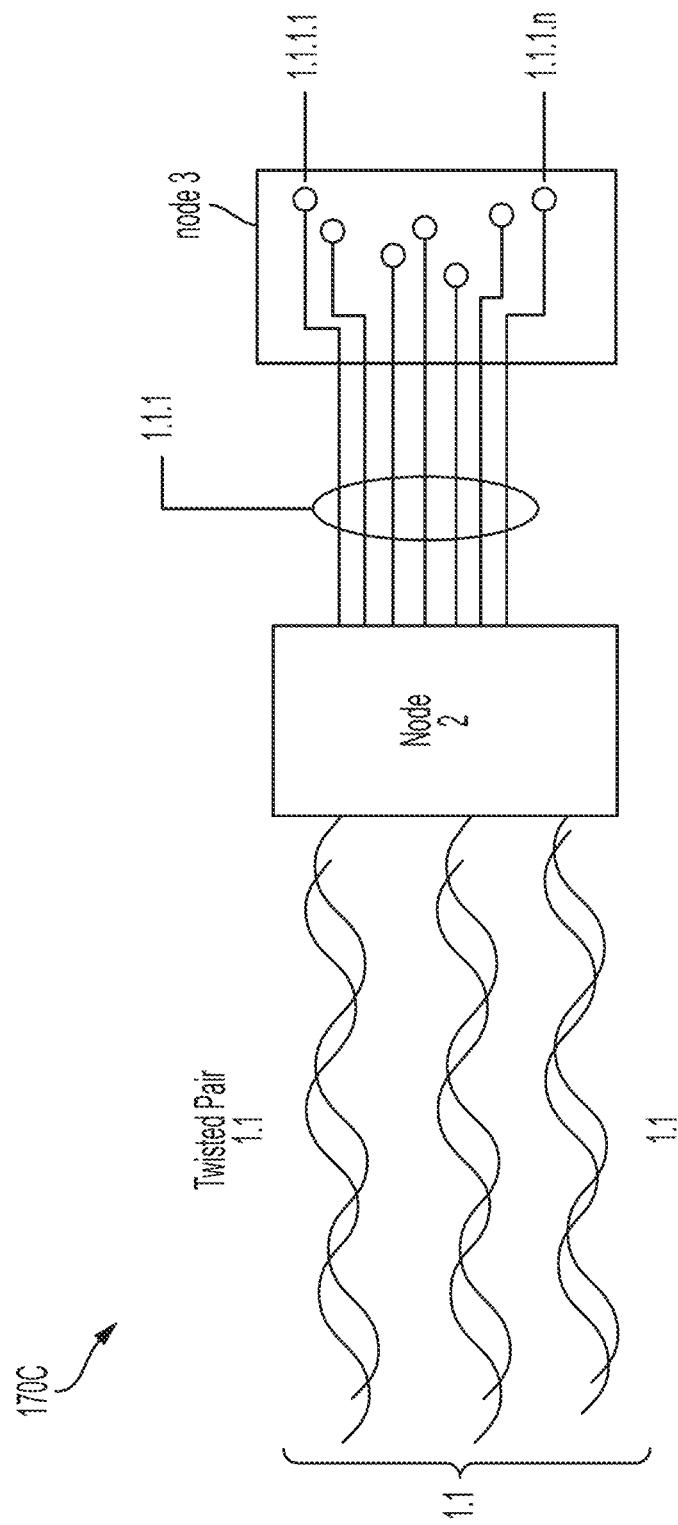
FIG. 1J schematically shows an exemplary arrangement of nodes suitable for use with an RF-based system embodiment in accordance with various aspects of the present teachings.

Specifically, as shown in FIG. 1I, each node in the Node 2 grouping connects or maps to n nodes in the Node 3 grouping. Accordingly, the node configuration 170B has each Node 0 connecting to n nodes at Node 1, with each of the n nodes at Node 1 connecting to a single node at Node 2, and then finally all of the n nodes at Node 2 each connect to n nodes at Node 3. This hierarchical mapping has a network topology of the form 1 to all n, each n to one n, and each n to all n moving from left to right from Node 0 to Node 3.

Figure 1K:
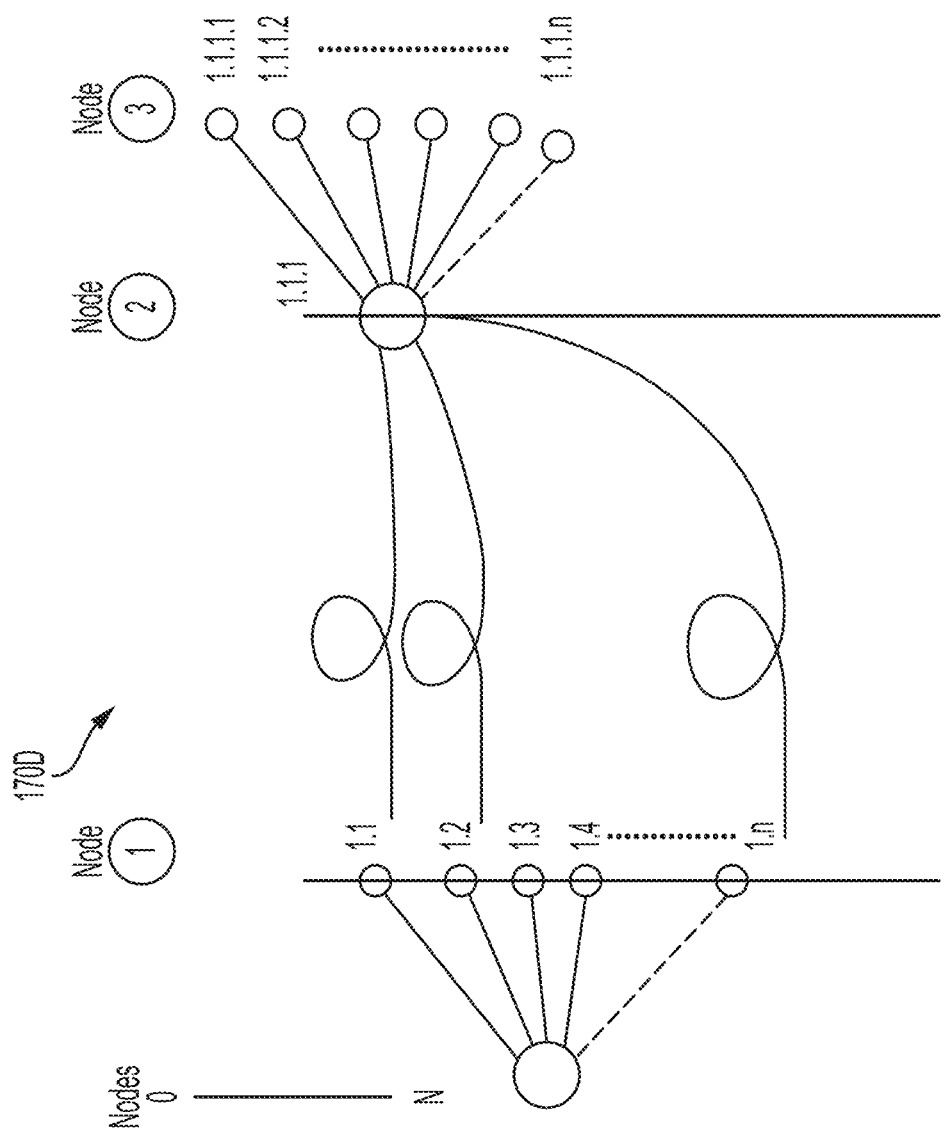
FIG. 1K schematically shows an exemplary alternative arrangement of nodes suitable for use with an RF-based system embodiment in accordance with various aspects of the present teachings.

Node 2 is responsible for turning on/off individual electrodes in the applicator. In one embodiment, Node 2 is also responsible for taking local measurement of individual current flowing out of each individual electrode. In contrast with FIG. 1I, FIG. 1K shows an alternative configure of nodes 170D in which each Node 0 connects to n nodes of the Node 1 type. In turn, all n of the Node 1 nodes connects to a single node at Node 2, shown as node 1.1.1. The only Node 2 node, node 1.1.1, connects to all of then nodes at Node 3. This configuration is of the form 1 to all n; all n to only 1 n, and only 1n to all n.

Based on the arrangement of node connections for node-based control system 170D in FIG. 1K, such local measurements cannot be performed at Node 1, but instead are measured at Node 2. This follows because Node 2 has each node at the Node 2 level connecting to a set of electrode groupings in the applicator such that all of the Node 2 nodes interface with all of the electrode nodes (Node 3) at the applicator. The ability of Node 2 nodes to be used to measure individual currents facilitates impedance mapping and individual addressing of electrodes in the electrode array.

The logical elements, such as FPGA's, ASICs, circuits, and combinations thereof are selected and arranged such that Node 1 can individually set all of the phase values for signals being output from Node 1 to other nodes such as Node 2 and Node 3, and sub-nodes of each. This is advantageous because it broadens the range of treatment options and RF profiles that can be achieved at the electrode array of Node 3. Specifically, as Node 1 can be selectively phased in different configurations based on the nodes selected, the phase of each node, and the timing of initiating phasing or waveform propagation from or to each node.

Various configurations for phasing Node 1 are possible. These may, include, without limitation, the following exemplary phasing sequences:

Phase nodes all in one phase as in: 1.1, 1.2, 1.3, . . . 1.n.

Phase the nodes individually as in: Phase node 1.1 then Phase node 1.7 then Phase node 1.2 then Phase node 1.16 then Phase node 1.1 then Phase node 1.2 then Phase node 1.3 then Phase node 1.n.

Phase the nodes in clusters as in: Phase nodes 1.1-1.6 then phase nodes 1.7-1.12 then phase nodes 1.13-1.18, then phase nodes 1.1-1.6, etc.

The foregoing are just examples, and any combination or all of the sub-nodes of Node 1 or subsets thereof can be phased in clusters, individually, collectively, in different sequences or orders of phasing, or combinations thereof. This flexibility to phase all together, individually, in clusters, etc. enables one to adapt treatment to contours of the patient's tissue being treated and enables one to adapt the treatment to the user placement. In general, although the exemplary control nodes are labeled or referenced by Node 0, Node 1, Node 2, and Node 3, each of the foregoing can be referenced as a first node, a second node, a third node, or fourth node without limitation.

Cable/Umbilical

As described herein with regard to FIG. 1A, the various conformable, rigid, semi-rigid, hybrid, disposable, re-usable, partially re-usable, and other applicators of RF energy described herein connect to a console such as console 110. The electrical connections to the applicator from a given console embodiment and one or more of the various control nodes electrical connections can be routed through an umbilical housing to safe guard the signal transmitting conductors. In one embodiment, one or more section of such an umbilical can house a RF transmission cable, sections thereof, and tubes or flow paths for circulating coolant to a given applicator.

In one embodiment, the lengths of the RF transmission cable, or sections thereof or lengths of conductor segments between the various control nodes, or subsets or combinations of the foregoing lengths should be selected to support operation of the RF-based systems described herein. In one embodiment, the disclosure relates to various operating lengths for various electrical conductor lengths used in the system that support its operation. In some embodiments, if these lengths are exceeded excessive noise, cross talk, or other deleterious effects can prevent the RF-based treatment systems disclosed herein from operating or can prevent the RF-based treatment systems from operating with the desired efficiency and effectiveness. Some examples of these length parameters can be seen by referring to FIG. 1G.

As shown in FIG. 1G, the distance between Node 1 and Node 2 is identified as length X. This length X may correspond to the length of an umbilical from a given console embodiment. Various suitable X length distances are discussed herein with regard to FIG. 1A. In addition, the distance between Node 2 and Node 3 is identified as length Y. Length Y can include the length of one or more conductors such as multiple conductors used in an RF-transmission cable. Length Y can be less than the flow path of coolant from Node 2 through the applicator. Length Y can be measured from the output of Node 2 to the input of the applicator. In addition, length Y can include traces or wires that extend into the applicator and terminate at a given electrode. Length Y can also include the average distance between the various conductors within the applicator to each electrode and the entry point for such conductors into the applicator added to the length of such conductors between the output of Node 2 and the input of Node 3. The input of Node 3 can include the opening or channel at which conductors from Node 2 enter the applicator. In general, the distance or length Y is the distance beyond Node 2 from the output of node 2 to the start of the applicator.

For the overall system to work well with all of the desired capacity, the distance selection of length or distance Y is important for successful operation of a given applicator-based RF treatment system. The selection of the length Y maintains Node 2's electrode activation and deactivation functions, and Node 2's current measurement functionality, and thus its contribution to impedance mapping and other derived functions. As part of the design effort and the node-based conductor configurations, it has been determined that in one embodiment Y ranges from about 0 inches to about 2 inches. This specification of the Y distances supports a system configuration that avoids wires or other conductors and uses a printed circuit board with conductive traces to improve impedance mapping and reduce cross coupling below a threshold level. In one embodiment, the range of from about 0 to about 2 inches includes the tracings on the PCB. In yet another embodiment, the distance Y ranges from about 0 to about 6 inches. In still another embodiment, the distances Y ranges from about 0 to about 1 foot. Alternatively, the distance Y can range from about 1 foot to 2 feet. In still other embodiments, Y is less than about 3 feet.

With the foregoing discussion, of exemplary system and the description of various electrode configurations and arrangements, it is informative to consider additional details relating to various treatment parameters and other features of the disclosure. As will be appreciated by a person skilled in the art in light of the present teachings, exemplary systems can provide the following benefits and/or include some or all of the following features:

Treatment Temperatures and Cooling of Patient Skin

In various aspects, it can be important to enforce uniformity of delivered RF energy so as to safely raise the target tissue to a desired temperature. In particular, to provide an efficacious treatment, it can be important to raise target tissues to an intended temperature range but also maintain the tissue in the targeted region at that elevated target temperature for a given duration. That is, "time at temperature" can be important to confer the desired clinical benefit. For example, temperatures may range between about 39° C. to about 47° C., or between about 39° C. to about 44° C., or between about 42° C. to about 47° C. within the fat layer, with from about 41° C. to about 42° C. providing a typical tissue temperature for treating tissue within the fat layer or within other similar tissues at a depth. In some aspects, the temperature ranges from about 41° C. to about 42° C. can be used to preferentially stimulate collagen development. Higher temperatures up to about 46-47° C. can be used to target tissues with more damage, thus providing a more aggressive treatment, e.g., in deeper tissue layers. However, the range of 46–47° C. may not be able to be tolerated directly on the skin surface due to the uncomfortable sensation of the relatively high temperature felt by the patient. In some aspects, treatment temperatures of tissue beneath the mucosa may be able to tolerate higher temperatures, up to about 70° C., or from about 40° C. to about 60° C. Treatment time at temperature could range from about 5 minutes to about 25 minutes and may vary with, for example, depth or volume of targeted tissue. As such, it can be important that the RF energy is actively controlled as otherwise discussed herein to distribute through targeted tissues in the targeted treatment zone in a substantially homogenous fashion, substantially uniformly, predictably and automatically (without user intervention). In some embodiments, the tissue surface temperature (e.g., skin surface and/or mucosal tissue surface) may be controlled to be held at a range from about 15° C. to about 40° C., or from about 25° C. to about 40° C. during the treatment of the tissue at a depth. Higher temperature ranges at a depth (e.g., from about 46-47° C.) may be tolerated and thereby realized during treatment due to temperature control ranging from about 15° C. to about 40° C., or from about 25° C. to about 40° C. at the skin surface.

Cooling of patient skin surface can protect the epidermis and also improve patient comfort. Adequate surface cooling (e.g., cooling water at a temperature from about 10° C. to about 40° C., or at a temperature from about 25° C. to about 40° C. or about 25° C. to about 35° C.) can allow the application of higher RF powers safely and comfortably than could be applied in the absence of such cooling. This can be important as most target tissues are located at some depth from the surface such that surface cooling acts to protect the intervening tissue layers which are not targeted.

As discussed below, the electrode array can have a variety of configurations, though in some exemplary aspects, the electrode array can be attached to an applicator comprising a metal coolant housing (e.g., bonded or adhered via an adhesive). An electrical insulating and thermal conducting layer (Kapton or ceramic, $AlO_2$ or the like) can be located between the cooling housing (e.g., containing a reservoir or bladder of temperature-controlled cooling water) and the electrode array such that the cooling water cools the electrode array and the patient's skin surface in accordance with various aspects of the present teachings. As noted above, the cooling water can be circulated from the console 110 of FIGS. 1A and 1B via one or more pumps through one or more fluid conduits (e.g., via one or more umbilical 133 to the respective applicator connected thereto), with the chiller/heater 138 being configured to detect and/or maintain the temperature of the cooling water as desired.

RF Pulse Duration in View of Target Tissue Selected for Treatment

A variety of treatment regimens can be provided in accordance with various aspects of the present teachings. In various aspects, both long duration (e.g., greater than 1 second, CW), low power RF energy (e.g., from about 1 $W/cm^2$ to about 5 $W/cm^2$) and short duration (e.g., less than 500 ms, or less than 100 ms), high energy RF pulses (e.g., from about 10 to about 1000 $J/cm^2$ per pulse, 10 $J/cm^2$-500 $J/cm^2$, 10 $J/cm^2$-300 $J/cm^2$, 10 $J/cm^2$-100 $J/cm^2$) regimens are envisioned and can provide different benefits depending on the biological target selection and biological target treatment. Without being bound by any particular theory, the method of action can be thermal in nature where delivered RF power acts to primarily or preferentially heat (or even coagulate) selected tissues. Thermal diffusion or conduction to adjacent tissues is also envisioned as a treatment regimen. More precisely, because different tissues have different electrical impedances and RF energy tends to propagate through anatomical structures or tissues exhibiting the lowest impedance, connective tissues (e.g., fibrous septae tissue that interpenetrate fat layers) can represent a relatively-low impedance preferential path through which the RF will be conducted. As such, heat will tend to accumulate in the relatively low-impedance RF conduction path. For example, the connective fibers of the septae tissue would begin to heat relative to adjacent tissue. As low impedance tissues accumulate heat (e.g., exhibit a temperature rise), they also begin to thermally conduct to nearby adjacent tissues such as fat, for example, which has a relatively higher electrical impedance compared to the connective fibers (e.g., the septae tissue). In light of the present teachings, it will be appreciated that the pulse duration of the applied RF can therefore provide a method to select anatomical target tissues as discussed in detail below.

Short duration, high power RF pulses can act to heat or even coagulate low impedance tissue (e.g., connective fibers of the septae tissue), whereas long duration, low power RF energy tends to heat the low impedance tissues at a sufficiently slow rate that heat is conducted into adjacent high electrical impedance tissues (e.g., fat). For example, by applying RF energy in short duration, high power pulses, fibrotic structures can be rapidly heated without being able to conduct heat away into adjacent higher resistance tissues (e.g., fat) sufficiently fast enough to dissipate the rapid buildup of heat within the fibrotic tissue. Short pulse duration, high magnitude RF power can thus deposit a temperature increase in tissues having a low electrical impedance within the treatment region (beneath the applicator). Short duration (e.g., from about 10 ms to about 500 ms, preferably <100 ms) and high magnitude RF pulse energies (e.g., from about 10 to 1000 $J/cm^2$) can be used to selectively treat low impedance tissues such as septae or other fibrotic structures within the patient's tissues. Since the preponderance of electrical current will flow through fibrotic structures located for example in more resistive, higher impedance fat layers, rapid delivery of such short duration RF treatment pulses acts to preferentially accumulate a temperature rise in the fibrous connective tissue structures such as septae. Given the short duration of the RF pulse, the rapidly heated fibrotic structures are unable to conduct heat away into adjacent higher resistance tissues (e.g., fat) fast enough to counter the rapid buildup in fibrotic tissue temperature rise. This pulse duration effect can thus act to "select" the fibrous tissues or septae for treatment, by accumulation of temperature rise, whereas the surrounding tissues remain relatively cool. This method can be useful for selectively heating fibrotic structures such as septae (a main component causing the cottage cheese or dimpled appearance of cellulite). This approach can be useful for coagulation of fibrotic structures such as septae in the tissue. While the example of septae and surrounding fat is used, the ability to target or "select" tissues of distinct electrical impedances can be applied to many other tissue types or layers.

On the other hand, relatively long duration, low power RF energy can be preferred to heat (more or less uniformly) tissue layers exhibiting differing electrical impedances. That is, longer pulse durations or even CW (continuous RF emission) can be used to treat all tissue types within the treatment area because the low impedance connective/fibrotic tissue or septae is heated slowly enough to allow the heat to transfer via thermal diffusion and/or conduction into the surrounding relatively higher impedance tissues. The result can thus be more or less bulk heating of all tissue within the treatment area (e.g., beneath the electrode array applicator). Thus, long pulse duration or CW emission (from about 1 second to continuous (CW)) with relatively lower magnitude RF power (e.g., from about 1 to about 5 $W/cm^2$) can be used to homogenously treat a block or zone of tissue regardless of tissue components and their differing electrical impedances of the tissues within the zone. Long pulse duration, low magnitude RF power tends to generate a temperature increase in all tissues in the target region through thermal conduction, regardless of electrical impedance. Because fat cells have a lower damage tolerance (elevated temperature tolerance) compared to the connective fibers, the fat cells can therefore be lysed while the connective tissue remains largely undamaged. The present teachings thus provide, for example, a method to perform lipolysis by providing low magnitude, long pulse duration (or CW) heating of connective fibers (septae) which then heat the adjacent fat cells. It will further be appreciated in light of the present teachings that pulse durations can be fine-tuned to optimize temperature accumulation in desired target tissues, while protecting surrounding tissues from exposure to excessive temperature rise.

Electrode Array

In various aspects, a large electrode face (e.g., an electrode pad) can be broken into a mosaic of smaller electrodes (e.g., an array of multiple individual electrodes). An electrode array can have a variety of configurations but is generally configured such that the plurality of the electrodes comprising the array can be placed in electrical contact with the tissue so as to provide RF energy thereto. The individual electrodes that comprise the electrode array can exhibit a variety of numbers of electrodes and have a variety of shapes, sizes, and layouts (e.g., pitch). Suitable individual electrodes can each have a diameter that ranges from about 3 mm to about 100 mm, from about 10 mm to about 70 mm, from about 10 mm to about 30 mm, by way of non-limiting example. In one embodiment, for example, each individual electrode of a given electrode array can measure approximately 1 cm in diameter. In some aspects, a group of electrodes in an electrode array or multiple electrode arrays can be arranged in a pattern covering from about 1 $cm^2$ to about 500 $cm^2$. The electrode array(s) can form a shape, for example, hexagonal, rectangular, circular, elliptical, rhombus, trapezoid, or other shape suited to target particular tissue areas for treatment. The number of individual electrodes in a single electrode array can also vary. In some aspects, for example, there can be from about 2 to about 100 individual electrodes in an electrode array, while in another embodiment there can be from about 6 to about 20 individual electrodes in an electrode array. In one non-limiting example, 19 individual electrodes are arranged in a hexagonal pattern covering about 20 $cm^2$ of surface area. A larger area of tissue may be treated by providing several applicators or groups of electrodes (e.g., several electrode arrays) that cover a desired surface area of tissue.

Individually Switched Electrode Array

As will be appreciated in light of the present teachings, substantially uniform deposition of energy can be achieved by breaking the large electrode face into a plurality of smaller electrodes, where each electrode within the array can be addressed and activated individually. In order to achieve uniform deposition of energy, one or more individual electrodes within the array can be individually addressed and activated based on tissue feedback including temperature and/or impedance feedback, for example, as discussed further below. In some aspects, for example, only one electrode (or a subset of the electrode array) may be activated based on the tissue feedback to help provide substantially uniform heating of tissue. In other aspects, individually controlling the electrodes can help ensure or control that the heated zone remains centered within the desired treatment zone location (e.g., beneath the electrode array applicator) as well as to maintain substantial homogeneity and consistency of the temperature rise within the desired treatment area despite variations in the patient's underlying tissue electrical impedance or despite nearby or adjacent anatomical structures.

By way of example, distribution electronics of the applicator(s) 130*a-d* of the system 100 of FIGS. 1A and 1B can be utilized to provide the same or different RF signals to the individual electrodes of the electrode array(s) 160 so as to provide improved control of the treatment procedure, for example, by adjusting one or more of power, RF frequency, pulse width, and/or duty cycle. In such aspects, each of the individual electrodes in the electrode array in contact with the patient can be independently addressed (e.g., switched to gate the RF power or duty cycle applied thereto), with each individual "channel" capable of also providing current, voltage, and/or phase angle feedback information useful for calculating power and impedance of individual electrodes. In some aspects, the independently-switched electrodes in the array can be switched (e.g., via controller 137) to gate RF power simultaneously to each of the individual electrodes in the array, or alternatively, the independently-switched patient contact electrodes in the array may be switched to gate RF power sequentially first to one of the electrodes in the array and next to another electrode in the array until all or substantially all of the electrodes in the array are addressed (e.g., during impedance mapping discussed below).

In some aspects, an individually-controlled RF electrode array can be employed to disrupt connective tissues that interpenetrate fat layers (e.g., fibrous septae tissue present in cellulite through septae disruption). In such exemplary aspects, the electrode array can be placed over the tissue region to be treated, with the septae beneath the electrode array being targeted for treatment by individually addressing one of the electrodes (or a subset of the electrodes) in the array of multiple electrodes with short duration (e.g., less than 100 ms), high energy pulse(s) (e.g., from about 10 to about 1000 J/cm$^2$). After the short pulse or series of pulses is completed by the first electrode (or subset of electrodes), another electrode or subset of electrodes in the array can be addressed with a short pulse or series of pulses, with the process being repeated until multiple electrodes or all electrodes in the array have been addressed with a short duration, high power RF pulse so as to target all of the tissue region below the array. Optionally, the individual electrodes are addressed sequentially with short pulses of high power RF energy. In one embodiment, all or substantially all of the RF energy available to the entire electrode array is gated to an individual electrode so that, due to the relatively low impedance of the septae tissue, the septae tissue is preferentially heated by the relatively short pulse. Alternatively, a greater power supply is employed that enables the desired and/or required high magnitude energies (e.g., from about 10 to about 1000 J/cm$^2$) to be gated to an individual electrode to thereby preferentially target septae tissue.

In another embodiment, an individually-controlled RF electrode array can be employed to disrupt connective tissues that interpenetrate fat layers as well as to provide for treatments of laxity (and/or lipolysis). By way of example, a RF electrode array can first be employed using relatively short pulses of high magnitude power as discussed above to disrupt (e.g., break) the septae in the tissue region below the array. That is, after each short pulse is completed by an electrode (or subset of electrodes), another electrode or subset of electrodes in the array can be addressed with a short pulse, with the process being repeated to target all of the tissue region below the array. Thereafter, the same electrode array can be used to heat the same tissue region as a whole (including septae tissue and other tissue in the region including fat, dermis, hypodermis, the dermal/hypodermal junction) by utilizing relatively long, low power RF pulses (e.g., from about 1 to about 5 W/cm$^2$) to provide for relatively bulk heating, for example, for a lipolysis and/or laxity treatment. For example, after the septae tissue has been targeted with the short pulse, high power RF treatment, the RF electrode array can be used to treat same tissue region for laxity by simultaneously addressing all or substantially all of the electrodes with a relatively long pulse or series of long pulses (e.g., from about 1 second to continuous (CW)) and for an exposure time ranging from about 5 minutes to about 35 minutes, or from about 10 minutes to about 30 minutes, or for about 25 minutes to maintain the target tissue within the treatment temperature range. It will also be appreciated that in some aspects, the thermal treatment of the tissue region via long pulses of multiple and/or all RF electrodes in the array can occur first, with the targeted treatment of the septae occurring thereafter via a sequential application of a short pulse by one (or possibly a few) of the electrodes in the array of multiple electrodes.

Flexible Electrode Arrays

In accordance with various aspects of the present teachings, flexible electrode arrays are envisioned wherein the electrode array allows for an improved connection to curved surfaces or contours of a patient's body. In such aspects, the applicator array can include a plurality of electrodes (e.g., individually-controlled electrodes), with the individual electrode units each exhibiting an active area of about 1 cm$^2$, for example, and comprising a thin metallic surface integrated on a flexible substrate. In some aspects, the individual electrodes can also be flexible (e.g., capable of bending) due to the limited thickness of the electrode's conductive material (e.g., a metal). Alternatively, the electrode can comprise, for example, a woven metal (e.g., copper) cloth that itself exhibits flexibility so as to conform to the contours of the tissue surface. An electrode array can thus be comprised of rows and columns of the rigid or flexible electrode units disposed on a flexible substrate that is scaled so as to provide an applicator with an area ranging from 1's to 100's of cm$^2$. Such flexibility allows treatment uniformity to be achieved on both a small and large scale. Custom shaped array patterns are also envisioned such that any shape suitable for a given treatment area may be employed, for example, a boomerang shape, a rectangle shape, or a trapezoid shape may be useful for sub-mental or chin treatments. It will be appreciated in light of the present teachings that many variations in shapes and sizes are possible. Various electrode arrays suitable for conforming to and attaching to a tissue surface having various non-standard shapes and sets of standard shapes are shown in FIGS. 2B-D and FIGS. 2E-F, respectively.

Disposable Applicators

In some aspects, the applicator (e.g., applicator 130*a* of FIG. 1A) or a portion thereof can be provided as a disposable. By way of example, the skin contacting portion of the applicator containing the treatment electrodes and a portion of the cooling conduits can be configured to couple to a non-disposable umbilical side (which couples the applicator to the console) containing relatively more-expensive distribution electronics that can be removably coupled (e.g., via pins) to the electrodes in the disposable portion of the applicator. The umbilical side can also contain one or more fluid conduits for delivering fluid to the disposable portion of the applicator (e.g., via one or more fluid coupling elements). In various aspects, an adhesive gel can be applied to the face of the applicator that is covered by a protective sheet. The sheet can be removed (e.g., torn off) and the applicator applied to the skin. Optionally, the adhesive gel pad can be discarded after one or more treatments, while the remainder of the applicator can be reused. Alternatively, in some aspects, the entire applicator can be disposable. In such aspects, the relatively expensive fittings and circuitry can be relegated to the umbilical side such that the cost of the disposable applicator can be minimized.

Figure 2A:
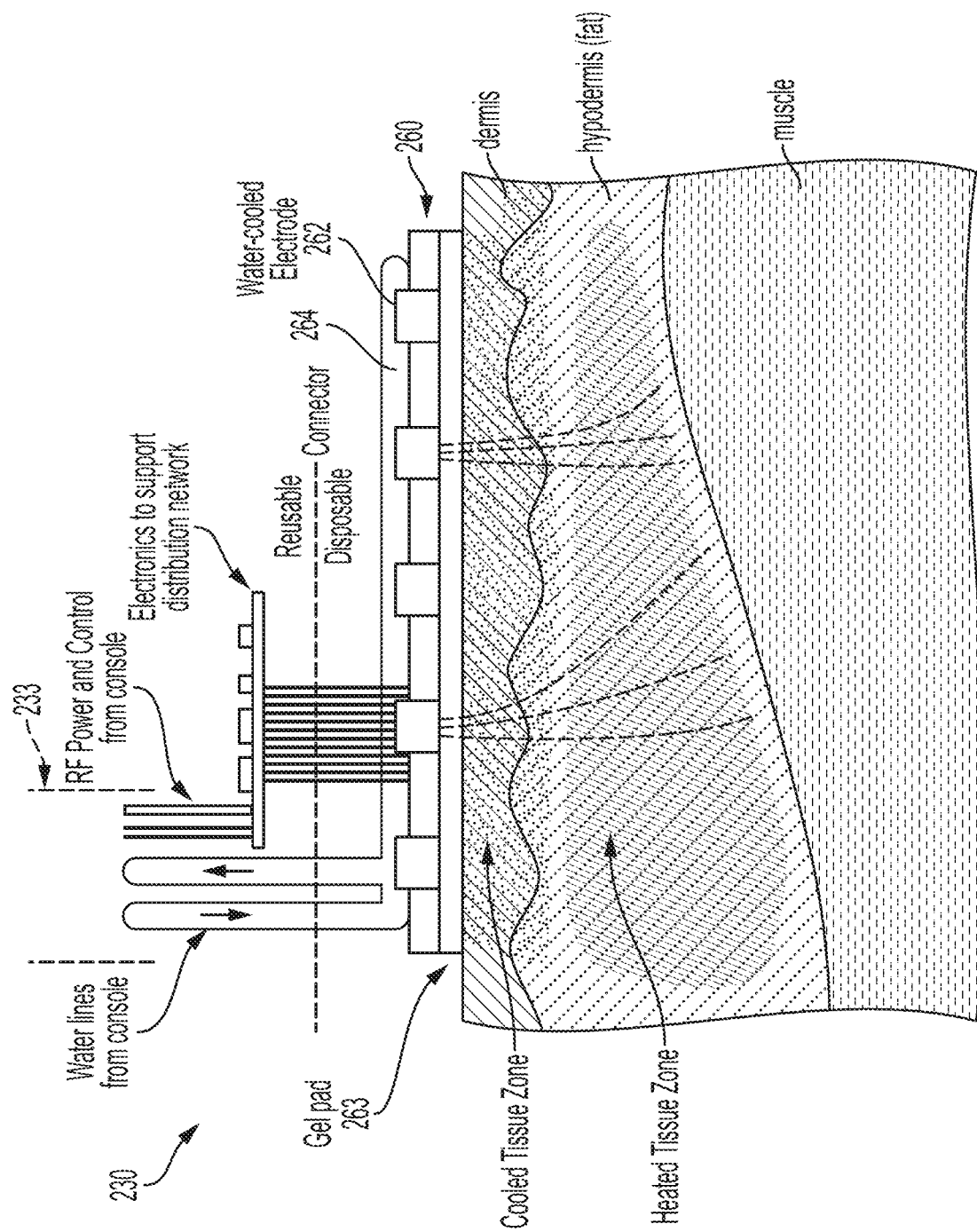
FIG. 2A schematically depicts an exemplary, disposable system for providing RF treatment of a target region of a patient's body in accordance with various aspects of the present teachings.

With reference now to FIG. 2A, a portion of another exemplary system for RF treatment in accordance with these and other aspects of the present teachings is shown schematically. FIG. 2A depicts a cross section of the skin including dermis, hypodermis (mostly fat), and muscle layers with an exemplary RF applicator 230 adhered to the skin's surface. As discussed otherwise herein, coolant from the console (e.g., console 110 of FIGS. 1A and 1B having a temperature-controlled water circulator 138) flows through cooling lines in the umbilical 233 and the flowing coolant can maintain the surface temperature of the skin while RF energy is applied to an array 260 of electrodes 262 to heat the skin. The ratio of cooling to heating can regulate the skin's surface temperature and can be used to adjust the distribution of heat in the skin so as to enable selection of a target treatment zone (e.g., treatment depth). Generally, less cooling for the same RF power tends to shift the heated zone toward the skin surface (e.g., to heat the dermis for tightening and increasing the thickness of the skin). If cooling is increased, the heated zone will tend to push down to lower tissue layers. As discussed below, short duration pulses of RF energy in combination with cooling will tend to preserve the skin (e.g., prevent bulk tissue heating), while preferentially heating those tissue of lowest impedance (e.g., the septae). In this manner, regulation of the skin's surface temperature can be used to adjust the distribution of thermal energy in the skin.

In various aspects, the disposable applicator 230 can also be flexible as discussed above, and may include a sticky adhesive on the patient facing side of the electrodes such that the flexible pad sticks to the patient surface. In certain aspects, contact with the patient's skin surface can be made through an adhesive gel. Though in some aspects the gel layer can be thermally conductive in order to enable skin cooling, the gel layer need not be electrically conductive, because most of the power coupling can be capacitive due to the high RF frequencies used. As shown in FIG. 2A, for example, a disposable portion of the flexible applicator 230 can include an adhesive gel pad 263 that can be disposed between the electrodes 262 to which the RF signal is applied and the tissue surface. Additionally, a bladder 264 through which heated or cooled water can be flowed can be provided such that the coupling of the disposable portion (i.e., below the broken line) to the umbilical side of the applicator allows for a fluid pathway. As discussed below, the bladder 264 can be flexible such that the applicator 230 generally adopts the contours of the tissue surface when applied (e.g., adhered thereto). Also shown interspersed within the applicator 230 are electrodes 262 each of which can in some aspects by individually-addressed via leads, for example, that can electrically couple to pins of the distribution electronics provided on the umbilical side of the applicator 230.

In certain aspects, these electrodes and the area around them can be ideally cooled, though it will be appreciated that cooling only a fraction of the applicator area can nonetheless be effective for certain applications. Also shown is that there can be different amounts of energy that are applied to the different electrodes depending on the impedance underneath; where there is thicker fat and higher impedance, more energy would be deposited accordingly. The exemplary connector concept shown in FIG. 2A is intended to describe at least one non-limiting disposable concept, where the expensive components used to accurately distribute RF and monitor the electrodes are on the reusable side and a multi-trace array connector and water lines are formed as the disposable portion (including the relatively low cost flexible electrodes).

Electrode and Applicator Geometry and Surface Coverage

Figure 2B:
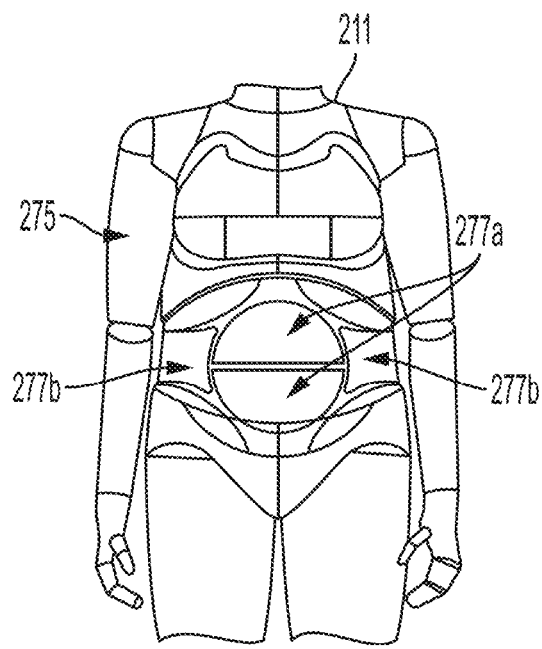
FIGS. 2B-D schematically depict various attachable electrode arrays having different shapes tailored to cover various regions of a patient's skin for targeted RF-based treatment in accordance with various aspects of the present teachings.
Figure 2C:
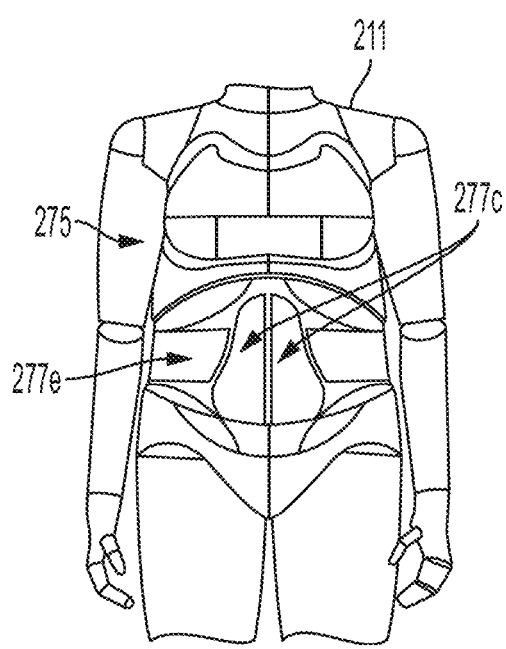
Figure 2D:
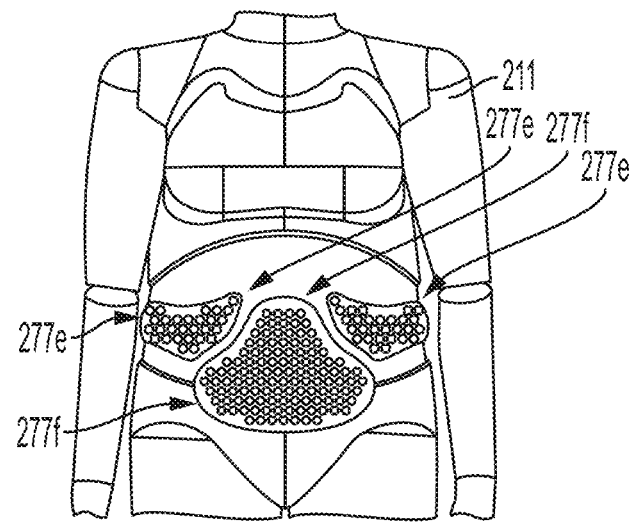

Various geometric shapes can be used for the skin/tissue contacting or skin/tissue facing region of a given electrode array. FIGS. 2B-C show a representation of a patient 211 that is a candidate for one or more RF-based cosmetic, medical, or other tissue surface treatments. The patient may have treatment regions 275 for which an applicator that includes an electrode array has not yet been applied as well as other regions for which various non-standard shaped tissue surface contacting applicator-based electrode arrays have been applied such the half circle applicators 277a and the elongate flared applicators 277b having slightly chamfered or rounded corners. Two half pear shaped applicators 277c can also be used to cover the stomach or other treatment regions of interest for a given patient. Complementary applicators 277b, 277e can also be used to approximate the edges of other specialized non-standard applicators. The complementary applicators can be side-piece applicators that are positioned on either side of larger primary applicator. Various complementary applicator embodiments 277b, 277e are shown. As shown in FIG. 2C, complementary applicators 277e interface closely with the two half pear-shaped applicators 277c to cover the majority of the stomach region of patient 211.

Other non-standard applicator shapes can be used, without limitation, such as a rounded wedged shaped applicator 277f and complementary applicators 277e that include curved boundaries that mimic the curves of the rounded wedge-shaped applicator 277f. In one embodiment, a primary nonstandard electrode is packaged with or otherwise provided with other non-standard complimentary applicators that track one or more edges or boundaries of the primary nonstandard applicator in order to cover or tile the treatment surface efficiently with a minimal amount of uncovered tissue in a given treatment area.

In general, gaps between electrode arrays of applicators can result in irregular treatments and unwanted boundary effects such as ridges or other anomalies that follow from uneven lipolysis or other variations in tissue response when gaps are present between electrode arrays. In one embodiment, the primary applicators are sized to cover a larger surface area relative to the smaller complementary applicators. In one embodiment, the surface area covered by a given primary applicator ranges from about 100 $cm^2$ to about 300 $cm^2$. In one embodiment, the surface area covered by a given primary applicator ranges from about 150 $cm^2$ to about 250 $cm^2$. In one embodiment, the surface area covered by a given complementary applicator or side piece applicator ranges from about 50 $cm^2$ to about 100 $cm^2$. In one embodiment, the surface area covered by a given complementary applicator or side piece applicator ranges from about 70 $cm^2$ to about 120 $cm^2$. The foregoing ranges can also be used to specify the area of a set of standard applicators wherein each applicator in the set has the same shape.

Figure 2G:
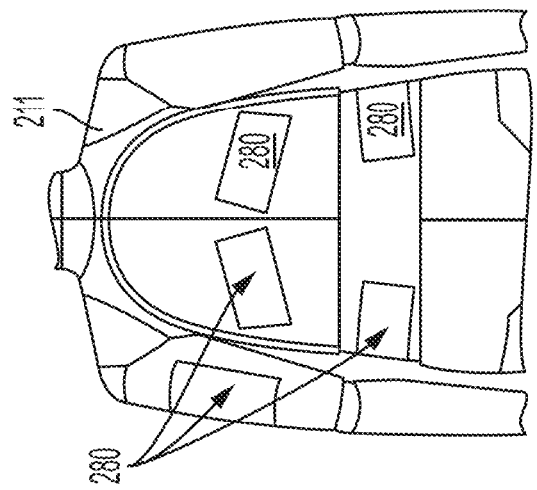
FIGS. 2E-G schematically depict various attachable electrode arrays having the same shape tailored to cover or tile various regions of a patient's skin for targeted RF-based treatment in accordance with various aspects of the present teachings.
Figure 2F:
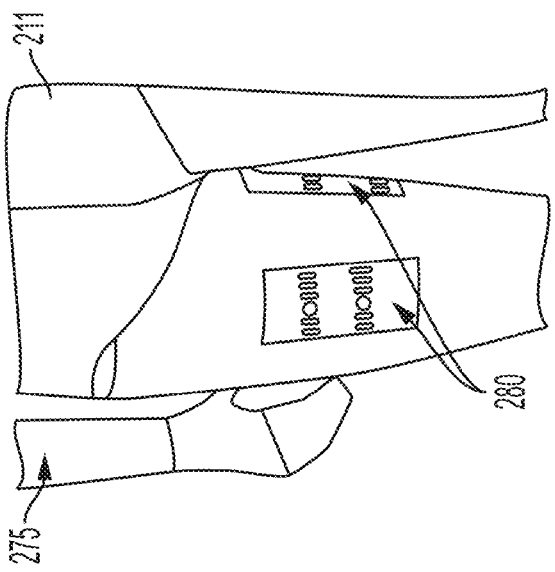
Figure 2E:
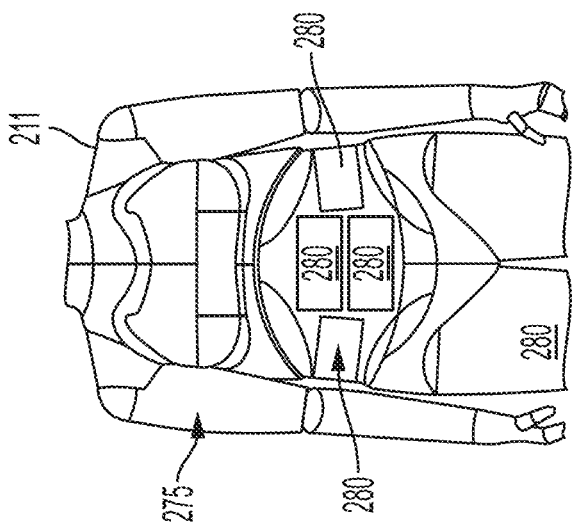

FIGS. 2E-G show a representation of a patient 211 that is a candidate for one or more RF-based cosmetic, medical, or other tissue surface treatments and various standard conformable applicators 280 in position or suitable or placing on an uncovered treatment region 275. In contrast with the non-standard applicators described with regard to FIGS. 2B-D, the use of standard applicators, such as the rectangular applicators 280 shown in FIGS. 2E-2G has the advantage of being able to tile or cover a tissue treatment region without having to use specialized shapes that have a higher manufacturing cost. The use of standard applications allows such applicators to be sold in a kit or other grouping. These applicators typically include a gel pad for adhering the electrode array of the applicator a tissue surface. These applicators effectively fill the space of a tissue surface and reduce the number of gaps. Regular polygons, fractal shapes, pairs of complementary shapes, and other repeating patterns can be used to specify kits of standard applicators that efficiently cover the surface area required for a given treatment regimen.

Figure 2H:
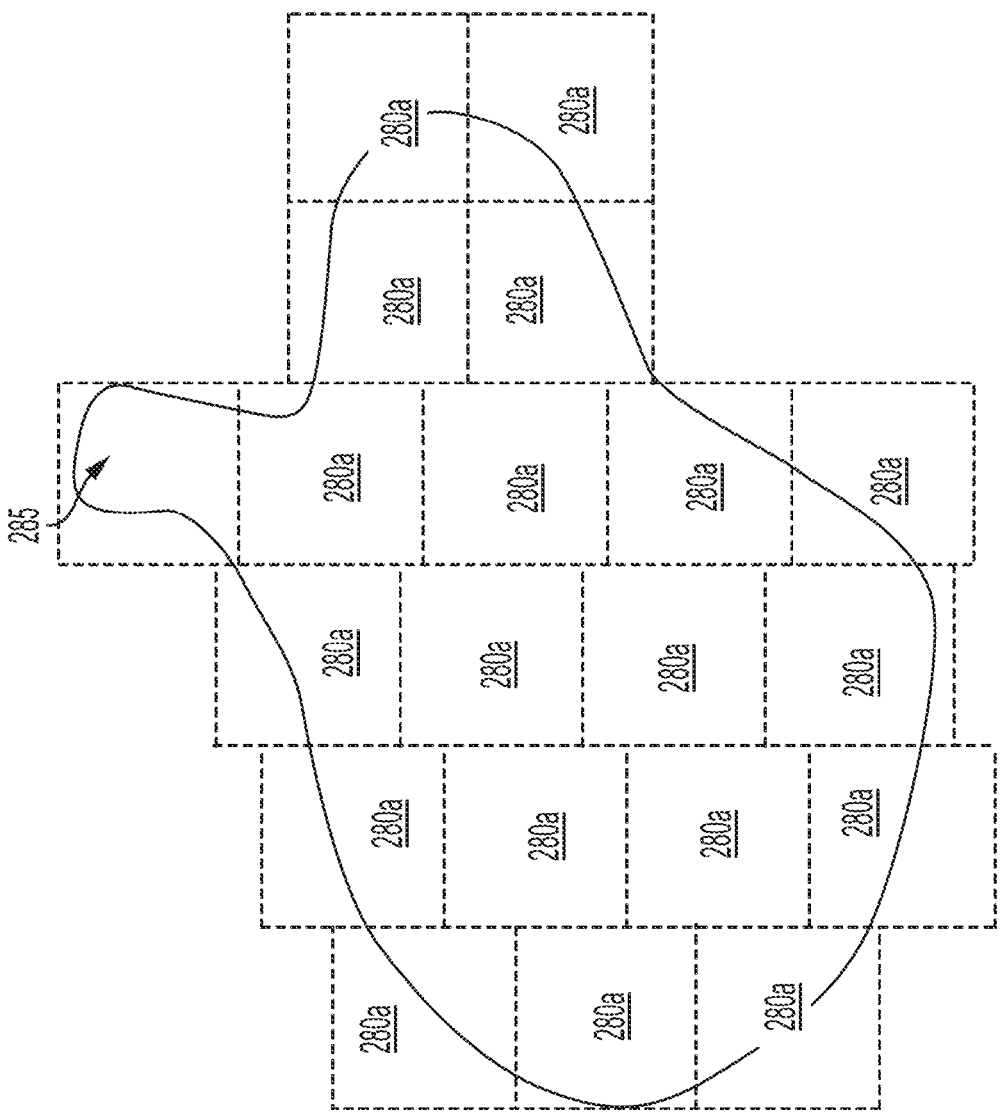
FIG. 2H schematically depicts a target tissue region that has been tiled or covered with multiple tissue attachable electrode arrays having the same shape as part of a kit or set of applicators in accordance with various aspects of the present teachings.

FIG. 2H is a schematic representation of a target region 285 of a tissue surface of a patient. For various tissue types or as otherwise constrained by patient specific parameters and the desired outcome for a particular treatment regimen, an electrode array that may be affixed to the skin surface may often by desirable. These electrodes can be positioned and remain in place during treatment. These conformal electrodes are also the type used in the embodiments described above relative to FIGS. 2B-G. A specific example of a standard applicator shape having electrode array is described and depicted herein with regard to FIG. 2H. The applicators 280a may be attached to the tissue surface using various materials having suitable adhesion properties. Further, the adhesive material also is tailored to release from the skin in response to manual manipulation.

In order to affect an RF-based treatment of the target region 285 various electrodes array geometries can be used that are space filing or otherwise amenable to efficiently tiling a surface such that gaps between applicators are reduced. Various specialized electrode geometries were introduced with regard to FIGS. 2B-D, although such specific geometric designs are suitable for particular procedures and use cases, manufacturing and cost per unit factors can come into play when a given electrode is a one-time-use device.

As shown the target region 285 has an irregular boundary. A custom electrode for this boundary would be expensive to make and would likely have limited applicability to the general population of candidates for RF treatment. Accordingly, in one aspect, the disclosure relates to kits or sets of attachable electrode arrays that include a set of electrode arrays that may be positioned and aligned to efficiently fill a two-dimensional region using K shapes per a given kit. K can range from 1 shape to about 20 shapes. In other embodiments, K can range from about 1 to about 10 shapes. In still other embodiments, K can range from about 1 to about 5 shapes. K can also be a positive integer greater than or equal to 1 and less than 50. The shapes are selected so that they are all the same shape in one embodiment, such as shown by the square electrodes 280a having a dotted border. The square shapes of the electrodes 280a effectively tile the area that defines treatment region 285. Pairs of shapes such hexagons and pentagons and other similar groupings can be used to cover an area while reducing gaps between applicator edges.

Figure 3A:
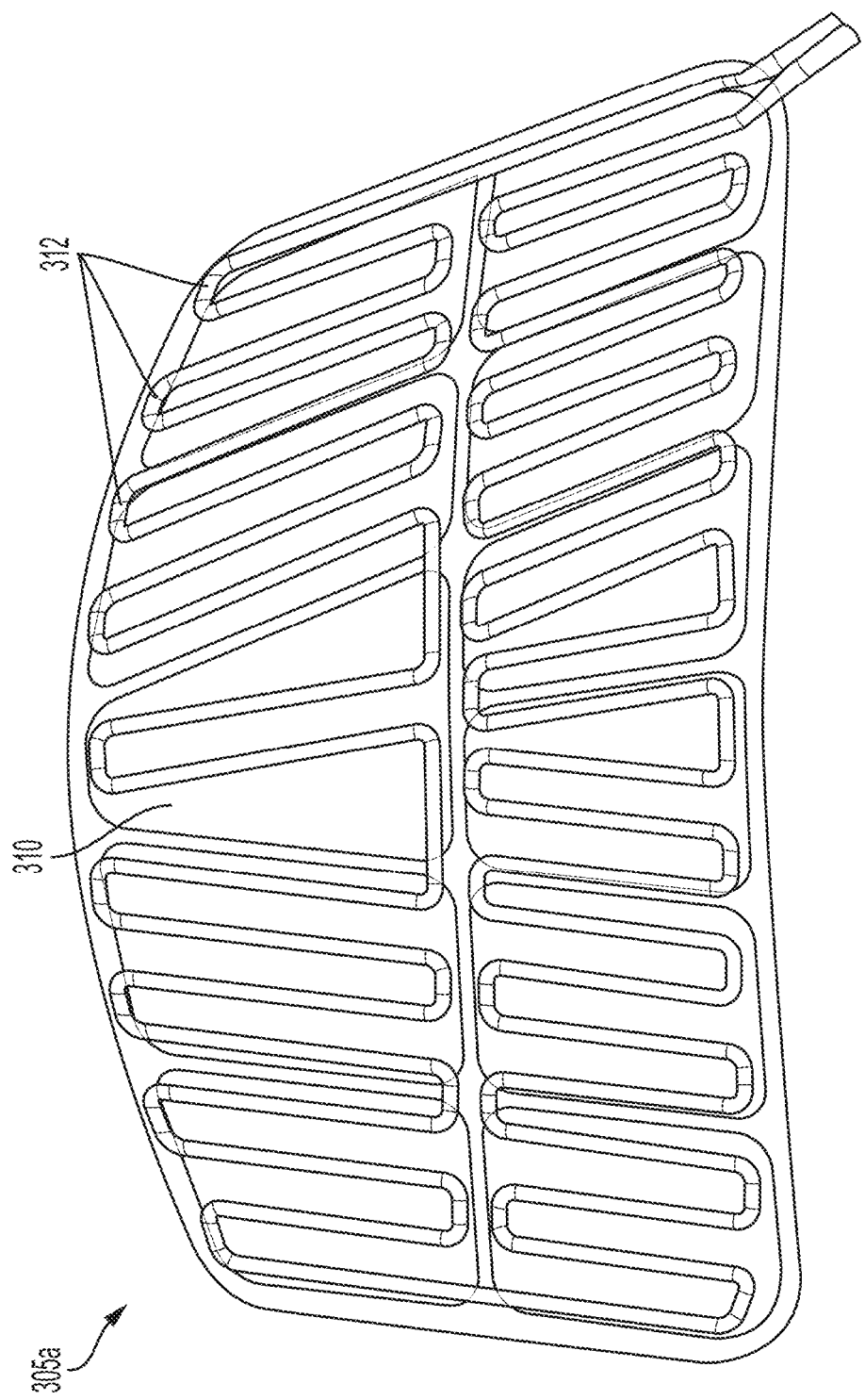
FIG. 3A schematically depicts an exemplary system for cooling a flexible electrode array and/or the patient's skin in accordance with various aspects of the present teachings.

As noted above, a flexible electrode can be supplied with a cooling water flow path which thermally conducts through an electrically insulating layer to the backside (not patient-connected side) of the electrodes such that the cooling water controls the patient's skin surface temperature during the treatment. For example, FIG. 3A depicts an exemplary flexible cooling bladder layer 305a for a flexible applicator that is configured to bend over a compound curve such as the submental area or a flank. A multi-layer adhesive pad design can thus comprise electrodes made of thin plated copper foil or fine plated copper fabric (e.g., die-cut to shape) and embedded in the adhesive laminate. The flexible cooling water manifold/bladder layer 305a depicted in FIG. 3A can include the top layer of the disposable pad, with the manifold using two layers of polymer sheet (e.g., die cut and thermally bonded in a labyrinth pattern at various locations 310) so as to define one or more fluid flow paths 312 therebetween. In various aspects, the electrodes can be cooled directly with the water rather than relying on conduction through the flexible substrate. Parallelograms, squares, rectangles, trapezoids, regular polygons, and other shapes can be used to provide kits that include one or more applicators sized and shape to efficiently cover or tile a tissue surface.

Electrode layers that may be used in association with the flexible cooling bladder layer 305a of FIG. 3A can be any electrode array as otherwise discussed herein including in association with a rigid, semi-rigid, conformable, hybrid, or flexible electrode array as described above, for example, with reference to the system of FIGS. 1A-1F and FIG. 2A and the applicators of FIGS. 3A-F and 3I-3X. Various cooling bladder embodiments can be integrated with different applicator designs. For a given applicator design, the bladder may be sandwiched between one or more layers or other assemblies. Various exemplary alternative cooling bladder embodiments are described and depicted in more detail. In some embodiments, the cooling bladders are part of an applicator that includes a disposable portion and a re-usable portion. In turn, each disposable portion and re-usable portion can include various components and subassemblies.

FIG. 3B shows an applicator 320A that may be implemented as a held in place applicator using a fastener or it can be used with adhesive tabs or strips and be adhered to a given patient as a conformal applicator. Applicator 320A is a hybrid applicator that can be combined with attachment devices or adhesives such as the gel pads disclosed herein. In addition to the mechanism of affixing it relative to a target tissue region, applicator 320A is also a hybrid applicator in the sense that it may include disposable components and re-usable components. When adhesive is not used to attach applicator 320A to a tissue surface, various mechanical attachment devices can be used such as belts, clamps, straps, and other devices.

In one embodiment, a belt 317 is used in conjunction with an applicator coupler 319 that includes a slot or other mechanism to receive the belt. The applicator coupler 319 is shown as including two slots to receive and slidably affix to the belt 317. This is but one possible configuration of the belt 317 and the applicator coupler 319. The belt and coupler can be of various shapes and configurations so long as they facilitate securing the applicator 320A to the patient for a given treatment session. The applicator coupler 319 includes a bottom surface having a deformable cylindrical shell having slits 318 spaced along at sides. The slits facilitate expansion of the cylindrical shell and gripping of one or more raised structures 340d, 340e on applicator such that the belt can be selectively secured to remove from the applicator 320a.

In one embodiment, the applicator 320A includes a plurality of electrodes (not shown) which are individually addressable and form an array disposed on first surface 340a. Surface or support 340a is applied to skin or another tissue targeted for treatment. Although shown as one surface or structure, support 340a can be formed from multiple layers, for example, the layers may include one or more of electrode, electrical insulating material, a thermal conducting layer, electrical leads and contacts, and others.

In one embodiment, the applicator also includes a second support 340b which is disposed on or adjacent to the first support 340a. The second support 340b can include one or more compressible materials such as a foam or other flexible material that conforms to the contours of the patient. The second support can include slots, clips or other attachment mechanisms so that it is separable from other components of the applicator to facilitate the reuse of one or more components of the application. The applicator 320A also includes a third support 340c that includes a rigid or semi-rigid material that forms the upper surface of the applicator 320A. The third support can include one or more attachment mechanisms to interface with a belt or other apparatus to secure the applicator to the tissue surface such that the electrodes are in close proximity thereto or in contact with the tissue surface. The third support 340c and the second support 340b are designed to slide appear or tear along a pre-scored line or region to facilitate reusing the rigid or semi-rigid third support 340c.

The electrode array of the applicator can be formed in or on flexible substrate such as by printing deposition or other manufacturing techniques. Such a flexible substrate can constitute one or more layers of the first support 340a. Each electrode is connected to an electrical trace or lead that extends and connects to one or more other electrodes or an electrical contact. For example, as shown flexible substrate 350a can be part of the first support 340a and extend therefrom as tab or a flexible ribbon. The portion of the flexible substrate 350a extending from the rear facing side of the applicator as shown has a plurality electrical contacts. Each such contact 350b is in electrical communication with one or more electrodes arranged relative skin contacting surface applicator on tissue facing surface of support 340a. These contacts 350b can be electrical traces or printed electrical leads or other electrical leads in various embodiments.

The applicator may also include one or more cooling mechanisms 305 such as a closed-loop bladder having multiple flow channels such as shown in FIG. 3A. As shown in FIG. 3B, two fluid transport ports 351 are shown that support cooling fluid ingress and egress. During a given treatment session, water or another suitable coolant circulates in one port 351 and out the other port 351 after circulating through a series of channels within the applicator in order to draw out heat and thereby cool treatment region receiving RF energy from the electrode array. FIG. 3C shows an alternative view of applicator 320A with the ports and flexible substrate 350b shown in front. The two and three-dimensional shape of each of the first, second and third supports can vary over a virtually unlimited range of shapes.

Although the overall shape of the first support 340a is substantially square or substantially rectangle, the shape of the support and the surfaces thereof can be any suitable regular or irregular shape. For example, in FIG. 3D, an alternative applicator embodiment 320B is shown that includes a first support 340g that is round. Similarly, the second support 340b is also shown as having around or curved shape. In addition, FIGS. 3E and 3F show two additional alternative embodiments of applicators 341a, 341b that are triangular and moon shaped, respectively. The applicator and the tissue contacting surface thereof can include any suitable two-dimensional shape, including regular and irregular shapes. These shapes are shown as exemplars and any suitable shape can be used in various embodiments. These embodiments can include fluid flow paths 351 for cooling bladders and also include electrical connectors 350d, which may be flexible substrates or include wires or other electrical conductors.

FIG. 3G shows a flexible applicator embodiment 325A. An exploded view of the applicator 325A is shown in FIG. 3H. The applicator 325A includes a plurality of temperature sensors 364. Suitable temperature sensors can include thermistors, but may implemented using other devices. The applicator also includes a flexible electrode 362. This electrode 362 can be an array of electrodes. FIGS. 3G and 3H show an embodiment of an electrode with no mapping and no cooling that offers the opportunity to provide substantially uniform heating and flexibility to provide good conformance to the target treatment regions. Although one electrode is shown in FIGS. 3G and 3H, an array of electrodes can be used in other embodiments for a given flexible applicator embodiment 325A and variations thereof. The applicator may include one or more regions of adhesive 370, which is typically disposed around the border of the applicator 325A. The regions 370 can include gel or other materials. An electrical cable 368 has a terminal contact or connector 368a. The electrical cable 368, such as an RF transmission cable attached to the applicator at a connection terminal or electrical contact 369. The connector 368a of cable 368 receives the contact 369 in one embodiment.

As shown in FIG. 3H, the applicator 325A can include one or more coatings 361 to facilitate manufacture or contact with patient. These can include gels, gel, Kapton pads or other materials. In the exploded view, various electrical tracings or leads 365 are shown. These are in electrical communication with the cable 368. The applicator may also include an electrical insulating and thermal conducting layer 367 as shown. Various layers of the applicators and electrode arrays described herein can include one or more an electrical insulating and thermal conducting layer (e.g., Kapton® polyimide or a ceramic, such as $AlO_2$ or the like) located between a cooling device and one or more electrodes or electrical connections. In various embodiments, different dielectric materials can be used to form portions of a given electrode array or otherwise support or be disposed relative to metal layers and conductor traces. Kapton may be used as suitable dielectric material in various embodiments, although other dielectrics suitable for RF applicators for patient directed applications may be used.

For various RF delivery applicator embodiments, suitable dielectric materials can include Kapton and other polyesters. In these embodiments, dielectric materials are selected to have some of the following characteristics: dielectric constant in the range of about 3 to about 4, which provides a good balance of capacitance vs. dielectric thickness; flexibility; ability to conform to patient tissue geometry such as skin surface geometry and others; low thermal energy losses/dissipation factor; tissue safe, skin same, biocompatible, cost effective, high temperature tolerant to allow soldering without material destruction; and durable and tough.

Figure 3J:
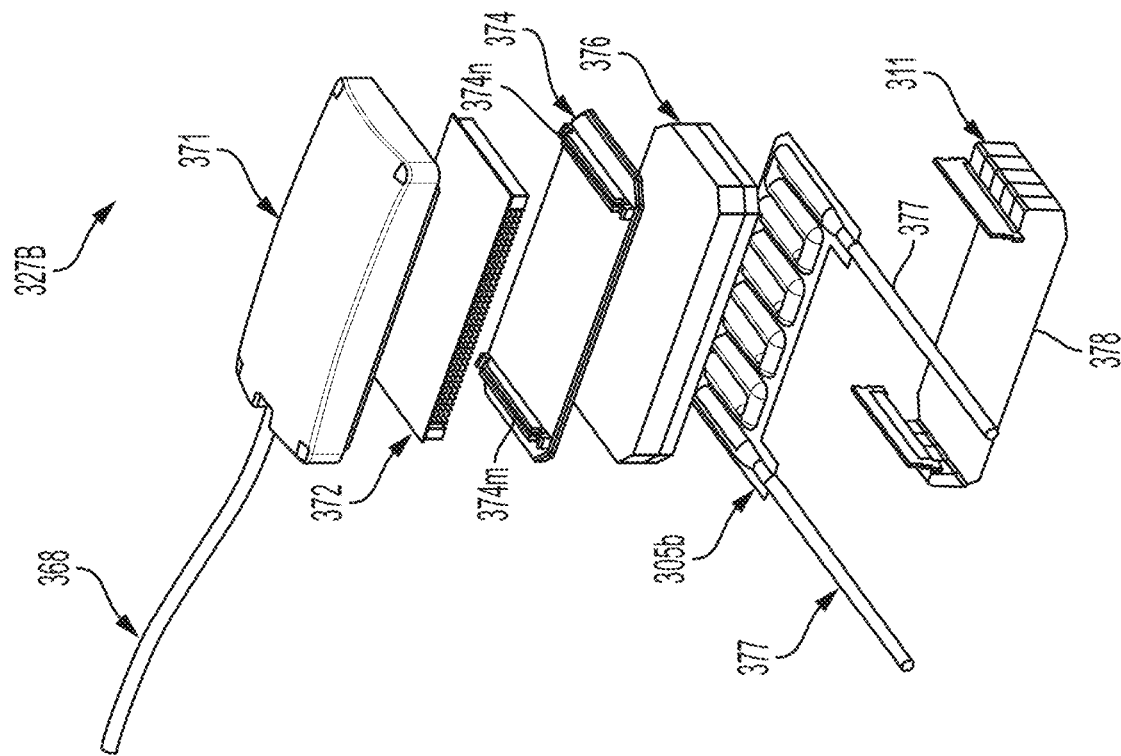
FIGS. 3I-J schematically depict various exemplary separable applicator embodiments that include a disposable component and a reusable component in accordance with various aspects of the present teachings.
Figure 3I:
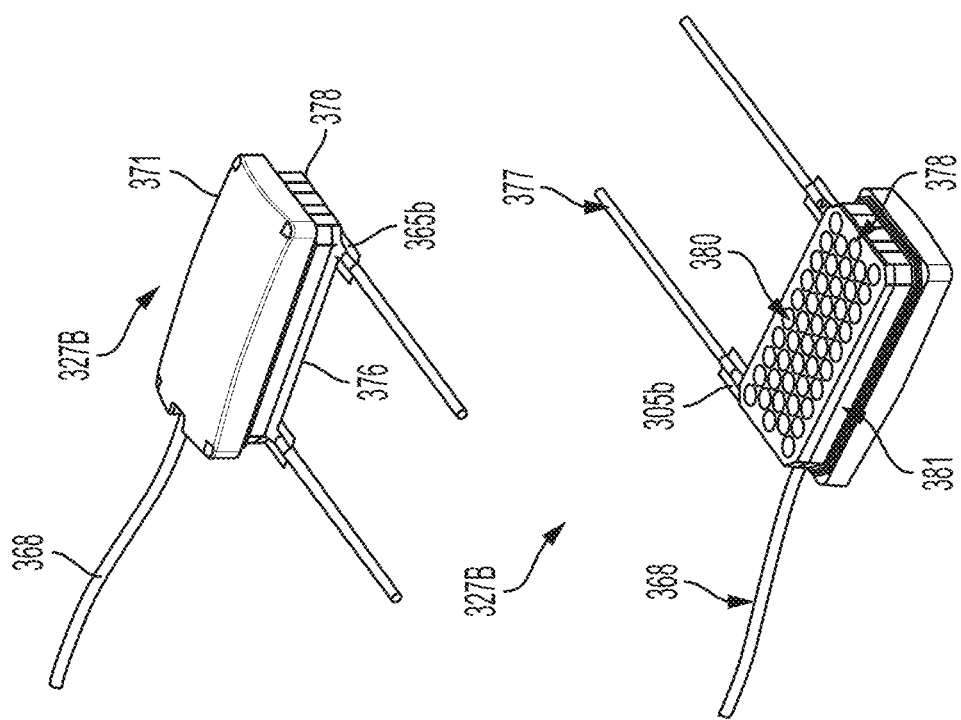

FIG. 3I shows a first view of another applicator embodiment 327B with the tissue facing surface facing downwards and a second view with the tissue facing surface facing upwards such that the electrodes 380 are visible. FIG. 3J shows an exploded view of the applicator 327B of FIG. 3I. The applicator 327B is a type of hybrid applicator that includes a disposable assembly and a reusable assembly. A rigid or semi-rigid housing 371 protects some of the components nested there within such as a print circuit board stack 372. A rigid substrate 374, which is typically a hard polymer such as a plastic, sandwiches the PCB stack 372 so that the stack is secured in the housing. The rigid substrate 374 may include one or more elongate members 374m, 374n or fins extending therefrom. These members can be received by slits or grooves 374r, 374s in the PCB stack 372 or in the housing 371. These three components, the housing, the rigid substrate, and the PCB stack can be treated as a set of reusable elements in one embodiment.

A compressible or conformal substrate 376 such as a layer of foam may also be present. As shown in FIGS. 3J and 3N, a cooling bladder 305b is also present in some embodiments and used to cool tissue when exposed to RF treatments. The cooling bladder 305b connects to fluid transport lines 377. A flexible electrode array 378 is the bottom element shown in FIG. 3J. An array of 48 electrodes that are part of the flexible array 378 are shown in FIG. 3I. Flexible or rigid electrical traces or leads 311 can bend around and connect to electrode array 378 as shown in FIG. 3J. The applicator 327B includes a cable 368 suitable for transmitting RF signals and receiving impedance measurements that extends from housing 371. In part, the disclosure relates to flexible cooling bladders that include quick release connections such as connections 382a shown in FIG. 3N. These arrays facilitate cooling and with a quick release connector, it is possible to start a procedure and end procedure quickly. Various bladder designs also benefit from being disposable components in one embodiment.

Figure 3K:
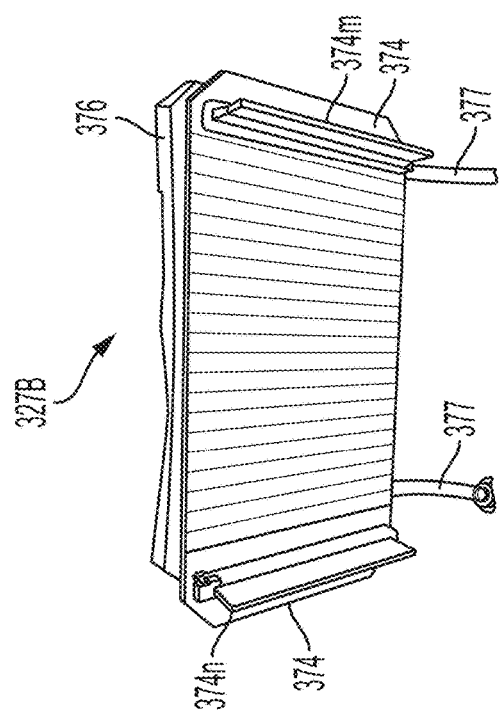
FIGS. 3K-3Q depict various images of exemplary separable applicator embodiments in accordance with various aspects of the present teachings.
Figure 3L:
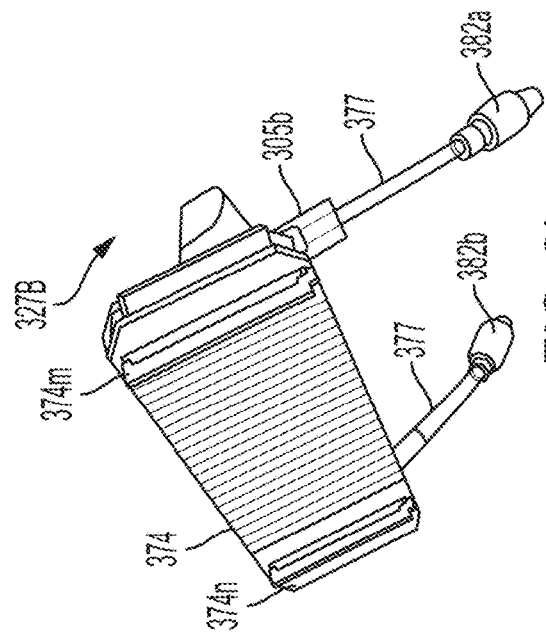
Figure 3M:
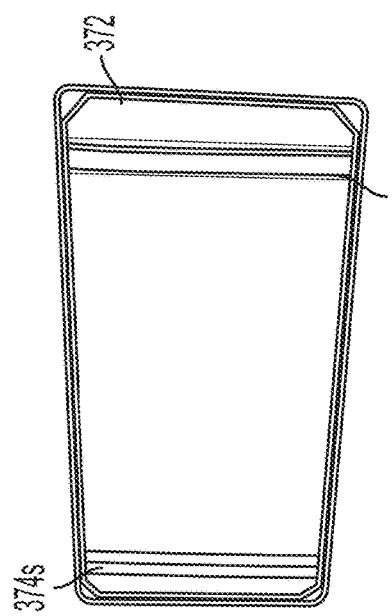
Figure 3N:
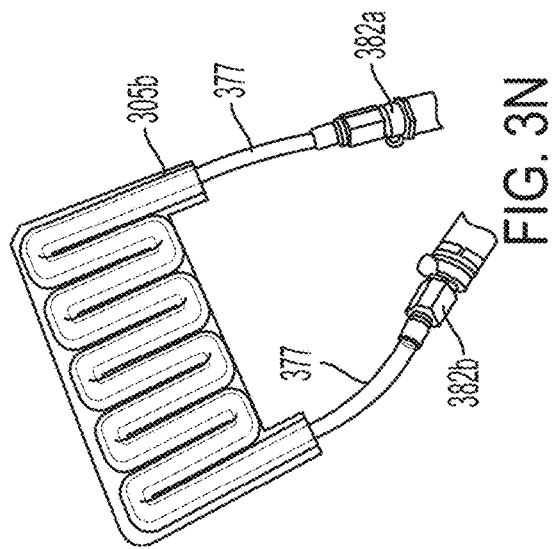

FIGS. 3K-S show images of alternative embodiments of the different components of applicator 327B shown in FIGS. 3I and 3J. FIG. 3K shows a bottom view of the PCB stack 374 combined with the foam layer 376 and the electrode array and the cooling bladder 305b. FIG. 3L shows a perspective view with the rigid substrate 374 shown as well as the inputs and outputs 377 for the cooling bladder. Connectors to the fluid inputs and outputs 382a, 382b are also shown in FIG. 3L and FIG. 3N. The groove or slits 374s, 374r of the PCT stack 372 are shown in FIG. 3M, the slits or grooves receive members 374 n, m. These slits or groove can also be formed in housing 371 or not used in some embodiments.

Figure 3O:
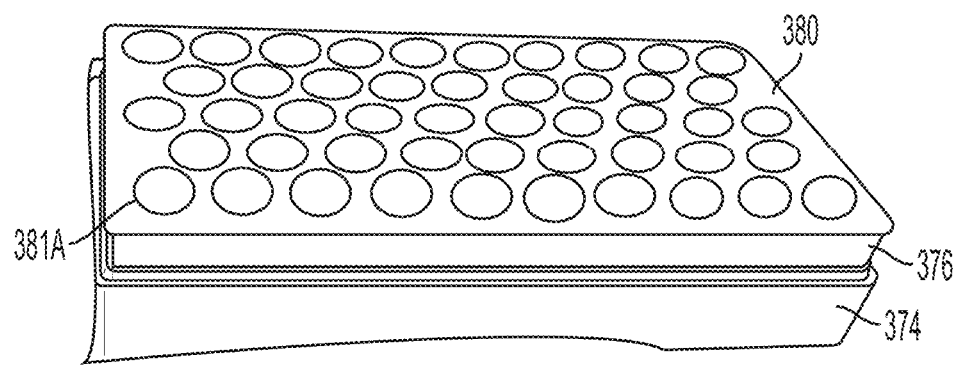
Figure 3P:
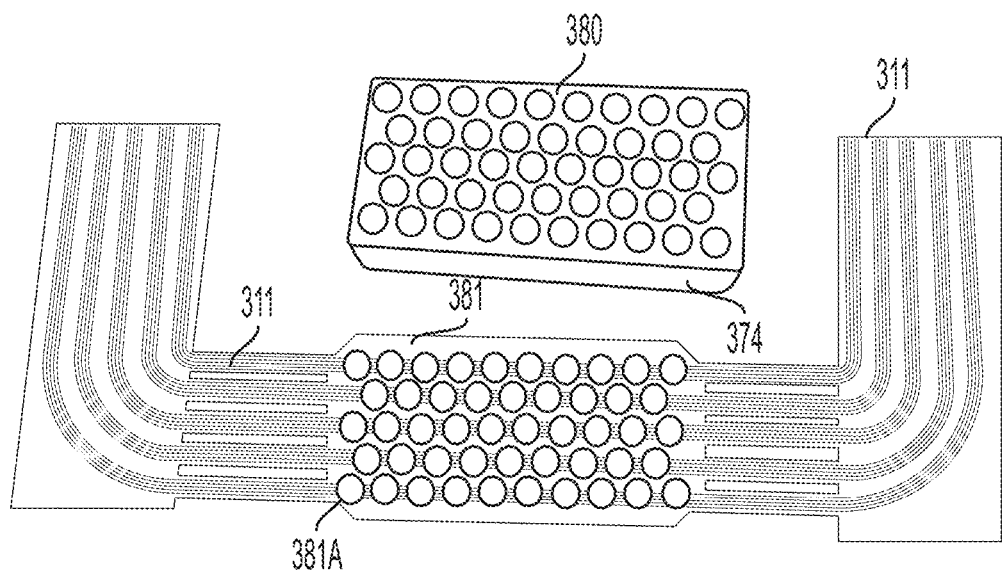
Figure 3Q:
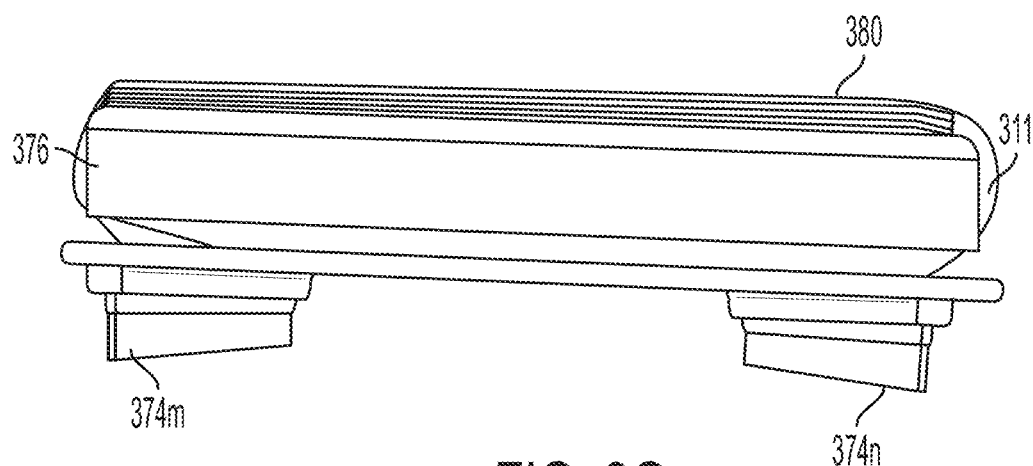

FIG. 3O shows a top perspective view of the electrode array 380 sandwiching foam layer 376 and the rigid substrate 374 and an exemplary electrode 381A. FIG. 3P shows the electrode array 380 and rigid substrate of FIG. 3O relative to the flexible substrate 381 that forms the electrode array 380. The flexible substrate includes various individual electrodes, for example electrode 381A, that connect to one or more electrical leads or tracings 311. Various electrical contacts or traces formed along the flexible substrate 381 are shown. These traces are also shown on either side of the foam layer 376 in FIG. 3Q. The arrangement of a flexible substrate 380 with electrode 381A as part of the array and the comfortable/compressible layer 376 combined with a substrate 374 offers the benefits of a conformal applicator while facilitating disposing of the flexible substrate array and conformable/compressible layer while saving the expensive electronic components for re-use.

FIGS. 3R-3T and 3U show alternative applicator embodiments 333A and 333B that incorporate a rigid electrode array 395a, 395b with individual electrodes 394. An outer housing 388a, 388b is used to protect various electronic components such as those on PCB stack 390. A cooling bladder 305c is also incorporated with cooling inlets and outlets 377. These inlets and outlets extend from housing at one or more channels 393. An electrical cable 368 provides signals and power to the array and is in electrical communication with various control nodes as described herein. These rigid applicators are particularly suitable for scanning patients and generating before and after impedance scans and other data derived therefrom. As discussed herein, various types of applicators can be to perform a RF-based tissue treatment. In addition, with regard to each applicator various electrode sizes can be used in a given single electrode or electrode array embodiment.

Electrode Size and Pitch

Electrode size and pitch can be manipulated to achieve the desired RF deposition uniformity, while maintaining flexibility and reducing electrical complexity. A rigid portion of electrode area of approximately 1 $cm^2$ can allow for a sufficient area to safely couple RF power to the skin (e.g., without high fluxes) and still allow for flexibility between adjacent electrodes so as to contour to most anatomical structures. If the electrode itself is flexible, such as a woven copper cloth, size limitations of the electrode may be governed by edge effects in which high frequencies are concentrated to the periphery of the electrodes, thereby inducing a non-uniform deposition of RF and consequently non-uniform heating. By balancing edge effects with the thermal properties of the tissue, the electrode area can be optimized resulting in substantially uniform heating of the skin and underlying tissue. The pitch or distance between adjacent electrodes in an array can also be optimized to heat the targeted area over the treatment time. Suitable pitch between adjacent electrodes may range from about 0.1 mm to about 2 cm, for example, from about 1 mm to about 1 cm. Suitable electrode diameter size may range from about 3 mm to about 20 mm, or about 10 mm in the case of a resistively-coupled electrode. Suitable electrode diameter size in the case of a capacitively-coupled electrode may range from about 3 mm to about 200 mm, or about 10 mm.

For the case of fractionally ablative RF treatment discussed below, for example, in an array of electrodes the size and pitch can be relatively small, ranging from about 0.1 mm to about 10 mm, or from about 0.5 mm to about 5 mm, with each electrode in close proximity to one another to cover substantially all of the applicator area. Because, for the case of fractionally ablative RF treatment, the pulse is so short (e.g., less than about 100 ms, or from about 5 ms to about 35 ms) that there is no time for thermal diffusion between the particular tissue addressed by each electrode and the short pulses at relatively high energies can ablate the tissue.

In the case of tissue heating and laxity applications, exposures may be long (e.g., 10-30 minutes) with the thermal properties of the skin/fat dictating the heat distribution and allowing for larger electrodes and greater pitches to accomplish bulk heating to tissue.

In the case of septae disruption, short duration, high power RF pulses are delivered to targeted tissue, and one can use a single electrode or an array of electrodes, and the electrode can be applied to the tissue and used hands free as discussed herein or, due to the short pulse associated with septae disruption, the single electrode or the array of electrodes can be constructed as a handpiece that is used in a stamping mode.

Electrode Clusters

In some aspects, electrode clusters (i.e., a node comprising a plurality of electrodes of an array sharing common electrical control) may be utilized to reduce electrical complexity while still capitalizing on the use of smaller electrodes that help with uniformity, flexibility, and reducing edge effects. In the simplest case, instead of driving each individual electrode of an array of electrodes, clusters of two, three, or more electrodes could be subject to similar control (e.g., identical RF signals) since the resolution of the thermal effect may not require more specific control, though it may nonetheless be preferable to maintain a high number of electrodes. Electrode clusters may be used, for example, to treat connective tissues that interpenetrate fat layers (e.g., fibrous septae present in cellulite) with short duration, high power RF pulses to one electrode cluster followed by short duration high power RF pulses to another electrode cluster in the electrode array, and so on, until all or substantially all electrode clusters in the array have been addressed. In one embodiment, all or substantially all of the RF energy available to the entire electrode array is gated to a single electrode cluster so that, due to the relatively low impedance of the septae tissue, the septae tissue is preferentially heated by the relatively short pulse. Alternatively, a greater power supply can be employed that enables the desired and/or required high magnitude energies per pulse (e.g., from about 10 to about 1000 $J/cm^2$) to be gated to an individual single electrode cluster to preferentially target septae tissue. As discussed further below, monitoring and/or knowing the impedance of each electrode (or most of the electrodes or substantially all of the electrodes) in real time can enable determination of contact integrity of each electrode (or most of the electrodes or substantially all of the electrodes) to the tissue and thereby enables avoidance of unintentional over treatment of a smaller area than the targeted area (e.g., burns can be avoided).

Patient Impedance Mapping

Various detection and/or feedback mechanisms are contemplated to help provide improved RF treatments in accordance with various aspects of the present teachings. RF treatment uniformity can be assisted by utilizing tissue impedance mapping alone or in combination with surface perimeter temperature feedback, as discussed below. In some aspects, a patient's tissue impedance may be "mapped" by detecting the impedance of the tissue region to be treated (or undergoing treatment) such that impedance differences can be compensated for, by way of example, by controlling or modifying the distribution of RF power (or total treatment time, or duty cycle) delivered through each individual electrode in an electrode array based upon the information gathered via impedance mapping and/or surface perimeter temperature feedback. Such impedance mapping can adjust for and/or prevent accumulation of heat in an untargeted region (e.g., outside of the applicator perimeter). Such impedance mapping can adjust for and/or prevent non-uniformity of the treatment zone whether due to anatomical variation or tissue layer thickness variations, and/or unintended non-uniformity of RF deposition.

In certain aspects, electrical impedance mapping of individual electrodes in the electrode array can occur by polling electrodes of the electrode array placed against the patient's tissue surface to determine an individual impedance of the tissue between each electrode pair of the pair of applicators, and thus, the corresponding tissue impedance beneath each electrode. By way of example, a mapping step can be performed at very low RF power (e.g., sub-treatment powers that do not substantially raise the temperature of the tissue) with two exemplary electrode arrays being disposed in contact with the tissue surface (or with different tissue surfaces). Impedance can then be detected for every combination of one electrode from one array and one electrode from the other array, for example, by selectively activating individual electrodes. After tissue impedance for one combination is determined, the electrodes can be deactivated and other electrodes "polled" to determine impedance along this particular path, and so on, until each of the individual electrodes in the two arrays (e.g., in the left and right arrays) are addressed.

Optionally, this process can be repeated so that each of the individual electrodes in only one array are addressed. In this manner, the tissue impedance will be measured in the tissue lying below each electrode in the array. It will be appreciated that this process can be repeated at various RF frequencies and can be performed just before application of RF treatment power or at various times during treatment. For example, this initial step of impedance mapping can be performed in less than about a minute (e.g., about 30 seconds). Based on these measurements, it will be appreciated in light of the present teachings that the relative thickness of the subcutaneous fat layer can be calculated due to differences in the impedance between fat and muscle, for example. A map of the patient's impedance under each discrete electrode provides a corresponding map of tissue impedance throughout the treatment zone.

In addition to having such a mapping on a per electrode basis, one or more applicators can be scanned across a patient's tissue to generate a baseline map or report which can include various representations that show impedance values or values derived or calculated based on such values including fat layer thickness, muscle regions, variations in tissue type, and other tissue specific parameters such a tissue type, hydration level, and others. An example applicator-based scan of multiple regions of a patient are shown with regard to FIG. 2A and discussed in more detail herein. In addition, the treatment of mucosal tissue, such as vaginal tissue can also be scanned using a moving array or a fixed array that is multiplexed. An array can be selectively addressed such that a sequence of electrodes are energized to cover different tissue regions.

As discussed above in association with FIGS. 1A-1F, distribution electronics of the applicator(s) 130*a* can thus be utilized to provide the same or different RF signals to the individual electrodes 162*a* of the electrode array 160*a* so as to provide improved control of the treatment procedure. In some related aspects, the distribution electronics can also be controlled such that each of the electrodes in the electrode array can be independently switched (e.g., to gate RF power to individual electrodes), with each individual channel providing current, voltage, and/or phase angle feedback information useful for calculating power and impedance of individual electrodes. To map the tissue, for example, the independently-switched contact electrodes in the electrode array may be switched to gate RF power sequentially first to one of the electrodes in the array and next to another electrode in the array until all or substantially all of the electrodes in the array are addressed, during an exemplary impedance mapping step as described below with reference to FIG. 4A. It will be noted that though FIG. 4A depicts an impedance mapping step between two electrodes in two different applicators, a person skilled in the art will appreciate that such a description is equally applicable to any number of applicators and electrode arrays.

Figure 4A:
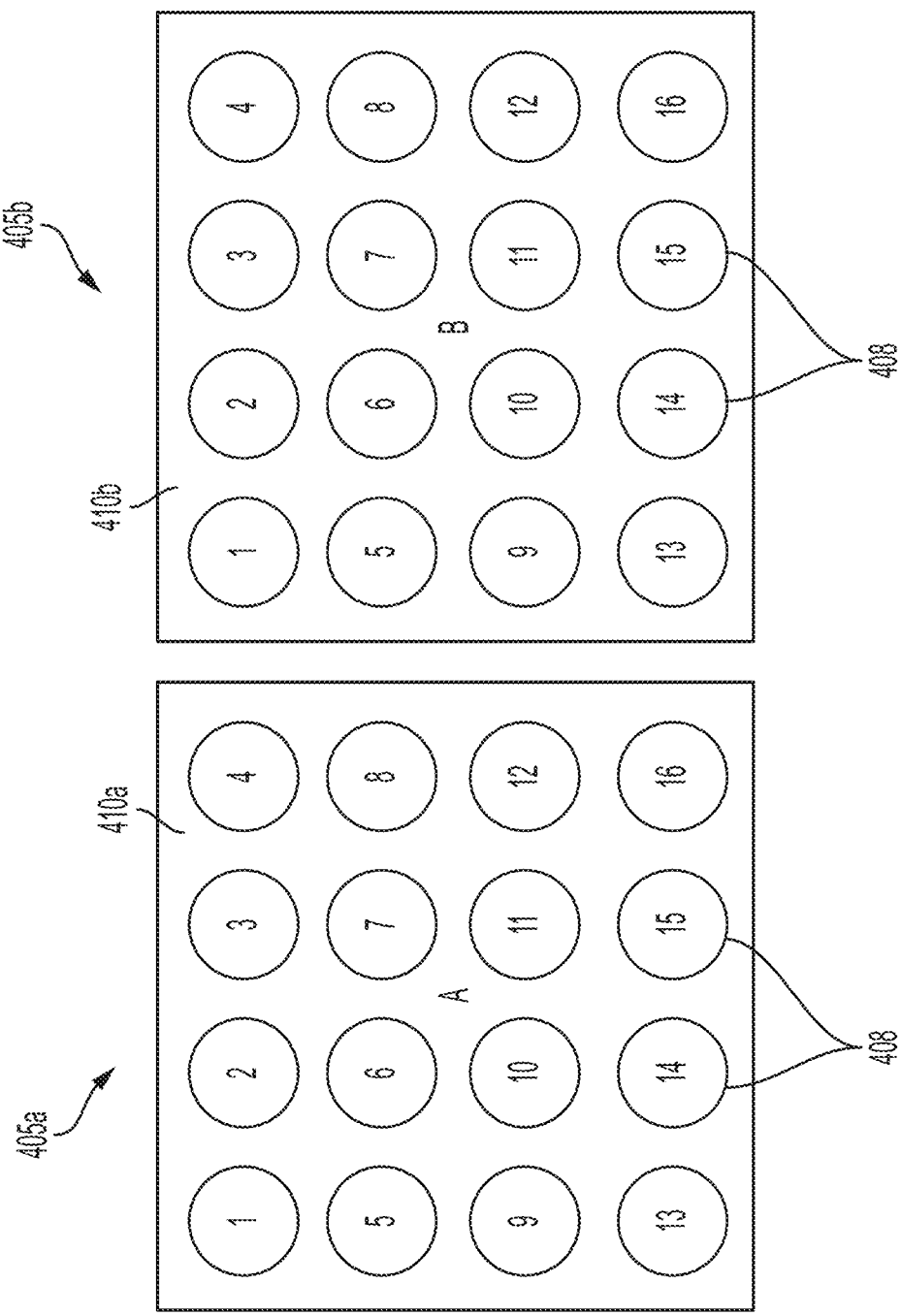
FIG. 4A depicts an exemplary array of electrodes that can be individually addressed according to an exemplary method for monitoring and/or controlling the distribution of RF energy provided by the electrode arrays in accordance with various aspects of the present teachings.

As shown schematically in FIG. 4A, two applicators 405*a*, 405*b*, each of which comprises an array 410*a*, 410*b* of 16 electrodes 408, can be disposed in contact with the tissue surface. With these applicators coupled to the tissue surface at the intended treatment locations, an impedance mapping step can be performed before applying treatment RF energy (i.e., energy of a sufficient power to effectuate a treatment in the target tissue) in order to determine the impedance (tissue resistance to RF energy) for every combination of one electrode 408 from applicator 405*a* and one electrode 408 from applicator 405*b*. For example, the electrodes 408 of the two applicators can be selectively activated so as to run very low RF current (e.g., sub-treatment energy) from A1 to B1, A1 to B2, A1 to B3, and so on, until a 16×16 matrix of resistance values has been generated such that the tissue resistance is known between every electrode in applicator 405*a* to every electrode in applicator 405*b*. When applicators 405*a*, 405*b* are disposed on tissue adjacent to one another as depicted (e.g., as opposed to distant from one another or on opposed tissue surfaces), it is generally observed that the lowest impedance would be exhibited between adjacent edges of applicators 405*a*, 405*b*. That is, the resistance measured between A4 and B1, A8 and B5, A12 and A9, and A16 and A13 would tend to be among the lowest impedance measured (depending on the tissue type, as discussed otherwise herein). Such an observation would indicate that the highest RF current and highest heating would also occur along these low-impedance pathways during treatment.

The impedance topography revealed by this method can thereby identify variations in patient tissues' electrical impedance and can therefore be used to re-apportion or adjust the RF power and/or treatment time delivered to each discrete electrode so as to improve uniformity of the deposition of heat (temperature rise) for more effective adipose destruction, dermal tightening, collagen heating, or septae targeting, as well as to center the treated zone beneath the applicator (e.g., electrode array) in order to achieve more uniform tissue temperatures. For example, individual electrodes which detect lower impedance relative to the mean impedance of all electrodes will tend to deposit more RF energy (and result in a relatively larger temperature rise) than electrodes which encounter a higher impedance. Thus, to homogenize the treated zone for uniformity and centering within the treated zone, the impedance topography map can be used to select individual electrodes at lower impedance locations for a reduction in RF power and/or to select individual electrodes at higher impedance locations for an increase in RF power. The increase or reduction in RF power delivered via individual electrodes can be proportional to the variation in electrode impedance with respect to the mean or average electrode power. Thus, in certain aspects, the distribution electronics of the applicator(s) can be utilized to adjust RF signal to the individual electrodes of the electrode array to account for the differences in impedance. For example, independently-switched contact electrodes 408 in the arrays 410*a*, 410*b* can be switched (e.g., under the influence of controller 137 of FIGS. 1A-1F) to modify the RF power provided to each of the individual electrodes 408 to assist in the uniform deposition of thermal energy within the treatment region.

With reference again to FIG. 4A, the data collected during the impedance mapping step can be used to adjust the electrode activation pattern (e.g., RF power, pulse width, total treatment time, duty cycle) to help maintain uniform heating under the applicators 410*a*, 410*b*. For example, one possible method to mitigate the edge effects between the electrodes of the adjacent edges is to alternate between activating electrodes A{1, 2, 5, 6, 9, 10, 13, 14} and B{1, 2, 5, 6, 9, 10, 13, 14} for a first duration (while the other electrodes are inactive), and activating electrodes A{3, 4, 7, 8, 11, 12, 15, 16} and B{3, 4, 7, 8, 11, 12, 15, 16} during a second duration so as to promote more even spacing and more uniform heating. Alternatively, electrodes A{4, 8, 12, 16} and/or B{1, 5, 9, 13} could have their RF power substantially reduced and/or permanently disabled, for example, for the duration of the treatment. The second-to-adjacent rows of electrodes between the applicators, namely electrodes A{3, 7, 11, 15} and B{2, 6, 10, 14} would still have a slight proclivity to send current laterally to each other, and so would heat the area under the electrodes which have been turned off. Such a pattern (e.g., generated by distribution electronics under the effect of a controller) would allow for more uniform heating under two adjacent electrodes operating in bipolar mode, for example.

Further, during a treatment, the RF power applied to each electrode 408 can also be tracked and controlled, with ongoing impedance monitoring (e.g., sampling) being employed to track changes in tissue impedance and with power to each array location being adjusted accordingly based on such feedback and/or to determine an endpoint in treatment. For example, during a treatment, the distribution electronics can be controlled such that each of the electrodes 408 in the electrode arrays 410*a*, 410*b* can occasionally be sampled (e.g., by gating RF power to individual electrodes), with each individual "channel" providing current, voltage, and/or phase angle feedback information useful for calculating power and impedance of individual electrodes. That is, this impedance mapping can also be done real time during the treatment (e.g., at intervals during the treatment). Ideally, this control feedback mechanism can inform a power-homogenizing algorithm to monitor and/or adjust treatment conditions. Such impedance mapping can be especially useful during the early portion of a treatment, for example, before temperature changes have accumulated on the tissue surface adjacent to the target treatment zone that can be detected by the temperature detectors as discussed in detail below. Later in the treatment when surface temperature rises can be observed, the impedance mapping feedback can optionally be summed with the feedback provided by the detection of the tissue surface temperature (e.g., around the perimeter of the applicator) so as to provide additional feedback information. Summing the two feedback mechanisms together (e.g., take 50% of the RF correction factor from the impedance topography map and 50% from RF correction factor indicated by surface temperature observation) is one non-limiting exemplary approach. Another feedback approach would be to shift toward use of the surface temperature feedback method after detectable differences in surface temperature manifest (e.g., a ½ to 1 degree C. difference or more), by way of non-limiting example. It is also possible in accordance with various aspects of the present teachings to rely entirely on impedance mapping to re-apportion RF power applied through each electrode to achieve optimum treatment placement, optimum homogeneity, the desired uniformity, and to acquire temperature information about the target tissue (e.g., the tissue beneath the surface of the skin or the mucosa).

Figure 4B:
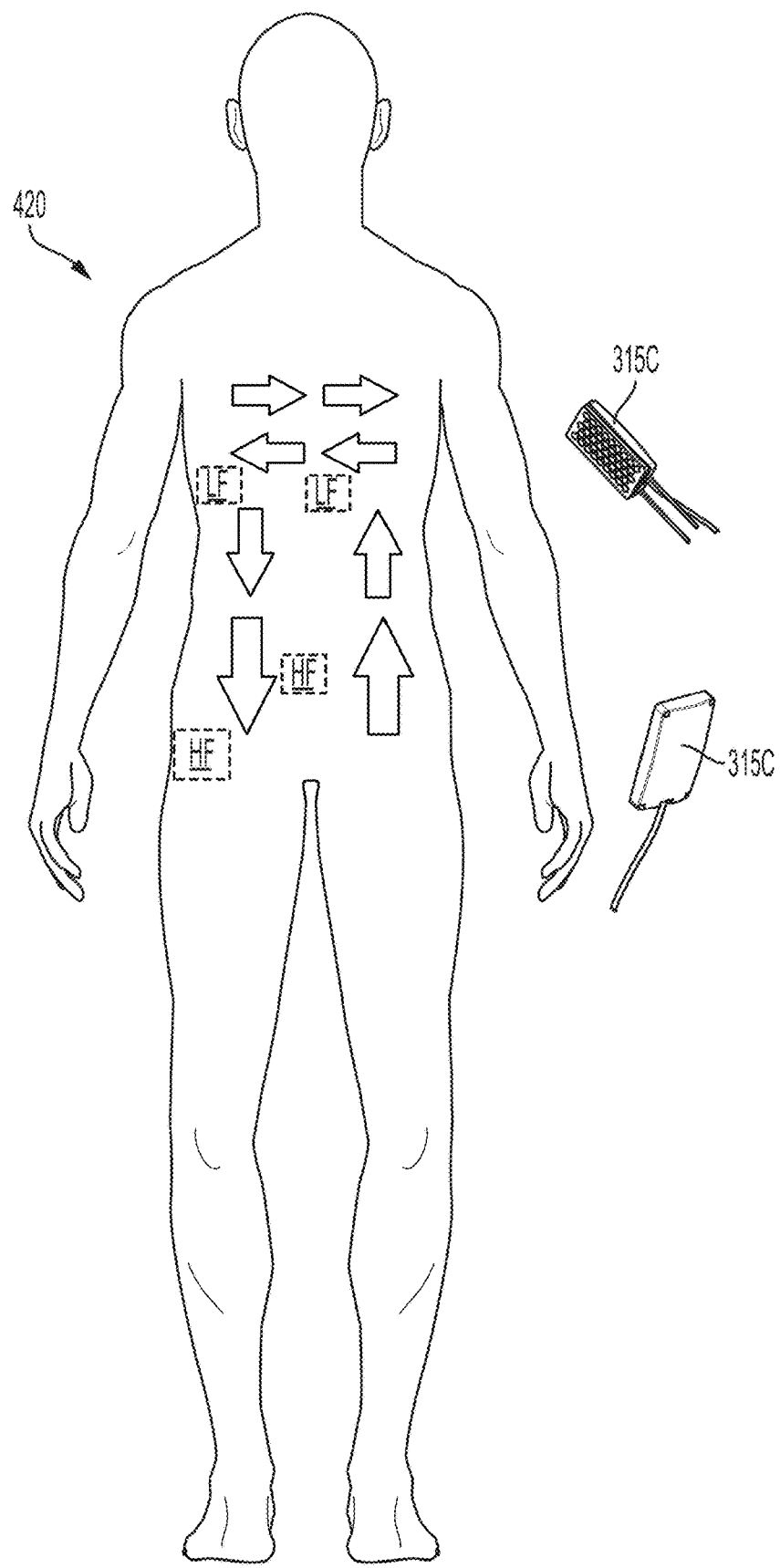
FIG. 4B schematically depicts an exemplary scan of a patient using one or more RF-based applicators to generate a tissue assessment or other outputs of interest in accordance with various aspects of the present teachings.

FIG. 4B shows a patient 420 that is a candidate for one or more RF-based treatments. One or more of the applicators described herein or other RF applicators or delivery devices can be used to scan one or more tissue surfaces of a patient to generate an impedance mapping. In FIG. 4B, the skin of portions of the patient's skin and torso are scanned. The scan can be performed by moving an applicator, such as applicator embodiment 315C, along the surface of the patient 420 according to various scan patterns such as shown by the exemplary directional arrows shown. Any suitable scan pattern can be used.

As an alternative to moving one or more applicators over a tissue surface, a set of applicators or electrode arrays can be disposed on the patient and scanned by multiplexing/ selectively addressing the different electrodes or by collecting impedance measurements with regard to the tissue at one or more instances in time.

In general, scanning a patient before treatment and then after treatment over time has various beneficial outcomes for users of the RF-based treatment systems herein. The temporal measurements can be taken over the course of one treatment sessions or multiple treatments sessions. In some embodiments, one or more impedance mappings are obtained with regard to the candidate tissues areas for treatment before a treatment session begins. The pattern of left and right oriented scans and up and down scans shown by the arrows in FIG. 4B are examples of the types of scanning that can be performed to identify impedance values associated with different locations on the patient and fat distribution relative thereto. The impedance values can be correlated with areas of more fat/high fat levels HF as present relative to same threshold and less fat LF is present relative to the same or different threshold. The boundaries of the higher fat levels HF and less or lower fat levels LF are shown by dotted lines. Other indicia and representations can be shown on a representative tissue scan. In light of the results of the scanning shown, it is clear that more treatments on the lower torso and upper thighs is likely warranted given the increased fat levels HF.

In this way, a "before" impedance map can be generated and stored for subsequent comparison to additional impedance mappings over time. Such a "before" or pre-treatment impedance mapping and an "after" treatment impedance mapping can be used to provide evidence of treatment efficacy, increase and sustain patient motivation when assessing benefits of ongoing treatment, and to also provide diagnostic information with regard to treatment parameters such as fat levels and a reduction in fat over time.

Figure 4C:
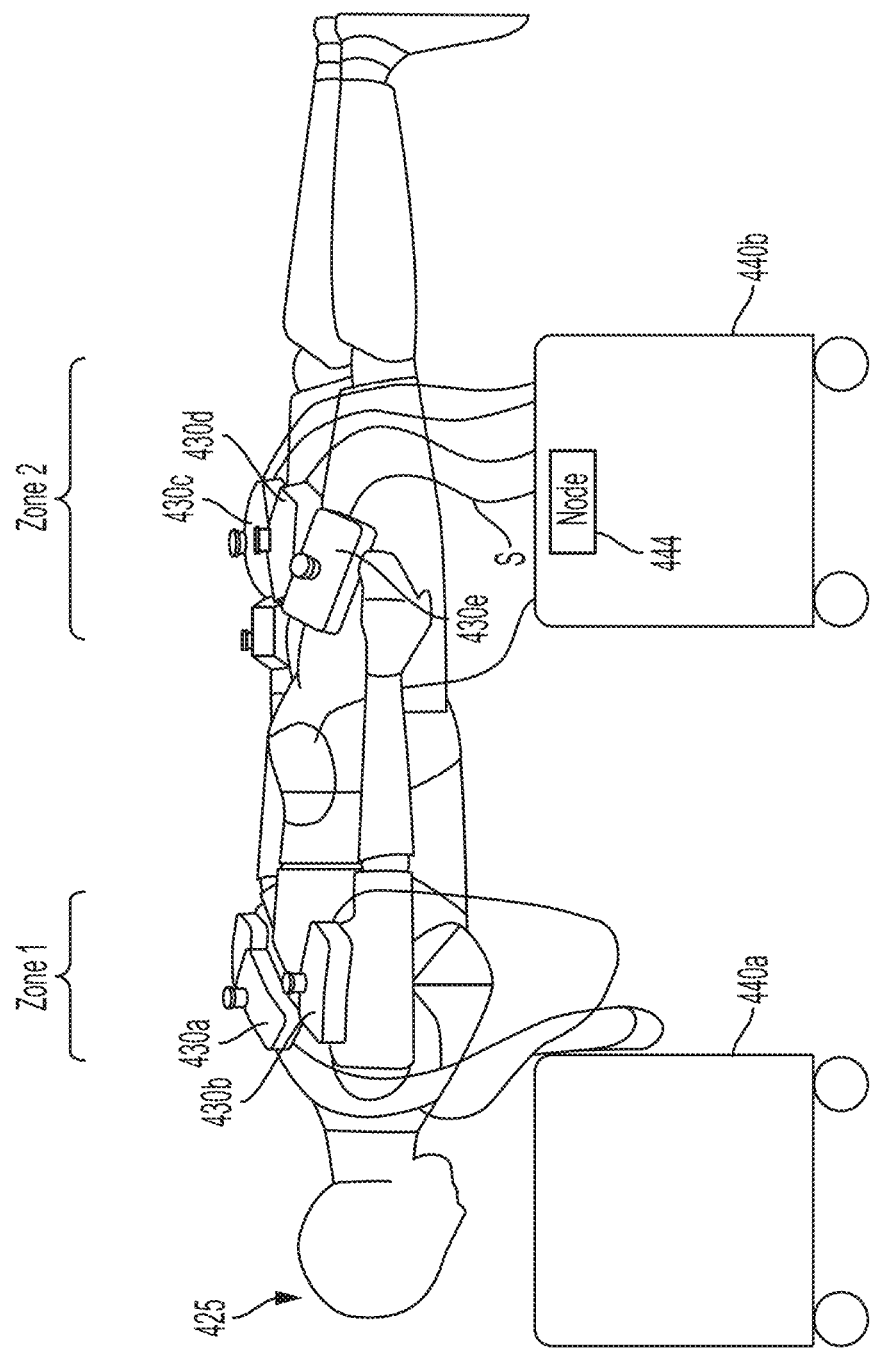
FIG. 4C depicts a patient undergoing RF-based tissue treatment with regard to two sections of the patient with multiple tissue regions being treated using RF applicators contacting the patient in each such section in accordance with various aspects of the present teachings.

FIG. 4C depicts a patient 425 undergoing RF-based tissue treatment with regard to two sections of the patient with multiple tissue regions being treated. Specifically, multiple RF applicators 430a, 430b, 430c, 430d, and 430e are used and placed in contact with the patient. Although any suitable applicator can be used, a conformable applicator or a rigid applicator is typical for the multizone treatment shown in FIG. 4C. Applicators 430a, 430b are positioned in a first treatment zone Zone 1 that includes the upper back torso while applicators 430c, 430d, and 430e are positioned in a second treatment zone Zone 2 that includes the upper back part of each thigh. The applicators shown can be held in place with one or more attachment mechanisms such as belts, clips, clamps, straps, fasteners, and other devices suitable for holding an applicator in a given position relative to a target treatment region of the patient 425.

Alternatively, the applicators can be adhered to the skin in each of the treatment zones using suitable adhesive strips, gel, gel pads, tabs, or other regions of adhesives that will hold the applicator in place but can be removed without patient discomfort at the end of the treatment. Each of the applicators is in electronic communication with one or more RF system components 440a, 440b as shown. These components 440a, 440b may include a console such as console 110 described herein or one or more components or subsystems of a given console 110. The applicators are in electrical communication with one or more electronic devices such as one or more control nodes as discussed herein. In one embodiment, the RF drive electronics are disposed in the applicator.

Each applicator can have one or more leads and one or more cables to provide control signals, power, transmit impedance measurements or for the transmission of other electronic signals as disclosed herein. For example, each applicator may include one or more transmission cables. In one embodiment, the distance of cable section (or the straight-line distance) between output of a control node 444 and a connection point of transmission cable with an applicator 430e is S. In one embodiment, control node 444 is a controller that generates control signals to measure individual current flow for one or more electrodes of the electrode array of applicator 430e. Each applicator used in a given embodiment may connect, directly or indirectly though other electrical device, to one or more control nodes, such as Nodes 0, 1, 2, 3 disclosed herein.

In one embodiment, the distance S is a target operational range suitable to maintain device operation and/or accuracy of applicator outputs relative to expected or baseline applicator outputs for a given set of input signals and/or power. In one embodiment, S ranges from about 0 to about 2 inches. In one embodiment, S ranges from about 0 to about 6 inches. In one embodiment, S ranges from about 0 to about 12 inches. In one embodiment, S ranges from about 0 to about 24 inches. In one embodiment, control node or node 444 includes a radio frequency printed circuit board (RF PCB) stack that is disposed in a housing or other assembly such within component 440b. In one embodiment, each of the applicators depicted in FIG. 4C is in electrical communication with one or more control nodes such as a node the same as or similar to node 444.

In one embodiment, it is desirable to simultaneously treat two or more sections or zones of patient in order to reduce the overall amount of time that would be spent in treatment. As a result, parallel treatment of different tissue regions in different parts of the body simultaneously with RF is one advantage of the disclosure. In some instances, additional treatment zones can be treated in addition to those zones. In some embodiments, each tissue zone can be treated in an alternating sequence, first zone is active with applicators delivering RF energy and second zone is inactive, and vice versa for a certain period of time or number of alternating iterations. This approach can be used to the extent such an approach is most comfortable to the patient or if a particular treatment regimen benefits from a rest period or alternating RF exposure during a given RF treatment.

Figure 4D:
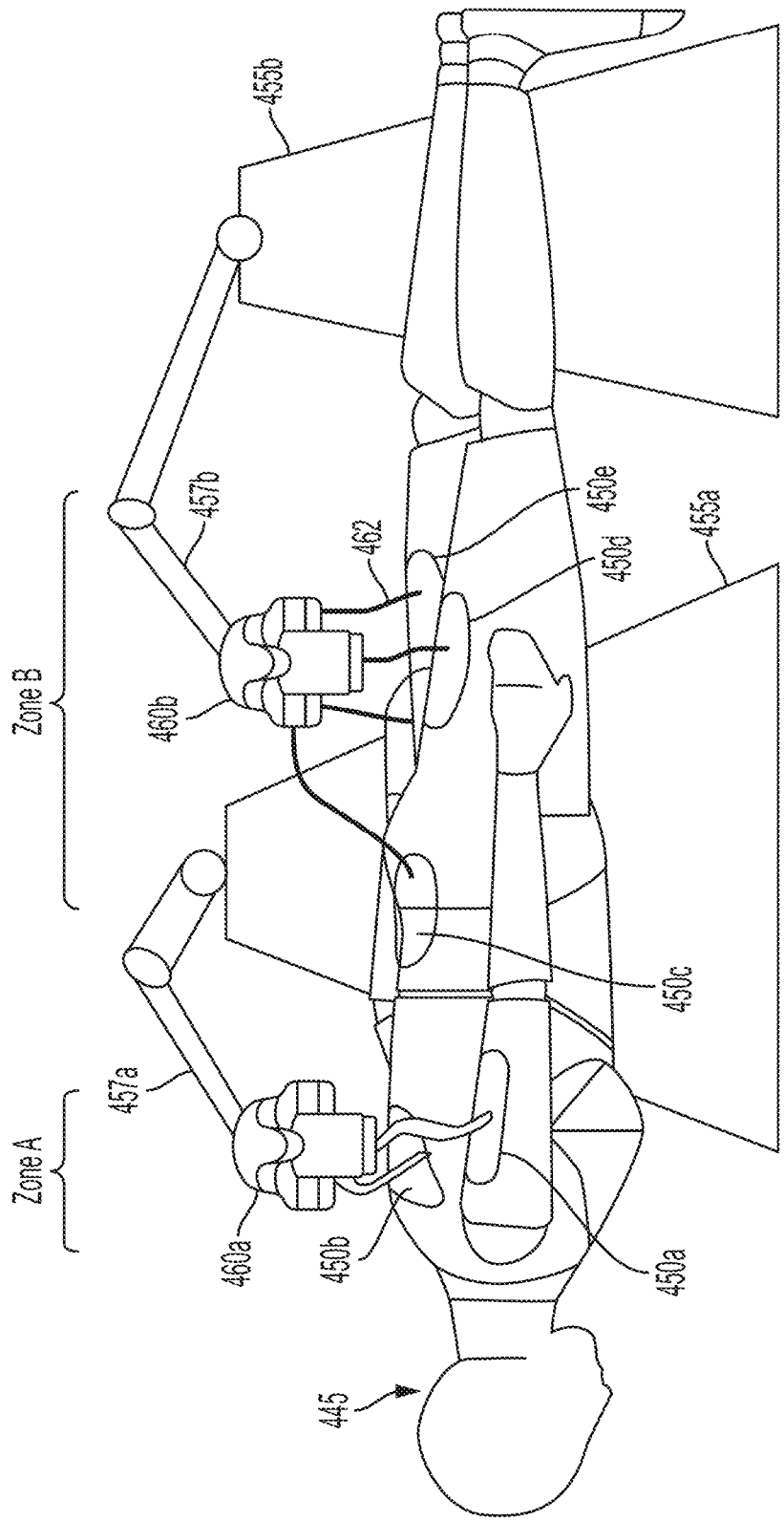
FIG. 4D depicts a patient undergoing RF-based tissue treatment with regard to two sections of the patient with multiple tissue regions being treated using multiple applicators positioned relative to supports relative to each such section in accordance with various aspects of the present teachings.

FIG. 4D depicts a patient 445 undergoing RF-based tissue treatment with multiple tissue regions being treated using multiple applicators positioned relative thereto. The applicators are typically conformable applicators that are stuck or otherwise adhered to the skin. In some embodiments, other applicators can be used. In more detail, FIG. 4D depicts a patient 445 undergoing RF-based tissue treatment with multiple tissue regions being treated in two different sections or zones of their body Zone A, Zone B.

Specifically, multiple RF applicators 450a, 450b, 450c, 450d, and 450e are used and placed in contact with the patient. Two supports such as supports 455a, and 455b are also shown having extension arms 457a, and 457b which support distribution devices 460a, 460b. The benefit of such a configuration supports the multi-zone treatment benefits discussed above with regard to FIG. 4C. The use of separate distribution devices 457a, 457b in electrical communication with the applications 450a, 450b, 450c, 450d, and 450e via cables such as cable 462 facilitate the use of thin conformable electrodes in a multi-zone treatment setup.

Although any suitable applicator can be used, a conformable applicator is typical for the multizone treatment shown in FIG. 4C. Given that the conformal applicators can be thin flexible sheets or stacks of layers, it is advantageous to separate the drive electronics such that they are located near the electrode array of such an applicator. With this in mind, the embodiment of FIG. 4D has conformable applicators having electrode arrays arranged as shown with the drive electronics and other electronic components such as one or more control node disposed in a distribution devices 460a, 460b as shown.

Each distribution device 460a, 460b can include multiple arms that have a connection port or direct connection to a transmission cable 462 that connects each arm of the distribution device to a given applicator. As shown each distribution device has four arms, with three of them visible in the figure and the fourth positioned on the other side of the device opposite the middle arm for each such device. The drive electronics in the distribution devices transmits power and control signals to the electrode array of each applicator that it is connected to and receives impedance data when an impedance mapping is performed relative to the various tissue treatment regions in Zone A and Zone B.

Applicators 450a, 450b are positioned in a first treatment zone Zone A that includes the upper back and the triceps area of each arm while applicators 450c, 450d, and 450e are positioned in a second treatment zone Zone B that includes the lower back and the upper back part of each thigh. The simultaneous or alternating treatment zones depicted in FIG. 4D facilitate the use of conformal applicators that stay fixed relative to the target treatment regions. These configurations can reduce treatment visits and also improve treatment outcomes with the placement of conformal applicators on specific tissue regions. Some further benefits of selective tissue targeting are discussed in more details as follows in the context of RF energy selection.

As noted above, short duration relatively-higher magnitude RF energy can be used to "selectively target" tissues such as fibrotic or connective tissue, septae or even blood or lymphatic vessels, which structures are found within all tissues and exhibit relatively lower electrical impedance compared to bulk tissue. In accordance with various aspects of the present teachings, the measured impedance of the tissue region (including septae) can be monitored and tracked during the application of the RF pulse(s) to determine changes in tissue composition in real-time. For example, during the RF pulse emission, the current, voltage and their phase relationship can be monitored so as to calculate the impedance of the tissue to which the RF energy is being applied. With reference now to FIGS. 5A-F, in various aspects of the present teachings, impedance tracking of the individual electrodes and/or the average impedance of the electrodes of the array during treatment can also be used to determine when to terminate treatment. As indicated above, certain tissue types (e.g. fibrotic structures such as septae) generally exhibit lower impedance relative to fat tissue, for example. Accordingly, in accordance with certain aspects of the present teachings, monitoring of the impedance can indicate when those lower-impedance tissues have been sufficiently altered by the application of RF energy to indicate that a desired outcome has been achieved.

Figure 5A:
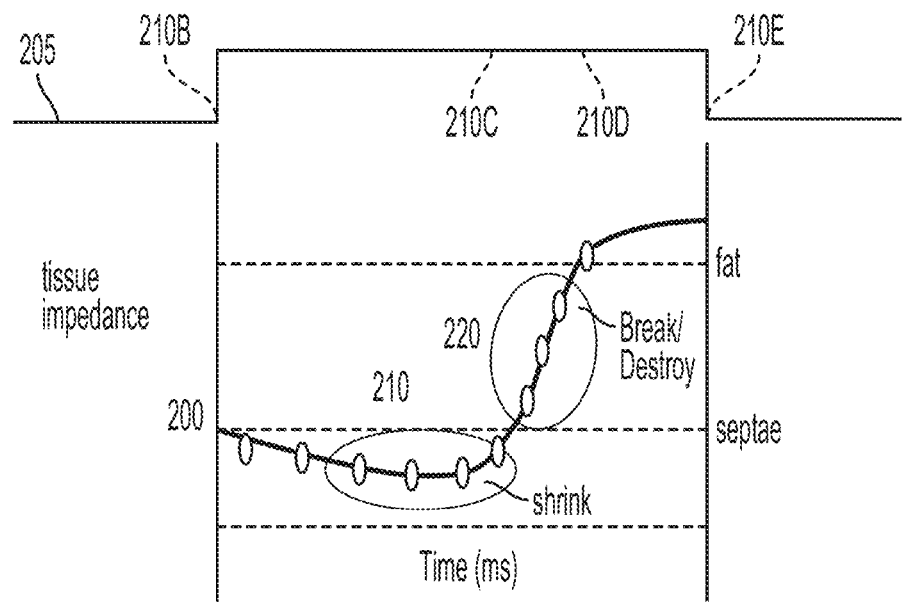
FIGS. 5A-F schematically depict an exemplary treatment targeting septae and exemplary method for monitoring and/or controlling the distribution of RF energy in accordance with various aspects of the present teachings.
Figure 5B:
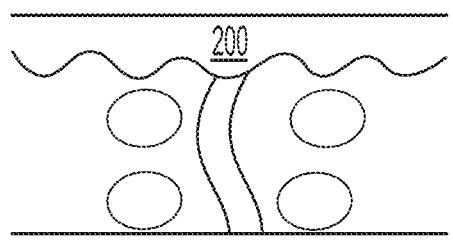
Figure 5C:
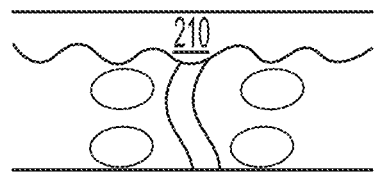

FIG. 5A represents a plot of impedance of tissue during the application of an exemplary RF signal 205 that is intended to provide a 500 ms pulse of high power RF energy, starting at time 210B as shown at the top of the figure. By way of example, prior to the initiation of the pulse at time 210B, the impedance of the native tissue schematically depicted as FIG. 5B can be determined utilizing a sub-treatment threshold low RF-power between an active electrode and a drain pad (or another active electrode on a second applicator). As discussed otherwise herein, this relatively low impedance detected at time 210B would be understood to represent the RF energy propagating through the untreated septae 200 depicted in FIG. 5B. However, as shown in FIGS. 5A and 5C, the application of the treatment RF energy following the initiation of the pulse at 210B can result in changes in the impedance of the tissue during the heating. For example, largely due to the RF energy propagating within the septae 200 between the initiation of the pulse at 210B and the time point 210C (e.g., about 300 ms), the impedance measurements generally indicate a decrease in impedance in the tissue between an active electrode and a drain pad (or another active electrode on a second applicator) as the septae heat and/or shrink as shown schematically by the decreased septae 210 length of FIG. 5C. For example, in some aspects, a small change in the impedance during the RF energy pulse, (e.g., the measured impedance drops a discernible amount, about 3%, greater than 3%, from about 3% to about 20%, or about 10%) can indicate a temperature rise in the septae and/or be indicative of septa shrinking and/or tightening. As heat continues to accumulate in the septae, the impedance suddenly increases rapidly between time 210C and 210D as shown in FIG. 5A.

Figure 5D:
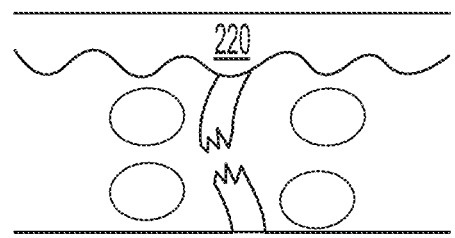
Figure 6A:
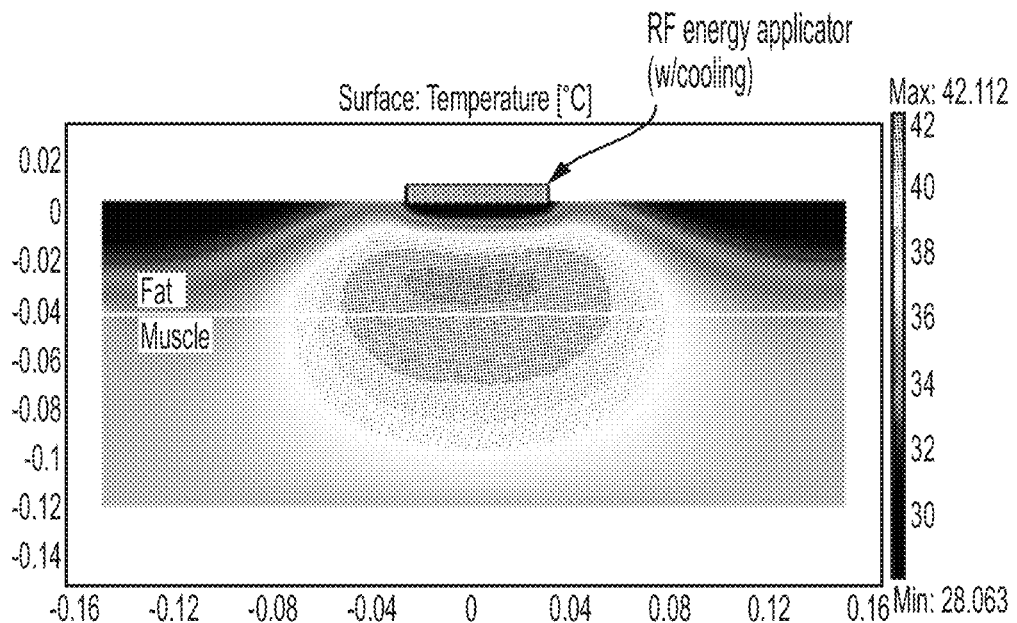
FIG. 6A depicts an exemplary plot of tissue temperature for a target region including a fat region of relatively uniform thickness during an exemplary treatment in accordance with various aspects of the present teachings.

Without being limited by any particular theory, this drastic increase in impedance can be attributed to a dramatic shift in the structure and/or composition of the tissue between the active electrode and the drain pad (or another active electrode on a second applicator). With reference to FIG. 5D, for example, this impedance rise can be attributed to the breaking of the septae caused by the RF energy such that the low-impedance path through the bulk tissue is no longer present and the detected impedance increases to a level more in line with bulk tissue (which includes the high impedance fat tissue). For example, in some aspects, after the initial decrease in impedance noted above, a drastic increase in the impedance during the RF energy pulse, (e.g., the measured impedance quickly increases a discernible amount, about 3%, greater than 3%, from about 3% to about 20%, about 10%, greater than 10%, or greater than 20% can indicate a large temperature rise in the septae causing coagulation, denaturation, breaking, and/or destruction of the septae. As shown in FIG. 6A, after time 210D (e.g., about 400 ms) the detected impedance stays relatively level though the exemplary RF pulse continues to be applied for its entire duration of 500 ms (time 210E). It will thus be appreciated in light of the present teachings that by monitoring the impedance of the tissue during treatment, it can be determined if a desired outcome has been achieved, and in some aspects, such changes can be used to determine the end point of the application (terminating treatment) and/or to adjust the treatment parameters (e.g., increase power, increase pulse width, apply additional RF pulses). For example, treatment can be terminated (e.g., by ending the pulse or series of pulses) at time 210D when this drastic increase in impedance is observed.

In various aspects, the sampling rate of the monitored impedance (e.g., as indicated by the black dots of FIG. 5A) can be selected to achieve the desired fidelity in the result. By way of example, the sampling rate of monitoring can include any of a number of sample times and frequencies during the pulse emission, for example, the sampling rate of monitoring can occur about 5 times, about 10 times, about 100 time, or about 1000 times during the RF pulse emission.

Figure 5E:
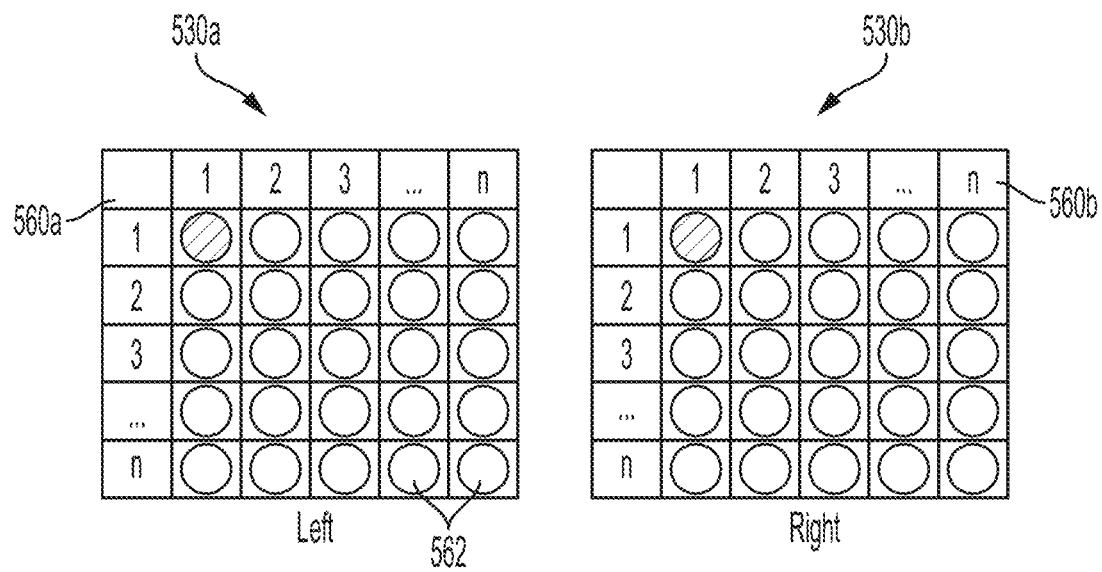
Figure 5F:
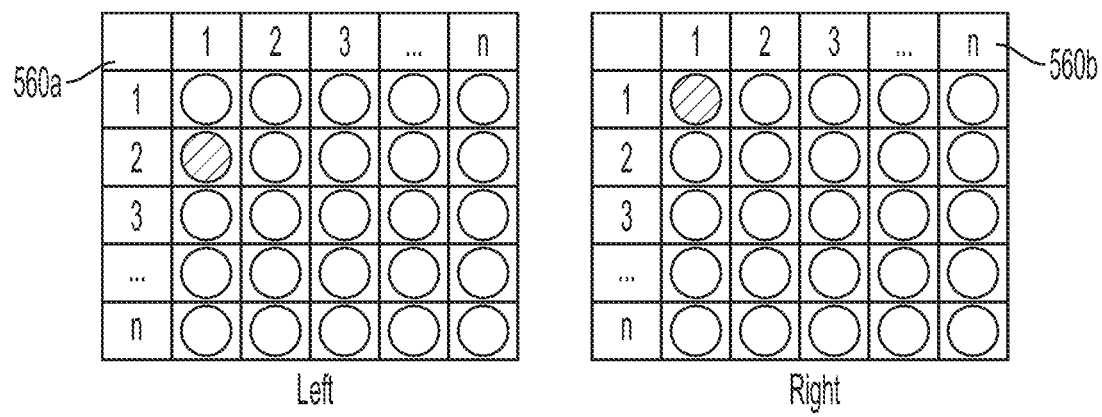

The above description of impedance tracking during RF treatment can be utilized with either a pulsed, single electrode applicator (e.g., applicator 130d of FIG. 1A) or an applicator having a plurality of electrodes (e.g., applicator 130a of FIGS. 1A, 1B, 1D and 1E). In various aspects for applicators containing an array of individually-addressable electrodes, after the sufficient impedance change of tissue between one electrode 562 (or a cluster of electrodes) of an array 560a on one applicator 530a and one electrode 562 (or a cluster of electrodes) of an array 560b on a second applicator 530b as indicated by FIG. 5E, a similar treatment can then be performed utilizing a different combination of electrodes 562 between the two applicators (or between one applicator and a drain pad) to address a different region of tissue and septae under the array of electrodes as shown in FIG. 5F.

In various aspects, electrode monitoring can also be provided to monitor the electrical condition of every electrode to satisfy open circuit (no contact) conditions so as to determine if the electrode(s) are in sufficient contact with the tissue. In such aspects, uniform attachment of the applicator and any drift in its electrical conditions from the point of application (e.g., the start of treatment) to the finish of the procedure (e.g., dehydration of the gel adhesive) can be optimized to avoid misinterpretation of tissue impedance conditions. Because the electrode array can be comprised of many individual electrodes, and the impedance of each array location can be continually monitored, a robust method of electrode array monitoring can be provided for automatically.

Patient Surface Temperature Feedback: Patient Surface Temperature Perimeter Feedback Used for RF Uniformity Compensation.

As discussed above, various detection and/or feedback mechanisms are contemplated to help provide improved RF treatments in accordance with various aspects of the present teachings. For example, RF treatment uniformity can be assisted by utilizing surface temperature feedback alone or in combination with impedance mapping, as discussed above. For example, by detecting temperature differences at various portions of the tissue surface adjacent the target region, the distribution of RF power (or total treatment time or duty cycle) delivered through each individual electrode in an electrode array can be controlled or modified to adjust for and/or prevent accumulation of heat in an untargeted region (e.g., outside of the applicator perimeter) or non-uniformity of the treatment zone whether due to anatomical variation or tissue layer thickness variations.

In exemplary aspects, the surface temperature of the patient's skin in areas around the perimeter of the applicator electrode array can be monitored by IR sensors, thermocouples, or the like (by way of non-limiting example) so as to identify uneven heating of skin surface areas adjacent to the intended treatment zone. Based on these signals (alone or in combination with the impedance mapping), a controller (including a microprocessor and algorithm as in FIG. 1A) can provide correction factors to the RF power set-point for individual electrodes so as to optimize treatment uniformity, homogeneity, and placement of the treatment zone.

As discussed above, skin laxity and other treatments requiring bulk heating may require "time at temperature" to be maintained for a given tissue type, anatomical area, and desired treatment endpoint, by way of example. A suitable treatment temperature range can be from about 42-47° C. and a suitable total treatment time can range from about 10-35 minutes, by way of non-limiting example. However, dosimetry methods in which a total energy versus volume approach is utilized may fail to recognize wide variations in patient perfusion (e.g., the cooling effect) or variations in the thermal capacity of differing tissue types (e.g., nearby or adjacent bone, viscera, and/or thick fat layers all cause variation in temperature deposition when exposed to a fixed dose of Joules/volume).

Predictable RF uniformity is important for efficacy and safety in an applied RF treatment and can become a concern in the case of non-uniform fat layers. However, application of uniform RF energy (e.g., 1 MHz) through a patient's skin and then into deeper tissues (e.g., a fat layer) is complicated by various tissue types and differing impedance variations. For example, as discussed above, fibrous structures and other connective tissues have a lower impedance to RF energy relative to fat tissue. Additionally, tissue layers below the fat layer including muscle, large vessels, etc. likewise have a much lower impedance than fat. Consequently, RF energy will preferentially travel along these lower-impedance pathways as opposed to the fat tissue such that the RF energy tends to preferentially heat (at least initially) these low-impedance tissues prior to being diffused into the adjacent fat cells.

In particular, RF treatment applicators that are placed on a tissue surface directly over a fat layer of non-uniform thickness (e.g., one side of the applicator is above a 20 mm thick fat layer and the opposite side of applicator is over a 40 mm thick fat layer) can cause uneven distribution of heat and/or the treatment of non-targeted tissue. That is, because fat cells have a higher impedance relative to the deeper muscle tissues, for example, the RF energy uniformly delivered at the surface will "drift" toward the direction of least impedance, in this case toward the muscle. Because RF energy will generally progress to the deeper tissues via the shortest path length through the high impedance fat layer, the RF energy will tend to be delivered through the 20 mm thick fat layer such that the temperature of that side of the applicator increases more than on the side of the applicator of the 40 mm thick fate layer. This causes the "treated zone" (area of tissue exposed to temperature rise) to drift toward the shallowest fat layer such that the actual treated zone is offset from beneath the applicator toward the shallowest fat layer side, an undesirable and somewhat difficult to predict effect.

Such non-uniform energy distribution effects and the benefits provided by various aspects of the present teachings can be further understood with reference to FIGS. 6A-E. First, with reference to FIG. 6A, the temperature profile of a relatively uniform thickness of a fat layer of 40 mm is depicted during a treatment in which the same RF power is delivered by each of a plurality of electrodes. In FIG. 6A, the left vertical axis is the distance from the patient skin surface measured in meters (e.g., a depth below the skin surface), while the horizontal axis is the distance from the applicator center measured in meters. The right vertical axis is the temperature in degrees C. As shown, uniformity of temperature aggregated in the treated zone can be observed, with the treated zone being symmetric and located directly below the RF energy applicator.

Figure 6B:
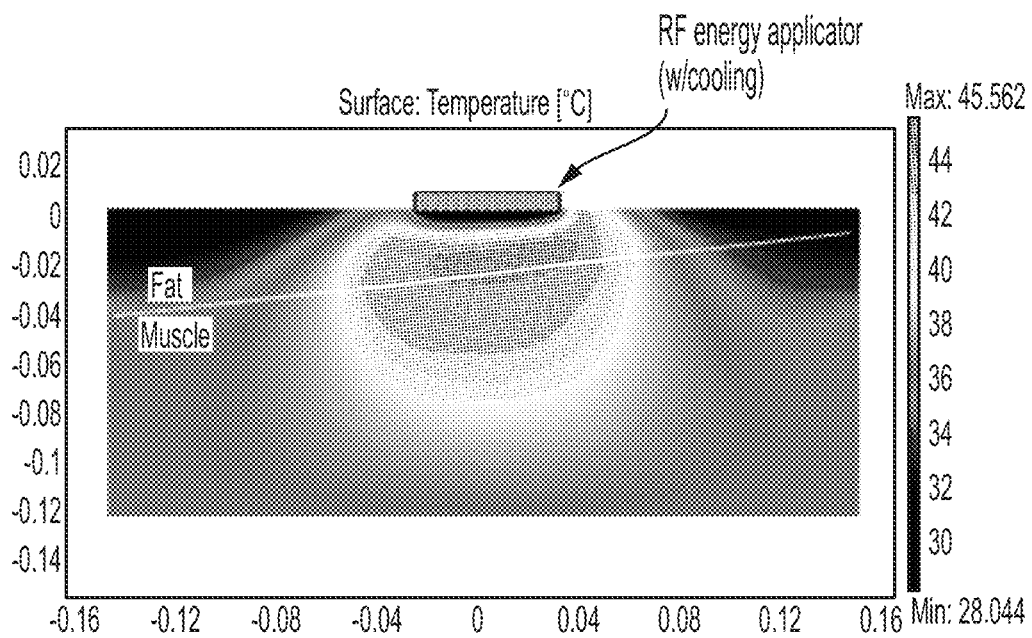
FIG. 6B depicts an exemplary plot of tissue temperature for a target region including a fat region of relatively non-uniform thickness during an exemplary treatment in accordance with various aspects of the present teachings.
Figure 6C:
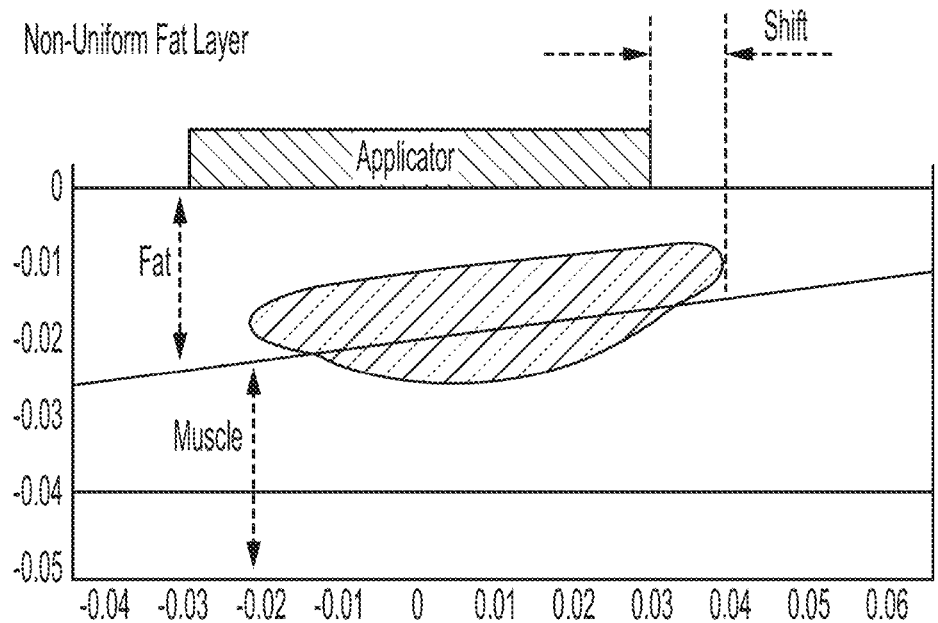
FIG. 6C schematically depicts treatment zone shift due to a fat region exhibiting a relatively non-uniform thickness during RF treatment.

FIG. 6B, on the other hand, shows the temperature profile of a non-uniform fat layer during the same RF treatment as in FIG. 6A. In particular, the left side of FIG. 6B exhibits a fat layer of about 40 mm thickness, while the right side of FIG. 6B has a fat layer about 20 mm thick. Asymmetry and drift of treated zone temperature away from the thicker fat layer can be observed such that the treated zone is not directly below the RF energy applicator (shifted toward the thinner fat layer on the right side of FIG. 6B), which can be an undesirable result. FIG. 6C schematically depicts this treatment zone drift with the vertical axis representing depth and the horizontal axis representing distance parallel to the skin surface from the applicator center (measured in meters).

As shown, the zone exhibiting the target treatment temperature is asymmetric and shifted away from the center of the applicator.

Figure 6D:
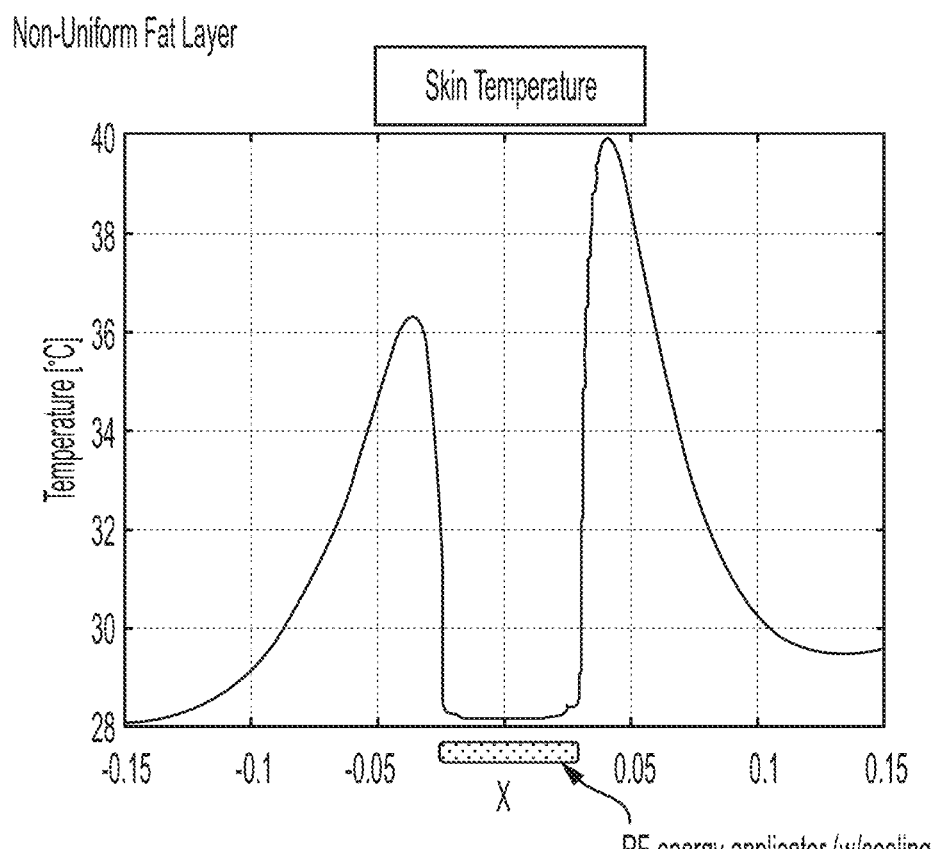
FIG. 6D depicts an exemplary plot of tissue temperature due to a treatment zone shift of a fat region exhibiting a relatively non-uniform thickness during RF treatment.

FIG. 6D depicts the exemplary temperature profile of the tissue surface based on the simulation of FIGS. 6B and 6C, with the left vertical axis as temperature in degrees C., while the horizontal axis is distance from the applicator center (along the skin surface) measured in meters. As shown in FIG. 6D, two heated lobes are observed, with each lobe disposed on a side of the perimeter of the applicator's cooled surface. In case of a uniform fat layer thickness, these two lobes would have been expected to be equal magnitude to each other. In this case, however, more RF energy was deposited toward the right side of the depicted treatment area due to the shallower fat layer such that the lobes are asymmetric. As such, correcting and/or preventing non-uniform treatment zones or treatment zone drift from beneath the applicator is one object of this disclosure.

In various aspects as discussed otherwise herein, a more uniform treatment can be attained by delivering proportionately more RF energy to the thicker fat layer side and proportionately less RF energy to the thinner fat layer side of the applicator. In this exemplary case, the electrode being an array of a plurality of independently switchable skin surface contact electrodes (e.g., 19 electrodes arranged in a hexagonal array for the depicted example). This electrode array can be electrically isolated from but thermally bonded to a water-cooled plate (e.g., as discussed with reference to FIGS. 2A and 3A). The switched electrode array allows for RF energy to be apportioned non-uniformly to the tissue to counter the tendency of the treatment zone to drift toward the thinnest fat layers. Specifically, drift can be prevented by increasing RF power delivered to the thick fat layer side of the applicator while simultaneously decreasing the RF power switched to independent electrodes on the thinner fat layer side of the applicator. This non-uniform applicator power approach forces the treated zone to remain centered beneath the applicator despite tissue impedance and/or fat thickness variations.

FIG. 6E shows improved uniformity on the right side due to the reapportionment of RF power to provide a non-uniform RF power input to compensate for the non-uniform fat layer as compared to the uniform RF power input approach provided on the left side as was shown above in association with FIG. 6C. The left hand image of FIG. 6E providing uniform RF power input generates an offset to the right of the highest temperature region that extends well outside the applicator's dimensions. The right hand image of FIG. 6E, however, provides non-uniform RF applicator power input by which power has been modulated to compensate for the underlying tissue thickness variation (e.g., as determined by impedance mapping). The right hand image in FIG. 6E depicts the highest temperature region, which is directly adjacent the applicator's dimensions and is illustrative of the modulated system's ability to cause the tissue heating to occur under the applicator despite the variation in tissue impedance caused by a non-uniform fat layer in accordance with various aspects of the present teachings. For example, each of the independently switched electrodes can be operated in a closed loop with regard to power. Additionally, each electrode may act as a discrete impedance detector by monitoring delivered amps, volts, phase angle, etc. This impedance information may be used to derive a "map" of general tissue layer non-uniformity proximal to the applicator so as to provide the control system with a starting RF applicator power correction term such that individual electrodes located over high impedance regions (e.g., above thicker fat layers) are "corrected" to add a compensating increase of RF power. And where individual electrodes are located over a relatively lower impedance region, the RF powers are "corrected" so as to generate a uniform thermally-treated zone which remains centered beneath the applicator.

The tissue impedance map approach described above is used for providing feedback to the control system for use to reapportion (add a plus or minus correction term to RF power command) RF power delivered through each individual electrode for the purpose of controlling the treatment to remain within the desired treatment zone, centered beneath the applicator.

In addition, in the case of a non-uniform tissue impedance or thickness (e.g., a fat layer), where no correction term is applied to individual electrode power or where insufficient correction is applied, the resulting skin surface temperature adjacent to the perimeter of the applicator can be asymmetric. That is, the skin surface adjacent the perimeter of the applicator edge located over the thinner fat layer (of lower impedance) will tend to get hotter than the skin adjacent the applicator perimeter side located over the thicker fat layer (of higher impedance). Thus, even when the electrode array is uncompensated or undercompensated with regard to the re-apportionment of RF power to the individual electrodes based on impedance mapping, monitoring of the skin surface temperature rise adjacent the applicator perimeter can provide a useful control feedback mechanism to correct for asymmetry or drift of the intended treatment zone. In some aspects, monitoring the patient surface adjacent to the perimeter of the electrode (a few mm's away from the cooled patient cooling block edge) alone can provide sufficient feedback for the control algorithm to re-apportion or correct RF power delivered to individual electrodes such that the treated zone is controlled to remain uniform and symmetric with respect to the applicator center (e.g., the treated zone is centered beneath the applicator).

In accordance with various aspects of the present teachings, patient surface temperatures outside the perimeter of the actively cooled patient water cooling block and electrode array can therefore give an indication of the tissue temperature located deeper (i.e., below the skin surface). An asymmetry in surface temperatures around the perimeter of the applicator, for example, can indicate an asymmetry in or drift of the resulting "treated zone" (zone of tissue temperature rise which reaches the target temperature). Specifically, individual electrodes closest to areas of the applicator with the highest skin surface temperature would be switched to reduce RF power whereas the opposite side of the applicator would be switched to increase the duty cycle of applied RF power. For example, a side of a given electrode array that is overheating can be shut off (or its duty cycle reduced) in favor of another portion of the same array that has a lower skin surface temperature. Therefore, the skin surface temperature around the perimeter of the applicator electrode array can act to indicate that RF power must be modified so that the temperature rise of the skin surface can be controlled to remain consistent and homogenous around the perimeter of the applicator.

Maintaining homogeneity of skin surface temperature rise by monitoring temperature of the perimeter of the electrode array and/or impedance mapping by individually monitoring impedance of the individual electrodes in the array alone or in combination can thus provide feedback to the control system for the purpose of homogenizing and centering the treated zone beneath the center of the applicator electrode array.

Impedance Measurements and Temperature Feedback of Subcutaneous Tissue

One of the primary goals of hyperthermic treatments, including those applied to adipose destruction and tissue tightening, is to raise the temperature of tissue beneath the superficial surface of the skin to a range of from about 39° C. to about 47° C., from about 39° C. to about 44° C., from about 41° C. to about 42° C., from about 42-47° C. while preserving the temperature of the skin surface to a normal temperature of about 35° C. or less. However, temperature at depth is typically unknown or requires an invasive method to monitor the temperature beneath the surface, such that it has heretofore been difficult to directly infer subcutaneous temperatures from the surface temperature due to active cooling of this tissue surface. It has thus been common to use the patient's sensation to determine the proper heating rate or dose.

Applicant has discovered, however, that the measured impedance and subcutaneous temperature can be closely related. As discussed above, the impedance of the area under the electrode array can be mapped to determine where more or less energy should be deposited to compensate for anatomical variations. Through observations of the impedance mapping during treatments, a strong correlation was observed between the impedance and the temperature of the tissue beneath the surface, which can further be applied to a closed-loop feedback mechanism whereby the system can determine the temperature of the subcutaneous volume under a specific electrode, under a cluster of electrodes, or under an electrode array. It will further be appreciated that one advantage of knowing the temperature under the tissue surface is that treatment temperature variations can be minimized by compensating for changes in perfusion or regional anatomical hot spots that might be dictating the overall sensation.

The plots described below depict exemplary aspects of the identified correlation between impedance and subcutaneous tissue temperature. As shown in FIG. 7A, the tissue temperature at a depth of 1.5 cm was determined by an invasive temperature sensor (a fluorophore tipped optical fiber, which is not influenced by RF like a conventional thermocouple) during an exemplary RF treatment. The power in Watts is positioned on the right vertical axis, the resulting temperature in degrees Celsius is positioned on the left vertical axis, and treatment time is on the horizontal axis. As shown, the plot exhibits a ramp up phase as the tissue temperature increases in the first several minutes of the treatment, after which the RF power is reduced so as to maintain an approximate plateau at about 45° C. That is, the target tissue can be raised to the therapeutic temperature range (e.g., 42-47° C.) during an initial heating or build phase in which the RF power (or duty cycle) is increased, after which the RF power (or its duty cycle) can be reduced to maintain the target tissue in the desired therapeutic temperature range (e.g., at its plateau of about 45° C.).

Figure 7B:
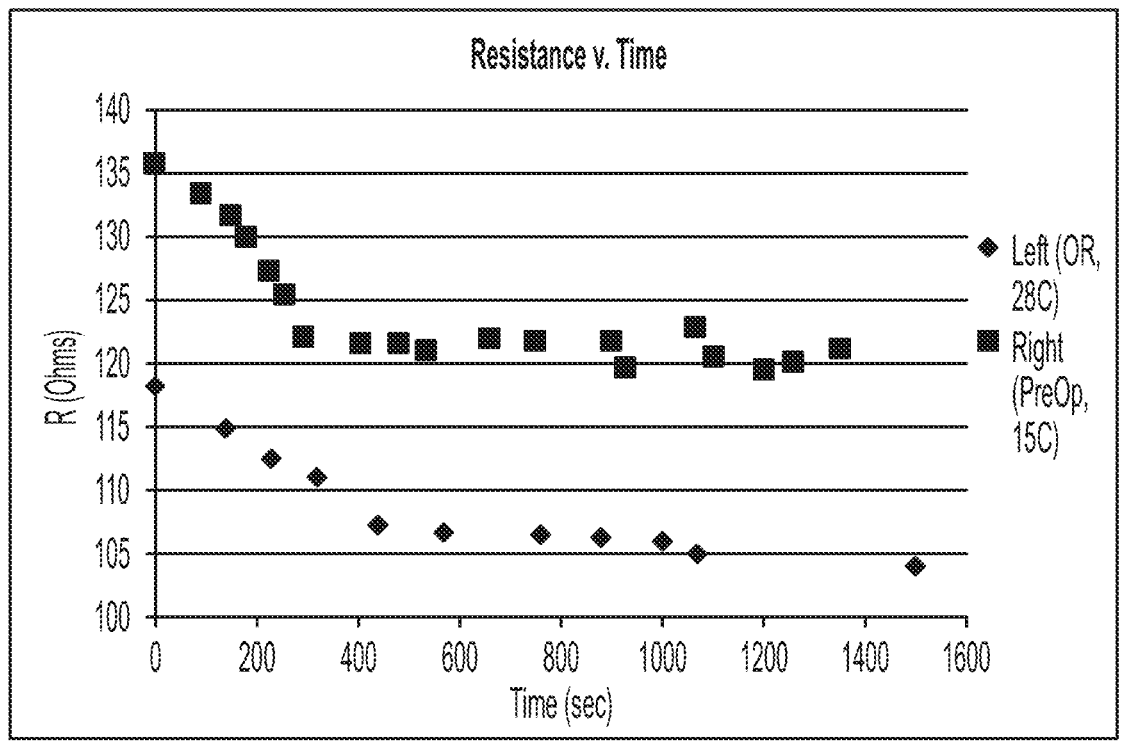
FIG. 7B depicts a plot of tissue impedance during the exemplary treatment of FIG. 7A, while utilizing different cooling temperatures.
Figures 1, 7C:
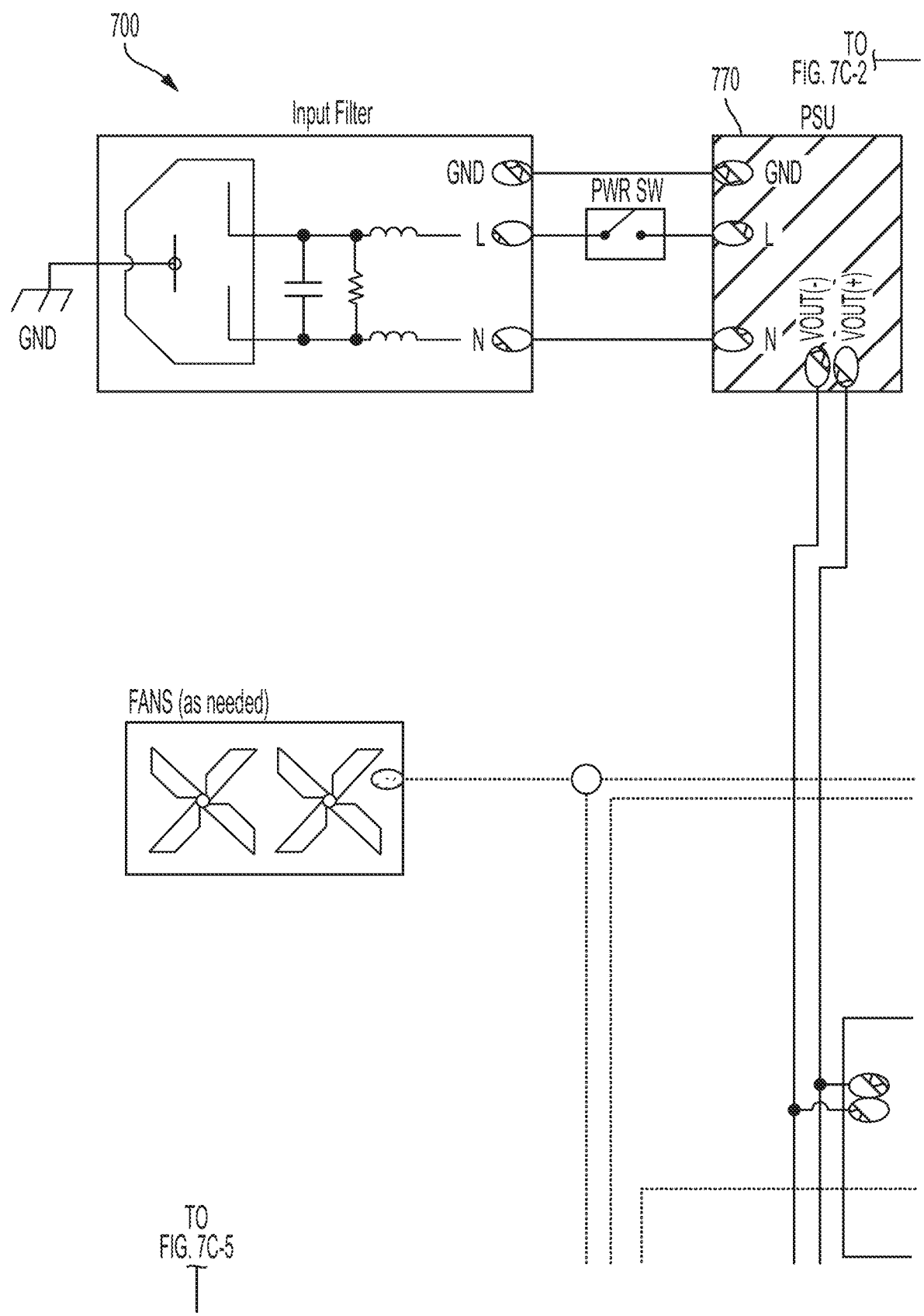
FIGS. 7C-1-7C-8 depicts exemplary electronics for an applicator having an electrode array in accordance with various aspects of the present teachings.
Figures 2, 7C:
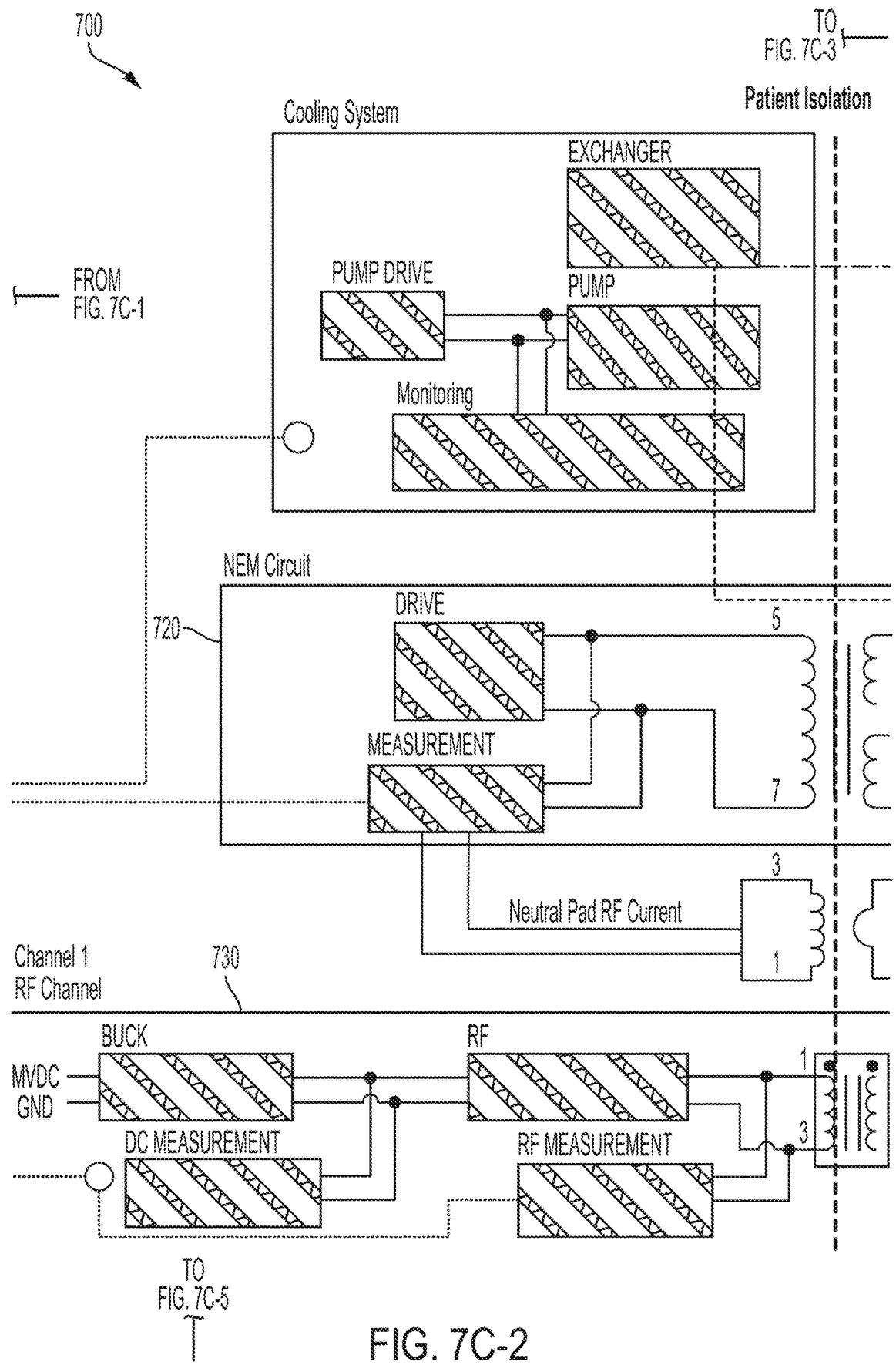
Figures 3, 7C:
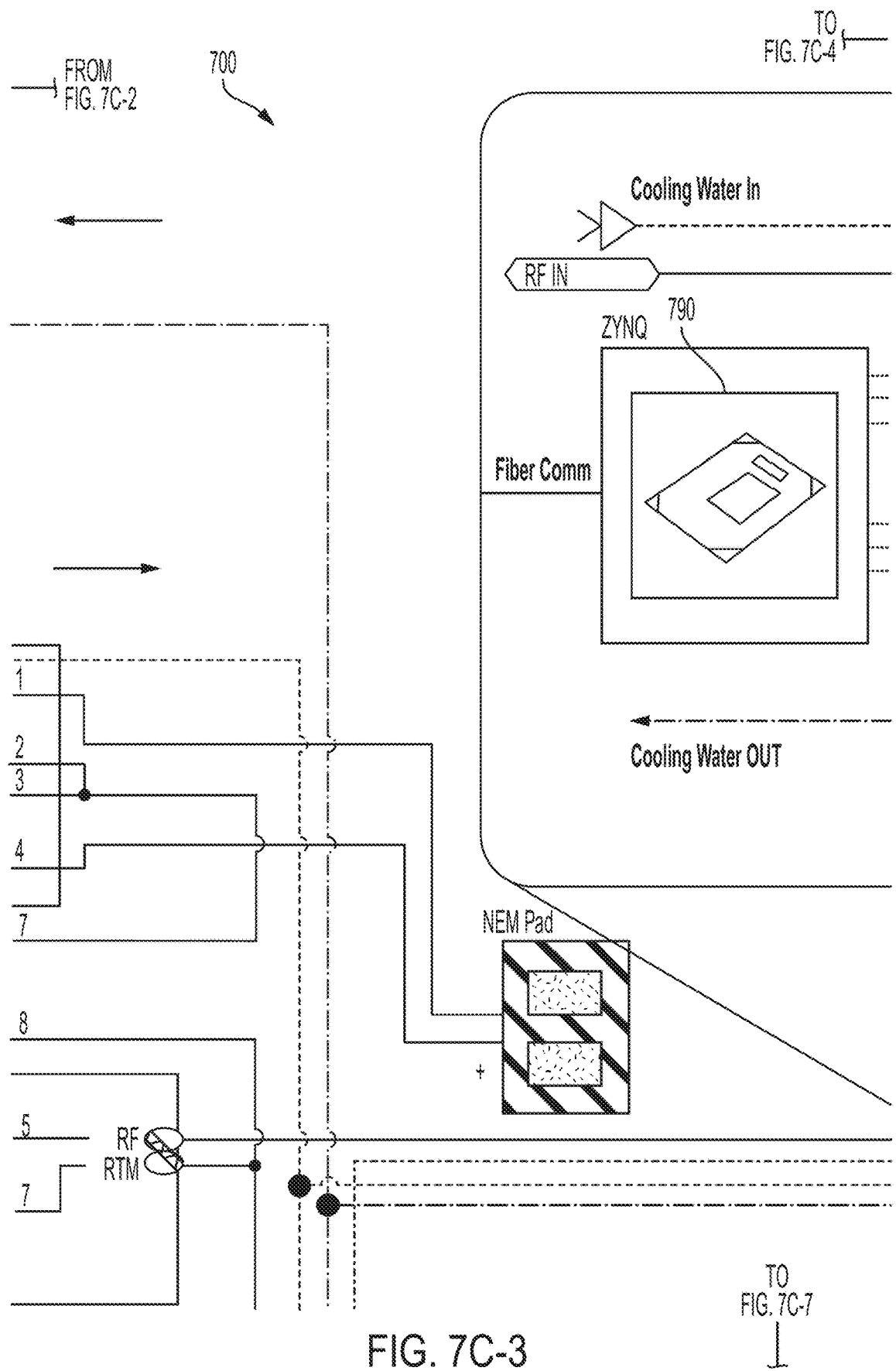
Figures 4, 7C:
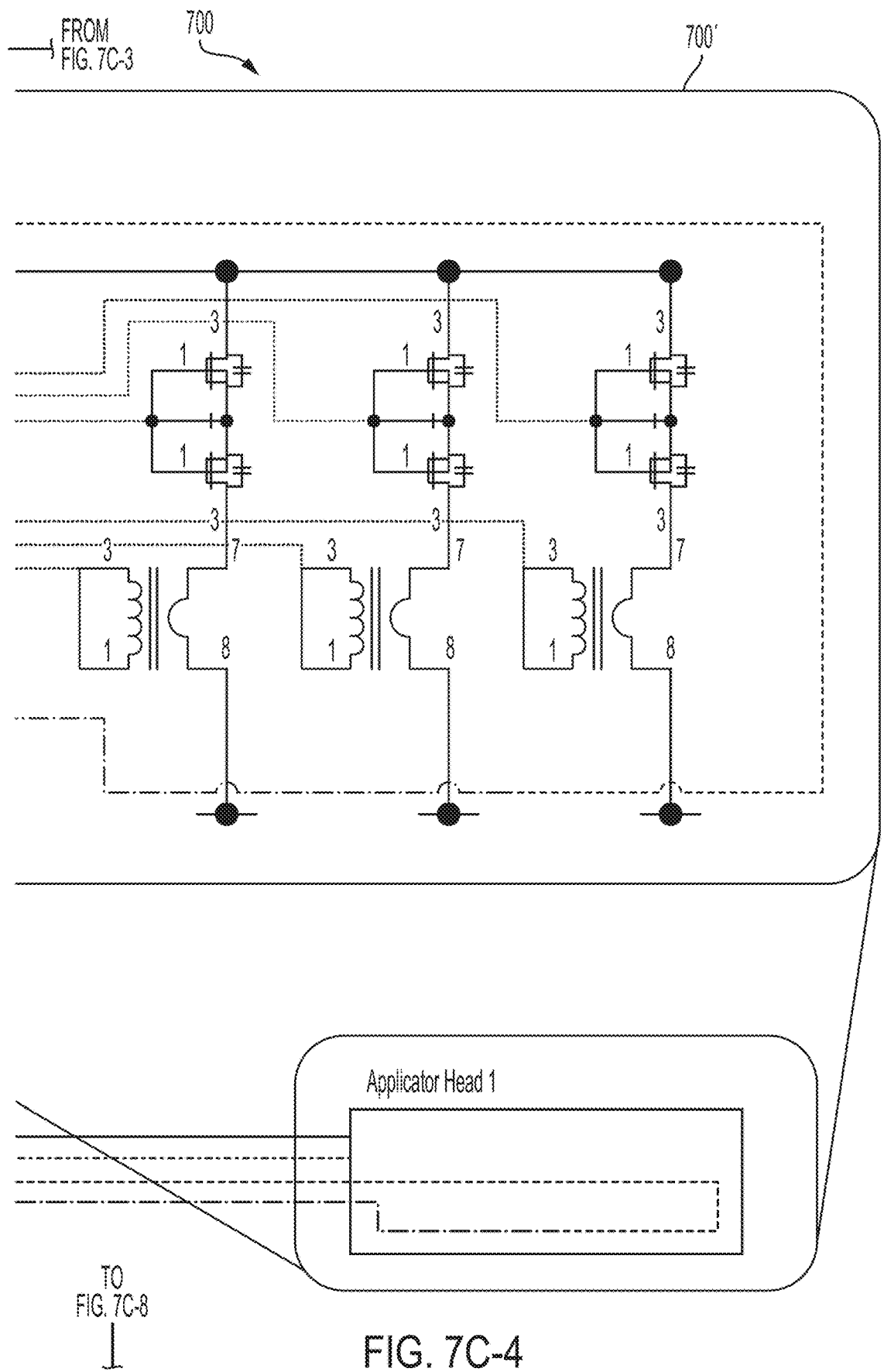
Figures 5, 7C:
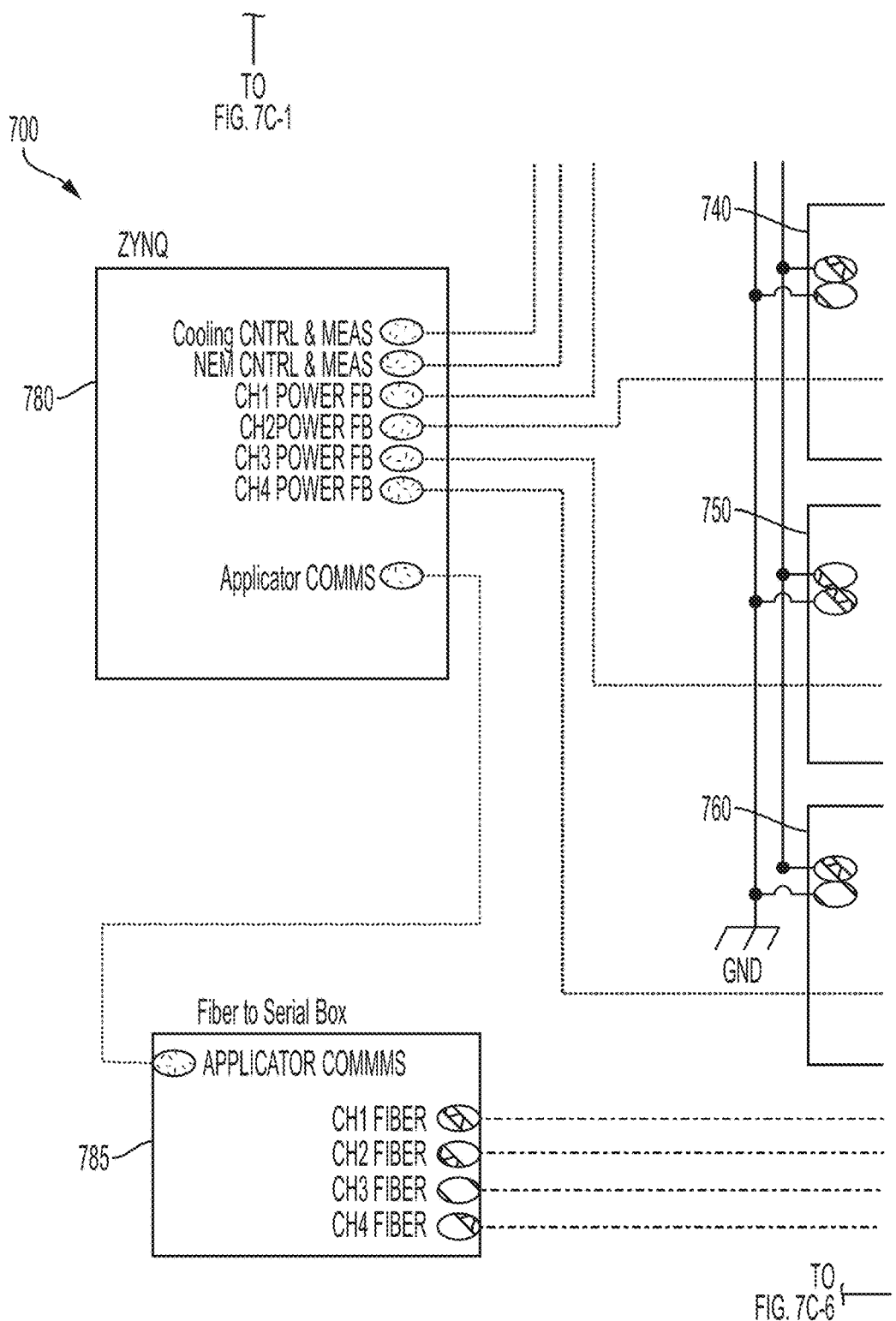
Figures 6, 7C:
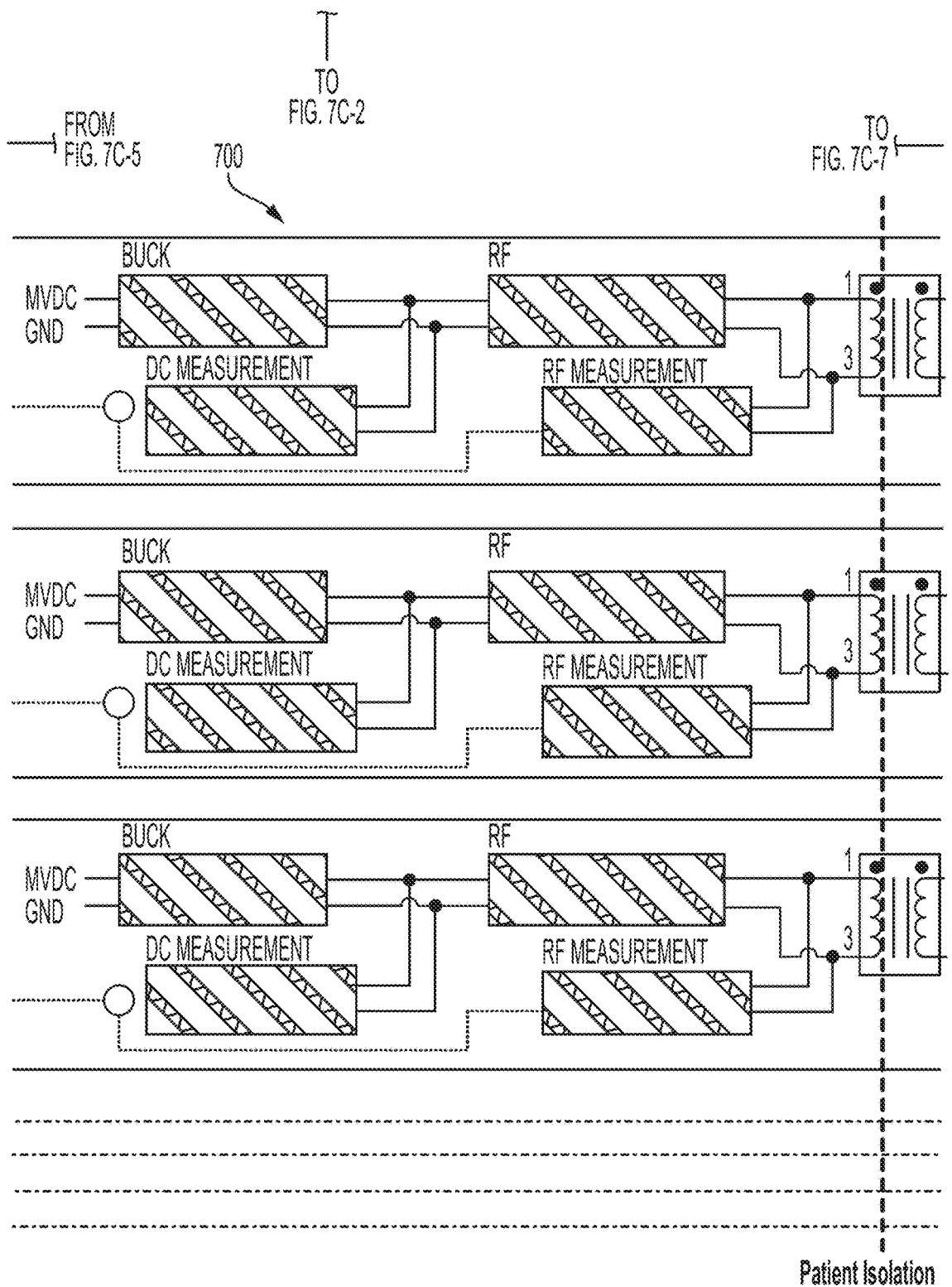
Figures 7, 7C:
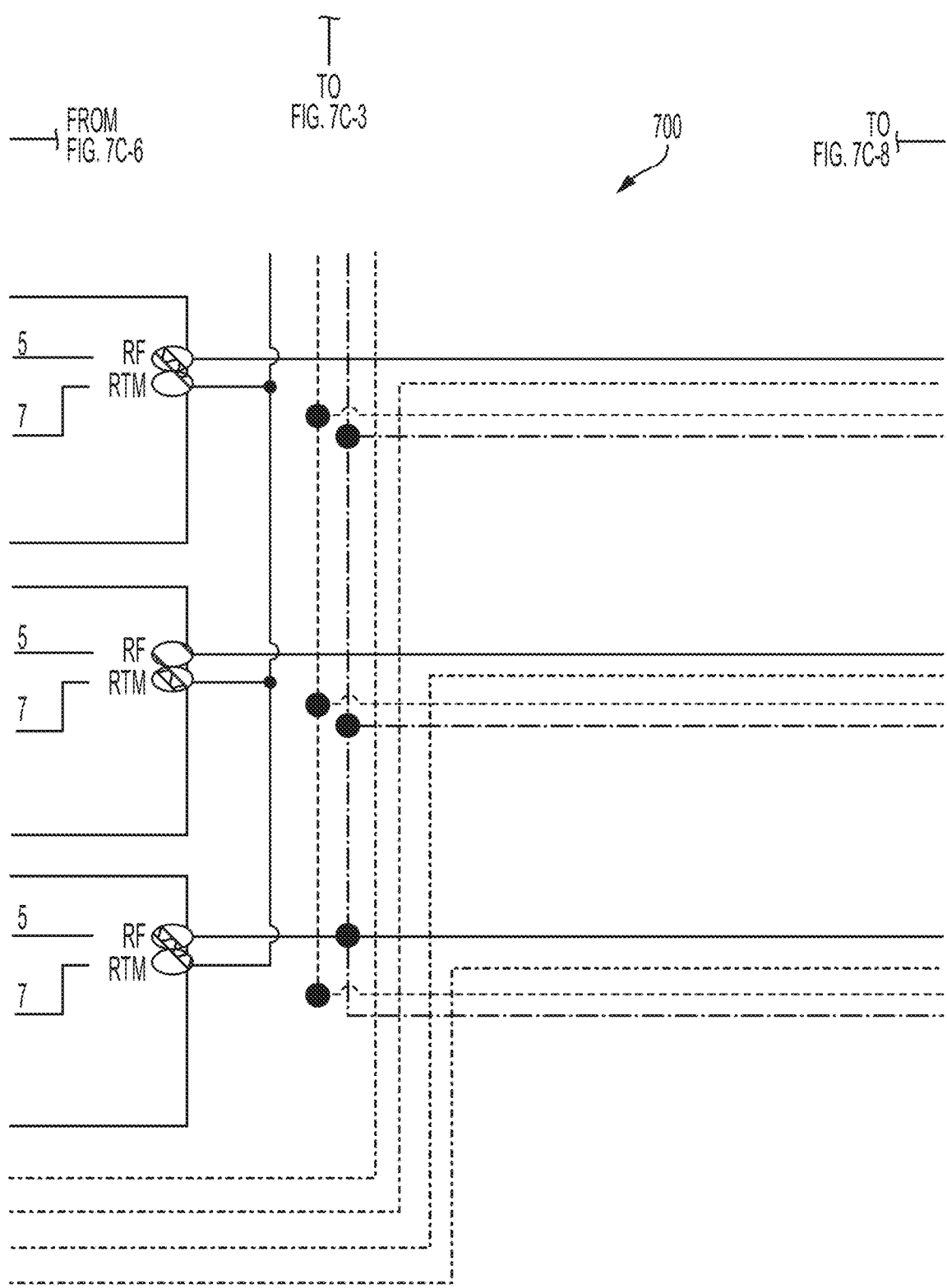
Figure 7C:
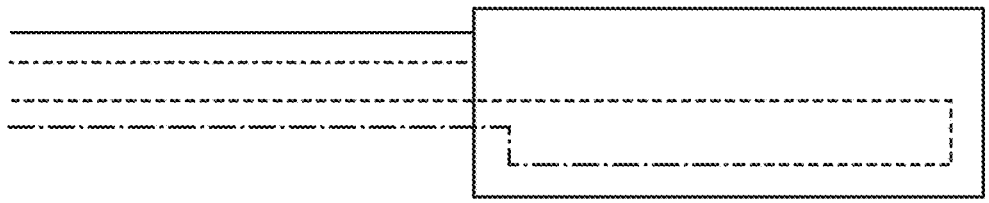
Figure 7:
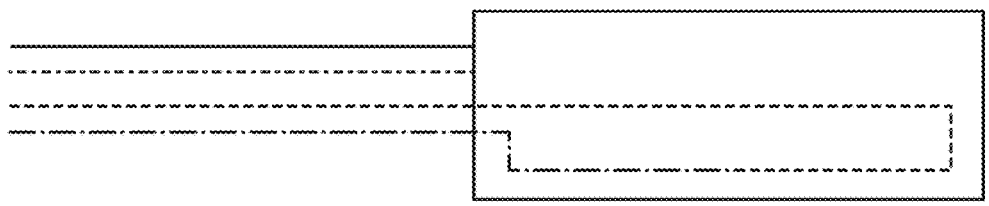

The same exposure is plotted another way in FIG. 7B. Instead of temperature, FIG. 7B depicts the total impedance of the combined array of electrodes plotted against exposure time for two different cooling temperatures, 15° C. as indicated by the squares and 28° C. as indicated by diamonds. Based on the plot and in light of the present teachings, a person skilled in the art would appreciate a clear relationship between the ramp and sustain phases where the impedance is inversely proportional to the tissue temperature depicted in FIG. 7A. In accordance with the present teachings, a person skilled in the art would therefore appreciate that this observation can be utilized to determine an absolute or relative calibration based on the impedance measurements (e.g., relative to the starting point and a recorded delta) that can aid in maintaining the consistency and efficacy of RF treatments.

The plot of FIG. 7B also demonstrates that the detected impedance generally reflects an offset between the different cooling settings (e.g., lower temperature correlates to a higher impedance). In this case, the 15° C. cooling water (as indicated by squares) conductively cools the patient surface and adjacent deeper tissue layers more than the 28° C. cooling water (as indicated by diamonds), thereby resulting in differing offsets or differing nominal starting impedances. Without being bound by any particular theory, this phenomenon may be because the cooler tissue constricts blood vessels, thus resulting in a higher impedance for the cooler 15° C. surface temperature. It can be seen that for the tissue under the 15° C. water-cooled area, the electrode starts at a higher impedance (resistance) than the tissue under the less-cooled area (28° C. cooling water), with the impedances differing by about 19-20 ohms. As noted above, the patient impedance is inversely proportional to the temperature rise at a given depth such that when comparing the FIGS. 7A-B, a person skilled in the art would appreciate in view of the present teachings that a tissue temperature rise of about 11-12° C. at 1.5 cm depth corresponds to about a 19-20 ohms decrease in resistance of the patient tissue. Moreover, in both the 28° C. and the 15° C. curves, a similar delta or decrease in patient tissue resistance (impedance) is observed, indicating a similar temperature at depth. In light of this relationship, the delta in impedance which occurs during the course of the treatment can be effectively used in accordance with various aspects of the present teachings, for example, to determine the treatment endpoint and in order to help maintain a consistent treatment temperature at depth, thereby reducing side-effects due to overtreatment and improving efficacy. Thus, in accordance with various aspects of the present teachings, a control scheme can be provided in which the change in patient tissue impedance can be monitored during the treatment and where the energy emission to the patient is decreased or increased in order to maintain, for example, a target value decrease in resistance (e.g., approximately 19-20 Ohm). That is, the RF signal can be adjusted or modulated to approach and then maintain the impedance at a target value by means of a closed loop algorithm.

Multiple Treatment Pads

Multiple treatment pads can be used in accordance with various aspects of the present teachings. In its simplest form of treatment pads, one array can be used as the "source" and another array as a "return." The two electrode arrays can cover the same area and the clinical endpoint can be the same for the two areas. In this case, there is no return electrode where current is uselessly completing the circuit, but rather the return current is doing the exact same tissue heating as the source current. A multiple electrode array, e.g., two or more electrode arrays or three or more electrode arrays, could also be supported by this method.

Running Multiple Treatment Pads

In some aspects, two or more treatment pads (e.g., treatment applicators having an electrode array) may be run in a bipolar or hybrid configuration as discussed herein in association with FIGS. 1A and 1E. In an embodiment where there can be two or more treatment applicators, each can have an active electrode array that is given its own DC and RF drive circuit, which can be independently controllable, including voltage and phase.

The two or more treatment applicators each have RF drive circuits that operate at the same RF frequency, however, each of the treatment applicators operate at various phases (e.g., the phases are not necessarily the same). In some aspects, for the two or more treatment applicators, all of the RF transformer secondaries (e.g., the "output" side of each transformer that is connected to a subject or patient) are connected together and are referenced to a single drain electrode.

In one embodiment, only one active electrode array is utilized and the drain electrode serves as the return electrode. In this case, all of the RF current flows through both the active electrode array and the drain (return) electrode.

In another embodiment, two or more active electrode arrays are utilized and a minimal amount of current flows through the drain electrode. The RF applied to each of the two or more active electrodes can be controlled, in voltage and/or phase, in order to achieve all or almost all of the current flowing among and between the two or more active electrode arrays, with a minimal amount of current flowing through the drain electrode. This approach can be employed for any number of active electrode arrays greater than one, including odd numbers or even numbers of active electrode arrays. For example, it is feasible using phasing, to have three active electrode arrays sharing all of the current between the three active electrode arrays with minimal current flowing through the drain electrode.

In the case of multiple active electrode arrays, the drain electrode can be used for two purposes: (1) to monitor the voltage among the secondaries of the RF transformers (e.g., the output side of each transformer that is connected to a subject or patient) and hence monitor the body voltage; and/or (2) to act as a "dump" or "drain" of small amounts of RF energy in the case where the anatomy underlying all or a portion of an active RF electrode requires less current than the other of the two or more active RF electrode arrays. In such cases, the phasing can be arranged to divert some of the current to the drain so as to reduce some of the current flowing through one of the multiple active RF electrodes in the array to achieve uniform tissue heating or uniform tissue temperature despite varying anatomy.

Active electrode phasing can also be adjusted to compensate for the anatomical placement of the various active electrodes. In the case of four electrodes, for example, if two are placed adjacent on the body, the active electrodes can be phased so that the two adjacent electrodes are in-phase and do not pass current through the skin between them, but rather act as one large electrode array, effectively heating the desired tissue. Phase control of signal transmitted to electrode can be used to effectively steer energy, current, RF signals, power delivery and other parameters in or near a given target treatment area to facilitate targeted tissue treatment or other objectives of a given treatment.

It will be appreciated that this exemplary architecture can therefore provide for use of any number of active electrode arrays to achieve large area tissue heating without limitations of return electrode size and also with more flexibility as to the placement of the active electrodes.

In one exemplary configuration, three treatment applicators can be connected in a wye or a star configuration, wherein each applicator is provided an RF output 120 degrees out of phase from each other and wherein the RF currents sum to substantially zero on the neutral pad (e.g., drain electrode or return electrode) such that a minimal amount of current flows through the drain electrode. Other exemplary configurations would include an even number of applicators (e.g., two or four treatment applicators) and where the phase angles of the RF power signal to each applicator are 180 degrees out of phase. In the case of four applicators, two of the four applicators could have a phase angle of 0 degrees, for example, and the other two could have a phase angle of 180 degrees, wherein RF power returning via the drain electrode would be substantially zero, or sum to zero.

Any even number of applicators can be applied with a result of substantially zero neutral or minimal amount of return current flowing through the return pad by providing an equal number of electrodes with phase angle 0 and phase angle 180 degrees. In the case of an odd number of applicators, multiples of three may be utilized with a result of substantially zero neutral return current or a minimal amount of return current by delivering a phase angle difference of 120 degrees and where the number of applicators operated at each phase angle is equal with respect to each node. In the case of six applicators, for example, a RF signal of phase angle 0 could be applied to two applicators, a different RF signal of phase angle 120 degrees could be applied to two other applicators, and a different RF signal of phase angle 240 degrees could be applied to the remaining two applicators.

In the case of an odd number of applicators which are not divisible by 3 (e.g., 5, 7, 11, 13, etc.), the return current will not sum out to substantially zero. However, the neutral return current will be substantially equivalent to the RF power provided to a single applicator and the remaining applicators all cancel out one another, and as a result, they sum to substantially zero return current.

For such cases of odd number of applicators which are not divisible by 3, there can be two equal groups at 180 degrees out of phase from each other, and the remaining electrode can be operated at any phase angle. Alternatively, the number of applicators can be divided into three groups of equal numbers, with each group operated at 120 degrees out of phase, with the remaining ungrouped applicator operating at any phase angle. In both of these examples (two groups 180 degrees out of phase, or three groups 120 degrees out of phase), all applicators sum to substantially zero return current except for a single applicator, which would not sum to zero and where the neutral return current would be substantially equivalent to that of a single applicator regardless of how many odd number of applicators that is not divisible by 3 is used.

The utility of these approaches where the neutral return currents sum to zero (except for one treatment applicator) is that any number of treatment applicators can be used without concern of overheating the return pad. As a result, a very large area of the body can be simultaneously treated/covered with treatment applicators, while requiring the use of only a single return pad. Optionally, multiple return pads can also be used. In this case, the individual applicator size could increase since the return current (substantially corresponding to only one applicator as described above) will be distributed amongst the multiple return pads. This can allow the treatment applicator size and number of treatment applicators/electrode arrays to be scaled to properly address a given treatment area. In these examples, substantially zero presumes a substantially equivalent amount of energy delivered to each treatment applicator (e.g., a substantially even underlying anatomy). However, where small variations in the RF power delivered to each treatment applicator or electrode array are observed due to variation in the anatomy underlying each applicator or electrode array, a minimal amount of return current may flow to the drain (return) electrode.

Referring now to FIG. 7C, the exemplary electronics for a system 700 in accordance with various aspects of the present teachings is depicted, with inset 700' representing a block diagram of the single electrode array/applicator. Element 720 represents the neutral electrode return circuit. Elements 730, 740, 750, 760 represents four separate RF amplifiers (e.g., RF energy sources) which are connected in wye configuration and may be operated at any phase angle with respect to each other. Each RF amplifier is connected to a single electrode array/treatment applicator. For example, RF amplifier 730 is connected to electrode array 700'. As shown, an adjustable 48V isolated DC power supply 770 provides electrical power to the four RF power amplifiers. A block diagram of the system controller 780 determines the operating level and phase angles at which each RF amplifier operates. The isolated communication circuit 785 connects each applicator to the system controller 780. The applicator/electrode array controller 790 switches individual electrodes within a single array and also monitors individual electrode voltages, currents and phase, within the single array and this electrical feedback is used to determine the impedance of each individual electrode within an electrode array/applicator. As discussed otherwise herein, the controller 790 is capable of adjusting the duty cycle of RF energy applied to each individual electrode within the electrode array so as to enable the uniform deposition of thermal energy in tissue below the array.

In some exemplary aspects, a system for treating a patient's tissue can include two or more treatment applicators that are employed to treat a single region of patient tissue (e.g., the abdomen) or to treat differing regions of patient tissue (e.g., the upper arm and the thigh). To be capable of both types of treatment, each treatment applicator can have its own individually-controllable RF energy source and each of the RF energy sources can operate at the same fundamental frequency (e.g., at a single fundamental frequency), but the phases and the amplitudes of each of the two or more RF energy sources can be controllable. Specifically, the phases and the amplitudes of each of the two or more RF energy sources may be controlled relative to one another to enable sharing of current amongst the two or more applicators. In various aspects, this capability to share current amongst the two or more applicators can enable the flexible placement of the applicators on the body of the subject such that the two or more applicators may be placed in the same treatment region (e.g., the abdomen) or in two distinct treatment regions (e.g., one applicator placed on the upper arm and the other applicator place on the thigh) so that each distinct treatment region can have a suitable amount of RF energy delivered thereto. For example, in an embodiment where one applicator is placed on the upper arm, any excess current flowing to the upper arm that would be unnecessary to treat the targeted tissue can be shared with (e.g., diverted to) the other applicator to treat the thigh tissue, a region of higher tissue density than the arm. In some embodiments, a return or drain electrode can additionally be employed. In various aspects, the two or more treatment applicators each can have a plurality of treatment electrodes (e.g., an array of treatment electrodes) configured to be disposed in contact with a surface of a patient's tissue and to deliver RF energy thereto, wherein the plurality of treatment electrodes comprises at least two individually-addressable treatment electrodes to which RF signals can be applied.

Drain Pad

A drain pad may be used to balance two treatment pads, for example. If multiple arrays are used, one may heat up faster than the other requiring that some of the RF energy be drained off to a third, non-treatment return electrode.

Water Temperature Changes

Water temperature changes can be induced by changing the set-point of the coolant and thereby changing the heating profile in the skin. Colder temperatures would drive the heated zone deeper, and conversely, heating the water will bring the zone closer to the dermis for tightening. In various aspects, the circulating water can be configured to maintain the temperature of the skin in a range of about 15-35° C. during the treatment, with adjustments occurring to effect the sensation/patient comfort and/or to control the depth of the heated zone as discussed otherwise herein.

RF Modulation

Modulation of the RF power may be utilized to improve the sensation (e.g., reduce patient pain). By way of example, the hyperthermic treatment can be confined to the target tissue while keeping temperatures of tissue (e.g., epidermal and/or dermal tissue) above the targeted tissue at depth below injury threshold (i.e., lower than about 46-47° C.). For example, the RF treatment parameters (such as delivery pattern, power, pulse duration, etc.) can be modulated over the treatment time, and in some aspects by taking into account the cooling rate on the skin surface, an optimized temperature profile/gradient in the target tissue (e.g., tissue about or below the dermal/hypodermal junction such as hypodermal tissue) can be achieved during the treatment.

Electrode Sampling

Sampling of each individual electrode for control purposes can be preferably done at frequencies that avoid the enervation of muscular nerves. While the fundamental frequency is between 0.5-4 MHz (lower frequencies may be preferred to reduce cross talk between electrodes), the control loop may operate at frequencies closer to 100 Hz. The modulation of the duty cycle of each electrode should be staggered to reduce the effects of nerve enervation.

Exemplary Treatments of Mucosal Tissues

As noted above, systems and methods in accordance with various aspects of the present teachings can also be utilized to provide treatment to various internal tissues by applying RF energy to mucosal tissue surfaces via a water-cooled treatment electrode or electrode array operating in either monopolar or bipolar mode, the RF energy propagating from the mucosal tissue surface into the deeper tissue layers. In such aspects, tissue remodeling, for example, can be accomplished by the heat generated within sub-tissue surface regions by tissue-penetrating RF energy, while the cooling can protect overlying tissue. In some embodiments, the RF electrode array for treatment of mucosal tissues is uncooled. Though described below with reference to exemplary treatments of the vagina (e.g., vaginal laxity, rejuvenation, urinary incontinence, and other genitourinary conditions), it will be appreciated that the present teachings can be adapted to provide a desired treatment to other internal tissue surfaces (e.g., esophagus, oral cavity, treatment of fecal incontinence and digestive tract).

Stress urinary incontinence (*SUI*), for example, is a condition characterized by the inability to prevent involuntary urination when the body is stressed, e.g., during coughing, sneezing, or vigorous physically activity. It is commonly the result of weakened muscle strength at the neck of the bladder and around the urethra. *SUI* is often reported by postmenopausal women and is believed to be associated with vaginal changes that occur during menopause that weaken the vaginal wall or the muscles that lay between the vaginal wall and the urethra. While surgical interventions are known and sometimes necessary in severe cases of vaginal laxity, surgery is often undesirable because of the costs, time-consuming recovery periods, and potential side effects and complications. Non-surgical devices and methods of treating *SUI* and other genitourinary conditions, particularly in women, would therefore meet a long-felt need.

In various aspects, the methods and systems in accordance with the present teachings can deliver a controlled amount of heat through the application of RF energy to the vaginal wall to remodel tissue, e.g., the anterior vaginal wall so as to treat *SUI*. The tissue can be the vaginal wall itself or tissue adjacent to the vagina in the vicinity of the urethra. For example, a target region for localized heating can be the tissue between the vaginal wall and the mid-urethra. In certain aspects, the target tissue can be heated to about 40° C. to about 45° C., or from about 41° C. to about 43° C., or to about 42° C. (e.g., without surface cooling). The RF energy can be applied for a period of time, preferably less than 30 minutes, or less than 10 minutes, or in some instances less than five minutes. For example, RF energy can be applied for about one minute to attain the desired temperature in the target tissue region and continue to be applied to maintain the desired temperature for about 5 minutes. Thereafter the heat source can be deactivated, and the treatment probe can be allowed to cool and removed from the vagina. In some instances, the entire procedure can be completed in less than 10 minutes. Optionally, if surface cooling of the mucosal tissue (e.g., vaginal tissue) is utilized, the tissue can be heated to temperatures higher than in a range from about 40° C. to about 45° C., for example, from about 40° C. to about 70° C., or from about 45° C. to about 60° C.

In certain aspects, the method can include the step of applying RF energy to the anterior vaginal wall, to a treatment depth of about 2 to 9 cm, preferably about 5 to 8 cm, or more specifically to about 7 cm beyond the outer vaginal wall surface. In such embodiments, the anterior portion encompasses about 120 degrees of the vaginal wall closest to the urethra, e.g., from about 10 to 2 o'clock, from 11 to 1 o'clock, from half past 11 to half past 12 o'clock, with the 12 o'clock defined by the portion of vaginal wall closest to the urethra.

In certain aspects, it can be desirable to uniformly heat the entire target volume. Various methods of ensuring uniform heating by varying the power delivered by individual electrodes as discussed otherwise herein. However, in some aspects, the methods of the disclosure can also include using an array of electrodes to deliver heat to multiple loci of tissue within a target region. This fractional heating creates a lattice of hyperthermic islets, with each islet surrounded by relatively unaffected tissue. Such "fractional" therapy can be a desirable method of tissue remodeling because damage occurs within smaller sub-volumes or islets within the larger volume being treated. Because the resulting islets are surrounded by neighboring healthy tissue that is substantially spared from the damage, the healing process can be thorough and fast.

Devices and methods of treating female genitourinary conditions, such as urinary incontinence, particularly stress urinary incontinence, are disclosed to remodel tissue in the anterior region of the vaginal wall and/or in the muscles adjacent to the vaginal wall in the vicinity of the urethra.

The devices can include a probe adapted for vaginal insertion having a surface configured to apply heat to the anterior vaginal wall. In certain embodiments, the probe can take the form of an elongated tube or wand having one or more therapy pads, e.g., RF energy radiating electrode arrays, to deliver energy to the tissue either in contact with the probe or in proximity to it. As described previously, each electrode within the array can be addressed and activated individually. The individually programmable electrodes in the array not only permit delivery of tailored therapy but can also serve as sensors when not active, thereby permitting control of the applied energy to achieve a desired heating regime and homogeneity of treatment within a target region regardless of variations in the patient's underlying tissue electrical impedance or anatomical structures.

The probe can also include one or more temperature sensors to monitor the temperature of the vaginal wall surface and/or the target tissue. For example, the temperature sensors can be thermistors or infrared (IR) sensors configured to detect black body radiation emitted by heated tissue. Alternatively, temperature monitoring can be implemented by one or more of the electrodes operating as an impedance measuring electrode. The relationship of impedance changes with temperature is described in this application. The probes can also include cooling pads to avoid overheating of the vaginal wall surface and thereby permit heat to be primarily delivered to subsurface target tissue regions.

In certain embodiments, the probe can include an array of pads or electrodes, programmable such that a subset of the array components can be activated to deliver heat to a specific region or in a specific pattern. For example, RF electrodes can be distributed over all or part of the probe's surface to heat either the entire vaginal vault or section of the vaginal wall. A plurality of electrodes allows for not only mono-polar treatments (characterized by an energy path from at least one electrode to a remotely located return pad) but also bi-polar treatments (with energy flowing between electrodes). In certain embodiments, the plurality of electrodes can also be employed to monitor tissue impedance (or simply resistance) in order to map the underlying tissue and/or to further control procedures. For example, adjustment of power gated to individual electrodes based on the tissue impedance map can be used to homogenize the temperature rise across all treated areas. Controlling individual electrodes output power (e.g., via gate duty cycle) also permits the clinician to achieve a controlled and consistent tissue temperature rise across all treated tissue ranges. This is especially useful for a device that is fixed to the anatomy, activated and subsequently only monitored by the physician or staff member.

In certain embodiments, the probe can also include one or more fixation devices. For example, a locking sleeve or sheath can be provided that can be inserted into the vagina before the probe can be employed to fix the probe in place at a desired orientation and depth for treatment. The probe can also include one or more inflatable elements which can be inflated following probe insertion to force the energy-delivering elements of the probe into proper contact with the anterior vaginal wall. The devices of the present disclosed herein can be handheld or computer-directed. The probes can include markings to indicate depth of penetration.

Systems incorporating the devices are also encompassed by the present teachings including, for example, controllers, power supplies, coolant reservoirs, monitors and alarms, all or some of which can be incorporated into a console providing a graphic user interface and displaying various parameters. The systems can also include imaging elements, either within the probes themselves or partially within the probes and used in conjunction with an ancillary transurethral catheter, to help identify the target tissue region.

Alternatively, the probes can be used in conjunction with stand-alone imaging systems, such ultrasound, x-ray or fluoroscopic imagers.

In other aspects, the devices and methods disclosed herein can be used to treat other genitourinary conditions by delivering a controlled pattern of heating or RF energy to other regions of the vagina. One or more embodiments of this disclosure can further be used to rejuvenate vaginal tissue generally and provide relief from numerous genitourinary syndromes of menopause (GSM).

It is believed that the close proximity of the urethra and the vagina influences the improvement in SUI symptoms. Without being bound by any particular theory, it is further believed that heating of the vaginal wall and adjacent tissue between the vagina and urethra leads to tissue remodeling by contraction of the target tissue, collagen regeneration, enervation or combination thereof, such that urinary leakage symptoms improve.

Figure 8:
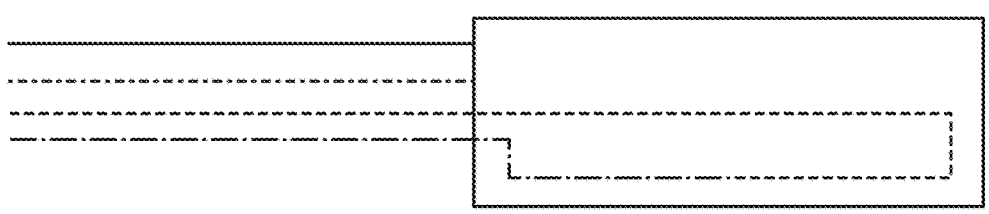
Figure 8:
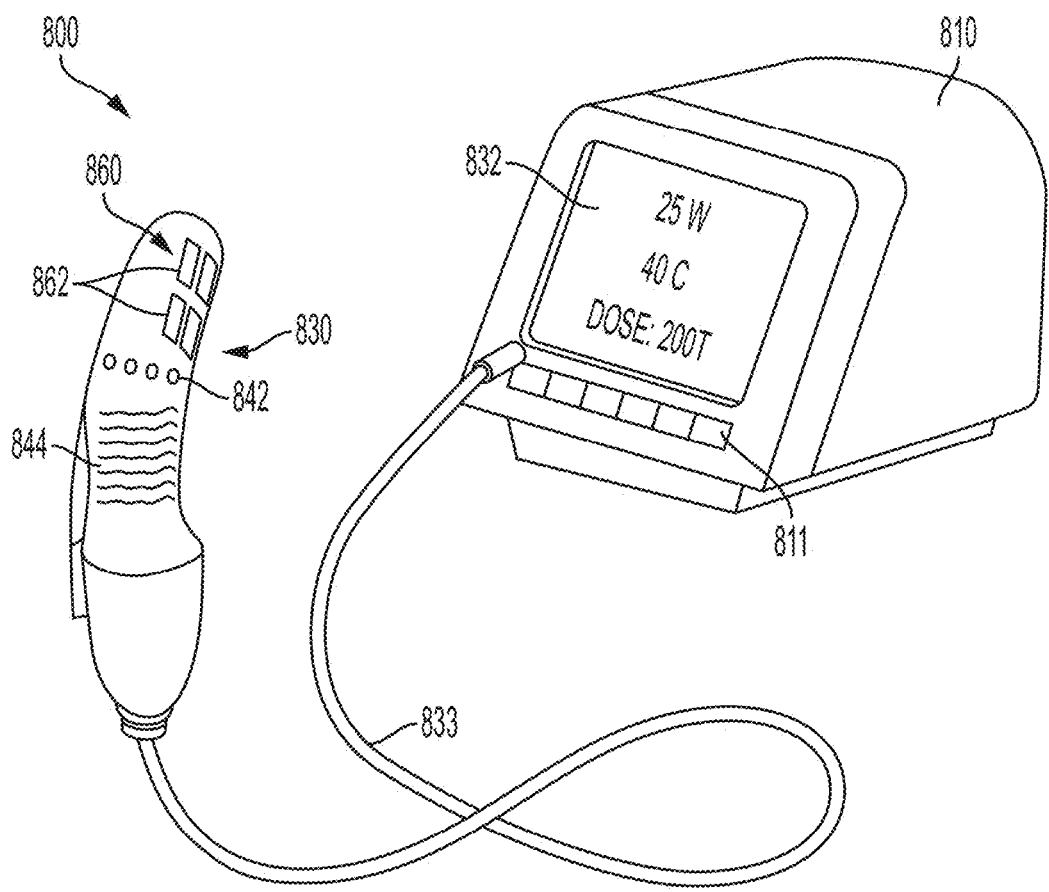

With reference now to FIG. 8, an exemplary system 800 in accordance with various aspects of the present teachings is schematically depicted. As shown, the system 800 includes a console 810 that houses an RF generator and other electronic components (e.g., one or more microprocessors) and provides a display 832, for example, of the operating parameters. In one embodiment, the RF generator is designed to incorporate one or more features described herein with regard to Node 1. Node 1 may be disposed in or near console 810 in various embodiments. The display 832 can be a touch sensitive screen, for example, that provides a graphic user interface (GUI) and/or the console 810 can provide separate user controls 811. As noted above, though some exemplary applicators are described herein as being generally planar (rigid or flexible) arrays of electrodes, in some exemplary aspects, the applicator can be configured for insertion into a patient (e.g., through a lumen or natural body orifice) so as to provide for the application of RF energy to a mucosal tissues surface (e.g., vaginal wall, esophageal lining). By way of example, as shown in FIG. 8, the applicator can comprise a generally tubular probe 830 (e.g., a wand-like applicator) that can be sized and shaped to be inserted into the vagina or esophagus for RF treatment thereof. The console 810 can be connected to the intelligent, temperature controlled probe 830 via a cable or umbilical 833, for example, for delivery of RF energy from a generator disposed within the console 810 to the probe 830. In certain aspects, the console 810 can also house a coolant source to provide circulating coolant to the applicator probe 830 via a cable or umbilical 833, as discussed otherwise herein. It will be appreciated that in certain aspects, the probe 830 can instead be wireless and contain its own RF generator, electronics, cooling and power supply (e.g., rechargeable batteries)).

As shown in FIG. 8, the probe 830 can be used for tissue heating and can include an array 860 of electrodes 862 which range from two to several hundred that can have an individual area of approximately 1 cm², by way of non-limiting example. As will be understood by a person skilled in the art in light of the discussion herein, the probe 830 can comprise a plurality of electrodes (or groups of electrodes or groups of arrays of electrodes) that can be activated to apply RF energy to the target tissue in monopolar or bipolar mode. By way of example, in some aspects, one electrode or a group of electrodes of the probe 830 can represent the "active" electrodes while another electrode or a group of electrodes can represent the neutral "return" electrode. Alternatively, it will be appreciated that a return pad can be placed on the skin surface (e.g., near the pubic region, on a portion of a patient's leg) during a vaginal treatment to provide a return path for the RF energy provided by the electrodes to the mucosal lining of the vagina. Further, as discussed in detail below with respect to FIG. 11 for a separate probe 1130, the electrode array 1160a can consist of pin-point electrodes 1162a configured to fractionally ablate the mucosa (e.g., 50 individual electrodes in a 5×5 mm area). With reference again to FIG. 8, the probe 830 can further include one or more temperature sensors 842. In various aspects, the probe 830 can further include markers 844 to indicate the depth of its penetration into the vagina.

Figure 9:
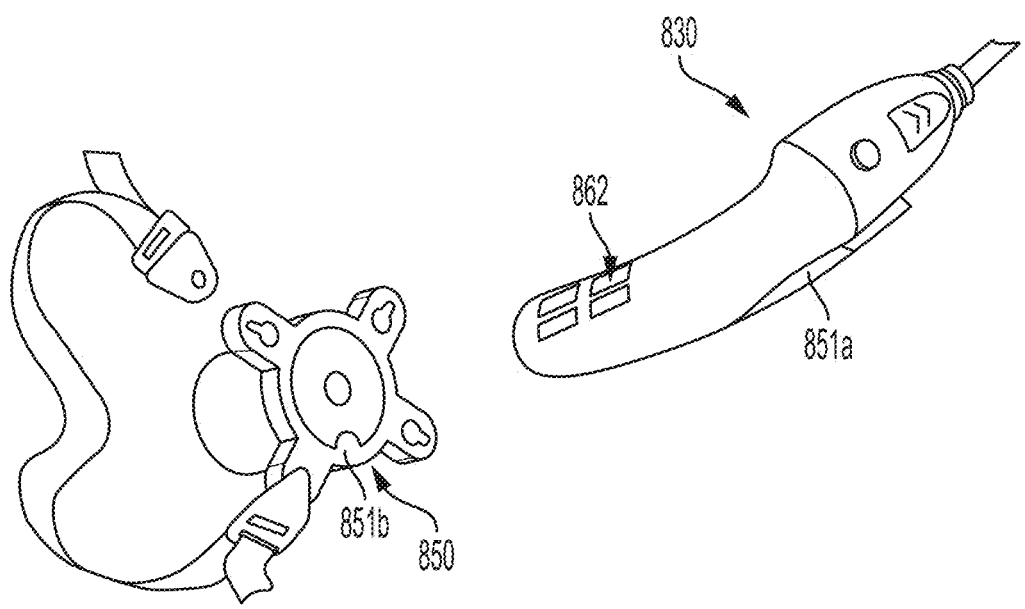
FIG. 9 is schematic perspective view of a probe and an introducer according to various aspects of the present teachings.

As shown in FIG. 9, the system 800 can also include a locking sleeve or sheath 850 (or introducer) that can be useful for guiding the treatment, for example, to ease insertion, provide alignment, and/or to set a depth based on sounding of bladder neck with a Foley catheter or manual sounding of the vagina. By way of example, the probe 830 can include a groove 851a to mate with a corresponding ridge 851b on the introducer 850, though other mating or locking mechanisms can be substituted as will be appreciated by the person skilled in the art in light of the teachings herein.

Figure 10A:
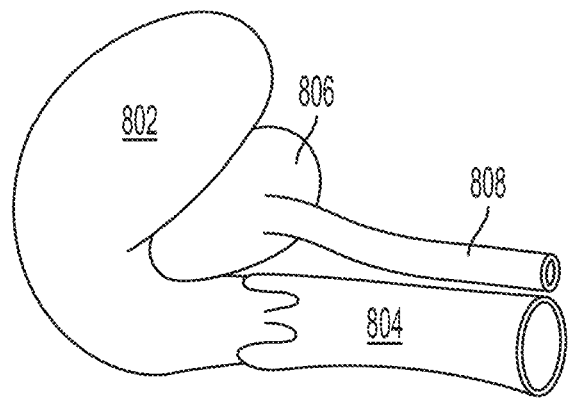
FIG. 10A is a schematic illustration of a female genitourinary tract.
Figure 10B:
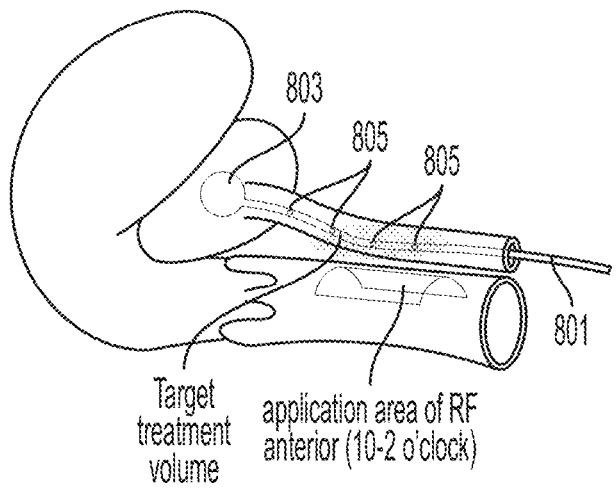
FIG. 10B is a schematic illustration of a female genitourinary tract showing insertion of a monitoring catheter into the urethra.
Figure 10C:
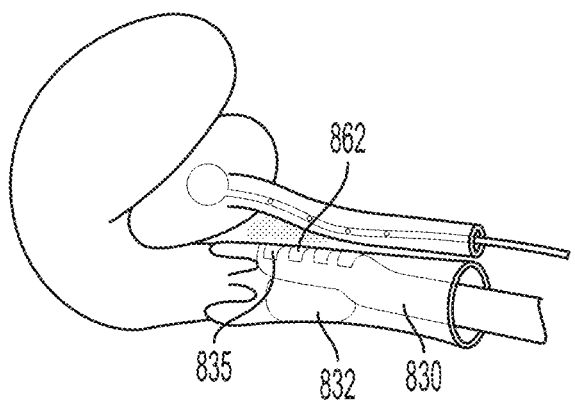
FIG. 10C is a schematic illustration of a female genitourinary tract showing insertion of a vaginal treatment probe in accordance with various aspects of the present teachings.

With reference now to FIGS. 10A-C, an exemplary method of treating SUI in accordance with various aspects of the present teachings is illustrated. In particular, FIG. 10A provides a schematic illustration of the female genitourinary tract including the uterus 802, vagina 804, bladder 806, and urethra 808. At the vaginal opening, the urethra 808 and vaginal wall are anatomically close. However, as the urethra 808 nears the bladder neck, the urethra 808 is separated from the vaginal wall. In various exemplary aspects, this is the region targeted for the RF-based heat therapy (e.g., near the mid urethra).

With reference now to FIG. 10B, the insertion of a catheter 801 (e.g., a Foley catheter) is shown after insertion into the urethra 808. As shown, the catheter 801 can be inserted in to the urethra 808 until its distal end reaches the bladder 806, after which a balloon 803 can be inflated to stabilize and fix the catheter 801 in place. The urethra's full length can be identified by the external orifice and its termination at the bladder neck. Identification of the bladder neck is a routine clinical practice by inserting a catheter, inflating the balloon, and retracting it until the balloon hits the neck.

In certain aspects, the catheter 801 can include one or more temperature sensors 805 disposed along its length and configured to measure, for example, a temperature rise in the urethra 808 and/or to monitor the temperature of tissue remote to the tissue-electrode interface (e.g., at the target tissue that is intended to be heated). The catheter 801 can also be connected to the console 810 of FIG. 8 such that current to the RF probe 830 can be controlled by monitoring impedance to ensure contact between the probe electrodes 862 (e.g., individually-monitored electrodes) and the vaginal wall, as discussed otherwise herein.

As noted above, in certain aspects, the target region targeted for the RF-based heat therapy (e.g., near the mid urethra) can be located at about the mid-urethra as the urethra 808 becomes separated (e.g., diverges) from the vaginal wall. In various exemplary aspects, the target region 809 can be the tissue that lies beyond the vaginal wall between the vagina 804 and urethra 808. To heat this region via application of RF energy, it is preferable that the probe's electrodes 862 should be disposed in contact with the anterior wall of the vaginal vault, as shown in FIG. 10B.

With reference now to FIG. 10C, exemplary procedures in accordance with various aspects of the present teachings are depicted in which the probe 830 is disposed in contact with the desired regions of the vaginal wall such that one or more electrodes 862 can heat the vaginal wall via the application of RF thereto. It will be appreciated that more than one electrode 862 can be used simultaneously to apply RF energy, for example, if it is desired to heat a larger length or width of the vaginal tissue with a less tiring hand motion (or to automate the procedure). In various exemplary aspects, the probe 830 can further include an inflatable balloon 832 to stabilize the probe 830 in contact with the vaginal wall surface. As discussed otherwise herein, the electrodes 862 can be connected to a common node (e.g., one or more electrode clusters) or can be individually controlled to only deliver power to those electrodes in contact with the vaginal wall, for example. In various aspects, each of the plurality of electrodes 862 (or groups of electrodes 862) can be activated to apply RF energy to the target tissue in monopolar or bipolar mode. Alternatively, it will be appreciated that a return pad (e.g., pad 130e of FIG. 1C) can be placed on the skin surface (e.g., near the pubic region, or on a patient's thigh) during a vaginal treatment to provide a return path for the RF energy provided by the electrodes 862 to the mucosal lining of the vagina 804. Alternatively, in various aspects, the catheter 801 can serve as a return path to focus the energy into the tissue between the vagina 804 and the urethra 808. It will be appreciated that configuration can help concentrate tissue heating to the vaginal wall immediately adjacent to the urethra 808, any muscle in between, and the urethra 808 itself. In yet another aspect, the probe electrodes 862 can be bi-polar such that one electrode 862 in the array 862 (or a group of electrodes) act as a therapeutic "active" electrode emitting RF energy, while one or more other electrodes in the array 860 act as a "return" (grounding) electrode to provide an electrical return path for the RF energy. In certain aspects, pulsed RF, concentrating high energies in short pulses, can be preferred.

In certain aspects, a hands free set-up can be preferred. For example, after sounding the vagina and bladder neck, a practitioner can adjust the probe 830 to apply the RF to the correct zone along the urethra 808, fix the probe 830 into place with a balloon 832 or other means, and employ feedback to determine that the probe 830 (and its electrodes 862) are in contact in order to initiate the application of RF. In accordance with various aspects of the present teachings, the probe 830 can then be operated so as to uniformly deposit RF energy, maintain a uniform desired temperature range in the target region, provide consistent dosimetry, and/or provide surface cooling as discussed otherwise herein.

The probe 830, for example, can also include a cooling mechanism 835, such as one or more cooling surfaces interspersed with the electrodes 862 that cool the vaginal wall surface by circulation of a coolant through the probe 830. Alternatively, in various aspects, cooling can be achieved by thermoelectric (Peltier) devices or the use of a phase change material (e.g., ice) in thermal contact with a patient contact surface (e.g., via the electrodes). As discussed otherwise herein, controlling the temperature of the electrode-tissue interface can be useful to control the depth of targeted tissue. Cooling can change the therapeutic goal such that heating the target tissue is not limited due to patient tolerance (e.g., in a range from about 40° C. to about 45° C.). With cooling, for example, the target temperature can be increased to a temperature in a range from about 40° C. to about 70° C., or from about 45° C. to about 60° C.

Figure 11:
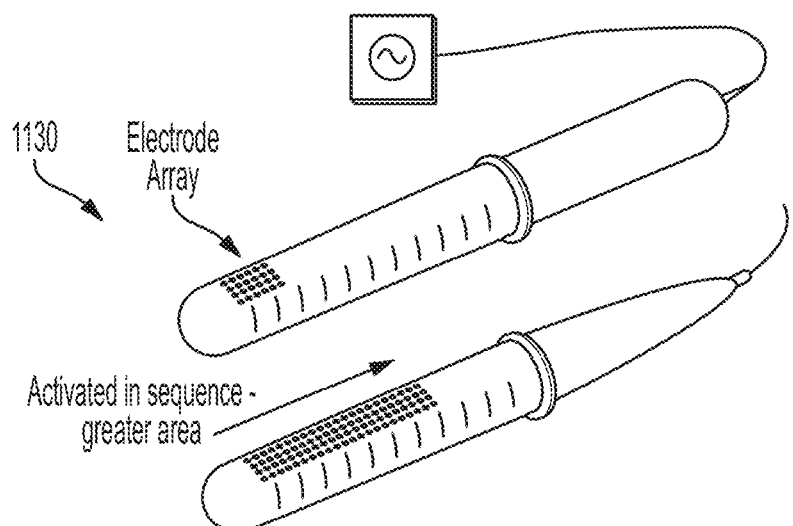
FIG. 11 is a schematic illustration of a probe according to exemplary aspects of the present teachings for operating in two different modes.

With reference now to FIG. 11, another exemplary probe 1130 according to various aspects of the present teachings is depicted. As shown, the probe 1130 can include a plurality of distinct electrodes 1162 disposed over the entire surface of the probe 1130, as opposed to the anterior, distal region of the probe. It will be appreciated in view of the present teachings that the advantages of such a probe 1162 includes the ability to treat the entire vagina 804 by means of switching differing electrodes on and off. This type of probe (electrodes over entire surface) could treat vaginal conditions (rejuvenation) other than SUI, throughout the vagina. However, to address the SUI-treatment target tissue region alone, the electrodes 1162 within the desired anterior vaginal region (e.g., in the 10 o'clock to 2 o'clock positions) could be energized, while the other electrodes remain off. Additionally, such a probe can allow the clinician to adjust ranges greater than the 10 o'clock to 2 o'clock positions, for example, by energizing more electrodes and thereby treating a larger area of tissue up to including the entire circumference of the vagina. Such a probe can likewise allow the clinician to adjust ranges narrower than the 10 o'clock to 2 o'clock positions, for example, by energizing fewer electrodes and thereby treating a smaller area of tissue. Any desired region (or the entirety of the vagina) can thus be selected for treatment.

Various aspects of the control of the RF therapy can be based on the feedback from multiple temperature sensors along the urethra. If the urethra is the target to be heated for stimulation of the tissue and surrounding musculature, having a monitor within the urethra can help standardize clinical outcomes and significantly improve safety. Thus, monitoring temperature at discrete locations along the catheter can be beneficial to enable detection of any thermal anomalies, e.g., hot spots. Additionally or alternatively, these discrete temperature sensors can inform the treatment endpoint decision. Variations in patient anatomy and tissue perfusion can thus be compensated for by monitoring the actual tissue temperature rise during the application of the RF energy.

In various aspects, both long duration, low irradiance (~1-5 W/cm$^2$) and short duration, high fluence (~10-1000 J/cm$^2$) regimes discussed previously herein are also envisioned for tissue accessed internally and can provide contrasting benefits as to biological target selection and treatment. Without being bound by any particular theory, the method of action can be thermal in nature where delivered RF power acts to heat or even coagulate selected tissues. For long, continuous exposures, uniform heating of structures can be accomplished. For short bursts of concentrated energy, foci of ablated tissue can be created. In various aspects, it can also be desirable to ensure uniformity of delivered RF energy. To provide efficacious treatment in some applications, it can be desirable to not only raise the temperature of target tissues to a temperature range, but also to hold the target tissue in the targeted region at an elevated target temperature for a given duration. That is, maintaining the temperature for a period of time can confer a desired clinical benefit. It can also be advantageous to actively control the RF energy as discussed herein to distribute energy through targeted tissues in the targeted treatment zone in a homogenous fashion, uniformly, predictably and automatically (e.g., without user intervention). In addition, RF pulse duration can be used to select and/or target particular tissue. High magnitude, short duration RF pulses, when concentrated to small electrode-tissue interface areas, can generate sufficient flux or current density to coagulate and vaporize tissue, thereby resulting in the "fractional" treatment discussed above.

Figure 12:
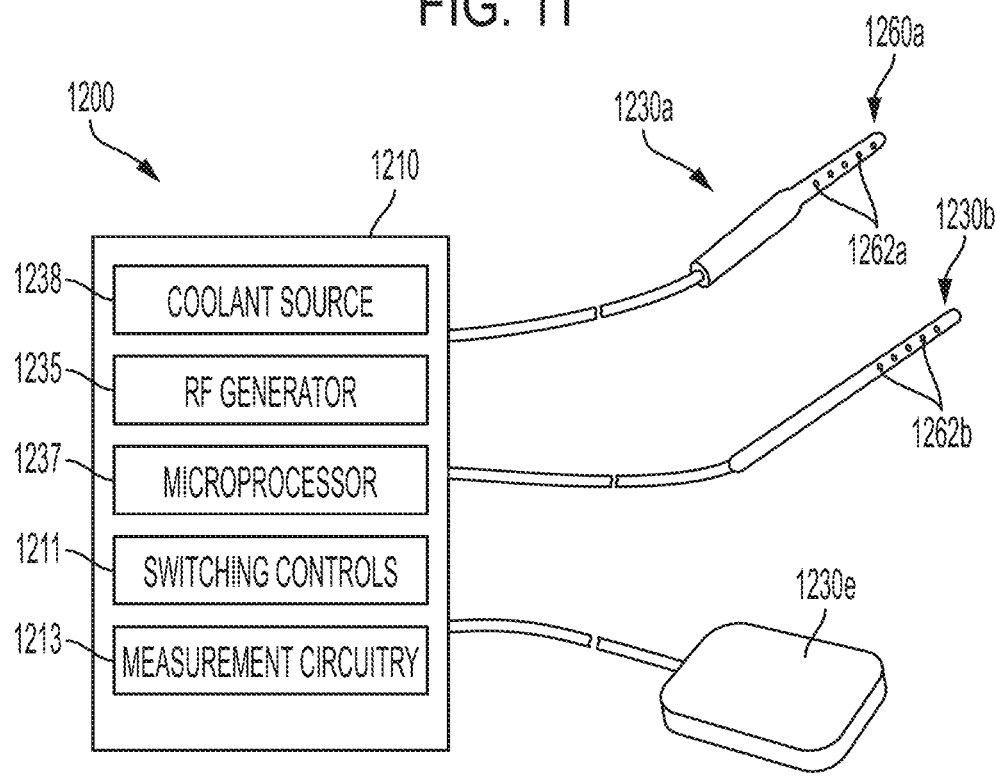
FIG. 12 is a schematic illustration of a RF system including exemplary electronics according to various aspects of the present teachings.

With reference now to FIG. 12, another exemplary system 1200 in accordance with the present teachings is depicted.

As show, system 1200 can include a console 1210, a coolant source 1238, a microprocessor 1237, an RF power source 1235, switching controls 1211 and measurement circuitry 1213 (which can be separate or housed together in a single console 1210). The system 1200 further includes at least one probe 1230a with an associated array 1260a of electrodes 1262a. The individual electrodes 1262a of the array 1260a can be independently switched by the switching controls 1211 to gate RF energy to individual electrodes in the array. Electrodes not actively receiving RF energy can be monitored by the measurement circuitry 1213 such that each electrode serves as a signal channel, providing current, voltage, and/or phase angle feedback useful for calculating the power and impedance at each of the individual electrodes 1262a. The system 1200 can further include an optional second probe 1230b to provide an electrical return path. Probe 1230b can also include an array 1260b to either deliver RF energy or provide another mechanism for sensing impedance and/or other electrical parameters and/or temperature. In some embodiments, probe 1230b can be incorporated into a catheter for disposition in the patient's urethra. Alternatively or in addition, the system 1200 can also include a return (ground or neutral) pad 1230e, for example, to be connected to the patient so as to provide a drain for applied electrical current. The system 1200 can be used with other applicators disclosed herein in various embodiments.

As discussed otherwise herein, electrode arrays suitable for use on internal tissue surfaces can also have a variety of configurations in accordance with the present teachings. For example, the electrode array can be configured as a probe including of a metal coolant housing, with an electrical insulating and thermal conducting layer (e.g., Kapton® polyimide or a ceramic, such as A102 or the like) located between a coolant circuit and the electrode array. The electrode array can be attached to the applicator cooling housing via an adhesive such that a circulating coolant, e.g., chilled water from a coolant source, can cool the electrode array and the patient's internal tissue surface to which the electrodes are disposed in contact (e.g., the vaginal wall).

In various exemplary aspects, for example, the electrode array applicator can have 50 individually controlled electrodes arranged in a square, circular, or hexagonal pattern. Additionally or alternatively, the surface temperature of the patient's tissue surface (e.g., the vaginal wall) in areas around the perimeter of the applicator electrode array can be monitored by IR sensors, thermocouples, or the like (by way of non-limiting example) so as to identify uneven heating of vaginal wall surface areas adjacent to the intended treatment zone. Based on these signals, a microprocessor and algorithm can provide correction factors to the RF power setpoint for individual electrodes so as to optimize treatment uniformity, homogeneity, and placement of the treatment zone. In various aspects, the electrodes can be individually monitored for impedance as discussed otherwise herein, which can be used by the microprocessor and algorithm to define a map of the patient's impedance topography and to provide correction factors for changing the RF power setpoint to optimize treatment uniformity, homogeneity, and placement of the treatment zone.

Cooling of patient's internal tissue surface to which the electrodes are applied (e.g., the mucosal lining, the vaginal wall) can protect the tissue surface and also improve patient comfort during the procedure or minimize discomfort afterwards. Adequate surface cooling (e.g., via circulating water within the probe at about 10° C. to 35° C.) allows the application of larger magnitude of RF power safely and comfortably. This can be desirable as most target tissues are located at some depth from the internal tissue surface (e.g., the vaginal wall surface) and therefore surface cooling acts to protect the intervening tissue layers which are not targeted and allows the heat to penetrate deeper into the tissue. Because mucosal tissue tends to have nerve endings that are close to the surface, cooling the tissue surface enables higher temperatures to be tolerated by the subject at the desired treatment depth below the cooled surface.

As discussed above, individually-switched electrode arrays (e.g., individually controllable electrodes where RF power delivery can be independently adjusted/controlled) can be provided to help ensure or control the treated zone to remain centered with the desired treatment zone (beneath the electrode array applicator) as well as to remain homogenous and consistent in terms of temperature rise within the desired treatment area regardless of variations in the patient's underlying tissue electrical impedance or anatomical structures. Each electrode (or subsets of electrodes) within the array can be addressed and activated individually. By way of example, a map of the impedance can be generated for the entire vaginal vault and, based on this impedance information, govern the activation of only certain electrodes to avoid structures which are not targeted. Vaginal wall (and/or urethral) surface temperatures can also be monitored and used for RF uniformity compensation. Application of uniform RF energy (e.g., at a frequency of about 1 MHz) through the vaginal wall and then into deeper tissues is complicated by various tissue types and differing impedance variations. For example, fibrous structures and connective tissues have a lower impedance to RF energy relative to fat. Consequently, RF energy will preferentially travel along connective fibrous tissues opposed to fat. Heated connective tissues thereafter thermally diffuse and/or conduct heat from the fibers into adjacent fat cells and raise their temperature. Likewise, muscle tissue can have a much lower impedance than other tissue types. Because predictable RF uniformity is important for efficacy and safety in an applied RF treatment, non-homogeneous tissue structures in the target region should be taken into account. Since some tissue structures have a higher impedance relative to others (e.g., deeper muscle tissues), RF energy uniformly delivered at the surface can "drift" toward the direction of least impedance. The RF energy will typically progress to the deeper tissues via the shortest path length through the high impedance layer closest to the vaginal wall. Thus, as discussed otherwise herein, only one electrode (or a subset of the electrode array) can be activated based on tissue feedback (e.g., based on impedance and/or temperature feedback) and/or the power, duration, duty cycle, etc. of the RF signal provided to the individual electrodes can be individually adjusted to help provide uniform heating.

As discussed above in accordance with various aspects of the present teachings, the application of different RF pulse durations can be utilized to provide for the treatment of selective tissues and/or a variety of treatments. With respect to internal tissues, both long duration (e.g., greater than 1 second, CW), low power RF energy (e.g., from about 1to about 5 W/cm$^2$) and short duration (e.g., less than 500 ms, less than 100 ms), high energy RF pulses (e.g., from about 10 to about 1000 J/cm$^2$ per pulse, 10 J/cm$^2$–500 J/cm$^2$, 10 J/cm$^2$–300 J/cm$^2$, 10 J/cm$^2$–100 J/cm$^2$) regimens are envisioned, for example. In some aspects, high-magnitude, short duration RF energy pulses can be utilized to generate sufficient flux or current density to ablate, coagulate, and/or vaporize tissue. By way of example, the RF pulses can be concentrated (e.g., focused) to a small-area of the electrode-tissue interface so as to induce sufficient flux or current density to coagulate and vaporize tissue.

With reference to FIG. 13, the results of an exemplary RF-based treatment on bovine liver is depicted in which an array of electrodes are spaced and configured to deliver heat to multiple loci of tissue within a target region such that treated portions are separated by untreated portions. In particular, the exemplary electrode arrays each comprise 20 electrodes to which an RF signal was applied while the electrodes were in contact with the liver surface. The RF signal comprised a 25 ms pulse, a pulse energy of about 30 mJ per electrode in each electrode of the array of 20 electrodes. As shown in FIG. 13, this exemplary treatment can be utilized to provide damage (e.g., ablation, coagulation) to separated islets within a larger volume. In such a "fractional" treatment, the damaged islets (vaporized tissue) are surrounded by healthy tissue that was substantially spared from damage caused by the application of the RF energy. In various aspects, the neighboring, undamaged (e.g., healthy) tissue can improve the healing process of the islets of damaged tissue.

The results of another exemplary "fractional" treatment is depicted in FIGS. 14A-C. The RF signals applied to the two arrays of electrodes, each array having 20 electrodes for each of these figures exhibit the same pulse energy of about 30 mJ per electrode in each array but differ in the duration of the RF signal. FIG. 14A, for example, shows a plurality of separated islets of vaporized tissue on a patient's skin surface caused by the application of an RF pulse duration of 35 milliseconds and energy to each of the electrodes in the array. FIG. 14B depicts the separated islets caused by the use of a pulse duration of 25 milliseconds, and FIG. 14C depicts the separated islets caused by the use of a pulse duration of 12 milliseconds. It can be observed that shorter pulse durations for the same energy per pulse cause more damage (e.g., vaporization of tissue) at the foci.

As discussed herein the disclosure relates to various embodiments. These include various applicator and electrode array designs that sandwich or combine or connect various components such as re-usable and disposable components. Flexible electrode array printed circuit board-based designs can include any suitable rectangular, arcuate, round, regular, and/or irregular shapes and combinations thereof. These flexible electrode arrays can be paired with foams, gels, and other materials to facilitate conforming to a patient. They can also be paired with rigid components that house electronic components designed for re-use. This approach facilitates an approach that address the technical problem of creating RF-based treatment devices that can be used cost effectively in a timely manner to increase patient comfort.

Uniform Heating Systems and Methods and Additional Applicator Embodiments

In part, the disclosure describes a flexible non-invasive body contouring applicator suitable for directing RF-based energy. The flexible applicator can be relatively thin. In various embodiments, the thickness of the applicator ranges from about 3 mil to about 10 mil. In one embodiment, the thickness of applicator is less than about 10 mil. In one embodiment, the thickness of applicator is greater than about 5 mil and less than about 12 mil. In various embodiments, the flexible applicator includes multiple separate treatment zones, wherein each zone may be set to reach a target temperature using one or more control systems by selectively energizing regions in a pattern to gradually bring overall region into a preferred treatment temperature range. The applicator uses an RF energy source/generator to generate heat via each of the treatment zones using RF-heating through conductive traces and/or dielectric gradients. In some embodiments, the applicator is connected to an RF generator via an interface device that includes an electronic subsystem. The interface device secures and releasably connects to the disposable applicator and operates as a quick disconnect/connect device. The individual separate zones/regions of the applicator may be energized to achieve uniform heating for each such zone/region. Further, the zones/regions of the applicator are selectively energized to facilitate uniform heating of the overall region of tissue in contact with the applicator.

A given flexible RF applicator may be energized using an RF source having an operating frequency. In various embodiments, the operating frequency may range about 0.5 MHz to about 10 MHz and as otherwise disclosed herein. In one embodiment, the RF frequency used with the flexible applicator is about 3 MHz or about 4 MHz. Further, the zones or regions of the applicator may be addressed according to various schemes and patterns, with various delay periods and changes to the addressing pattern being controllable by operator, for example, by an individual operating the device and/or by achieving a predetermined temperature goal for each zone/region that temperature goal being held within temperature range for a predetermined time range. Various distribution systems may be used to connect and address a given applicator. Regions or zones of the applicator can be energized or addressed such that the input electrical signal to a given region or zone is conducted zone by zone or region by region using a random, round robin, alternating, zig zag, and other addressing/energizing scheme. Heating of one tissue region below each interrogated region of an applicator allows for uniform heating without uncomfortable sensations. This may be achieved by cycling through different regions and energizing them while heat from one region extends to other regions to promote heating of an overall aggregate tissue section or region below or extending beyond the applicator.

In various embodiments, all of the regions of an applicator are typically not energized at the same time, although this is possible in some instances. Generally, applicator regions are selectively energized according to one of the aforementioned schemes or patterns to facilitate uniform heating of the body region underlying the zones/regions of the applicator being heated. Further, the applicator includes multiple layers arranged in a stack or combinations of substacks. In turn, the applicator has a shape defined in part by an outer boundary or border. The overall shape of the applicator is generally curved with sharp edges and straight lines being avoided as part of the applicator's border. Elliptical, circular, arcuate contours, and curved boundaries and combinations and fractions of the foregoing are preferred to mitigate against edge effects and non-uniform heating.

Various flexible and/or conformable applicators can also be used to implement the RF-based treatments and methods of treatment, including cosmetic treatments as disclosed herein. FIG. 15A shows a flexible RF-based applicator 880 suitable for directing RF energy to one or more tissues and body regions/body volumes. As shown, the applicator 880 has six regions or zones R1, R2, R3, R4, R5, and R6 that are divided by seven kerfs K. The kerfs K facilitate the applicator 880 conforming to contours of patient tissue, such skin generally, abdomen, and other patient tissues without limitation. In one embodiment, a kerf is the gap between the regions implemented to allow a flat applicator to conform to a compound curved surface. In various embodiments, the shape in which the plurality of layers is cut defines the shape of the kerfs and circular or elliptical strain relief elements at the end of kerfs. These strain relief elements/terminal strain relief elements may be incorporated in various applicator designs disclosed herein.

In general, the applicator can include two or more regions in some embodiments with one or more kerfs K. In some embodiments, the applicator 880 may have one region and not include a kerf. The applicator is flexible and suitable for conforming to one or more surfaces of a patient's skin, tissue, muscles, organs, body lumens, organ systems, and other regions and surfaces on or within a patient. The applicator 880 include an electrical connector 890 that includes a plurality of electrical contacts 892. The contacts may connect to an electrical trace disposed in or on the applicator.

In one embodiment, electrical connector 890 is part of applicator 980. The electrical contacts 892 connect to electrical traces and other electrical components of the applicator. The applicator 880 may also include a strain relief device/element 885 disposed relative to such as by surrounding or sandwiching flexible layers of applicator and electrical connector 890. The electrical connector 890 may include one or more alignment devices 895 suitable for facilitating alignment of the electrical contacts 892 with corresponding electrical contacts of an interface device. The first surface 900 of the applicator may include one or more labels. In one embodiment, an integer N, or other variable may be used to refer to the N conductive traces such as copper traces that direct RF to N outer regions of an applicator. A given set of patterned traces arranged in a configuration such as spiral, loop, or other concentric or nested configuration can be used as a RF transmitter for a given applicator or region thereof.

Uniformity—Flexibility/Contour

In various embodiments, the applicator features kerfs K. The kerfs are voids or cut outs in the flexible layer stacks that functions in a manner akin to a dart in a garment that enables the applicator sheet to accept the contour of the body while maintaining contact. Use of kerfs enables improved tolerance in sheet thickness. When the applicator size is above a treatment area of about 50 $cm^2$ or so then kerfs are used to provide flexibility in the applicator. Kerfs K enable the applicator to contour to larger treatment areas and are used for multiple zones/regions R1-RN in a single applicator.

In general, the regions or zones of an applicator are separated with kerfs, channels, gaps, cavities, voids, or other defined spaces to facilitate the use of one flexible applicator that can bend and be adjustable relative to a tissue region such as stomach, abdomen, submental region, organs, organ systems, skin, subcutaneous tissue, body tissue, any of a number of areas of the face, arms, legs, and other regions, lumens, or volumes of a patient. The selective and alternating energizing of regions of a given applicator is performed to facilitate uniform heating of target tissue subject to the regions of a given RF-based applicator being separated along one or more boundaries, such as kerfs or channels.

A given applicator includes a stack of layers and has a first side 900 as shown in FIG. 15A. The second side or tissue facing side is the surface opposite the first side. Additional details relating to the layer stack are described with regard to FIGS. 18 and 19A and elsewhere herein. Generally, each applicator has a first side and a second side. In one embodiment, the first side 900 corresponds to a labelled side, also referenced to as a vinyl or polymer side or upper or top side. Alternatively, the second side refers to gel side, wet side, lower side, or patient facing side. The wet side refers to the presence of aqueous material or gel disposed on a side of the applicator. The gel or other aqueous material facilitates maintaining skin contact and positioning of applicator region for targeted RF energy transmission and subsequent tissue heating. References to first side and second side are not limiting and may refer to any of the foregoing sides of an applicator as informed by context.

Shapes/Scalability

In various embodiments, the applicators may have different shapes. Preferably, the applicators have a curved boundary, in contrast with straight edges such as polygonal boundary. Elliptical, circular, oval, curved and other shapes may be used for specifying shape of applicator and/or its outer edge or boundary. For example, in various embodiments, an applicator is shaped as an ellipse or football having a surface area tailored for a particular patient size or tissue of interest (i.e., about 225 $cm^2$ or about 300 $cm^2$). Larger applicators are designed for larger treatment areas, such as, but not limited to: the abdomen and thighs, while smaller applicators are for smaller treatment areas, such as the face or arms. The geometry, size and coverage of an applicator is scalable based on which potential areas on body will be treated. Further, in various embodiments, an applicator can include various number of zones or regions R, such as, but not limited to, 6 zones R1-R6, 12 zones, 48 zones, or another number of zones. Each zone is typically bounded by one or more kerfs. The limit on the geometry and size is configurable based on energy available from one or more of the systems described and depicted herewith such as systems 100, 800, 1200.

Figure 15C:
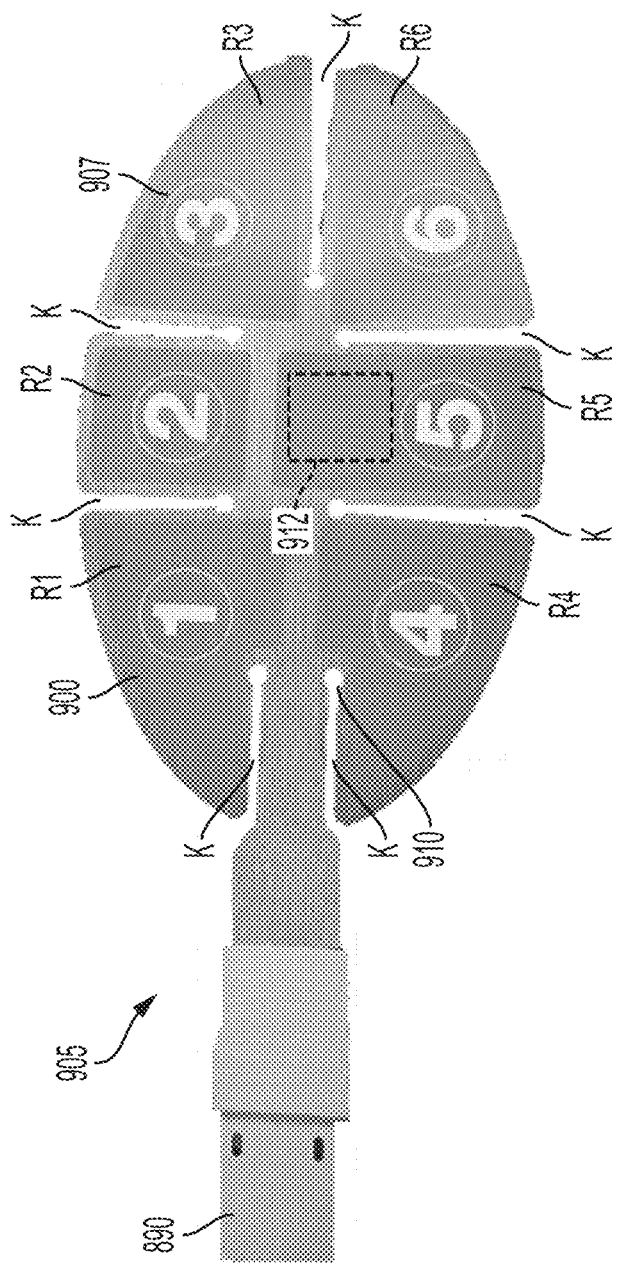
Figure 28A:
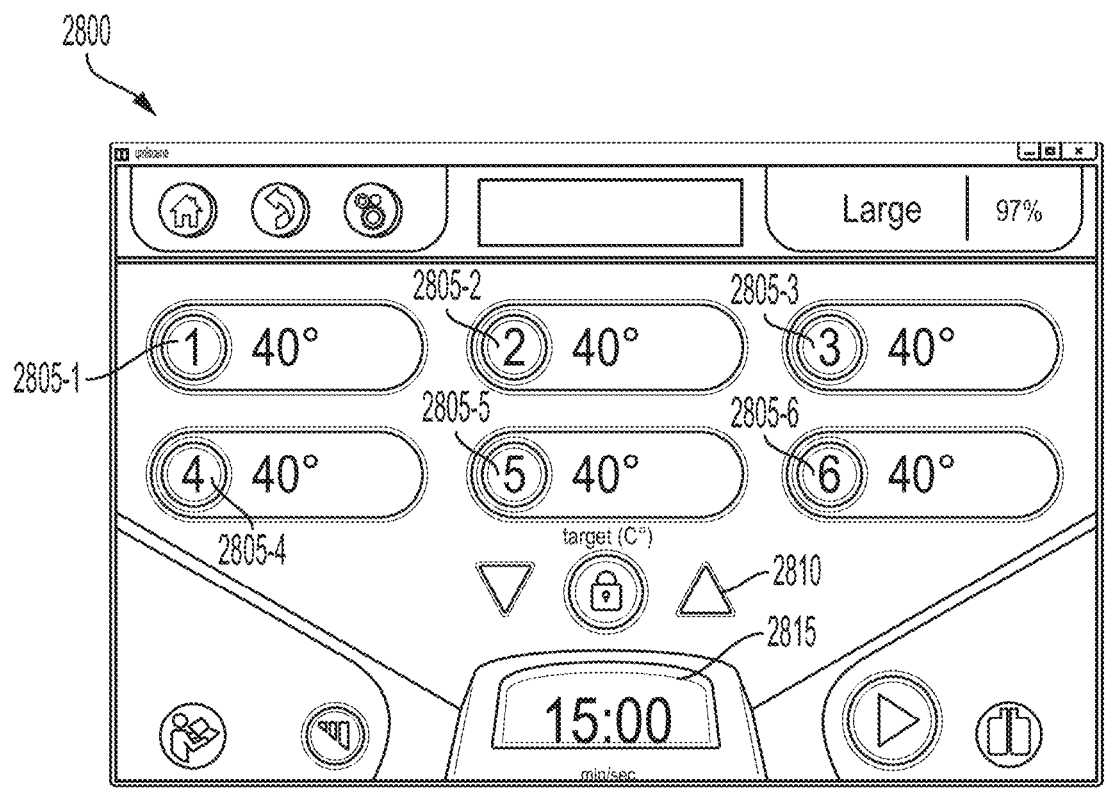
FIGS. 28A and 28B depicts a graphical user interface (GUI) for use with a treatment system using an applicator showing different configurations according to various aspects of the present teachings.
Figure 28B:
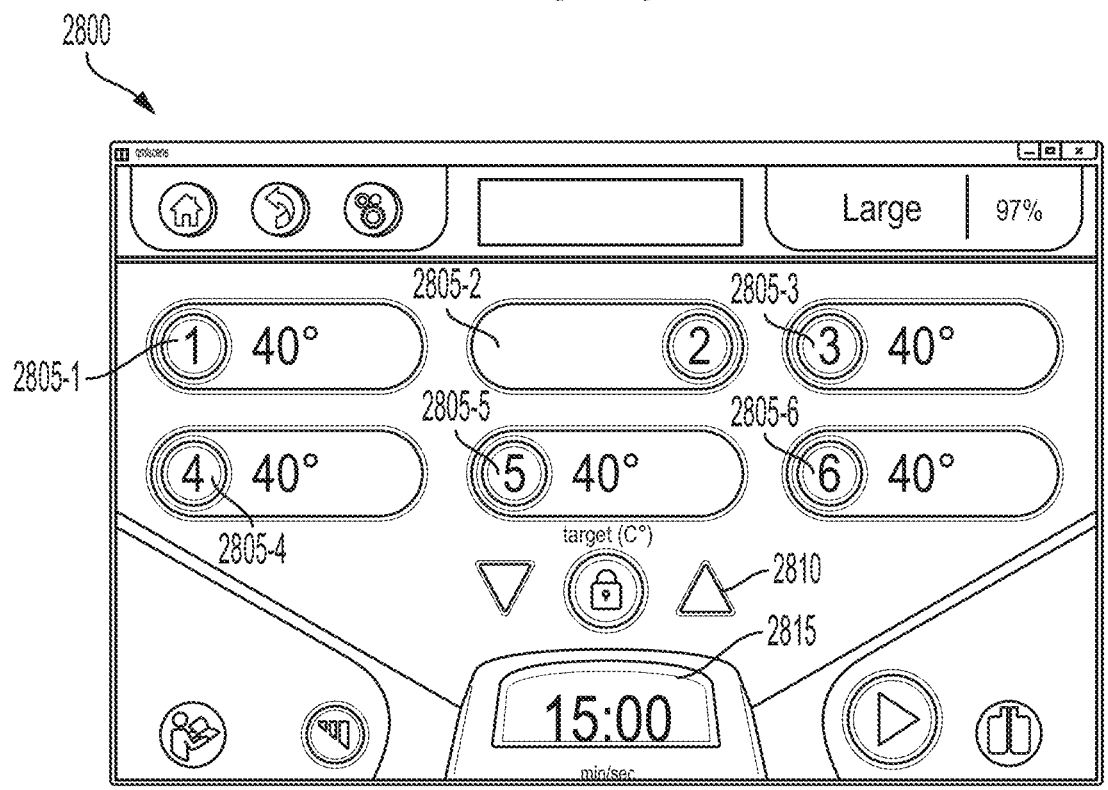

In various embodiments, an applicator can selectively control and/or turn on/off one or more zones. In some embodiments, a zone can be selectively sized to have an effective treatment a zone to be smaller than an adjacent zone. Further, in some embodiments, an applicator can be shaped to include one or more voids or regions free of RF-transmission elements or programmed to not energize certain RF transmission elements or regions to compensate for sensitive regions (i.e., belly button, scars, etc.). This can be controlled by a user interface on a display connected to system 100. An exemplary portion of an applicator that may be used to compensate for the presence of a navel, scar, or other depression is shown in FIG. 15C as region 912. As shown in FIG. 15C, region 912 is a portion of zone R5. In some embodiments, an entire region, such as region/zone R5 of applicator 905 may be selectively avoided such that RF energy is not transmitted to the navel or other sensitive region. In other embodiments, the region 912 could be enlarged, made smaller, and/or moved to other regions depending on the location of sensitive regions. The deactivation of regions of a user interfaces suitable for use with treatment systems and applicators disclosed herein is shown in FIGS. 28A and 28B.

In various embodiments, unwanted edge effects are avoided by selecting dielectric/trace for a given zone, in some embodiments one temperature sensor such as a thermistor is used per zone/region to regulate target tissue temperature such as skin temperature. In some embodiments, two thermistors are provided per zone for redundancy and to provide backup should one fail. For example, in region/zone R5 of applicator 900 in FIG. 15A, two temperature sensors H are shown. Each temperature sensor H connects to one or more electrical conductors that in turn are in electrical communication with one or more electrical contacts in the electrical connector 890. In some embodiments, one temperature sensor H is provided per each zone or region. The thermistors provide an outer temperature reading such as a tissue or applicator surface temperature reading and discerns the internal at depth temperature based on the outer temperature reading. In one embodiment, an outer surface of the tissue or the applicator surface temperature is measured using one or more applicator temperature sensors, such as thermistors. In turn, the internal at depth temperature is discerned from that reading. This follows from the internal temperature being correlated with surface temperature of tissue/applicator contacting the tissue.

The target skin surface temperature ranges from about 40° C. to about 44° C. This correlates to a temperature at depth that ranges from about 41-45° C. In some embodiments, the temperature range may extend to from about 42 to about 47° C. due to thermal accumulation.

In at least one embodiment, when applied to skin tissue, the applicator provides uniform heating up to a target surface temperature range (about 40 to about 44° C.), which corresponds to a range of (about 42 to about 47° C.) at the depth of fat tissue. In various embodiments, temperature is measured at the surface of the skin tissue and the temperature of the treated skin surface is used to determine the temperature of underlying tissue, i.e., the fat tissue below the target surface. One or more thermal/temperature sensors are incorporated in each region or section of a given applicator. In various embodiments, two thermal/temperature sensors such as for example thermistors are disposed in each applicator region.

In various embodiments, an applicator is capable of setting the temperature of each separate treatment zone individually. In some embodiments, one or more individual zones can have a different target temperature or can be shut off entirely depending on the prescribed course of treatment. For example, a treatment zone placed over the belly button region may be shut off due to sensitivity. In various embodiments, the amount of zone heating can be determined by ratio of change in resistance to resistance (ΔR/R), which is the change of impedance. During treatment, the applicator is configured to maintain a specified temperature in a target temperature range for at least about 12 minutes. In one embodiment, an example range for treatment time is from about 12 to about 15 minutes. In one embodiment, the time each region is energized is 12 to 15 minutes divided by number of applicator regions.

In various embodiments, the applicator is suited for applying energy to a uniform volume of tissue. Uniformity or overall uniformity is achieved using zone by zone uniformity across each treatment zone of the applicator. In some embodiments, each zone/region is heated for a time period of P or about P, wherein the total treatment time TTT is product of (about P or P)(number of applicator regions). In one embodiment, about P or P ranges from about 20 seconds to about 2 minutes. In one embodiment, about P or P ranges from about 40 seconds to about 3 minutes. In one embodiment, about P or P ranges from about 1 minute to about 2 minutes. In one embodiment, about P or P ranges from about 1.5 minutes to about 2.5 minutes. In one embodiment, about P or P ranges from about 1 minutes to about 10 minutes. In one embodiment, about P or P ranges from about 1 minutes to about 3 minutes. In one embodiment, about P or P ranges from about 2 minutes to about 8 minutes.

Outside the boundaries of the applicator, the energy applied by the applicator may cause thermal spread. For example, in at least one embodiment, the tissue under the kerfs eventually reaches a uniform temperature or within a particular treatment temperature range as a result of heat delivered by two or more regions of the applicator spreading and spanning tissue under a kerf. In one embodiment, kerfs terminate within boundary of applicator at a channel, hole or other opening such opening 910 shown in FIG. 15C. In some embodiments, the holes or openings are circular or elliptical. These holes or opening can serve as strain relief elements.

As shown in FIG. 15A, the applicator 900 includes zones or regions 1-6, R1-R6. In some embodiments, the applicator includes an outer label that shows and enumerates 1-6, R1-R6. Such a labelled outer layer is shown in applicator 905 in FIG. 15C, with regions 1-6 shown with a number printed on the applicator label with each number within a circular boundary. The printing of the numbers on the label is white in one embodiment, but may be any suitable color. In one embodiment, the label includes vinyl, plastic or another polymer material. The labelled regions 1-6 correspond to applicator regions or zones R1-R6. These zones may be displayed on a user interface to facilitate deactivating one or more zones prior to starting treatment.

In one embodiment, each zone or region is bounded by a two kerfs K with seven kerfs K in total. In some embodiments, applicators can use fewer zones, more zones, and/or have a different shape and size. The limits on geometry and size of an applicator depends on whether or not the RF generator can provide enough energy for heating the desired treatment zone. During the initial stages of treatment, each treatment zone of the applicator is activated sequentially in a clockwise manner R1 to R2, R2 to R3, R3 to R6, R6 to R5, and R5 to R4. A counterclockwise activation scheme or other activation schemes and patterns as described herein may be used. Thereafter, the temperature of each zone is measured using a temperature sensor H and modified as necessary to maintain a set surface temperature of (40-44° C.). Individually each treatment zone maintains a temperature in the range of (42-47° C.) to achieve the set surface temperature of (40-44° C.) for the overall region covered by the applicator. In this embodiment, the applicator covers an area 300 cm$^2$. In various embodiments, a size of an applicator can range from about 50 cm$^2$ to about 600 cm$^2$. In one embodiment, the label used on applicator surface 900 may include a polymer and designed to look like a metallic surface such as brushed chrome or another gray or silver metallic visual element. In one embodiment, the applicator includes a label that includes one or more pigments arranged to display a metal, metallic, or metal like appearance.

Flexibility

In various embodiments, applicator flexibility is enhanced by kerfs/voids that enable the applicator be flexible enough to conform to the contours of the body. For example, as shown in FIG. 15A, each kerf frees various portions/zones of an applicator to flex according depending on where the portion/zone is being applied on the body. The applicator shown in FIG. 15A has seven kerfs K in total. In various embodiments, the number kerfs employed depends on the size and shape of an applicator and how the applicator is intended to be applied to various body parts. In various embodiments, each applicator includes a plurality of kerf-free region such as an inner region or spine from which regions or zones extend and before which various kerfs terminate. An exemplary inner region 495 is shown within dotted lines in FIG. 22A. The inner region typically includes a high density of substantially parallel conductors that branch off to supply current to various regions. The density of conductors is high because an increased number of conductive traces are positioned next to each other in this region. As a result, the inner region can generate excess heat. As a result, the inner region can include one or more heat shields. The inner region 495 has a spyglass, skyscraper, stepped, or tapered configuration that follows from the number of adjacent traces decreasing in direction of dotted arrow AW moving away from the electrical connector 890 of the applicator.

The dielectric of the applicator has a dielectric constant that ranges about 3 to about 4, which provides a balance of capacitance vs. dielectric thickness while also having flexibility suitable for a patient tissue contacting applicator. As another consideration, when selecting dielectric material for an applicator, it is desirable for the material to have a low heat loss or heat dissipation factor and also be tolerant of high temperatures to permit soldering of components relative to conductors used with the dielectric material. Further, the selected dielectric of the applicator is skin safe and biocompatible. For example, in one embodiment, Kapton is one dielectric that fulfills these requirements. However, Kapton could be replaced by any dielectric that fulfills these requirements.

Uniform Heating—Applicator Considerations

In various embodiments, each zone of an applicator includes a plurality of RF traces to provide RF energy and/or heating from each of the zones. Without any management of the heat, RF traces can result in edge effects which makes providing uniform heating from an applicator difficult. A relatively flexible dielectric insulation, such as Kapton, can be selectively placed to promote uniform heating in a given treatment zone.

Figure 18:
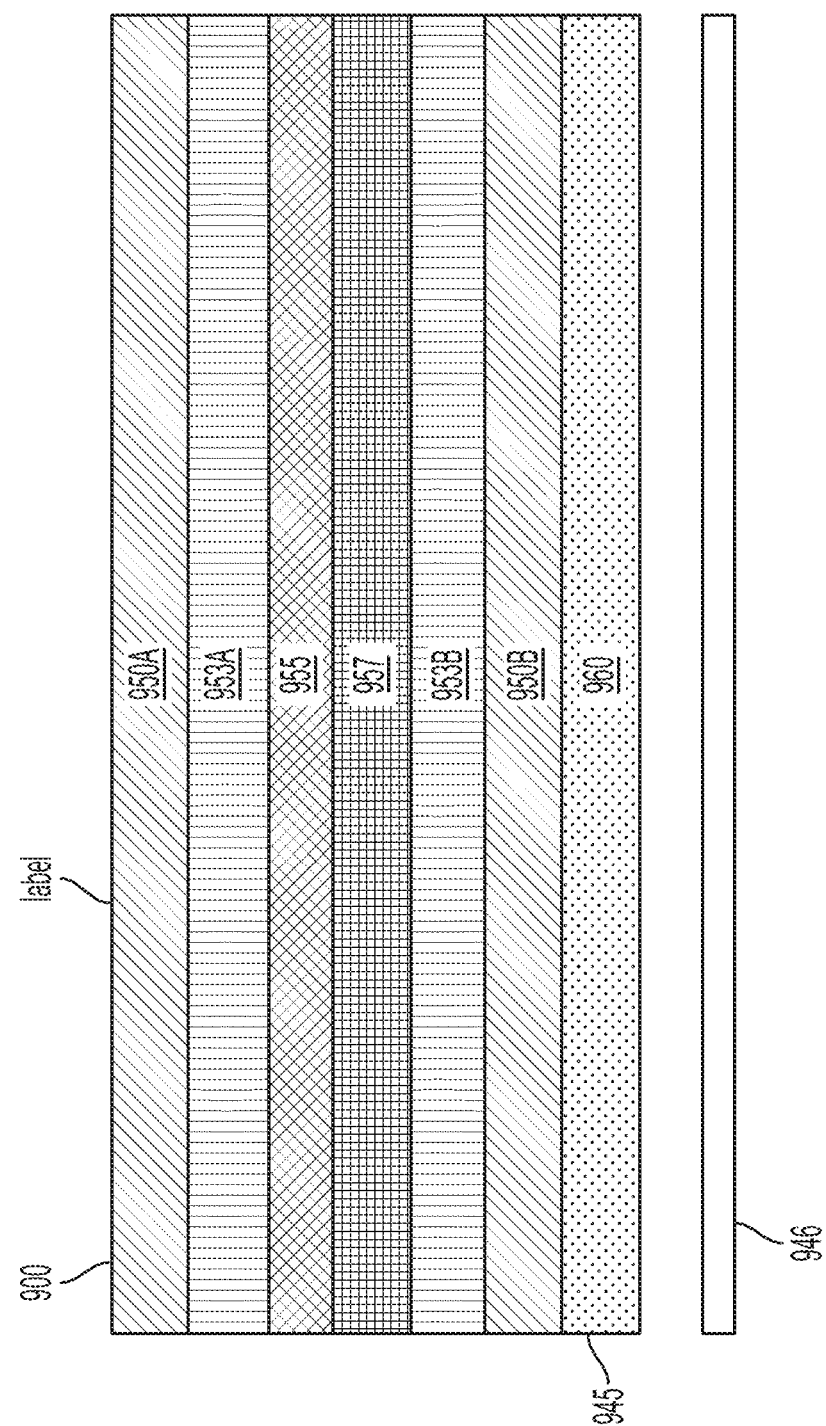
FIG. 18 schematically depicts various layers of a thin flexible RF-based applicator embodiment in accordance with various aspects of the present teachings.

FIG. 18 shows an exemplary arrangement of materials 940 of an applicator or a portion thereof such as a zone of an applicator, in accordance with an embodiment of the disclosure. These layers are also combined to form applicator 980 in FIG. 19A. As shown, there is a first side 900 and a second side 945. In one embodiment, the first side and second side correspond to a vinyl side and a wet side, or vice versa. Alternatively, in one embodiment, the first side and second side correspond to a patient facing side and an air facing side, or vice versa. During treatment, the wet side is placed in contact with patient tissue to be treated. In some embodiments, an aqueous gel such as a hydrogel is applied to the tissue facing/wet side to reduce or avoid air gaps. Further, the use of such a gel may improve the amount of current that can penetrate the tissue. In various embodiments, one or more thermistors are placed within each zone to monitor temperature during a given treatment method. Temperature sensor are in communication with a control system and can be used to change current levels when higher RF energy and associated current level may otherwise cause edge effects or instances of non-uniform heating. In at least one embodiment, a six zone applicator includes a thermistor in each of the zones.

As shown in FIG. 18, optional release liners 946 may be included with sterile disposable applicator and are peeled off prior to apply applicator to patient. The liner protects a gel layer 960 in some embodiments. Two dielectric material layers 950A, 950B sandwich a conductive layer 955 and a polyimide layer 957 using adhesive which may be disposed as two layers 953A, 953B. In various, embodiments the dielectric material layers may include a Kapton layer such as a cover or overlay. Layers 950A, 950B, 957 may be dielectric layers, such as first, second and third dielectric layers. The conductive layer 955 include a metal or an arrangement of electrical traces. The conductive layer includes copper or copper traces in various embodiments. The copper layer can include a continuous thin layer of copper metal. Alternatively, for various embodiments the copper layer comprises a plurality of copper traces extending into each region or zone of the applicator. The extent to which traces are placed closer to each other and more of them clustered in a parallel or concentric or other configuration results in increased trace density. A patient contacting layer 945, such as a water-based gel layer is also shown. An arrangement of the various layers of FIG. 18 are also shown relative to an exploded view of an applicator in FIG. 19A.

Figure 19B:
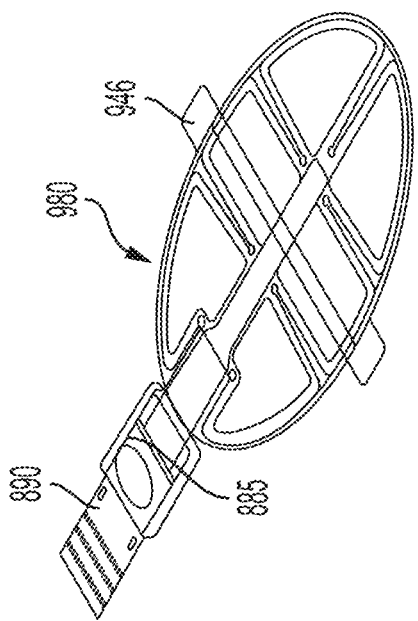
FIGS. 19B-19C schematically depict top perspective views of the thin Flexible RF-based applicator embodiment of FIG. 19A in accordance with various aspects of the present teachings.
Figure 19C:
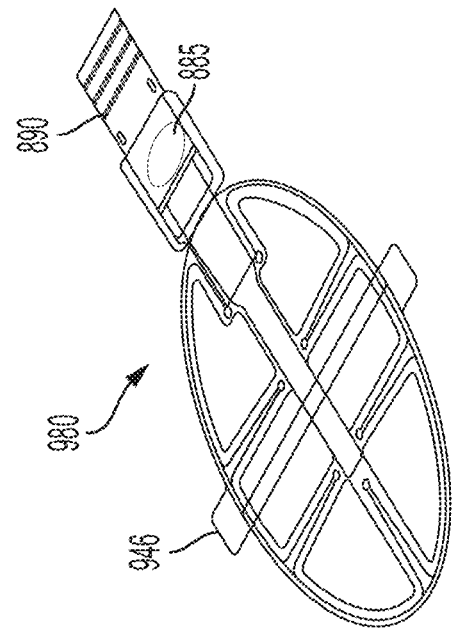
Figure 19A:
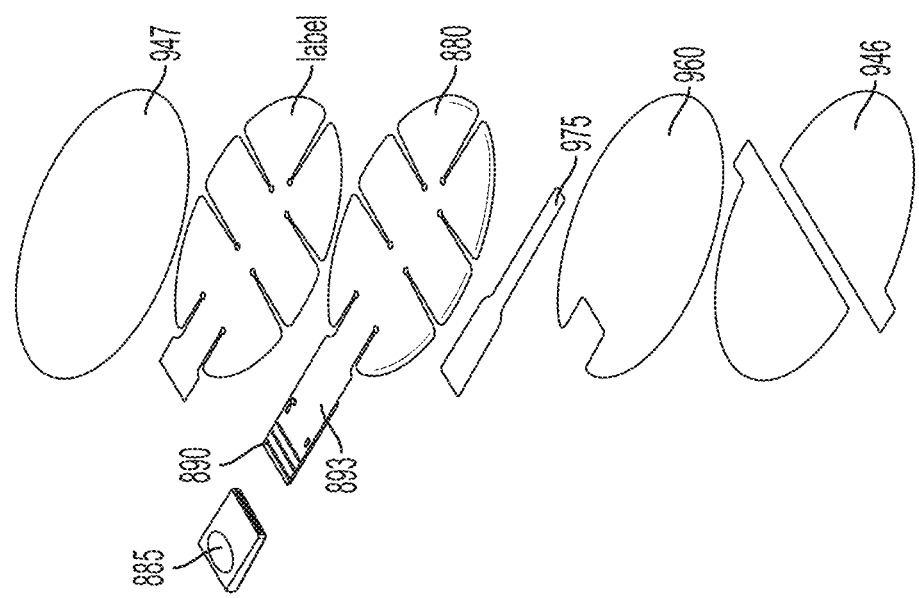
FIG. 19A schematically depicts an exploded view of various layers and components of a flexible RF-based applicator embodiment in accordance with various aspects of the present teachings.

In FIG. 19A, the releasable liner 946 is adjacent or below the gel layer 960. A heat shield layer 975 is also used to protect the inner region or spine of applicator. The heat shield layer 975 is elongate and optionally flared or tapered in some embodiments. The flexible applicator 880 includes the conductive layer, multiple dielectric layers, and adhesive layers discussed above. A label may be disposed on the applicator as discussed herein. In addition, another release liner 947 may also be used. A strain relief element 885 may also be used to reinforce extension region of applicator that includes electrical connector 890. In one embodiment, an elongate region 893 extends from applicator like a tail or parallel electrical cable that terminates in electrical connector 890. FIGS. 19B and 19C show different views of the combination of layers shown in FIG. 19A. In turn, FIGS. 20A-20F show different views of the applicator 980 with one or more release liners. FIGS. 21A-21F show various views of an applicator 981 that does not include a release liner.

Figure 22A:
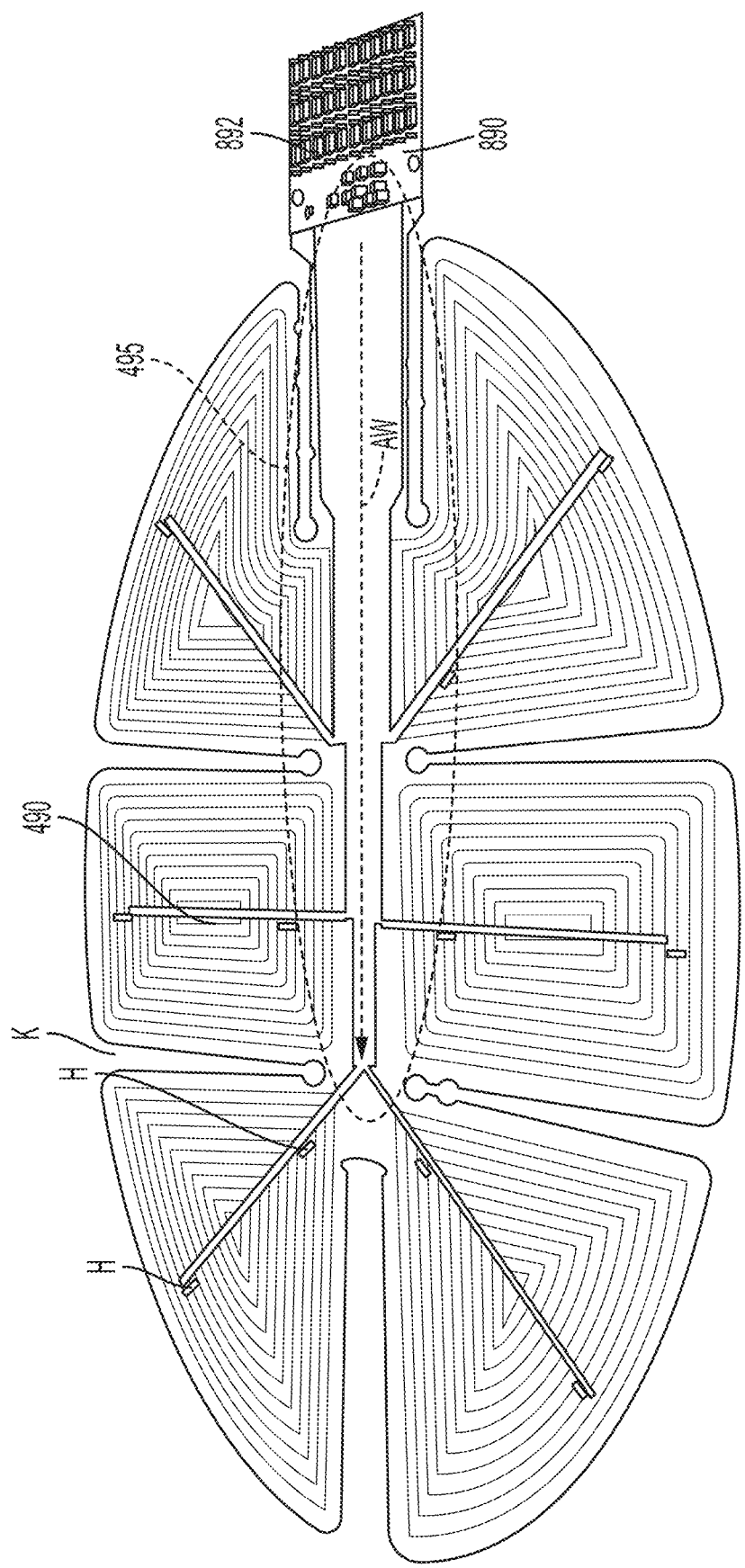
FIGS. 22A-22B schematically depict components of a flexible RF-based applicator showing regions with electrical traces of one or more conductive layers in accordance with various aspects of the present teachings.
Figure 22B:
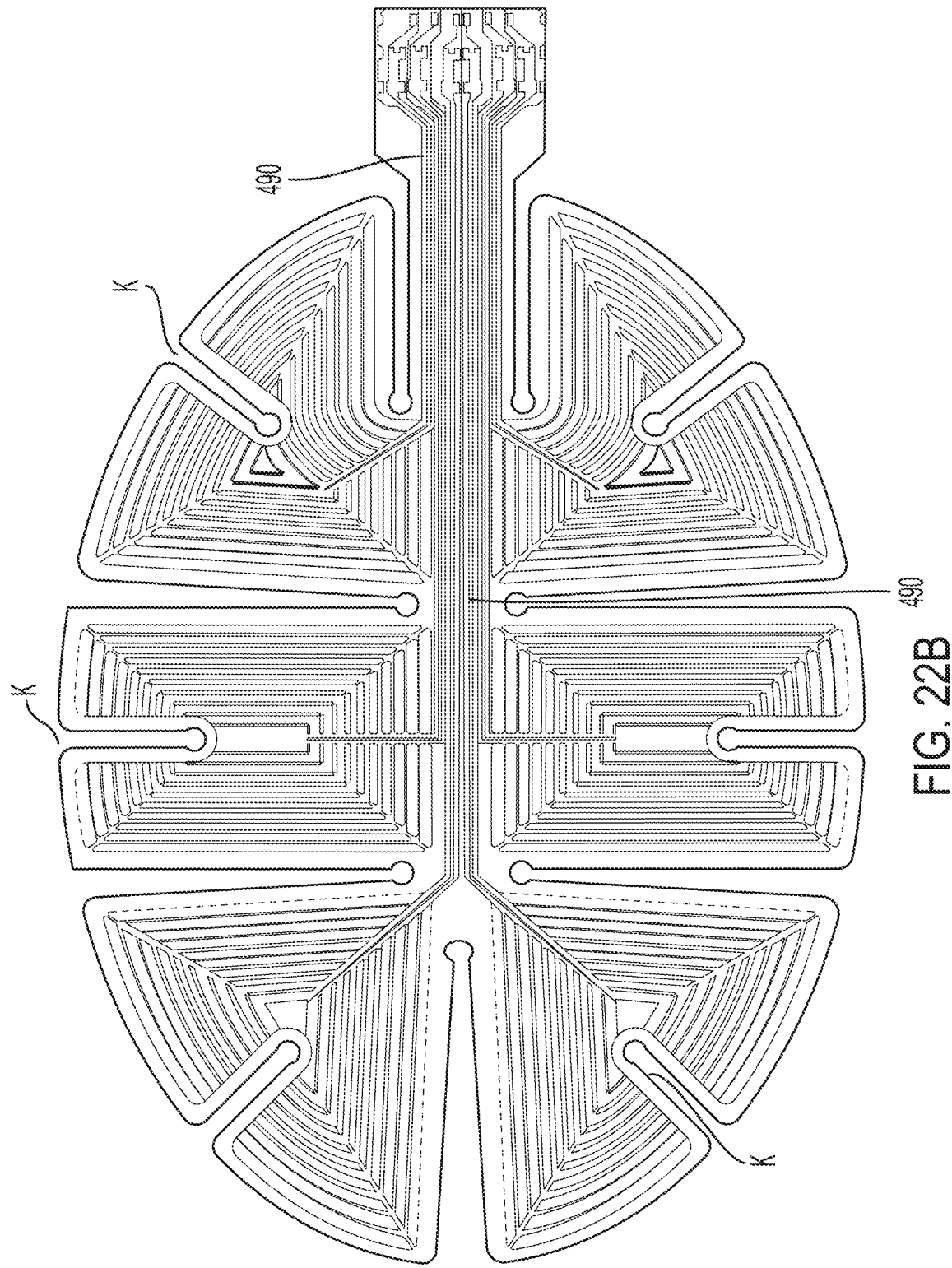
Figure 24F:
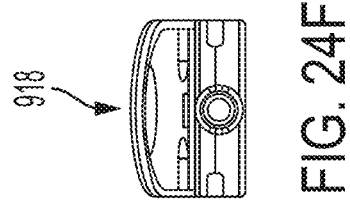
FIG. 24F schematically depicts a rear view of an interface device in accordance with various aspects of the present teachings.
Figure 24A:
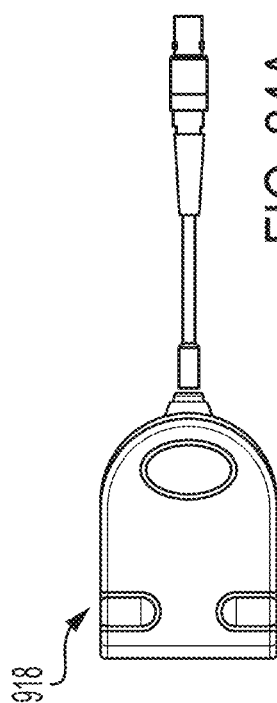
FIG. 24A schematically depicts a top view of an interface device in accordance with various aspects of the present teachings.
Figure 24B:
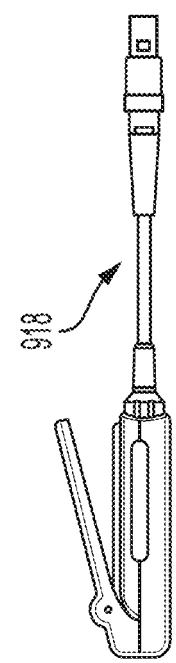
FIG. 24B schematically depicts a top side view of one side an interface device in accordance with various aspects of the present teachings.
Figure 24C:
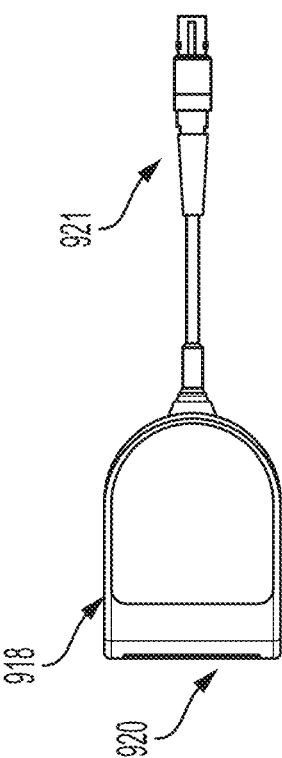
FIG. 24C schematically depicts a bottom view of an interface device in accordance with various aspects of the present teachings.
Figure 24D:
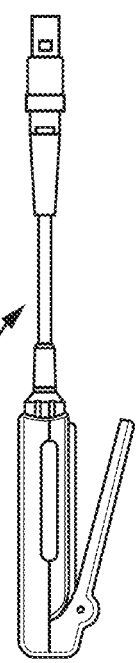
FIG. 24D schematically depicts a top side view of another side of an interface device in accordance with various aspects of the present teachings FIG. 24E schematically depicts a front view of an interface device in accordance with various aspects of the present teachings.
Figure 24E:
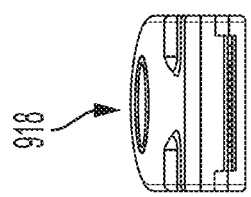

As shown in FIGS. 22A and 22B, the copper traces can be arranged in various patterns such as various paths. In some embodiments, the copper traces are arranged in spiral, area filling curves, nested rectilinear regions, nested curved regions and combinations thereof. Examples of conductive traces 490 are shown in FIGS. 22A and 22B. The center of a given zone includes a higher concentration of copper trace material, while the outer perimeter of the same zone shows thinner copper gradients towards the edges of the perimeter.

In various embodiments, the copper traces are arranged to have a greater positional density or be clustered at the center of the zone or in a particular part of the applicator. In some embodiments, there are higher concentration of copper trace material in the center portions of a given zone as a result of more copper traces being placed relative to each other. Thus, in one part of applicator in a given area more traces are placed next to each other than others, thereby increasing density or count of copper traces per unit area. A single set thickness is typically used for traces. Although that thickness can vary over suitable ranges such as from about 0.01 inches to about 0.3 inches. In some embodiments, a set of traces with a common width or thickness may be ore densely clustered in one area and less densely clustered in another area. As an example, in the spine area multiple traces are positioned next to each other in parallel, juxtaposed, adjacently, or otherwise. This can result in additional heating relative to the region of increased traces being positioned relative to each other and benefits from the inclusion of one or more heat shield layers.

In various embodiments, the Kapton can be replaced with another suitable dielectric, subject to the preferred dielectric properties described herein. Further, in these embodiments, the base polyimide can be replaced with another dielectric, i.e., polyester. In various embodiments, the thickness of each of the layers of FIG. 18 ranges from about 0.5 mil to about 1.5 mil. The optional hydrogel layer has a thickness greater than 1 mil in various embodiments.

Figure 16:
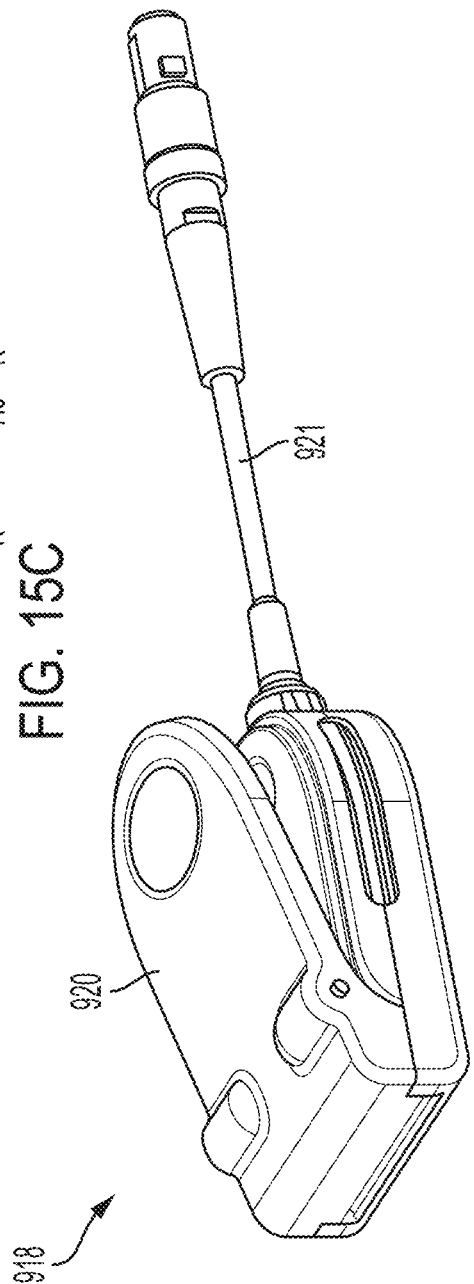
FIG. 16 schematically depicts an interface device suitable for quickly connecting and releasing an applicator according to various aspects of the present teachings.

The applicators are generally designed to be disposable and work in conjunction with a suitable interface device 905 as shown in FIG. 16. The interface device 905 is in electrical communication with a RF-based treatment system such as systems 100, 800, 1200 or other suitable systems disclosed herein. The interface device supports using sterile applicators and changing to applicators having different sizes, shapes and regions that facilitate alignment of electrical traces. The interface device 905 also supports quick connection and release of applicator from the interface device. The interface device shown is one exemplary device for connection of an applicator. In another embodiment, pluggable cable interfaces that releasably attach to an applicator's electrical terminus may be used and other interface devices suitable for making aligned contact with multiple electrical contacts at the electrical terminus of the applicator.

As shown, the interface device 905 of FIG. 16 depicts a clamp/clip device 920 and a cable adapter 921. The cable adapter 921 may include one or more electrical conductors and/or one or more optical connectors or optical devices such as a light pipe or optical fiber section. In various embodiments, a light pipe or optical fiber section is used as part of an interface device to support optically showing when applicator is energized or in a particular state or treatment. The clamp/clip device 920 may include one or more electrical to optical conversion devices. The cable adapter 921 may connect to other extension cables or subsystems. In one embodiment, cable adapter 921 connects to one or more of the systems disclosed herein such as systems 100, 800, 1200/Additional details of the interface device are discussed in more detail below.

As edge effects are present in RF traces, the applicators' use of selective dielectric insulation creating various gradients of dielectric insulation throughout the applicator surface and approach to graduating and/or scaling trace geometries by creating various gradients of copper trace throughout the applicator surface (FIGS. 22A, 22B) both manipulate edge effects to achieve better uniformity of temperature and flexibility.

Figure 17:
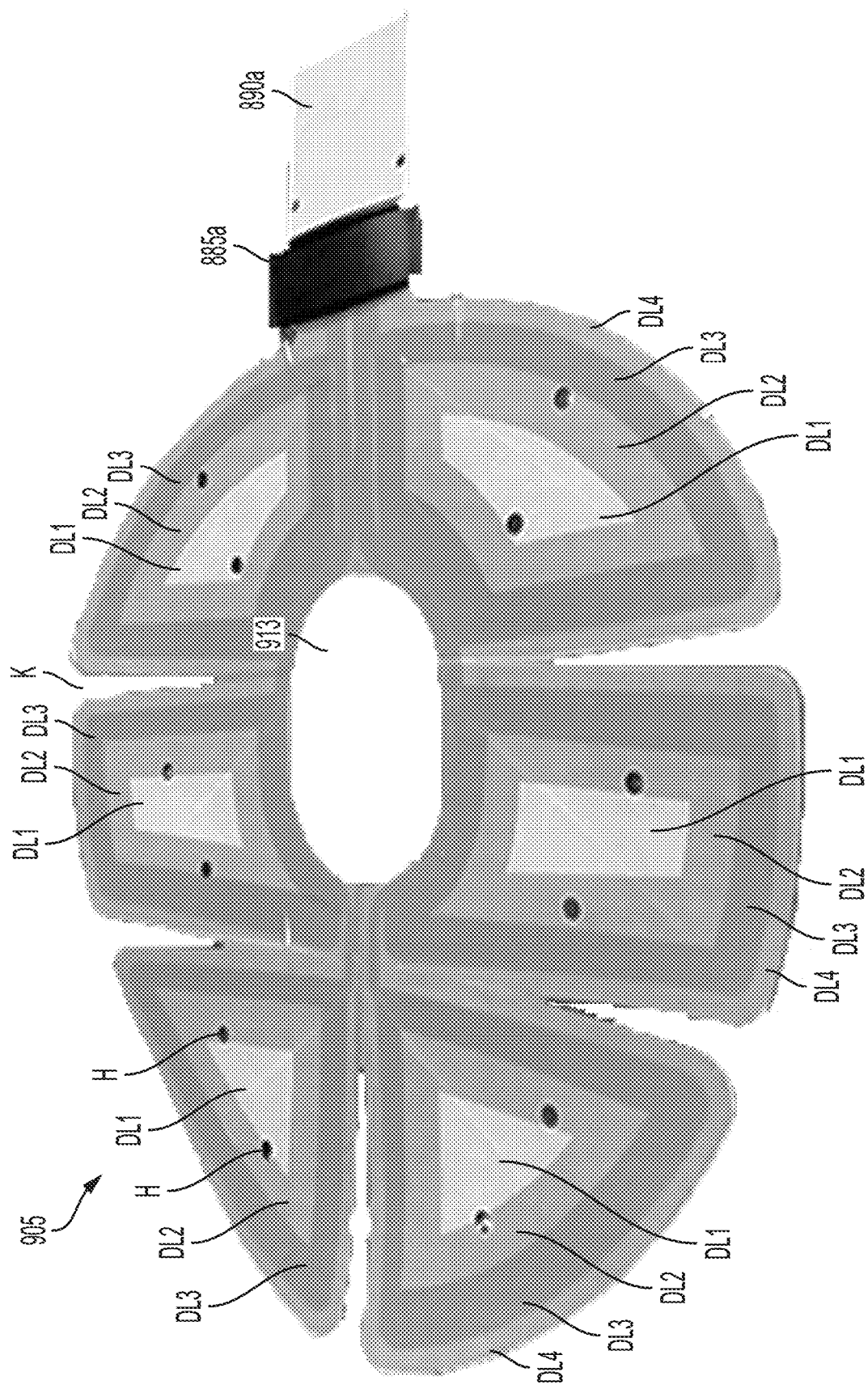
FIG. 17 schematically depicts a flexible RF-based applicator embodiment that includes dielectric material of varying thicknesses in different regions suitable for treating tissue in accordance with various aspects of the present teachings.

FIG. 17 shows an alternative applicator embodiment 905 that incorporates nested dielectric regions. Within the applicator, in one embodiment, a conductive layer that includes copper is evenly spread throughout. The surface of the applicator, shown in FIG. 17, is a gradient of dielectric with multiple layers of dielectric such that the center of a given zone features a single layer of the dielectric (1 mil thick). For each zone, when moving outwards from the center, each subsequent gradient has an additional layer. For example, the center has a single layer of dielectric DL1, the next gradient outwards has two layers DL2 of the dielectric (1 mil thick), the next gradient outwards has three layers of the dielectric (3 mils thick) DL3, and the final outer perimeter includes four layers of the dielectric DL4 (4 mils thick). The center region 913 is a hole defined by layered components of applicator and suitable for navel placement or over other sensitive regions.

In various embodiments, the applicator is a conformable applicator that applies RF energy to heat one or more zones. In at least one embodiment, the applicator is used with a waveform generator that operates at about 4 MHz. The 4 MHz generator facilitates providing RF energy uniformly across a dielectric using thin common materials over large areas. However, in other embodiments, other high frequency generators can be used. In one embodiment a 3 MHz generator is used. Suitable waveform generators for use with the flexible applicators disclosed herein are typically components of or in electrical communication with one or more the systems disclosed herein including systems 100, 800, and 1200.

In various embodiments, using RF energy and placing current into the body, for a given capacitive electrode area, is dependent on various properties. For example, as dielectric thickness decreases, RF current and the tendency of any air to ionize increase proportionally. The relative permittivity (i.e., the dielectric constant) of the dielectric layer increases, RF current and the tendency of any air to ionize increase proportionally. As voltage applied to the electrode increases, RF current and the tendency of any air to ionize increase proportionally.

As the frequency of the RF waveform increases, the RF current increases proportionally. In contrast, the tendency of any air to ionize does not increase proportionally. Thus, RF frequency may be increased to increase RF current per unit area without increasing the tendency of forming a corona discharge or a plasma in air in proximity to tissue undergoing treatment with an applicator. Accordingly, mitigating corona or plasma discharge is one advantage of the RF-based applicators disclosed herein. In various embodiments, the frequency range of RF generator is from about 1 to about 5 MHz. In some embodiments, a 4 MHz generator balances requirements because at higher frequencies inductance can be problematic and at lower frequencies the capacitive gradient required for uniform heating is more difficult to achieve.

In various embodiments, the applicator makes use of, or manipulates, edge effects via selective dielectric insulation placement and positioning, creating various gradients of dielectric insulation such by thickness variation throughout the applicator surface and graduating and/or scaling trace geometries by creating various gradients of copper traces throughout the applicator surface. Examples of such traces 490 are shown in FIGS. 22A and 22B. Graduating trace geometries creates multiple edges so that edge effects are present throughout the applicator surface providing a pattern that leads to substantially uniform heating. In addition to the temperature uniformity provided by the applicator, the flexibility of the applicator is also considered when determining the topology of dielectric gradient and/or copper trace gradients in the applicator.

In various embodiments, the pattern of materials sandwiched together is as follows: dielectric, copper, dielectric, etc. Various stacks of layers of material can be used for a given applicator. In turn, various sandwich constructions are possible in which one or more layers is sandwiched between two layers, a layer and a stack of layers, or two stacks of layers.

In various embodiments, a given applicator has a skin tissue contacting side 945. The skin contacting side includes a substance that is wet enough to conform to the stratum corneum therebetween. For example, in at least one embodiment, a thin adhesive that is micro-conformable (i.e., "wet") enough to conform to the stratum corneum will work well to allow coupling into the skin. The thin adhesive facilitates avoiding air gaps, which can reduce how much current can be coupled into the body. The air gap is filled with something water-based, and optimally water-based with a current-carrying ion, such as saline as part of various methods of treatment. For example, a suitable substances can include a hydrogel. In an alternate embodiment, an aggressive thin adhesive would also work, but should be made in a way to allow it to "wet" into the stratum corneum. In various embodiments, the applicator can be pre-wetted such that a cover is peeled off prior to application of the wet side to the subject's skin. Various embodiments include removable covers such as releasable liners for example such as those shown in FIGS. 19A, 19B, 19C, 20A and 20B For example, a conductive hydrogel, is loaded onto the subject facing side of the applicator, the hydrogel compensates for bumps, hairs and it sticks the applicator to the subject's body. The hydrogel hydrates the skin and makes it tacky or sticky. An alternative could be a conductive adhesive or pressure sensitive adhesive. However, another embodiment could include a dry surface and the subject's skin is wetted with the wetting substance (e.g., Ultrasound gel, hydrogel) and then the applicator is maintained in place. In some embodiments, a bandage is wrapped around the applicator and all or a portion of the subject's body to ensure the applicator is maintained in place. This applicator would likely be less convenient because proper placement might require two practitioners to apply the applicator and/or a cummerbund or wrap to maintain the applicator in place.

Quick Connect Interface Devices

An applicator may connect to a system, such as RF-based systems shown in FIGS. 1A-1F, 8 and 12 using various types of interface devices, connectors, and adapters. The relative placement of applicator and clamp 920 are shown in FIGS. 23A-23C. An exemplary interface unit is shown in FIG. 16. Additional views of interface device are shown in FIGS. 23A-24F. The interface unit 918 includes various components. A cable interface device/cable interface adapter extends 921 from clamp 920. In some embodiments, the cable is fixedly attached to the interface device, while in others it is releasably attached such as by being pluggable and unpluggable relative to the interface device. In some embodiments, the applicator includes a plurality of electrical traces at its connection interface. In light of the goal of matching up the electrical traces to corresponding interface device trace specific connections the interface device is a spring-biased clamp/clip. In this way, when interface device is compressed, it opens to receive a terminal portion of an applicator a shown in FIG. 23C. The applicator terminal includes one or more alignment features to facilitate the proper mating and alignment of terminal electrical connections in the applicator such as via alignment device 895. The alignment device 895 can include holes or other regions or shapes defined by connector 890 that are designed to mate with and align with connectors in interface device 920, such as pins, grooves, etc. In other embodiments, the interface device may be used with the other applicators disclosed herein. FIG. 23C shows the clamp in an open position ready to receive and electrically connect with electrical connector of a given applicator. FIGS. 24A-24F show various views of the interface device 918.

The interface device includes an upper or top housing, a lower or bottom housing, and an electrical subsystem that may include a printed circuit board. The top housing and the bottom housing sandwich the printed circuit board one or more optical connection Distributor Function The applicator is connected to the RF generator using an interface device such as a durable quick disconnect clamp embodiment and others as disclosed herein. The interface device is connected to an electrical distribution box that connects to the RF generator RFG. In one embodiment, the distribution box includes a printed circuit board and/or a collection of circuit elements. In one embodiment, the interface device includes a distribution box and provides distribution and/or control functions while also locking and releasing the disposable applicator. In a given distribution box/hub implementation, the box/hub is configured to monitor and control the various regions/zones of the applicator with minimal cross talk. Various distribution arrangements suitable for use with the flexible RF-based applicators and other applicators disclosed herein are shown in FIGS. 25A-25C.

In one embodiment, the distribution box/hub avoids use of multiple umbilicals that can lead to cross talk/signal interference. In one embodiment, a splitter for two or more umbilicals can be used simultaneously.

Figures 25A, 25B, 25C:
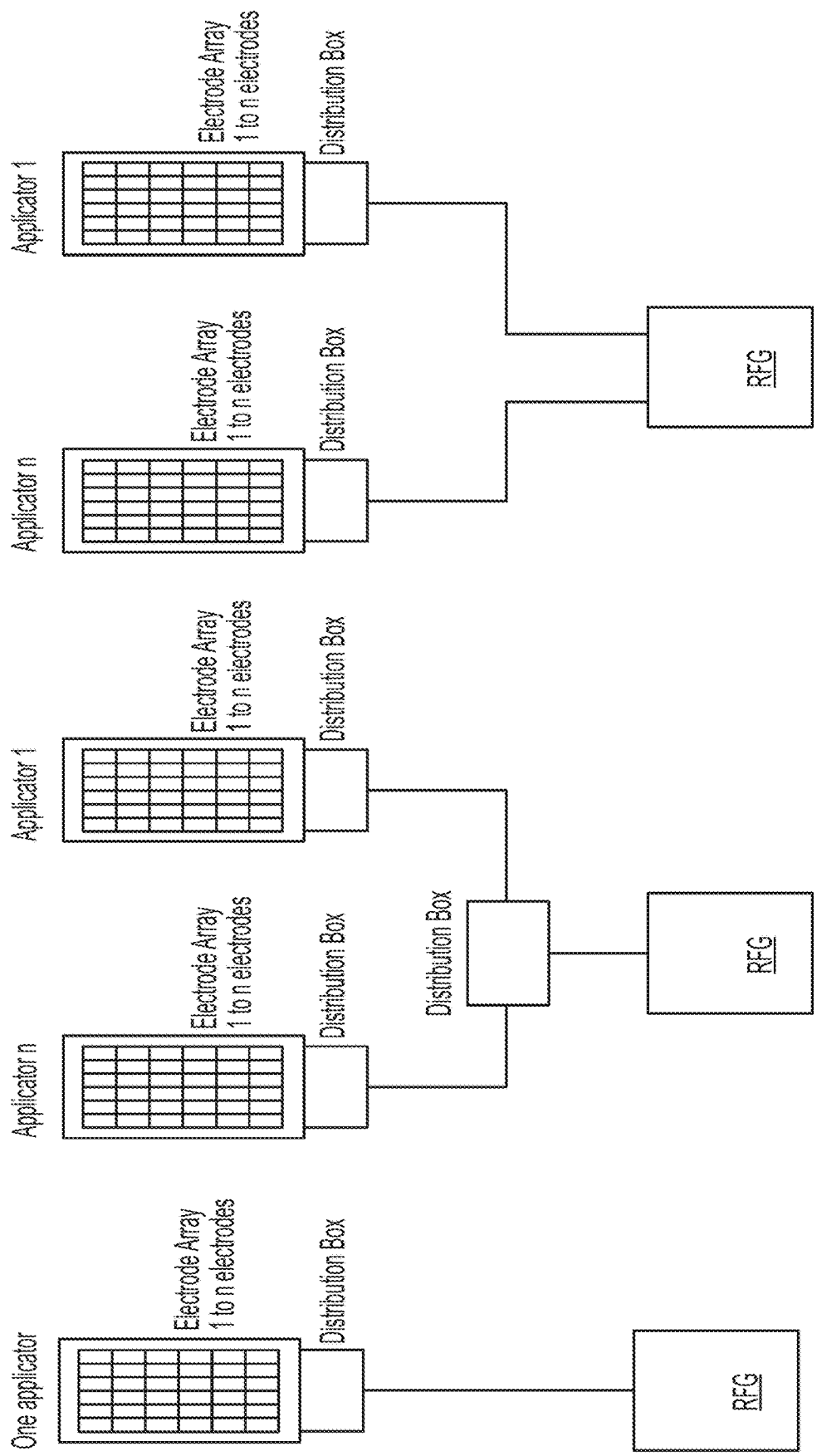
FIGS. 25A-25C schematically depict various distribution arrangements suitable for use with the flexible RF-based applicators and other applicators disclosed herein in accordance with various aspects of the present teachings.

FIG. 25A shows as distribution system that includes a distribution box local to the applicator which performs the task routing RF from the generator and locally distributing it to the individual electrodes to improve feedback control.

In various embodiments, the system shown in FIG. 25B includes a distribution box local to each of the applicators. The combination of applicator and distribution box obtains RF from the generator through a second distribution box. The architecture shown in FIG. 25C also has a distribution box local to each of the applicators. However, in this embodiment, each distribution box is directly connected to the generator. These and other applicator connection schemes can be used relative to a treatment system 100.

Exemplary RF-Based Treatment Methods

In various embodiments, the multi-zone/multi-region applicator that includes one or more kerfs and inner region/spine can be used to facilitate various treatment methods. These systems and methods can include various non-medical related cosmetic and/or aesthetic treatments, such as for skin tightening and/or body sculpting such as through causing lipolysis. In one method, a template is used to characterize one or more patient areas for treatment such that the patient and operator can reach consensus regarding the treatment approach and target regions. Once treatment is agreed upon, the patient may be marked up and otherwise measured and evaluated to determine which applicator to use and various other treatment parameters such as treatment time and target temperature range for uniform heating. Typically, marking up of patient's body is performed to outline regions of treatment that will receive one or more RF-based applicators.

In one embodiment, patient lies down (after neutral electrode pad or NEM attached) and operate prepares subject using one or more of the following use hydrogel predisposed on applicator, use pressure sensitive adhesive predisposed on applicator, layer hydrogel on the patient then apply it to patient, and/or layer ultrasound gel on patient then applicator and then bandage to maintain attachment of applicator. In various embodiments, operator accesses user interface of system 100 to identify a region such as belly button or select a small zone (e.g., zone 5 in FIG. 15C or a subset of a zone such as region 912) on belly button and then turn off zone 5 in GUI prior to treatment.

During initially heating phase, the operator selects a predetermined round robin region/zone activation scheme and then interrogates tissue with RF to reach target temperature. In one embodiment, each zone/region is heated for a set time such as a max time, such as about 10 seconds, and then each zone is sequentially heated for 10 seconds until target temperature is reached. In one embodiment, target temperature is reached in about 1 to about 60 seconds. A threshold of 42° C. may be set such that thermistors will cause a cessation of heating when this temperature is reached. In various embodiments, each zone/region is initially heated in a predetermined sequence (i.e., round robin) until a desired temperature is achieved. For example, in one embodiment, each zone/region is activated for a specified time (i.e., 10 seconds) to bring the tissue up to a desired temperature. As treatment progresses, the applicator zones are interrogated pursuant to an alternating pattern or scheme such as round robin, sequential based on region number, random, or others such that a given zone/region is actively being heated for a period of time and then another zone/region is switched to and also heated. In this way, shifting between different zones and actively heating them before again switching to another zone maintains the desired temperature or temperature range for the underlying tissue until the overall treatment time has been reached. In various embodiments, treatment time can be from about 10 minutes to about 15 minutes. In various embodiments, treatment time can be from about 12 minutes to about 24 minutes. In one embodiment, tissue is interrogated on a zone by zone or region by region basis so that the tissue underlying a given zone or region is maintained within the desired temperature region for the required time period, e.g., a zone is interrogated for 10 seconds to bring it within the range of about 42° C. to about 47° C. or from about 42° C. to about 44° C. and interrogated multiple times over the course of treatment such that overall treatment time of from about 10 min to about 15 min is achieved.

In other embodiments, compressible foam is used to bias tissue towards an applicator or array for contact to one or more electrodes to facilitate or support a given RF treatment of the tissue being contacted. In one embodiment, the electrodes are coupled electrically to reduce cross talk by providing a tacky but easy to remove adhesive applicator for pre-positioning on target treatment areas. Cross-talk may be reduced by including one or more insulating, conductive, semiconducting, materials such as gels or materials or layers. These layers can be doped with or formed using various insulating, conducting, and semiconducting materials to reduce cross-talk or other electrical interference when performing an RF-based treatment using one or more electrodes and/or applicators.

Figure 26C:
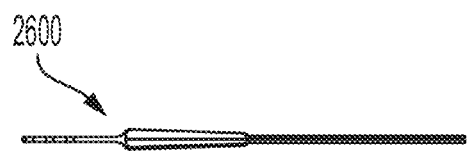
FIG. 26C schematically depicts a view of one side of an RF-based flexible applicator for submental treatment, in accordance with various aspects of the present teachings.
Figure 26E:
FIG. 26E schematically depicts a rear view of an RF-based flexible applicator in accordance with various aspects of the present teachings.
Figure 26A:
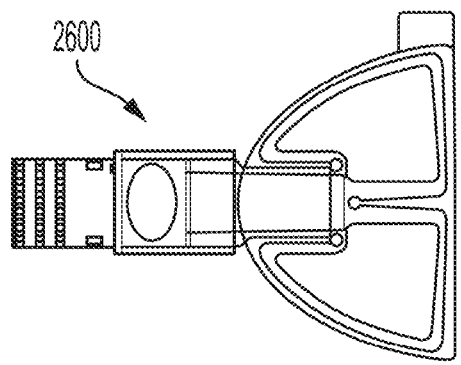
FIG. 26A schematically depicts a top view of an RF-based flexible applicator for submental treatment, in accordance with various aspects of the present teachings.
Figure 26F:
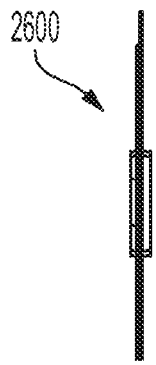
FIG. 26F schematically depicts a front view of an RF-based flexible applicator in accordance with various aspects of the present teachings.
Figure 26D:
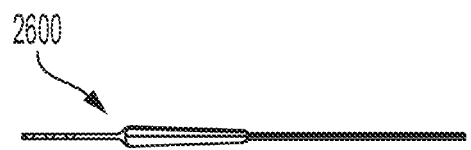
FIG. 26D schematically depicts a view of another side of an RF-based flexible applicator in accordance with various aspects of the present teachings.
Figure 26B:
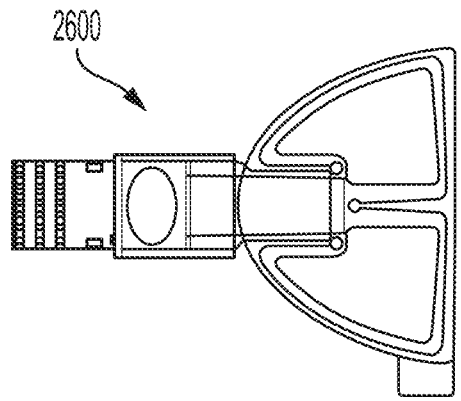
FIG. 26B schematically depicts a bottom view of an RF-based flexible applicator for submental treatment, in accordance with various aspects of the present teachings.

FIGS. 26A-26F show various different views of an applicator constructed and configured for use in the submental region (i.e., the neck and/or chin areas), in accordance with an embodiment of the disclosure. In one embodiment, a submental applicator includes two or more regions. In one embodiment, a submental applicator may have a shape that is a fraction of a circle or an ellipse, such a semicircle, a sector, or half or a third or another portion of an ellipse. FIG. 26A shows a top view of an RF-based flexible applicator 2600 for treating the submental region. FIG. 26B shows a bottom view of the applicator 2600 shown in FIG. 26A. FIG. 26C and FIG. 26D show side views of the applicator 2600. FIGS. 26E and 26F show a rear view and a front view of the applicator 2600 described herein. The submental applicator may include one or more release liners although such liners are optional for the applicators disclosed herein.

Figure 27A:
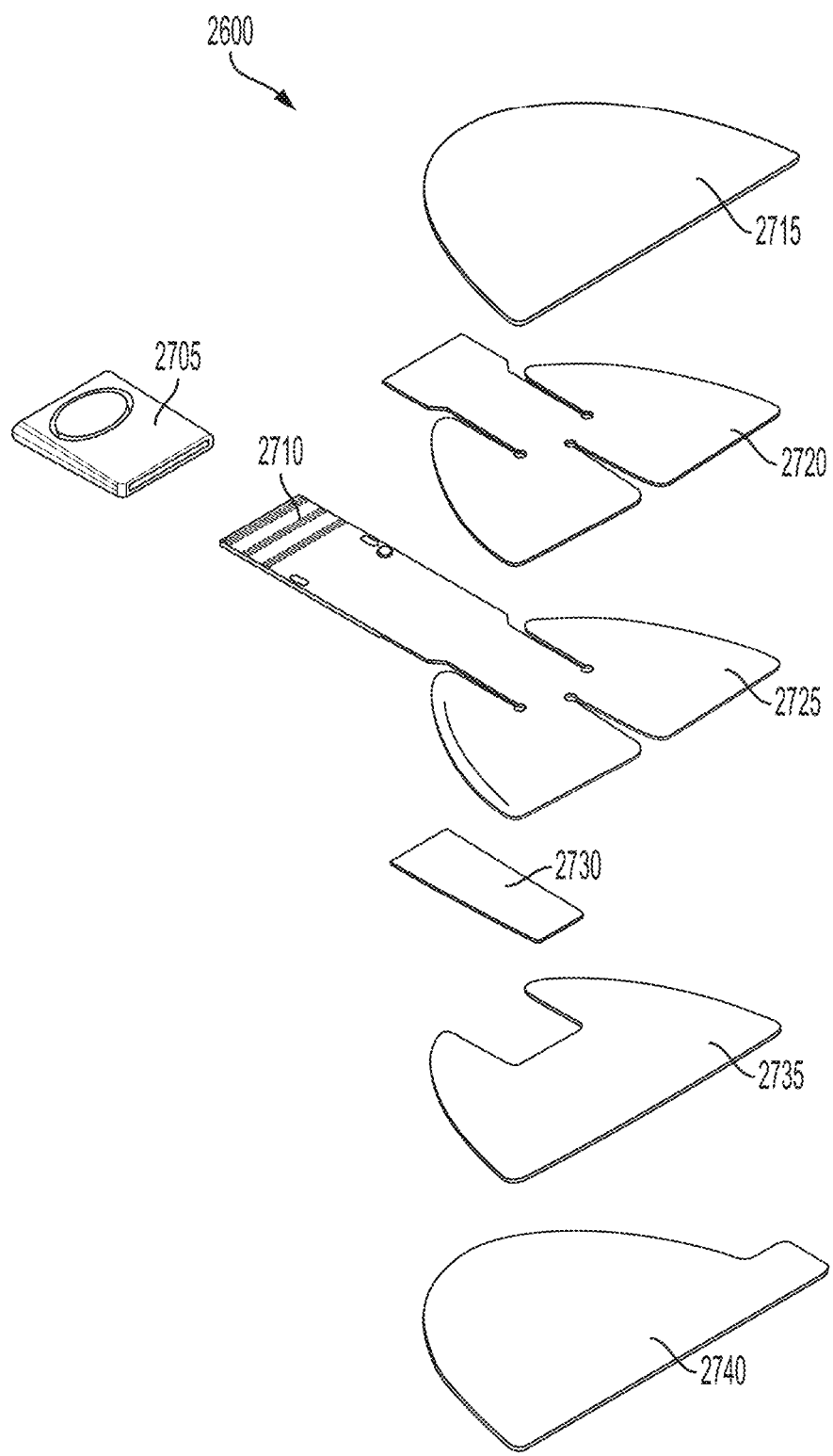
FIG. 27A schematically depicts an exploded view of various layers and components of a flexible RF-based applicator embodiment for treating the submental region, in accordance with various aspects of the present teachings.
Figure 27B:
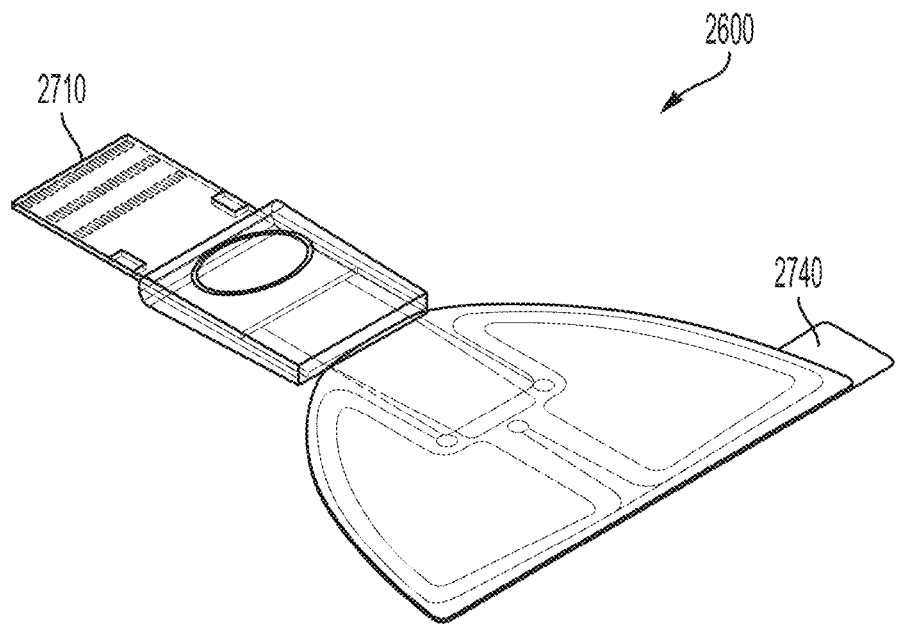
FIGS. 27B-27C schematically depict top perspective views of the Flexible RF-based applicator embodiment of FIG. 27A in accordance with various aspects of the present teachings.
Figure 27C:
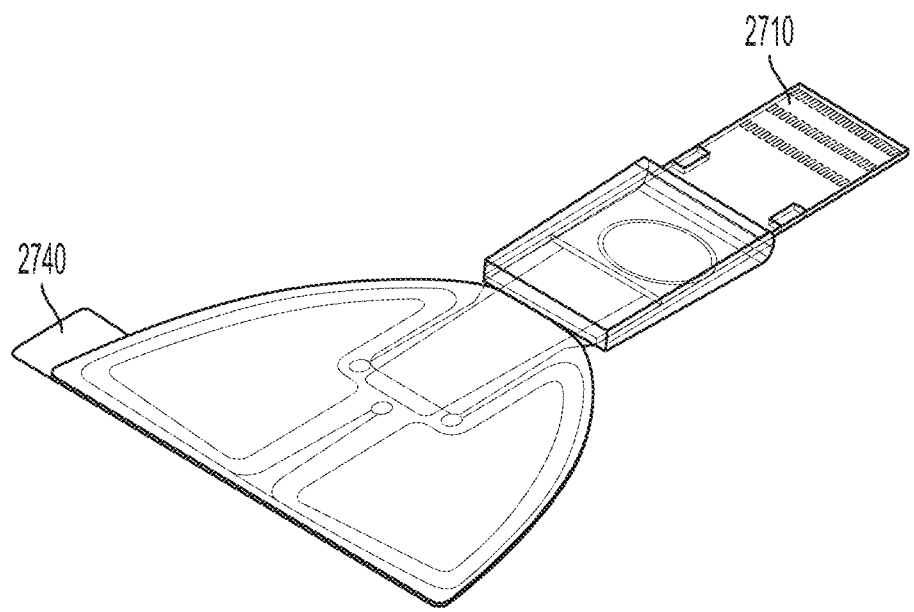

FIG. 27A shows an exploded view of the various layers of an applicator constructed and configured for use in the submental region, in accordance with an embodiment of the disclosure. Similar to the applicator shown in FIGS. 19A-19C, the applicator 2600 for treating the submental region (i.e., neck/chin) has multiple layers. As shown, the releasable liner 2740 is adjacent or below the gel layer 2735. A heat shield layer 2730 is also used to protect the inner region or spine of the applicator. The heat shield layer 2730 is optionally flared or tapered in some embodiments. The flexible applicator 2725 includes the conductive layer, multiple dielectric layers, and adhesive layers. A label 2720 may be disposed on the applicator as discussed herein. In addition, another release liner 2715 may also be used. FIGS. 27B and 27C show different views of the applicator with one or more release liners. The applicator electrical connector 2710 which is connected to the flexible applicator 2725. The system connects to the electrical connector 2710 using mated connector 2705 which may also operate to provide strain relief.

FIGS. 27B and 27C show two different perspective views of the applicator shown in FIG. 27A.

Graphical User Interface Features

The functioning of the display/GUI as it relates to the zones is helpful for protecting sensitive regions and showing temperature information to an operator of an applicator-based treatment system. The GUI 2800 of FIGS. 28A and 28B shows treatment temperature of each zone (zones 1 to 6 shown), identifies when zone is at treatment temperature and whether it is actively delivering RF. In some embodiments, such as applicator embodiment of FIG. 15C one or more of the plurality of layers comprises a label, wherein the label comprises W region identifiers, wherein each of the W region identifiers is disposed on one of the W regions. These regions are labeled 1 to 6 and correspond with regions/zones 1 to 6 shown in the GUI 2800. In some embodiments, W ranges from 2 to 16. In FIG. 15C W is six as shown by applicator label.

FIGS. 28A and 28B depicts a graphical user interface (GUI) for use with a system using an applicator, such as the applicator shown in FIG. 15C, in accordance with various aspects of the present teachings. FIG. 28A shows a GUI 2800 in communication with an applicator. The GUI 2800 is displayed on a display of one of the treatment systems 100, 800, 1200 and is implemented using one or more software modules that receive input signals from temperature sensors of applicator. FIG. 28A shows the graphics/buttons that are oriented in the same manner as the zones on the applicator. FIG. 28B shows one of the buttons grayed out which means the zone has been turned off for sensitive regions.

In this embodiment, the GUI 2800 configures/manages each zone of the applicator. In this case, buttons/controls 2805-1, 2805-2, 2805-3, 2805-4, 2805-5, and 2805-6 (2805 generally) correspond to six zones within the applicator. In other embodiments, an applicator can have more or less than six zones. Each of the buttons/controls 2805 designates a desired temperature for each zone. The controls 2810 can be used to modify the desired temperature for each zone or adjust the treatment time. Additionally, the GUI 2800 shows the treatment time in display 2815. As shown in FIG. 28B, button/control 2805-2 is grayed out, which indicates that zone two has been turned off due to sensitive regions being in close proximity to zone two. In various embodiments, the GUI 2800 is capable of deactivating one or more zones as needed.

All of the drawings submitted herewith include one or more ornamental features and views, each of which include solid lines any of which also incorporate and correspond to and provide support for dotted lines and alternatively, each of which include dotted lines any of which also incorporate and correspond to and provide support for solid lines.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the disclosure as if each value were specifically enumerated herein. In addition, smaller ranges between and including the upper and lower limits of a given range are contemplated and encompassed within the disclosure. The listing of exemplary values or ranges is not a disclaimer of other values or ranges between and including the upper and lower limits of a given range.

It should be appreciated that numerous changes can be made to the disclosed embodiments without departing from the scope of the present teachings. While the foregoing figures and examples refer to specific elements, this is intended to be by way of example and illustration only and not by way of limitation. It should be appreciated by the person skilled in the art that various changes can be made in form and details to the disclosed embodiments without departing from the scope of the teachings encompassed by the appended claims.

The invention claimed is:

1. A radiofrequency (RF)-based treatment system comprising:
   a flexible applicator comprising
      an inner region and
      a plurality of layers,
   the plurality of layers comprises
      a first dielectric layer,
      a second dielectric layer,
      an adhesive layer,
      a polyamide layer,
      an aqueous gel layer, and
      a conductive layer,
   wherein the first dielectric layer and the second dielectric layer sandwich the conductive layer,
   wherein the first dielectric layer is a continuous layer,
   wherein the second dielectric layer is a continuous layer,
   wherein the flexible applicator is configured to conform to a curved tissue surface,
   wherein one or more regions of the conductive layer is an RF transmitter,
   the plurality of layers define a plurality of kerfs and a plurality of strain relief elements,
   the inner region and N regions extending from the inner region,
   wherein the plurality of kerfs divide the applicator into N regions,
   wherein each strain relief element is hole extending through and defined by the plurality of layers,
   wherein two or more kerfs each define a gap between two of the N regions,
   wherein the gap extends from a strain relief element of the plurality of strain relief elements.

2. The RF-based treatment system of claim 1, wherein the N regions ranges from 2 regions to 12 regions.

3. The RF-based treatment system of claim 1, wherein the hole is a circular hole or an elliptical hole in the plurality of layers.

4. The RF-based treatment system of claim 3, wherein one or more of the plurality of kerfs terminate at the one or more strain relief elements, wherein the inner region is adjacent the one or more strain relief elements.

5. The RF-based treatment system of claim 1, wherein the inner region is a kerf-free region, wherein N regions is 6 regions.

6. The RF-based treatment system of claim 1, wherein the N regions comprises a first region and a second region, wherein each of the first and second regions define one or more areas, borders, or kerfs that are substantially the same.

7. The RF-based treatment system of claim 1, wherein the plurality of layers comprises a label, wherein the label comprises N region identifiers, wherein each of the N region identifiers is disposed on one of the N regions.

8. The RF-based treatment system of claim 1, wherein the applicator defines an applicator shape, wherein applicator shape is selected from the group consisting of elliptical, circular, substantially elliptical, substantially circular, pear shaped, substantially pear shaped, submental, and combinations thereof.

9. The RF-based treatment system of claim 1, wherein the conductive layer comprises a patterned region of copper traces in each of the N regions, wherein each of the patterned regions has one or more copper traces in electrical communication with copper traces arranged along the inner region.

10. The RF-based treatment system of claim 1, wherein the applicator further comprises an electrical connector, the electrical connector in electrical communication with one or more addressable regions of conductive layer.

11. The RF-based treatment system of claim 10, further comprising an RF generator, the RF generator having an operating frequency that ranges from about 0.5 MHz to about 10 MHz, wherein the RF generator is in electrical communication with the electrical connector.

12. The RF-based treatment system of claim 9, wherein the applicator further comprises an electrical connector, the electrical connector in electrical communication with one or more addressable regions of the conductive layer, the electrical connector comprising a plurality of electrical contacts, wherein the copper traces arranged along the inner region are in electrical communication with the electrical contacts.

13. The RF-based treatment system of claim 12, wherein the copper traces arranged along the inner region are arranged in a series of three or more adjacent sections, wherein the width of the three or more adjacent sections increase in width along a length of the three or more adjacent sections in a direction towards the electrical connector.

14. The RF-based treatment system of claim 1, wherein conductive layer comprises a continuous copper sheet, wherein the first dielectric layer and the second dielectric layer sandwich a portion of the continuous copper sheet disposed in each of the N regions.

15. The RF-based treatment system of claim 10, further comprising an RF treatment system comprising an interface device in communication with the RF treatment system, the interface device comprising a clamp and a cable adapter, wherein the clamp opens and closes to releasably connect and align with electrical connector, wherein cable adapter is in electrical communication with electric contacts of clamp.

16. The RF-based treatment system of claim 1, wherein area of the flexible applicator ranges from about 50 cm$^2$ to about 600 cm$^2$.

17. The RF-based treatment system of claim 1, further comprising a heat shield layer, wherein conductive layer comprises adjacent arrangements of electrical traces, wherein heat shield layer covers a portion of the inner region, wherein the portion of the inner region and the heat shield layer are disposed above the arrangements of electrical traces.

18. The RF-based treatment system of claim 1, further comprising one or more temperature sensors per each of the N regions.

19. The RF-based treatment system of claim 18, further comprising an RF treatment system in electrical communication with the applicator and each temperature sensor, further comprising a control system, wherein control system selectively addresses each of the N regions to transmit RF energy sequentially to facilitate uniform heating according to one or more patterns.

20. The RF-based treatment system of claim 18, further comprising an RF treatment system in electrical communication with the applicator and each temperature sensor, further comprising a control system, wherein the control system selectively bypasses one or more of the N regions in response to an operator selection that the one or more N regions is positioned above a sensitive tissue region.

21. The RF-based treatment system of claim 1, wherein the width of the gap increases along a length of the kerf.

22. A radiofrequency (RF)-based treatment system comprising:
- a flexible applicator comprising an elongate inner region and a plurality of layers,
- the plurality of layers comprises
  - a first dielectric layer,
  - a second dielectric layer, and
  - a conductive layer,
- wherein the first dielectric layer and the second dielectric layer sandwich the conductive layer,
- the plurality of layers define a plurality of kerfs, the elongate inner region and N regions extending from the elongate inner region,
- wherein the first dielectric layer is a continuous layer,
- wherein the second dielectric layer is a continuous layer,
- wherein the flexible applicator is configured to conform to a curved tissue surface,
- wherein the plurality of kerfs divide the applicator into N regions extending from the elongate inner region,
- wherein the conductive layer defines an arrangement of electrical traces in the elongate inner region,
- wherein the conductive layer further defines a plurality of patterned traces in each of the N regions,
- wherein each patterned trace in each of the N regions is in electrical communication with one or more electrical traces in the arrangement of electrical traces in the elongate inner region.

23. The system of claim 22, wherein the first dielectric layer comprises a flexible dielectric insulation, wherein the first dielectric layer is positioned in each of the N regions to manage heat by reducing edge effects from one or more of the patterned traces.

24. The system of claim 22, further comprising an RF treatment system in electrical communication with the applicator and the plurality of patterned traces, the RF treatment system further comprising a control system, wherein control system selectively addresses each of the N regions to transmit RF energy sequentially to facilitate uniform heating according to one or more patterns.

25. The system of claim 22, wherein the plurality of layers define a plurality of strain relief elements, wherein two or more kerfs each define a gap between two of the N regions, wherein the gap extends from a strain relief element of the plurality of strain relief elements.

26. The system of claim 25, wherein the width of the gap increases along a length of the kerf.

27. The system of claim 1, wherein the conductive layer comprises copper.

28. A cosmetic treatment system comprising:
- a flexible applicator comprising
- a plurality of layers;
- an elongate inner region; and
- four or more regions; each region separated from another other region by one or more kerfs, wherein each region defines two or more curved corners, each region extending from the elongate inner region,
- the plurality of layers comprises
  - a first dielectric layer,
  - a second dielectric layer, and
  - a conductive layer,
- wherein the first dielectric layer and the second dielectric layer sandwich the conductive layer,
- wherein the first dielectric layer is a continuous layer,
- wherein the second dielectric layer is a continuous layer,
- wherein the flexible applicator is configured to conform to a curved tissue surface,
- wherein the conductive layer defines an arrangement of electrical traces in the elongate inner region, wherein the conductive layer further defines a plurality of patterned traces in each region,
- wherein each patterned trace in each region is in electrical communication with one or more electrical traces in the arrangement of electrical traces in the elongate inner region.

29. The cosmetic treatment system of claim 28, further comprising a clip device operable to connect to and release from an electrical contact extending from the elongate inner region.

30. The cosmetic treatment system of claim 28, further comprising a releasable clip comprising a cable extending therefrom, wherein clip is configured to open and close on a region of the elongate inner region to electrically connect the flexible applicator to the cable.

31. The cosmetic treatment system of claim 28, wherein the four or more regions define an elliptical perimeter having gaps therein, wherein each gap is a portion of a kerf.

* * * * *